United States Patent
Grammenos et al.

(10) Patent No.: US 11,064,697 B2
(45) Date of Patent: Jul. 20, 2021

(54) PYRIDINE COMPOUNDS USEFUL FOR COMBATING PHYTOPATHOGENIC FUNGI

(71) Applicant: BASF SE, Ludwigshafen (DE)

(72) Inventors: Wassilios Grammenos, Ludwigshafen (DE); Christian Winter, Ludwigshafen (DE); Bernd Mueller, Frankenthal (DE); Antje Wolf, Ludwigshafen (DE); Ana Escribano Cuesta, Mannheim (DE); Erica Cambeis, Hessheim (DE); Jan Klaas Lohmann, Lambsheim (DE); Thomas Grote, Wachenheim (DE); Manuel Kretschmer, Washington, DC (US); Nadine Riediger, Schifferstadt (DE); Ian Robert Craig, Ludwigshafen (DE); Christine Wiebe, Mannheim (DE); Violeta Terterya-Seiser, Mannheim (DE); Andreas Koch, Birkenheide (DE); Marcus Fehr, Speyer (DE)

(73) Assignee: BASF SE, Ludwigshafen (DE)

( * ) Notice: Subject to any disclaimer, the term of this patent is extended or adjusted under 35 U.S.C. 154(b) by 232 days.

(21) Appl. No.: 15/746,866

(22) PCT Filed: Jul. 18, 2016

(86) PCT No.: PCT/EP2016/067039
§ 371 (c)(1),
(2) Date: Jan. 23, 2018

(87) PCT Pub. No.: WO2017/016915
PCT Pub. Date: Feb. 2, 2017

(65) Prior Publication Data
US 2020/0077653 A1 Mar. 12, 2020

(30) Foreign Application Priority Data
Jul. 24, 2015 (EP) .................................... 15178246

(51) Int. Cl.
C07D 401/04 (2006.01)
A01N 43/40 (2006.01)
C07D 401/14 (2006.01)
C07D 409/14 (2006.01)

(52) U.S. Cl.
CPC ........... *A01N 43/40* (2013.01); *C07D 401/04* (2013.01); *C07D 401/14* (2013.01); *C07D 409/14* (2013.01)

(58) Field of Classification Search
CPC .................................................. C07D 401/04
USPC ........................................ 546/144; 514/307
See application file for complete search history.

(56) References Cited

U.S. PATENT DOCUMENTS

| | | |
|---|---|---|
| 3,748,867 A | 7/1973 | Hamri et al. |
| 4,107,292 A | 8/1978 | Nemeth |
| 4,557,755 A | 12/1985 | Takahashi |
| 5,462,915 A | 10/1995 | Curtis |
| 5,705,174 A | 1/1998 | Benoff |
| 5,910,314 A | 6/1999 | Benoff |
| 7,232,926 B2 | 6/2007 | Hamprecht |
| 7,632,783 B2 | 12/2009 | Ito et al. |
| 7,737,275 B2 | 6/2010 | Hamprecht |
| 7,847,097 B2 | 12/2010 | Gebhardt |
| 8,357,695 B2 | 1/2013 | Schmidt |
| 8,362,026 B2 | 1/2013 | Schmidt |
| 8,741,968 B2 | 6/2014 | Gottsche |
| 8,999,358 B2 | 4/2015 | Amrhein |
| 9,150,538 B2 | 10/2015 | Umetani et al. |
| 2003/0119675 A1 | 6/2003 | Wolf |
| 2004/0115280 A1 | 6/2004 | Podszun |
| 2008/0171658 A1 | 7/2008 | Dyllick-Brenzinger |
| 2008/0275242 A1 | 11/2008 | Ito et al. |
| 2011/0212837 A1 | 9/2011 | Angermann |
| 2013/0324506 A1 | 12/2013 | Berrebi-Bertrand et al. |

FOREIGN PATENT DOCUMENTS

| | | |
|---|---|---|
| DE | 1695921 A1 | 9/1972 |
| EP | 0008207 A2 | 2/1980 |
| EP | 1736471 | 11/2008 |
| EP | 2103214 B1 | 10/2013 |
| EP | 2223919 B1 | 10/2014 |

(Continued)

OTHER PUBLICATIONS

English translation of description and claims of JP 2011/148714. (Year: 2011).*
Mollet et al., "Formulation Technology," 1st ed., Wiley-VCH Verlag GmbH, Weinheim 2001, Chapter 6.4, pp. 181-246.
Dietrich et al., "Amino Resin Microcapsules. II. Preparation and Morphology," Acta Polymerica, vol. 40, No. 5, (1989), pp. 325-331.
Mollet et al., "Formulation Technology," 1st ed., Wiley-VCH Verlag GmbH, Weinheim 2001, Chapter 14.2.2, pp. 389-398.

(Continued)

*Primary Examiner* — Patricia L Morris
(74) *Attorney, Agent, or Firm* — Marshall, Gerstein & Borun LLP

(57) ABSTRACT

The present invention relates to compounds I

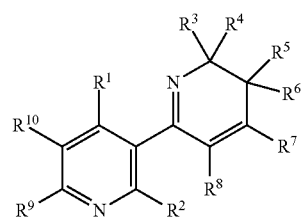

wherein the variables are defined as given in the description and claims. The invention further relates to uses, processes and intermediates for compounds I.

13 Claims, No Drawings

(56) References Cited

FOREIGN PATENT DOCUMENTS

| | | |
|---|---|---|
| EP | 2517562 B1 | 1/2017 |
| FR | 2161776 A1 | 7/1973 |
| JP | 2011148714 A | 11/2008 |
| WO | 9603041 A1 | 2/1996 |
| WO | 0027519 A2 | 5/2000 |
| WO | 0183459 A2 | 11/2001 |
| WO | 03097589 A1 | 11/2003 |
| WO | WO2004013094 A2 | 2/2004 |
| WO | 05054208 A1 | 6/2005 |
| WO | 05102044 A1 | 11/2005 |
| WO | 06094792 A1 | 9/2006 |
| WO | 06094978 A2 | 9/2006 |
| WO | 06125746 A1 | 11/2006 |
| WO | 2007011022 A1 | 1/2007 |
| WO | 08043835 A2 | 4/2008 |
| WO | 08043836 A1 | 4/2008 |
| WO | WO2005070917 A1 | 11/2008 |
| WO | WO2008035379 A2 | 11/2008 |
| WO | 11023758 A2 | 3/2011 |
| WO | 11023759 A2 | 3/2011 |
| WO | WO2011042918 A2 | 4/2011 |
| WO | WO2012051036 A1 | 4/2012 |
| WO | 12101070 A1 | 8/2012 |
| WO | 13134310 A1 | 9/2013 |
| WO | WO2013047749 A1 | 3/2015 |
| WO | 16169683 A1 | 10/2016 |
| WO | WO2016156129 A1 | 10/2016 |
| WO | 17037210 | 3/2017 |
| WO | WO2017060148 A1 | 4/2017 |
| WO | WO2017067784 A1 | 4/2017 |

OTHER PUBLICATIONS

Finch et al., "Microencapsulation," Ullman's Encyclopedia of Idustrial Chemistry, 6th Edition, 2001 Electronic Release.

Office Action, issued in co-pending U.S. Appl. No. 15/562,448, dated Jan. 22, 2019.

HCAPLUS Abstract 1947:3669 (1947).

De Lucca, "Harmful Fungi in Both Agriculture and Medicine," Revista Iberoamericana de Micologia, vol. 24, Issue 1, (2007), pp. 3-13.

Search Report, issued in EP Application No. 15178246.3, dated Sep. 7, 2015.

International Search Report, issued in PCT/EP2016/067039, dated Oct. 18, 2016.

International Preliminary Report on Patentability, issued in PCT/EP2016/067039, dated Jan. 30, 2018.

Basak, et al., "Catalytic enantioselective oxidation of sulfides and disulfides by a chiral complex of bis-hydroxamic acid and molybdenum", Tetrahedron: Asymmetry, vol. 17, Issue 4, Feb. 20, 2006, pp. 508-511.

Senecal, et al., "A General, Practical Palladium-Catalyzed Cyanation of (Hetero)Aryl Chlorides and Bromides", Angewandte Chemie, vol. 52, Issue 38, Sep. 16, 2013, pp. 10035-10039.

Tian, et al, "One-pot synthesis of 4-methylisoquinolines via a sequential Pd-catalyzed Heck reaction and intramolecular cycfization", Organic & Biomolecular Chemistry, vol. 11, Issue 42, 2013, pp. 7262-7266.

Yu, et al., "Development of Pd/C-Catalyzed Cyanation of Aryl Halides", The Journal of Organic Chemistry, vol. 76, Issue 2, 2011, pp. 665-668.

Chakravorti, et al., "Isoquinolylquinoline Derivatives: Part III-Synthesis of Some 4-Substituted 3-(3',4'-Dihydro-1'-isoquinolyl) quinoline Derivatives as Possible Antifilarial Agents", Indian Journal of Chemistry, Section B, vol. 24B, Issue 7, 1985, pp. 737-746.

Das, et al., "Isoquinolylquinoline Derivatives: Part IV-Synthesis of Some 4-Substituted 3-(3',4'-Dihydro-3'methyl-1'-isoquinolyl)-7-chloro-quinoline Derivatives as Possible Trypanocidal Agents", Indian Journal of Chemistry, Section B, vol. 25, Issue B, 1986, pp. 1072-1078.

* cited by examiner

PYRIDINE COMPOUNDS USEFUL FOR COMBATING PHYTOPATHOGENIC FUNGI

This application is a National Stage application of International Application No. PCT/EP2016/067039, filed Jul. 18, 2016. This application also claims priority under 35 U.S.C. § 119 to European Patent Application No. 15178246.3, filed Jul. 24, 2015.

The present invention relates to pyridine compounds and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

Surprisingly, this object is achieved by the use of the inventive pyridine compounds of formula I having favorable fungicidal activity against phytopathogenic fungi.

Accordingly, the present invention relates to the Compounds of formula I

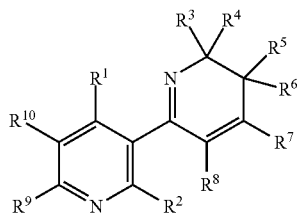

I wherein
$R^1$ is in each case independently selected from hydrogen, halogen, OH, CN, $NO_2$, SH, $NH_2$, $NH(C_1\text{-}C_4\text{-alkyl})$, $N(C_1\text{-}C_4\text{-alkyl})_2$, $NH\text{—}SO_2\text{—}R^x$, $C_1\text{-}C_6$-alkyl, $C_2\text{-}C_6$-alkenyl, $C_2\text{-}C_6$-alkynyl, $C_1\text{-}C_6$-alkoxy, $C_3\text{-}C_6$-cycloalkyl, five- or six-membered heteroaryl and aryl; wherein the heteroaryl contains one, two or three heteroatoms selected from N, O and S; and wherein
$R^x$ is $C_1\text{-}C_4$-alkyl, $C_1\text{-}C_4$-halogenalkyl, unsubstituted aryl or aryl that is substituted by 1, 2, 3, 4 or 5 substituents $R^{x1}$ independently selected from $C_1\text{-}C_4$-alkyl;
wherein the aliphatic moieties of $R^1$ are unsubstituted or substituted with identical or different groups $R^{1a}$ which independently of one another are selected from:
$R^{1a}$ halogen, OH, CN, $C_1\text{-}C_6$-alkoxy, $C_3\text{-}C_6$-cycloalkyl, $C_3\text{-}C_6$-halogencycloalkyl, $C_1\text{-}C_4$-halogenalkoxy, $C_1\text{-}C_6$-alkylthio and phenoxy, wherein the phenyl group is unsubstituted or carries 1, 2, 3, 4 or 5 substituents $R^{1a}$ selected from the group consisting of halogen, OH, $C_1\text{-}C_4$-alkyl, $C_1\text{-}C_4$-halogenalkyl, $C_1\text{-}C_4$-alkoxy and $C_1\text{-}C_4$-halogenalkoxy;
wherein the cycloalkyl, heteroaryl and aryl moieties of $R^1$ are not further substituted or carry 1, 2, 3, 4, 5 or up to the maximum number of identical or different groups $R^{1b}$ which independently of one another are selected from:
$R^{1b}$ halogen, OH, CN, $C_1\text{-}C_4$-alkyl, $C_1\text{-}C_4$-alkoxy, $C_1\text{-}C_4$-halogenalkyl, $C_3\text{-}C_6$-cycloalkyl, $C_3\text{-}C_6$-halogencycloalkyl, $C_1\text{-}C_4$-halogenalkoxy and $C_1\text{-}C_6$-alkylthio;
$R^2$ is in each case independently selected from the substituents as defined for $R^1$, wherein the possible substituents for $R^2$ are $R^{2a}$ and $R^{2b}$, respectively, which correspond to $R^{1a}$ and $R^{1b}$, respectively;
$R^3, R^4$ are independently selected from hydrogen, halogen, OH, CN, $NO_2$, SH, $C_1\text{-}C_6$-alkylthio, $NH_2$, $NH(C_1\text{-}C_4\text{-alkyl})$, $N(C_1\text{-}C_4\text{-alkyl})_2$, $NH\text{—}SO_2\text{—}R^x$, $C_1\text{-}C_6$-alkyl, $C_2\text{-}C_6$-alkenyl, $C_2\text{-}C_6$-alkynyl, $C_1\text{-}C_6$-alkoxy, $C_1\text{-}C_6$-halogenalkoxy, a saturated or partially unsaturated three-, four-, five-, six-, seven-, eight-, nine-, or ten-membered carbocycle or heterocycle, wherein in each case one or two $CH_2$ groups of the carbo- and heterocycle may be replaced by a group independently selected from $C(=O)$ and $C(=S)$, five- or six-membered heteroaryl and aryl; wherein the heterocycle and the heteroaryl contain independently 1, 2, 3 or 4 heteroatoms selected from N, O and S;
wherein the aliphatic moieties of $R^3$ and $R^4$ are independently not further substituted or carry 1, 2, 3 or up to the maximum possible number of identical or different groups $R^{3a}$ or $R^{4a}$, respectively, which independently of one another are selected from:
$R^{3a}, R^{4a}$ halogen, OH, CN, $NO_2$, SH, $NH_2$, $NH(C_1\text{-}C_4\text{-alkyl})$, $N(C_1\text{-}C_4\text{-alkyl})_2$, $NH(C(=O)C_1\text{-}C_4\text{-alkyl})$, $N(C(=O)C_1\text{-}C_4\text{-alkyl})_2$, $C_1\text{-}C_6$-alkoxy, $C_3\text{-}C_6$-cycloalkyl, $C_3\text{-}C_6$-halogencycloalkyl, $C_1\text{-}C_4$-halogenalkoxy, $C_1\text{-}C_6$-alkylthio, aryl and phenoxy, wherein the aryl and phenyl groups are independently unsubstituted or carry 1, 2, 3, 4 or 5 substituents selected from halogen, OH, CN, $NO_2$, SH, $NH_2$, $NH(C_1\text{-}C_4\text{-alkyl})$, $N(C_1\text{-}C_4\text{-alkyl})_2$, $NH(C(=O)C_1\text{-}C_4\text{-alkyl})$, $N(C(=O)C_1\text{-}C_4\text{-alkyl})_2$, $NH\text{—}SO_2\text{—}R^x$, $C_1\text{-}C_6$-alkylthio, $C_1\text{-}C_4$-alkyl, $C_1\text{-}C_4$-halogenalkyl, $C_1\text{-}C_4$-alkoxy and $C_1\text{-}C_4$-halogenalkoxy;
wherein the carbocyclic, heterocyclic, heteroaryl and aryl moieties of $R^3$ and $R^4$ are independently not further substituted or carry 1, 2, 3, 4, 5 or up to the maximum number of identical or different groups $R^{3b}$ or $R^{4b}$, respectively, which independently of one another are selected from:
$R^{3b}, R^{4b}$ halogen, OH, CN, $NO_2$, SH, $NH_2$, $NH(C_1\text{-}C_4\text{-alkyl})$, $N(C_1\text{-}C_4\text{-alkyl})_2$, $NH(C(=O)C_1\text{-}C_4\text{-alkyl})$, $N(C(=O)C_1\text{-}C_4\text{-alkyl})_2$, $NH\text{—}SO_2\text{—}R^x$, $C_1\text{-}C_4$-alkyl, $C_1\text{-}C_4$-alkoxy, $C_1\text{-}C_4$-halogenalkyl, $C_3\text{-}C_6$-cycloalkyl, $C_3\text{-}C_6$-halogencycloalkyl, $C_1\text{-}C_4$-halogenalkoxy, $C_1\text{-}C_6$-alkylthio, $C_1\text{-}C_6$-halogenalkylthio, $C_1\text{-}C_4$-alkoxy-$C_1\text{-}C_4$-alkyl, phenyl and phenoxy, wherein the phenyl groups are unsubstituted or substituted with substituents selected from the group consisting of halogen, OH, $C_1\text{-}C_4$-alkyl, $C_1\text{-}C_4$-halogenalkyl, $C_1\text{-}C_4$-alkoxy and $C_1\text{-}C_4$-halogenalkoxy;
and wherein $R^x$ is as defined above; or
$R^3, R^4$ together with the carbon atom to which they are bound (marked with * in formula I) form a saturated or partially unsaturated three-, four-, five-, six-, seven-, eight-, nine-, or ten-membered carbocycle or heterocycle; wherein the heterocycle contains 1, 2, 3 or 4 heteroatoms selected from N, O and S, wherein N may carry one substituent $R^N$ selected from $C_1\text{-}C_4$-alkyl, $C_1\text{-}C_4$-halogenalkyl and $SO_2Ph$, wherein Ph is unsubstituted phenyl or phenyl that is substituted by 1, 2 or 3 substituents selected from $C_1\text{-}C_4$-alkyl, and wherein S may be in the form of its oxide SO or $SO_2$, and wherein the carbocycle or heterocycle is unsubstituted or carries one, two, three or four substituents $R^{34}$ independently selected from halogen, OH, CN, $NO_2$, SH, $NH_2$, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_1$-$C_4$-alkoxy-$C_1$-$C_4$-alkyl, phenyl and phenoxy, wherein the phenyl groups are unsubstituted or substituted with substituents $R^{34a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein in each case one or two $CH_2$ groups of the carbo- or heterocycle may be replaced by a group independently selected from C(=O) and C(=S);

$R^5$ is halogen;

$R^6$ is selected from H or halogen;

$R^9$, $R^{10}$ are independently selected from H, halogen, CN, $NO_2$, $N(R^{91})(R^{92})$, $S(R^{93})$, $S(O)_{z94}(R^{94})$, $O(R^{95})$, $C_1$-$C_6$-alkyl, $C_2$-$C_6$-alkenyl, $C_2$-$C_6$-alkynyl, cycloalkyl, CO—$(R^{96})$;

$R^{91}$, $R^{92}$ are independently selected from H, alkyl, alkenyl, alkynyl, cycloalkyl, CO—$R^{(911)}$, and $S(O)_{z91}R^{912}$;

$R^{911}$ H or $R^{912}$;

$R^{912}$ is independently selected from alkyl, alkenyl, alkynyl, cycloalkyl, O—$R^{9111}$, and $N(R^{9112})(R^{9113})$;

$R^{9111}$ is alkyl, alkenyl, alkynyl or cycloalkyl;

$R^{9112}$, $R^{9113}$ are independently selected from H, alkyl, alkenyl, alkynyl, alkenyl and cycloalkyl;

z91 is 1 or 2;

$R^{93}$ is H, alkyl, alkenyl, alkynyl, or cycloalkyl;

$R^{94}$ is independently selected from alkyl, alkenyl, alkynyl, cycloalkyl, O—$R^{941}$, and $N(R^{942})(R^{943})$;

$R^{941}$ is independently selected from alkyl, alkenyl, alkynyl, and cycloalkyl;

$R^{942}$, $R^{943}$ are independently selected from H or $R^{941}$;

z94 is 1 or 2;

$R^{95}$ is independently selected from H, alkyl, alkenyl, alkynyl, cycloalkyl, carbonyl-$R^{951}$, $S(O)_{z95}R^{952}$;

$R^{951}$ is H or $R^{95}2$;

$R^{952}$ is independently selected from alkyl, alkenyl, alkynyl, cycloalkyl, O—$R^{9521}$, $N(R^{9522})(R^{9523})$;

$R^{9521}$ is independently selected from alkyl, alkenyl, alkynyl, cycloalkyl; $R^{9522}$, $R^{9523}$ is independently selected from H and $R^{9521}$;

z95 is 1 or 2;

$R^{96}$ is independently selected from H, alkyl, alkenyl, alkynyl, cycloalkyl, O—$R^{961}$, $N(R^{962})(R^{963})$;

$R^{961}$ is independently selected from H, alkyl, alkenyl, alkynyl, cycloalkyl;

$R^{962}$, $R^{963}$ are independently selected from H, alkyl, alkenyl, alkynyl, cycloalkyl; wherein the aliphatic moieties of $R^9$, $R^{10}$ are unsubstituted or substituted by identical or different groups of $R^{9a}$, wherein $R^{9a}$ independently of one another are selected from: halogen, OH, CN, $C_1$-$C_6$-alkoxy, alkenyloxy, alkynyloxy, $C_3$-$C_6$-cycloalkyl, $C_3$-$C_6$-halogencycloalkyl, $C_1$-$C_4$-halogenalkoxy, $C_1$-$C_6$-alkylthio;

or $R^9$ & $R^{10}$ together with the carbon atoms to which they are bound form a five-, six-, or seven-membered heterocyclic or heteroaromatic ring; wherein the ring contains 1, 2, 3 or 4 heteroatoms selected from N, O and S, wherein N may carry one substituent $R^N$ selected from $C_1$-$C_4$-alkyl, $C_1$-$C_4$-akyl and $SO_2Ph$, wherein Ph is unsubstituted phenyl or phenyl that is substituted by 1, 2 or 3 substituents selected from $C_1$-$C_4$-alkyl, and wherein S may be in the form of its oxide SO or $SO_2$; and wherein in each case one or two $CH_2$ groups of the carbo- or heterocycle may be replaced by a group independently selected from C(=O) and C(=S); and wherein the heterocyclic or heteroaromatic ring is substituent by $(R^{11})_m$, wherein m is 0, 1, 2, 3 or 4;

$R^{11}$ is in each case independently selected from halogen, OH, CN, $NO_2$, SH, $NH_2$, $NH(C_1$-$C_4$-alkyl), $N(C_1$-$C_4$-alkyl$)_2$, NH—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains 1, 2 or 3 heteroatoms selected from N, O and S; and wherein in each case one or two $CH_2$ groups of the carbo- or heterocycle may be replaced by a group independently selected from C(=O) and C(=S); and wherein $R^x$ is $C_1$-$C_4$-alkyl, $C_1$-$C_4$-halogenalkyl, unsubstituted aryl or aryl that is substituted by 1, 2, 3, 4 or 5 substituents $R^{x1}$ independently selected from $C_1$-$C_4$-alkyl;

wherein the aliphatic moieties of $R^{11}$ are unsubstituted or carry 1, 2, 3 or up to the maximum possible number of identical or different groups $R^{11a}$ which independently of one another are selected from:

$R^{11a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or unsubstituted or substituted with $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heteroaryl and aryl moieties of $R^{11}$ are unsubstituted or carry 1, 2, 3, 4, 5 or up to the maximum number of identical or different groups $R^{11b}$ which independently of one another are selected from:

$R^{11b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, and $C_1$-$C_6$-alkylthio;

$R^7$ and $R^8$ together with the carbon atoms to which they are bound form a ring A, wherein the ring A is phenyl or five- or six-membered heteroaryl; wherein the heteroaryl contains one, two or three heteroatoms selected from N, O and S, and wherein the ring A is substituent by $(R^{78})_o$, wherein o is 0, 1, 2 or 3; and $R^{78}$ are independently selected from halogen, OH, CN, $NO_2$, SH, $NH_2$, $NH(C_1$-$C_4$-alkyl), $N(C_1$-$C_4$-alkyl$)_2$, $NH(C(=O)C_1$-$C_4$-alkyl), $N(C(=O)C_1$-$C_4$-alkyl$)_2$, NH—$SO_2$—$R^x$, CH(=O), C(=O)$C_1$-$C_6$-alkyl, C(=O)NH($C_1$-$C_6$-alkyl), CR'=NOR", $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, $C_2$-$C_6$-alkenyloxy, $C_2$-$C_6$-alkynyloxy, $C_3$-$C_6$-cycloalkyl, $C_3$-$C_6$-cycloalkenyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; wherein R' and R" are independently selected from $C_1$-$C_4$-alkyl, $C_2$-$C_6$-alkenyl, $C_2$-$C_6$-alkynyl, $C_3$-$C_6$-cycloalkyl, saturated or partially unsaturated three-, four-, five-, six-, seven-, eight-, nine-, or ten-membered heterocycle, five- or six-membered heteroaryl or aryl; wherein the heterocycle or heteroaryl contains one, two or three heteroatoms selected from N, O and S, and wherein R' and/or R" are independently unsubstituted or carry one, two or three R'" independently selected from halogen, OH, CN, $NO_2$, SH, $NH_2$, $NH(C_1$-$C_4$-alkyl), $N(C_1$-$C_4$-alkyl$)_2$, NH—$SO_2$—$R^x$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl; and wherein $R^x$ is defined above;
and
wherein the aliphatic moieties of $R^{78}$ are not further substituted or carry 1, 2, 3 or up to the maximum possible number of identical or different groups $R^{78a}$ which independently of one another are selected from:
$R^{78a}$ halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heterorayl, phenyl and phenoxy group is unsubstituted or unsubstituted or substituted with $R^{78aa}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;
wherein the alicyclic, phenyl, heterocyclic and heteroaryl moieties of $R^{78}$ are unsubstituted or substituted with identical or different groups $R^{78b}$ which independently of one another are selected from:
$R^{78b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, and $C_1$-$C_6$-alkylthio;
and the N-oxides and the agriculturally acceptable salts thereof.

The numbering of the ring members in the compounds of the present invention is as given in formula I above:

Compounds of formula I can be accessed e.g. starting from alcohols of type II with nitriles of type III in the presence of an acid in an organic solvent (see for example US 2008/0275242 or WO2005/070917). Preferably, sulfuric acid or a sulfonic acid, in particular triflic acid, are used as acid. Most suitable solvents are hydrocarbons, preferably benzene or dichloromethane. In the following schemes, the optionally substituted phenyl or heteroaryl formed by $R^7$ and $R^8$ is sketched by a circle named "A":

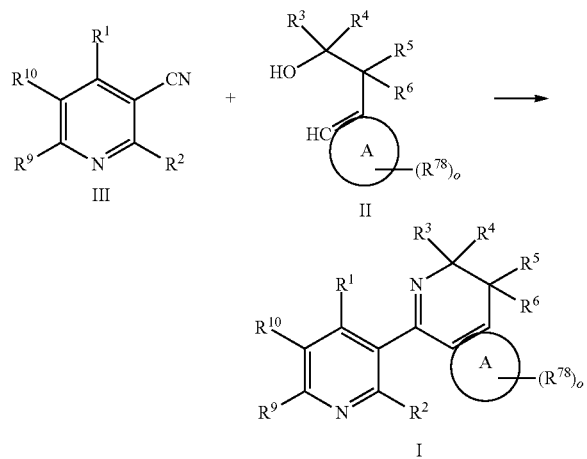

Depending on the nature of the starting materials, the reaction is performed at a temperature from −40° C. to 200° C., in particular from −10° C. to 120° C., more specifically from 0° C. to 100° C., even more specifically from room or ambient temperature (about 23° C.) to 80° C.

Nitriles of type III are either commercially available or can be prepared by a skilled person from the corresponding halides following literature procedures (see, for example Journal of Organic Chemistry, 76(2), 665-668; 2011; Angewandte Chemie, International Edition, 52(38), 10035-10039; 2013; WO2004/013094).

Alcohols of type II can be prepared as described below. A skilled person will realize that compounds of type III can be reacted with organometallic reagents, preferably alkyl Grignard or alkyl-Lithium reagents, in ethereal solvents, preferably THF at low temperatures and under inert conditions to furnish compounds of type II.

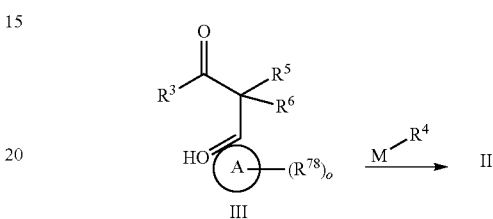

Alternatively, alcohols of type II can be prepared from epoxydes IIIa and compounds VI (see below):

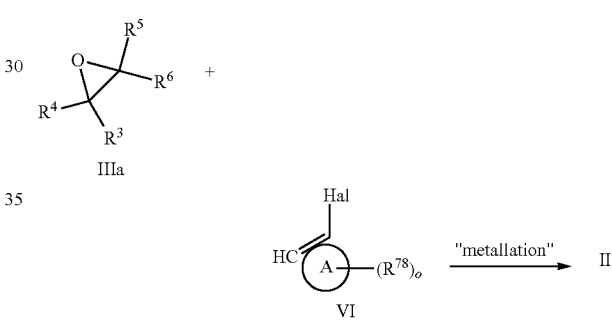

The metallation reaction may preferably be carried out using Lithium-organic compounds, such as for example n-butyl lithium, sec-butyl lithium or tert-butyl lithium to result in an exchange of halogen by lithium. Also suitable is the reaction with magnesium resulting in the formation of the respective Grignard reagents. A further possibility is the use of other Grignard reagents such as isopropyl-magnesium-bromide instead of Mg.

A typical preparation of compounds of type III can be achieved by reacting compounds of type IV with organometallic reagents, preferably alkyl Grignard or alkyl-Lithium reagents, in ethereal solvents, preferably THF at low temperatures and under inert conditions to furnish compounds of type III as previously reported (see for example WO2012051036; WO2011042918).

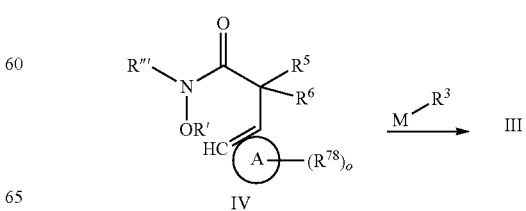

Compounds of type IV can be accessed by reacting a carbonyl compound of type V, preferably a carboxylic acid (X=OH) or an acid chloride (X=Cl), with NH(OR')R", wherein R' and R" are selected from $(C_1-C_4)$-alkyl, most preferably being methyl, in an organic solvent, preferably THF or dichloromethane. Typically the reaction is performed in a range between 0° C. and ambient temperature in the presence of an organic base, preferably $N(C_2H_5)_3$ or pyridine (see e.g. US 20130324506; Tetrahedron: Asymmetry, 17(4), 508-511; 2006). If X=OH, the addition of an activating reagent, preferably a carbodiimide, may be preferred (see for example ChemMedChem, 7(12), 2101-2112; 2012; 2011038204; Journal of Organic Chemistry, 76(1), 164-169: 2011).

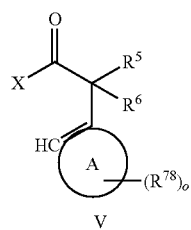

If required, compounds of type V can be prepared from the corresponding aryl halides of type VI (Hal is halogen, preferably Br or I). As described (Tetrahedron, 68(9), 2113-2120; 2012; Chemical Communications (Cambridge, United Kingdom), 49(60), 6767-6769: 2013), aryl halides will react with compounds of type VII in the presence of a transition metal catalyst, preferably a copper(I) salt, in an organic solvent, preferably DMF or DMSO, at elevated temperatures. Typically a base, preferably potassium phosphate, is added.

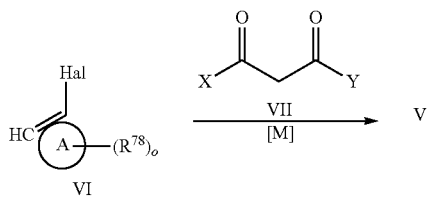

If appropriate, compounds of type II can be prepared as follows. A known or commercially available compound of type VIII can be reacted with an organometallic reagent of type IX, preferably a Grignard or an organolithium reagent, readily prepared by a skilled person. Preferably, the reaction is performed in a temperature range from −78° C. to room temperature under inert conditions in an ethereal solvent.

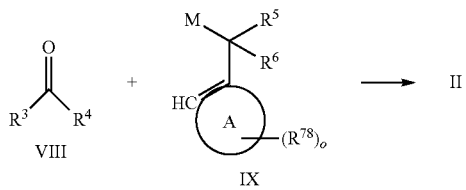

It may be preferred to access compounds I, where $R^5$ and $R^6$ are F (named compounds I-1) from the respective keto compound (named compounds IIA) as follows based on a literature precedent (US 2008/0275242). A skilled person will realize that compounds I-1 can be formed using a suitable halogenation agent, preferably diethyl aminosulfur trifluoride or phosphorus trihalides in an organic solvent, preferably a chlorinated hydrocarbon such as dichloromethane at, e.g., room temperature. If appropriate, the reaction can be performed at elevated temperatures.

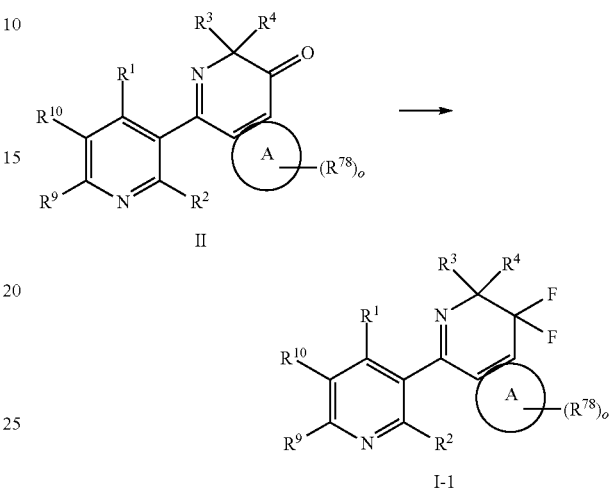

Compounds of type IIA can be accessed by reacting compounds of type 1-2 (where $R^5$ and $R^6$ are halogen substituents (Hal'), in particular bromo) under aqueous or mildly acidic conditions in an organic solvent.

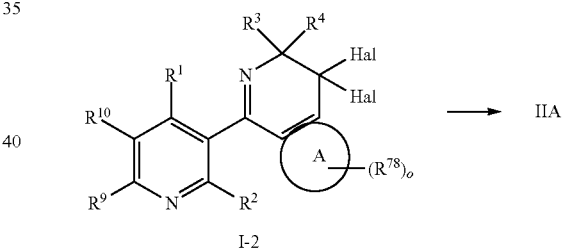

Said compounds 1-2 can be prepared from compounds 1-3 (where $R^5$ and $R^6$ are both hydrogen) by reaction with a halide source, preferably N-bromosuccinimide or 1,3-dibromo-5,5-dimethylhydantoin, in an organic solvent, preferably chlorobenzene or carbon tetrachloride in the presence of an initiator, preferably azo-bis-isobutyronitrile, at elevated temperatures (see for example WO 2008/035379).

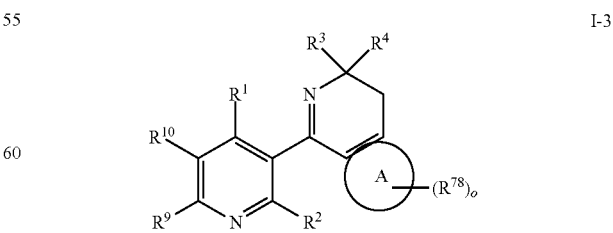

Alternatively, as described elsewhere (WO 2013/047749), compounds 1-1 can be prepared directly from compounds 1-2. To this end, compounds 1-2 are reacted with hydrogen fluoride triethyl amine (HF NEt$_3$) in an organic solvent, preferably an aromatic hydrocarbon and at elevated temperatures.

The N-oxides may be prepared from the inventive compounds according to conventional oxidation methods, e. g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

The intermediate compounds of formula IIA are novel. Consequently, one aspect of the present invention relates to compounds of formula IIA:

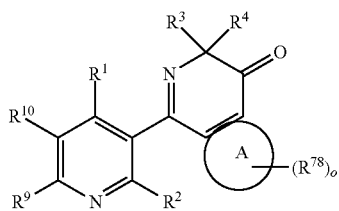

IIA wherein the substituents $R^1$, $R^2$, $R^3$, $R^4 R^9$, $R^{10}$ and o are as defined and preferably defined for formula I.

The compounds of formula IIA have fungicidal activity and the details below referring to the compounds I also apply to compounds IIA.

Particular embodiments of the compounds IIA are the following compounds IIA.A, IIA.B, IIA.C, IIA.D, IIA.E, IIA.F, IIA.G, IIA.H, IIA.I, IIA.J and IIA.K. In these formulae, the substituents $R^1$, $R^2$, $R^3$, $R^4$, $R^9$, $R^{10}$, $R^{78}$ and o are independently as defined or preferably defined herein:

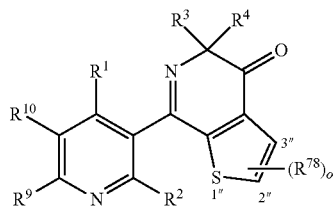

II.A.A

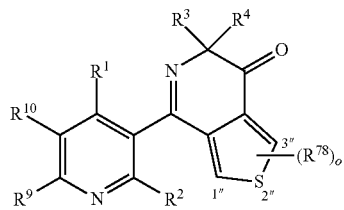

II.A.B

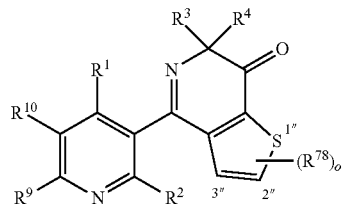

II.A.C

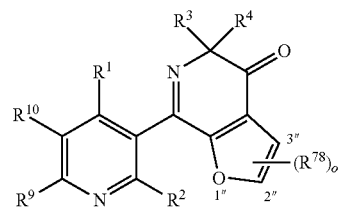

II.A.D

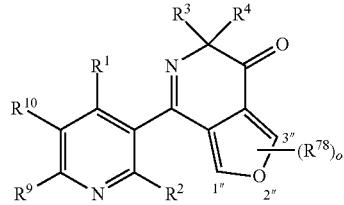

II.A.E

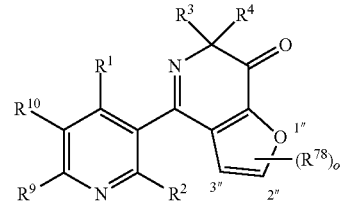

II.A.F

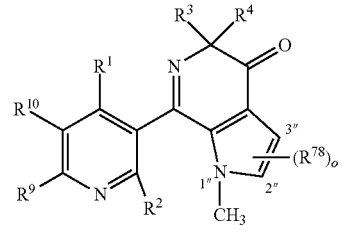

II.A.G

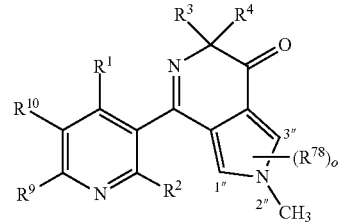

II.A.H

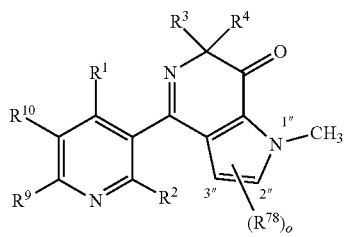
II.A.I

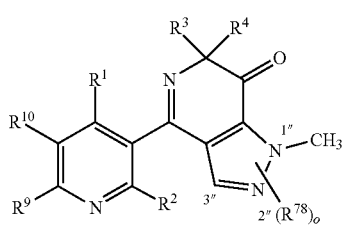
II.A.J

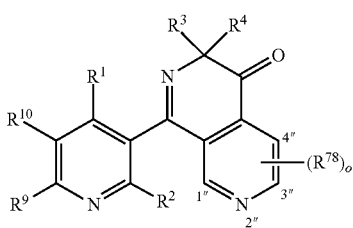
II.A.K

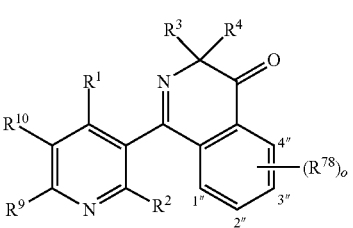
II.A.Ka

According to one embodiment, o in each of the formulae IIA.A, IIA.B, IIA.C, AD, IIA.E, IIA.F, IIA.G, IIA.H, IIA.I, IIA.J, IIA.K and II.A.L, respectively, is 0, i.e. the heteroaryl is not substituted. These compounds are named IIA.A.1, IIA.B.1, IIA.C.1, IIA.D.1, IIA.E.1, IIA.F.1, IIA.G.1, IIA.H.1, IIA.I.1, IIA.J.1, IIA.K.1 and II.A.Ka.1 respectively.

Further preferred compounds I are the following compounds IIA.L, IIA.M, IIA.N, IIA.O, IIA.P, IIA.Q, IIA.R, IIA.S, IIA.T and IIA.U. In these formulae, the substituents $R^1$, $R^2$, $R^3$, $R^4$, $R^9$, $R^{10}$, $R^{78}$ and o are independently as defined or preferably-defined herein:

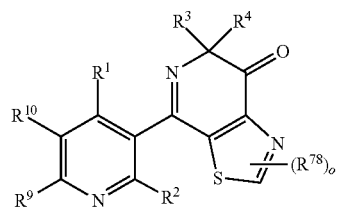
II.A.L

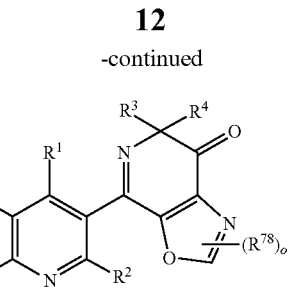
II.A.M

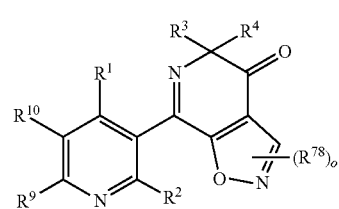
II.A.N

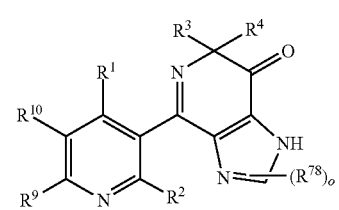
II.A.O

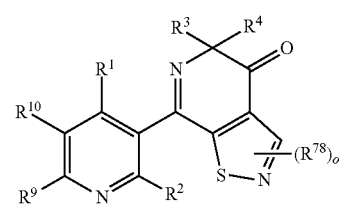
II.A.P

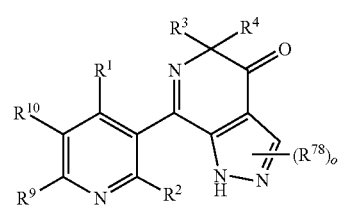
II.A.Q

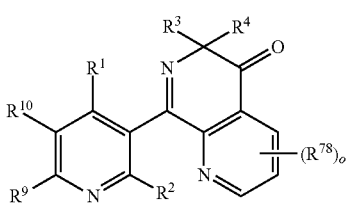
II.A.R

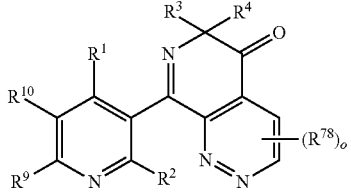
II.A.S

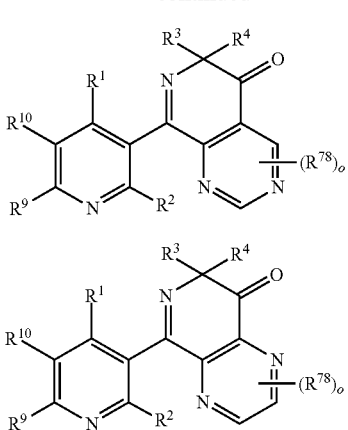

II.A.T

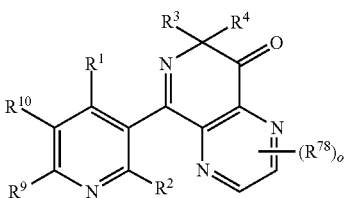

II.A.U

According to one embodiment, o in each of the formulae IIA.L, IIA.M, IIA.N, IIA.O, IIA.P, IIA.Q, IIA.R, IIA.S, IIA.T and IIA.U, respectively, is 0, i.e. the heteroaryl is not substituted. These compounds are named IIA.L.1, IIA.M.1, IIA.N.1, IIA.O.1, IIA.P.1, IIA.Q.1, IIA.R.1, IIA.S.1, IIA.T.1 and IIA.U.1, respectively.

Particular compounds II.A of the invention are the compounds of the formulae IIA.A, IIA.B, IIA.C, IIA.D, IIA.E, IIA.F, IIA.G, IIA.H, IIA.I, IIA.J, IIA.K and IIA.Ka that are compiled in the Tables 1-1 to 1-15, 2-1 to 2-15, 3-1 to 3-15, 4-1 to 4-15, 5-1 to 5-15, 6-1 to 6-15, 7-1 to 7-15, 8-1 to 8-15, 9-1 to 9-15, 10-1 to 10-8, 11-1 to 11-22, 12-1 to 12-24.

Each of the groups mentioned for a substituent in the tables is furthermore per se, independently of the combination in which it is mentioned, a particularly preferred aspect of the substituent in question.

Table 1-1 Compounds of formula IIA.A in which o is 0 and the meaning for the combination of $R^1$, $R^2$, $R^3$, $R^4$, $R^9$ and $R^{10}$ for each individual compound corresponds in each case to one line of Table A.

Table 1-2 Compounds of formula IIA.A in which o is 1, $R^{78}$ is 2"-F and the meaning for the combination of $R^1$, $R^2$, $R^3$, $R^4$, $R^9$ and $R^{10}$ for each individual compound corresponds in each case to one line of Table A.

Table 1-3 Compounds of formula IIA.A in which o is 1, $R^{78}$ is 2"-Cl and the meaning for the combination of $R^1$, $R^2$, $R^3$, $R^4$, $R^9$ and $R^{10}$ for each individual compound corresponds in each case to one line of Table A.

Table 1-4 Compounds of formula IIA.A in which o is 1, $R^{78}$ is 2"-Br and the meaning for the combination of $R^1$, $R^2$, $R^3$, $R^4$, $R^9$ and $R^{10}$ for each individual compound corresponds in each case to one line of Table A.

Table 1-5 Compounds of formula IIA.A in which o is 1, $R^{78}$ is 2"-$CH_3$ and the meaning for the combination of $R^1$, $R^2$, $R^3$, $R^4$, $R^9$ and $R^{10}$ for each individual compound corresponds in each case to one line of Table A.

Table 1-6 Compounds of formula IIA.A in which o is 1, $R^{78}$ is 2"-$OCH_3$ and the meaning for the combination of $R^1$, $R^2$, $R^3$, $R^4$, $R^9$ and $R^{10}$ for each individual compound corresponds in each case to one line of Table A.

Table 1-7 Compounds of formula IIA.A in which o is 1, $R^{78}$ is 2"-$OCHF_2$ and the meaning for the combination of $R^1$, $R^2$, $R^3$, $R^4$, $R^9$ and $R^{10}$ for each individual compound corresponds in each case to one line of Table A.

Table 1-8 Compounds of formula IIA.A in which o is 1, $R^{78}$ is 2"-$C_6H_5$ and the meaning for the combination of $R^1$, $R^2$, $R^3$, $R^4$, $R^9$ and $R^{10}$ for each individual compound corresponds in each case to one line of Table A.

Table 1-9 Compounds of formula IIA.A in which o is 1, $R^{78}$ is 3-F and the meaning for the combination $R^1$, $R^2$, $R^3$, $R^4$, $R^9$ and $R^{10}$ for each individual compound corresponds in each case to one line of Table A.

Table 1-10 Compounds of formula IIA.A in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 1-11 Compounds of formula IIA.A in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 1-12 Compounds of formula IIA.A in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 1-13 Compounds of formula IIA.A in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 1-14 Compounds of formula IIA.A in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 1-15 Compounds of formula IIA.A in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 2-1 Compounds of formula IIA.B in which o is 0 and the meaning for the combination of $R^1$, $R^2$, $R^3$, $R^4$, $R^9$ and $R^{10}$ for each individual compound corresponds in each case to one line of Table A.

Table 2-2 Compounds of formula IIA.B in which o is 1, $R^{78}$ is 1"-F and the meaning for the combination of $R^1$, $R^2$, $R^3$, $R^4$, $R^9$ and $R^{10}$ for each individual compound corresponds in each case to one line of Table A.

Table 2-3 Compounds of formula IIA.B in which o is 1, $R^{78}$ is 1"-Cl and the meaning for the combination of $R^1$, $R^2$, $R^3$, $R^4$, $R^9$ and $R^{10}$ for each individual compound corresponds in each case to one line of Table A.

Table 2-4 Compounds of formula IIA.B in which o is 1, $R^{78}$ is 1"-Br and the meaning for the combination of $R^1$, $R^2$, $R^3$, $R^4$, $R^9$ and $R^{10}$ for each individual compound corresponds in each case to one line of Table A.

Table 2-5 Compounds of formula IIA.B in which o is 1, $R^{78}$ is 1"-$CH_3$ and the meaning for the combination of $R^1$, $R^2$, $R^3$, $R^4$, $R^9$ and $R^{10}$ for each individual compound corresponds in each case to one line of Table A.

Table 2-6 Compounds of formula IIA.B in which o is 1, $R^{78}$ is 1"-$OCH_3$ and the meaning for the combination of $R^1$, $R^2$, $R^3$, $R^4$, $R^9$ and $R^{10}$ for each individual compound corresponds in each case to one line of Table A.

Table 2-7 Compounds of formula IIA.B in which o is 1, $R^{78}$ is 1"-$OCHF_2$ and the meaning for the combination of $R^1$, $R^2$, $R^3$, $R^4$, $R^9$ and $R^{10}$ for each individual compound corresponds in each case to one line of Table A.

Table 2-8 Compounds of formula IIA.B in which o is 1, $R^{78}$ is 1"-$C_6H_5$ and the meaning for the combination of $R^1$, $R^2$, $R^3$, $R^4$, $R^9$ and $R^{10}$ for each individual compound corresponds in each case to one line of Table A.

Table 2-9 Compounds of formula IIA.B in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 2-10 Compounds of formula IIA.B in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 2-11 Compounds of formula IIA.B in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 2-12 Compounds of formula IIA.B in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 2-13 Compounds of formula IIA.B in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 2-14 Compounds of formula IIA.B in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 2-15 Compounds of formula IIA.B in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 3-1 Compounds of formula IIA.C in which o is 0 and the meaning for the combination of $R^1$, $R^2$, $R^3$, $R^4$, $R^9$ and $R^{10}$ for each individual compound corresponds in each case to one line of Table A.

Table 3-2 Compounds of formula IIA.C in which o is 1, $R^{78}$ is 2"-F and the meaning for the combination of $R^1$, $R^2$, $R^3$, $R^4$, $R^9$ and $R^{10}$ for each individual compound corresponds in each case to one line of Table A.

Table 3-3 Compounds of formula IIA.C in which o is 1, $R^{78}$ is 2"-Cl and the meaning for the combination of $R^1$, $R^2$, $R^3$, $R^4$, $R^9$ and $R^{10}$ for each individual compound corresponds in each case to one line of Table A.

Table 3-4 Compounds of formula IIA.C in which o is 1, $R^{78}$ is 2"-Br and the meaning for the combination of $R^1$, $R^2$, $R^3$, $R^4$, $R^9$ and $R^{10}$ for each individual compound corresponds in each case to one line of Table A.

Table 3-5 Compounds of formula IIA.C in which o is 1, $R^{78}$ is 2"-$CH_3$ and the meaning for the combination of $R^1$, $R^2$, $R^3$, $R^4$, $R^9$ and $R^{10}$ for each individual compound corresponds in each case to one line of Table A.

Table 3-6 Compounds of formula IIA.C in which o is 1, $R^{78}$ is 2"-$OCH_3$ and the meaning for the combination of $R^1$, $R^2$, $R^3$, $R^4$, $R^9$ and $R^{10}$ for each individual compound corresponds in each case to one line of Table A.

Table 3-7 Compounds of formula IIA.C in which o is 1, $R^{78}$ is 2"-$OCHF_2$ and the meaning for the combination of $R^1$, $R^2$, $R^3$, $R^4$, $R^9$ and $R^{10}$ for each individual compound corresponds in each case to one line of Table A.

Table 3-8 Compounds of formula IIA.C in which o is 1, $R^{78}$ is 2"-$C_6H_5$ and the meaning for the combination of $R^1$, $R^2$, $R^3$, $R^4$, $R^9$ and $R^{10}$ for each individual compound corresponds in each case to one line of Table A.

Table 3-9 Compounds of formula IIA.C in which o is 1, $R^{78}$ is 3"-F and the meaning for the combination of $R^1$, $R^2$, $R^3$, $R^4$, $R^9$ and $R^{10}$ for each individual compound corresponds in each case to one line of Table A.

Table 3-10 Compounds of formula IIA.C in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 3-11 Compounds of formula IIA.C in which o is 1, $R^{78}$ is 3"-Br and the meaning for the combination of $R^1$, $R^2$, $R^3$, $R^4$, $R^9$ and $R^{10}$ for each individual compound corresponds in each case to one line of Table A.

Table 3-12 Compounds of formula IIA.C in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 3-13 Compounds of formula IIA.C in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 3-14 Compounds of formula IIA.C in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 3-15 Compounds of formula IIA.C in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 4-1 Compounds of formula IIA.D in which o is 0 and the meaning for the combination of $R^1$, $R^2$, $R^3$, $R^4$, $R^9$ and $R^{10}$ for each individual compound corresponds in each case to one line of Table A.

Table 4-2 Compounds of formula IIA.D in which o is 1, $R^{78}$ is 2"-F and the meaning for the combination of $R^1$, $R^2$, $R^3$, $R^4$, $R^9$ and $R^{10}$ for each individual compound corresponds in each case to one line of Table A.

Table 4-3 Compounds of formula IIA.D in which o is 1, $R^{78}$ is 2"-Cl and the meaning for the combination of $R^1$, $R^2$, $R^3$, $R^4$, $R^9$ and $R^{10}$ for each individual compound corresponds in each case to one line of Table A.

Table 4-4 Compounds of formula IIA.D in which o is 1, $R^{78}$ is 2"-Br and the meaning for the combination of $R^1$, $R^2$, $R^3$, $R^4$, $R^9$ and $R^{10}$ for each individual compound corresponds in each case to one line of Table A.

Table 4-5 Compounds of formula IIA.D in which o is 1, $R^{78}$ is 2"-$CH_3$ and the meaning for the combination of $R^1$, $R^2$, $R^3$, $R^4$, $R^9$ and $R^{10}$ for each individual compound corresponds in each case to one line of Table A.

Table 4-6 Compounds of formula IIA.D in which o is 1, $R^{78}$ is 2"-$OCH_3$ and the meaning for the combination of $R^1$, $R^2$, $R^3$, $R^4$, $R^9$ and $R^{10}$ for each individual compound corresponds in each case to one line of Table A.

Table 4-7 Compounds of formula IIA.D in which o is 1, $R^{78}$ is 2"-$OCHF_2$ and the meaning for the combination of $R^1$, $R^2$, $R^3$, $R^4$, $R^9$ and $R^{10}$ for each individual compound corresponds in each case to one line of Table A.

Table 4-8 Compounds of formula IIA.D in which o is 1, $R^{78}$ is 2"-$C_6H_5$ and the meaning for the combination of $R^1$, $R^2$, $R^3$, $R^4$, $R^9$ and $R^{10}$ 4 for each individual compound corresponds in each case to one line of Table A.

Table 4-9 Compounds of formula IIA.D in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 4-10 Compounds of formula IIA.D in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 4-11 Compounds of formula IIA.D in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 4-12 Compounds of formula IIA.D in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 4-13 Compounds of formula IIA.D in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 4-14 Compounds of formula IIA.D in which o is 1, $R^{78}$ is 3"-OCHF$_2$ and the meaning for the combination of $R^1$, $R^2$, $R^3$, $R^4$, $R^9$ and $R^{10}$ for each individual compound corresponds in each case to one line of Table A.

Table 4-15 Compounds of formula IIA.D in which o is 1, $R^{78}$ is 3"-C$_6$H$_5$ and the meaning for the combination of $R^1$, $R^2$, $R^3$, $R^4$, $R^9$ and $R^{10}$ for each individual compound corresponds in each case to one line of Table A.

Table 5-1 Compounds of formula IIA.E in which o is 0 and the meaning for the combination of $R^1$, $R^2$, $R^3$, $R^4$, $R^9$ and $R^{10}$ for each individual compound corresponds in each case to one line of Table A.

Table 5-2 Compounds of formula IIA.E in which o is 1, $R^{78}$ is 1"-F and the meaning for the combination of $R^1$, $R^2$, $R^3$, $R^4$, $R^9$ and $R^{10}$ for each individual compound corresponds in each case to one line of Table A.

Table 5-3 Compounds of formula IIA.E in which o is 1, $R^{78}$ is 1"-Cl and the meaning for the combination of $R^1$, $R^2$, $R^3$, $R^4$, $R^9$ and $R^{10}$ for each individual compound corresponds in each case to one line of Table A.

Table 5-4 Compounds of formula IIA.E in which o is 1, $R^{78}$ is 1"-Br and the meaning for the combination of $R^1$, $R^2$, $R^3$, $R^4$, $R^9$ and $R^{10}$ for each individual compound corresponds in each case to one line of Table A.

Table 5-5 Compounds of formula IIA.E in which o is 1, $R^{78}$ is 1"-CH$_3$ and the meaning for the combination of $R^1$, $R^2$, $R^3$, $R^4$, $R^9$ and $R^{10}$ for each individual compound corresponds in each case to one line of Table A.

Table 5-6 Compounds of formula IIA.E in which o is 1, $R^{78}$ is 1"-OCH$_3$ and the meaning for the combination of $R^1$, $R^2$, $R^3$, $R^4$, $R^9$ and $R^{10}$ for each individual compound corresponds in each case to one line of Table A.

Table 5-7 Compounds of formula IIA.E in which o is 1, $R^{78}$ is 1"-OCHF$_2$ and the meaning for the combination of $R^1$, $R^2$, $R^3$, $R^4$, $R^9$ and $R^{10}$ for each individual compound corresponds in each case to one line of Table A.

Table 5-8 Compounds of formula IIA.E in which o is 1, $R^{78}$ is 1"-C$_6$H$_5$ and the meaning for the combination of $R^1$, $R^2$, $R^3$, $R^4$, $R^9$ and $R^{10}$ for each individual compound corresponds in each case to one line of Table A.

Table 5-9 Compounds of formula IIA.E in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 5-10 Compounds of formula IIA.E in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 5-11 Compounds of formula IIA.E in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 5-12 Compounds of formula IIA.E in which o is 1, $R^{78}$ is 3"-CH$_3$ and the meaning for the combination of $R^1$, $R^2$, $R^3$, $R^4$, $R^9$ and $R^{10}$ for each individual compound corresponds in each case to one line of Table A.

Table 5-13 Compounds of formula IIA.E in which o is 1, $R^{78}$ is 3"-OCH$_3$ and the meaning for the combination of $R^1$, $R^2$, $R^3$, $R^4$, $R^9$ and $R^{10}$ for each individual compound corresponds in each case to one line of Table A.

Table 5-14 Compounds of formula IIA.E in which o is 1, $R^{78}$ is 3"-OCHF$_2$ and the meaning for the combination of $R^1$, $R^2$, $R^3$, $R^4$, $R^9$ and $R^{10}$ for each individual compound corresponds in each case to one line of Table A.

Table 5-15 Compounds of formula IIA.E in which o is 1, $R^{78}$ is 3"-C$_6$H$_5$ and the meaning for the combination of $R^1$, $R^2$, $R^3$, $R^4$, $R^9$ and $R^{10}$ for each individual compound corresponds in each case to one line of Table A.

Table 6-1 Compounds of formula IIA.F in which o is 0 and the meaning for the combination of $R^1$, $R^2$, $R^3$, $R^4$, $R^9$ and $R^{10}$ for each individual compound corresponds in each case to one line of Table A.

Table 6-2 Compounds of formula IIA.F in which o is 1, $R^{78}$ is 2"-F and the meaning for the combination of $R^1$, $R^2$, $R^3$, $R^4$, $R^9$ and $R^{10}$ for each individual compound corresponds in each case to one line of Table A.

Table 6-3 Compounds of formula IIA.F in which o is 1, $R^{78}$ is 2"-Cl and the meaning for the combination of $R^1$, $R^2$, $R^3$, $R^4$, $R^9$ and $R^{10}$ for each individual compound corresponds in each case to one line of Table A.

Table 6-4 Compounds of formula IIA.F in which o is 1, $R^{78}$ is 2"-Br and the meaning for the combination of $R^1$, $R^2$, $R^3$, $R^4$, $R^9$ and $R^{10}$ for each individual compound corresponds in each case to one line of Table A.

Table 6-5 Compounds of formula IIA.F in which o is 1, $R^{78}$ is 2"-CH$_3$ and the meaning for the combination of $R^1$, $R^2$, $R^3$, $R^4$, $R^9$ and $R^{10}$ for each individual compound corresponds in each case to one line of Table A.

Table 6-6 Compounds of formula IIA.F in which o is 1, $R^{78}$ is 2"-OCH$_3$ and the meaning for the combination of $R^1$, $R^2$, $R^3$, $R^4$, $R^9$ and $R^{10}$ for each individual compound corresponds in each case to one line of Table A.

Table 6-7 Compounds of formula IIA.F in which o is 1, $R^{78}$ is 2"-OCHF$_2$ and the meaning for the combination of $R^1$, $R^2$, $R^3$, $R^4$, $R^9$ and $R^{10}$ for each individual compound corresponds in each case to one line of Table A.

Table 6-8 Compounds of formula IIA.F in which o is 1, $R^{78}$ is 2"-C$_6$H$_5$ and the meaning for the combination of $R^1$, $R^2$, $R^3$, $R^4$, $R^9$ and $R^{10}$ for each individual compound corresponds in each case to one line of Table A.

Table 6-9 Compounds of formula IIA.F in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 6-10 Compounds of formula IIA.F in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 6-11 Compounds of formula IIA.F in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 6-12 Compounds of formula IIA.F in which o is 1, $R^{78}$ is 3"-CH$_3$ and the meaning for the combination of $R^1$, $R^2$, $R^3$, $R^4$, $R^9$ and $R^{10}$ for each individual compound corresponds in each case to one line of Table A.

Table 6-13 Compounds of formula IIA.F in which o is 1, $R^{78}$ is 3"-OCH$_3$ and the meaning for the combination of $R^1$, $R^2$, $R^3$, $R^4$, $R^9$ and $R^{10}$ for each individual compound corresponds in each case to one line of Table A.

Table 6-14 Compounds of formula IIA.F in which o is 1, $R^{78}$ is 3"-OCHF$_2$ and the meaning for the combination of $R^1$, $R^2$, $R^3$, $R^4$, $R^9$ and $R^{10}$ for each individual compound corresponds in each case to one line of Table A.

Table 6-15 Compounds of formula IIA.F in which o is 1, $R^{78}$ is 3"-C$_6$H$_5$ and the meaning for the combination of $R^1$, $R^2$, $R^3$, $R^4$, $R^9$ and $R^{10}$ for each individual compound corresponds in each case to one line of Table A.

Table 7-1 Compounds of formula IIA.G in which o is 0 and the meaning for the combination of $R^1$, $R^2$, $R^3$, $R^4$, $R^9$ and $R^{10}$ for each individual compound corresponds in each case to one line of Table A.

Table 7-2 Compounds of formula IIA.G in which o is 1, $R^{78}$ is 2"-F and the meaning for the combination of $R^1$, $R^2$, $R^3$, $R^4$, $R^9$ and $R^{10}$ for each individual compound corresponds in each case to one line of Table A.

Table 7-3 Compounds of formula IIA.G in which o is 1, $R^{78}$ is 2"-Cl and the meaning for the combination of $R^1$, $R^2$, $R^3$, $R^4$, $R^9$ and $R^{10}$ for each individual compound corresponds in each case to one line of Table A.

Table 7-4 Compounds of formula IIA.G in which o is 1, $R^{78}$ is 2"-Br and the meaning for the combination of $R^1$, $R^2$, $R^3$, $R^4$, $R^9$ and $R^{10}$ for each individual compound corresponds in each case to one line of Table A.

Table 7-5 Compounds of formula IIA.G in which o is 1, $R^{78}$ is 2"-$CH_3$ and the meaning for the combination of $R^1$, $R^2$, $R^3$, $R^4$, $R^9$ and $R^{10}$ for each individual compound corresponds in each case to one line of Table A.

Table 7-6 Compounds of formula IIA.G in which o is 1, $R^{78}$ is 2"-$OCH_3$ and the meaning for the combination of $R^1$, $R^2$, $R^3$, $R^4$, $R^9$ and $R^{10}$ for each individual compound corresponds in each case to one line of Table A.

Table 7-7 Compounds of formula IIA.G in which o is 1, $R^{78}$ is 2"-$OCHF_2$ and the meaning for the combination of $R^1$, $R^2$, $R^3$, $R^4$, $R^9$ and $R^{10}$ for each individual compound corresponds in each case to one line of Table A.

Table 7-8 Compounds of formula IIA.G in which o is 1, $R^{78}$ is 2"-$C_6H_5$ and the meaning for the combination of $R^1$, $R^2$, $R^3$, $R^4$, $R^9$ and $R^{10}$ for each individual compound corresponds in each case to one line of Table A.

Table 7-9 Compounds of formula IIA.G in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 7-10 Compounds of formula IIA.G in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 7-11 Compounds of formula IIA.G in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 7-12 Compounds of formula IIA.G in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 7-13 Compounds of formula IIA.G in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 7-14 Compounds of formula IIA.G in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 7-15 Compounds of formula IIA.G in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 8-1 Compounds of formula IIA.H in which o is 0 and the meaning for the combination of $R^1$, $R^2$, $R^3$, $R^4$, $R^9$ and $R^{10}$ for each individual compound corresponds in each case to one line of Table A.

Table 8-2 Compounds of formula IIA.H in which o is 1, $R^{78}$ is 1"-F and the meaning for the combination of $R^1$, $R^2$, $R^3$, $R^4$, $R^9$ and $R^{10}$ for each individual compound corresponds in each case to one line of Table A.

Table 8-3 Compounds of formula IIA.H in which o is 1, $R^{78}$ is 1"-Cl and the meaning for the combination of $R^1$, $R^2$, $R^3$, $R^4$, $R^9$ and $R^{10}$ for each individual compound corresponds in each case to one line of Table A.

Table 8-4 Compounds of formula IIA.H in which o is 1, $R^{78}$ is 1"-Br and the meaning for the combination of $R^1$, $R^2$, $R^3$, $R^4$, $R^9$ and $R^{10}$ for each individual compound corresponds in each case to one line of Table A.

Table 8-5 Compounds of formula IIA.H in which o is 1, $R^{78}$ is 1"-$CH_3$ and the meaning for the combination of $R^1$, $R^2$, $R^3$, $R^4$, $R^9$ and $R^{10}$ for each individual compound corresponds in each case to one line of Table A.

Table 8-6 Compounds of formula IIA.H in which o is 1, $R^{78}$ is 1"-$OCH_3$ and the meaning for the combination of $R^1$, $R^2$, $R^3$, $R^4$, $R^9$ and $R^{10}$ for each individual compound corresponds in each case to one line of Table A.

Table 8-7 Compounds of formula IIA.H in which o is 1, $R^{78}$ is 1"-$OCHF_2$ and the meaning for the combination of $R^1$, $R^2$, $R^3$, $R^4$, $R^9$ and $R^{10}$ for each individual compound corresponds in each case to one line of Table A.

Table 8-8 Compounds of formula IIA.H in which o is 1, $R^{78}$ is 1"-$C_6H_5$ and the meaning for the combination of $R^1$, $R^2$, $R^3$, $R^4$, $R^9$ and $R^{10}$ for each individual compound corresponds in each case to one line of Table A.

Table 8-9 Compounds of formula IIA.H in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 8-10 Compounds of formula IIA.H in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 8-11 Compounds of formula IIA.H in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 8-12 Compounds of formula IIA.H in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 8-13 Compounds of formula IIA.H in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 8-14 Compounds of formula IIA.H in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 8-15 Compounds of formula IIA.H in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 9-1 Compounds of formula IIA.I in which o is 0 and the meaning for the combination of $R^1$, $R^2$, $R^3$, $R^4$, $R^9$ and $R^{10}$ for each individual compound corresponds in each case to one line of Table A.

Table 9-2 Compounds of formula IIA.I in which o is 1, $R^{78}$ is 2"-F and the meaning for the combination of $R^1$, $R^2$, $R^3$, $R^4$, $R^9$ and $R^{10}$ for each individual compound corresponds in each case to one line of Table A.

Table 9-3 Compounds of formula IIA.I in which o is 1, $R^{78}$ is 2"-Cl and the meaning for the combination of $R^1$, $R^2$, $R^3$, $R^4$, $R^9$ and $R^{10}$ for each individual compound corresponds in each case to one line of Table A.

Table 9-4 Compounds of formula IIA.I in which o is 1, $R^{78}$ is 2"-Br and the meaning for the combination of $R^1$, $R^2$, $R^3$, $R^4$, $R^9$ and $R^{10}$ for each individual compound corresponds in each case to one line of Table A.

Table 9-5 Compounds of formula IIA.I in which o is 1, $R^{78}$ is 2"-$CH_3$ and the meaning for the combination of $R^1$, $R^2$, $R^3$, $R^4$, $R^9$ and $R^{10}$ for each individual compound corresponds in each case to one line of Table A.

Table 9-6 Compounds of formula IIA.I in which o is 1, $R^{78}$ is 2"-$OCH_3$ and the meaning for the combination of $R^1$, $R^2$, $R^3$, $R^4$, $R^9$ and $R^{10}$ for each individual compound corresponds in each case to one line of Table A.

Table 9-7 Compounds of formula IIA.I in which o is 1, $R^{78}$ is 2"-$OCHF_2$ and the meaning for the combination of $R^1$, $R^2$, $R^3$, $R^4$, $R^9$ and $R^{10}$ for each individual compound corresponds in each case to one line of Table A.

Table 9-8 Compounds of formula IIA.I in which o is 1, $R^{78}$ is 2"-$C_6H_5$ and the meaning for the combination of $R^1$, $R^2$, $R^3$, $R^4$, $R^9$ and $R^{10}$ for each individual compound corresponds in each case to one line of Table A.

Table 9-9 Compounds of formula IIA.I in which o is 1, $R^{78}$ is 3-F and the meaning for the combination of $R^1$, $R^2$, $R^3$, $R^4$, $R^9$ and $R^{10}$ for each individual compound corresponds in each case to one line of Table A.

Table 9-10 Compounds of formula IIA.I in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 9-11 Compounds of formula IIA.I in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 9-12 Compounds of formula IIA.I in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 9-13 Compounds of formula IIA.I in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 9-14 Compounds of formula IIA.I in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 9-15 Compounds of formula IIA.I in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 10-1 Compounds of formula IIA.J in which o is 0 and the meaning for the combination of $R^1$, $R^2$, $R^3$, $R^4$, $R^9$ and $R^{10}$ for each individual compound corresponds in each case to one line of Table A.

Table 10-2 Compounds of formula IIA.J in which o is 1, $R^{78}$ is 3"-F and the meaning for the combination of $R^1$, $R^2$, $R^3$, $R^4$, $R^9$ and $R^{10}$ for each individual compound corresponds in each case to one line of Table A.

Table 10-3 Compounds of formula IIA.J in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 10-4 Compounds of formula IIA.J in which o is 1, $R^{78}$ is 3"-Br and the meaning for the combination of $R^1$, $R^2$, $R^3$, $R^4$, $R^9$ and $R^{10}$ for each individual compound corresponds in each case to one line of Table A.

Table 10-5 Compounds of formula IIA.J in which o is 1, $R^{78}$ is 3-$CH_3$ and the meaning for the combination of $R^1$, $R^2$, $R^3$, $R^4$, $R^9$ and $R^{10}$ for each individual compound corresponds in each case to one line of Table A.

Table 10-6 Compounds of formula IIA.J in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 10-7 Compounds of formula IIA.J in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 10-8 Compounds of formula IIA.J in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 11-1 Compounds of formula IIA.K in which o is 0 and the meaning for the combination of $R^1$, $R^2$, $R^3$, $R^4$, $R^9$ and $R^{10}$ for each individual compound corresponds in each case to one line of Table A.

Table 11-2 Compounds of formula IIA.K in which o is 1, $R^{78}$ is 1"-F and the meaning for the combination of $R^1$, $R^2$, $R^3$, $R^4$, $R^9$ and $R^{10}$ for each individual compound corresponds in each case to one line of Table A.

Table 11-3 Compounds of formula IIA.K in which o is 1, $R^{78}$ is 1"-Cl and the meaning for the combination of $R^1$, $R^2$, $R^3$, $R^4$, $R^9$ and $R^{10}$ for each individual compound corresponds in each case to one line of Table A.

Table 11-4 Compounds of formula IIA.K in which o is 1, $R^{78}$ is 1"-Br and the meaning for the combination of $R^1$, $R^2$, $R^3$, $R^4$, $R^9$ and $R^{10}$ for each individual compound corresponds in each case to one line of Table A.

Table 11-5 Compounds of formula IIA.K in which o is 1, $R^{78}$ is 1"-$CH_3$ and the meaning for the combination of $R^1$, $R^2$, $R^3$, $R^4$, $R^9$ and $R^{10}$ for each individual compound corresponds in each case to one line of Table A.

Table 11-6 Compounds of formula IIA.K in which o is 1, $R^{78}$ is 1"-$OCH_3$ and the meaning for the combination of $R^1$, $R^2$, $R^3$, $R^4$, $R^9$ and $R^{10}$ for each individual compound corresponds in each case to one line of Table A.

Table 11-7 Compounds of formula IIA.K in which o is 1, $R^{78}$ is 1"-$OCHF_2$ and the meaning for the combination of $R^1$, $R^2$, $R^3$, $R^4$, $R^9$ and $R^{10}$ for each individual compound corresponds in each case to one line of Table A.

Table 11-8 Compounds of formula IIA.K in which o is 1, $R^{78}$ is 1"-$C_6H_5$ and the meaning for the combination of $R^1$, $R^2$, $R^3$, $R^4$, $R^9$ and $R^{10}$ for each individual compound corresponds in each case to one line of Table A.

Table 11-9 Compounds of formula IIA.K in which o is 1, $R^{78}$ is 3"-F and the meaning for the combination of $R^1$, $R^2$, $R^3$, $R^4$, $R^9$ and $R^{10}$ for each individual compound corresponds in each case to one line of Table A.

Table 11-10 Compounds of formula IIA.K in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 11-11 Compounds of formula IIA.K in which o is 1, $R^{78}$ is 3-Br and the meaning for the combination of $R^1$, $R^2$, $R^3$, $R^4$, $R^9$ and $R^{10}$ for each individual compound corresponds in each case to one line of Table A.

Table 11-12 Compounds of formula IIA.K in which o is 1, $R^{78}$ is 3-$CH_3$ and the meaning for the combination of $R^1$, $R^2$, $R^3$, $R^4$, $R^9$ and $R^{10}$ for each individual compound corresponds in each case to one line of Table A.

Table 11-13 Compounds of formula IIA.K in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 11-14 Compounds of formula IIA.K in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 11-15 Compounds of formula IIA.K in which o is 1, $R^{78}$ is 3"-$C_6H$ and the meaning for the combination of $R^1$, $R^2$, $R^3$, $R^4$, $R^9$ and $R^{10}$ for each individual compound corresponds in each case to one line of Table A.

Table 11-16 Compounds of formula IIA.K in which o is 1, $R^{78}$ is 4"-F and the meaning for the combination of $R^1$, $R^2$, $R^3$, $R^4$, $R^9$ and $R^{10}$ for each individual compound corresponds in each case to one line of Table A.

Table 11-17 Compounds of formula IIA.K in which o is 1, $R^{78}$ is 4"-Cl and the meaning for the combination of $R^1$, $R^2$, $R^3$, $R^4$, $R^9$ and $R^{10}$ for each individual compound corresponds in each case to one line of Table A.

Table 11-18 Compounds of formula IIA.K in which o is 1, $R^{78}$ is 4"-Br and the meaning for the combination of $R^1$, $R^2$, $R^3$, $R^4$, $R^9$ and $R^{10}$ for each individual compound corresponds in each case to one line of Table A.

Table 11-19 Compounds of formula IIA.K in which o is 1, $R^{78}$ is 4"-$CH_3$ and the meaning for the combination of $R^1$, $R^2$, $R^3$, $R^4$, $R^9$ and $R^{10}$ for each individual compound corresponds in each case to one line of Table A.

Table 11-20 Compounds of formula IIA.K in which o is 1, $R^{78}$ is 4"-$OCH_3$ and the meaning for the combination of $R^1$, $R^2$, $R^3$, $R^4$, $R^9$ and $R^{10}$ for each individual compound corresponds in each case to one line of Table A.

Table 11-21 Compounds of formula IIA.K in which o is 1, $R^{78}$ is 1"-$OCHF_2$ and the meaning for the combination of $R^1$, $R^2$, $R^3$, $R^4$, $R^9$ and $R^{10}$ for each individual compound corresponds in each case to one line of Table A.

Table 11-22 Compounds of formula IIA.K in which o is 1, $R^{78}$ is 1"-$C_6H_5$ and the meaning for the combination of $R^1$, $R^2$, $R^3$, $R^4$, $R^9$ and $R^{10}$ for each individual compound corresponds in each case to one line of Table A.

Table 12-1 Compounds of formula IIA.Ka in which o is 0 and the meaning for the combination of $R^1$, $R^2$, $R^3$, $R^4$, $R^9$ and $R^{10}$ for each individual compound corresponds in each case to one line of Table A.

Table 12-2 Compounds of formula IIA.Ka in which o is 1, $R^{78}$ is 4"-$OCHF_2$ and the meaning for the combination of $R^1$, $R^2$, $R^3$, $R^4$, $R^9$ and $R^{10}$ for each individual compound corresponds in each case to one line of Table A.

Table 12-3 Compounds of formula IIA.Ka in which o is 1, $R^{78}$ is 4"-$C_6H_5$ and the meaning for the combination of $R^1$, $R^2$, $R^3$, $R^4$, $R^9$ and $R^{10}$ for each individual compound corresponds in each case to one line of Table A.

Table 12-4 Compounds of formula IIA.Ka in which o is 1, $R^{78}$ is 1"-F and the meaning for the combination of $R^1$, $R^2$, $R^3$, $R^4$, $R^9$ and $R^{10}$ for each individual compound corresponds in each case to one line of Table A.

Table 12-5 Compounds of formula IIA.Ka in which o is 1, $R^{78}$ is 1"-Cl and the meaning for the combination of $R^1$, $R^2$, $R^3$, $R^4$, $R^9$ and $R^{10}$ for each individual compound corresponds in each case to one line of Table A.

Table 12-6 Compounds of formula IIA.Ka in which o is 1, $R^{78}$ is 1"-Br and the meaning for the combination of $R^1$, $R^2$, $R^3$, $R^4$, $R^9$ and $R^{10}$ for each individual compound corresponds in each case to one line of Table A.

Table 12-7 Compounds of formula IIA.Ka in which o is 1, $R^{78}$ is 1"-$CH_3$ and the meaning for the combination of $R^1$, $R^2$, $R^3$, $R^4$, $R^9$ and $R^{10}$ for each individual compound corresponds in each case to one line of Table A.

Table 12-8 Compounds of formula IIA.Ka in which o is 1, $R^{78}$ is 1"-$OCH_3$ and the meaning for the combination of $R^1$, $R^2$, $R^3$, $R^4$, $R^9$ and $R^{10}$ for each individual compound corresponds in each case to one line of Table A.

Table 12-9 Compounds of formula IIA.Ka in which o is 1, $R^{78}$ is 1"-$OCHF_2$ and the meaning for the combination of $R^1$, $R^2$, $R^3$, $R^4$, $R^9$ and $R^{10}$ for each individual compound corresponds in each case to one line of Table A.

Table 12-10 Compounds of formula IIA.Ka in which o is 1, $R^{78}$ is 1"-$C_6H_5$ and the meaning for the combination of $R^1$, $R^2$, $R^3$, $R^4$, $R^9$ and $R^{10}$ for each individual compound corresponds in each case to one line of Table A.

Table 12-11 Compounds of formula IIA.K in which o is 1, $R^{78}$ is 3"-F and the meaning for the combination of $R^1$, $R^2$, $R^3$, $R^4$, $R^9$ and $R^{10}$ for each individual compound corresponds in each case to one line of Table A.

Table 12-12 Compounds of formula IIA.Ka in which o is 1, $R^{78}$ is 3-Cl and the meaning for the combination of $R^1$, $R^2$, $R^3$, $R^4$, $R^9$ and $R^{10}$ for each individual compound corresponds in each case to one line of Table A.

Table 12-13 Compounds of formula IIA.Ka in which o is 1, $R^{78}$ is 3"-Br and the meaning for the combination of $R^1$, $R^2$, $R^3$, $R^4$, $R^9$ and $R^{10}$ for each individual compound corresponds in each case to one line of Table A.

Table 12-14 Compounds of formula IIA.Ka in which o is 1, $R^{78}$ is 3"-$CH_3$ and the meaning for the combination of $R^1$, $R^2$, $R^3$, $R^4$, $R^9$ and $R^{10}$ for each individual compound corresponds in each case to one line of Table A.

Table 12-15 Compounds of formula IIA.Ka in which o is 1, $R^{78}$ is 3"-$OCH_3$ and the meaning for the combination of $R^1$, $R^2$, $R^3$, $R^4$, $R^9$ and $R^{10}$ for each individual compound corresponds in each case to one line of Table A.

Table 12-16 Compounds of formula IIA.Ka in which o is 1, $R^{78}$ is 3"-$OCHF_2$ and the meaning for the combination of $R^1$, $R^2$, $R^3$, $R^4$, $R^9$ and $R^{10}$ for each individual compound corresponds in each case to one line of Table A.

Table 12-17 Compounds of formula IIA.Ka in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table A.

Table 12-18 Compounds of formula IIA.Ka in which o is 1, $R^{78}$ is 4"-F and the meaning for the combination of $R^1$, $R^2$, $R^3$, $R^4$, $R^9$ and $R^{10}$ for each individual compound corresponds in each case to one line of Table A.

Table 12-19 Compounds of formula IIA.Ka in which o is 1, $R^{78}$ is 4"-Cl and the meaning for the combination of $R^1$, $R^2$, $R^3$, $R^4$, $R^9$ and $R^{10}$ for each individual compound corresponds in each case to one line of Table A.

Table 12-20 Compounds of formula IIA.Ka in which o is 1, $R^{78}$ is 4"-Br and the meaning for the combination of $R^1$, $R^2$, $R^3$, $R^4$, $R^9$ and $R^{10}$ for each individual compound corresponds in each case to one line of Table A.

Table 12-21 Compounds of formula IIA.Ka in which o is 1, $R^{78}$ is 4"-$CH_3$ and the meaning for the combination of $R^1$, $R^2$, $R^3$, $R^4$, $R^9$ and $R^{10}$ for each individual compound corresponds in each case to one line of Table A.

Table 12-22 Compounds of formula IIA.Ka in which o is 1, $R^{78}$ is 4"-$OCH_3$ and the meaning for the combination of $R^1$, $R^2$, $R^3$, $R^4$, $R^9$ and $R^{10}$ for each individual compound corresponds in each case to one line of Table A.

Table 12-23 Compounds of formula IIA.Ka in which o is 1, $R^{78}$ is 4"-$OCHF_2$ and the meaning for the combination of $R^1$, $R^2$, $R^3$, $R^4$, $R^9$ and $R^{10}$ for each individual compound corresponds in each case to one line of Table A.

Table 12-24 Compounds of formula IIA.Ka in which o is 1, $R^{78}$ is 4"-$C_6H_5$ and the meaning for the combination of $R^1$, $R^2$, $R^3$, $R^4$, $R^9$ and $R^{10}$ for each individual compound corresponds in each case to one line of Table A.

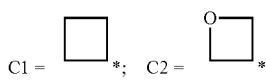

The carbon atom, which is part of the dihydroisoquinoline ring, is marked *.

TABLE A

| line | R¹ | R² | R³ | R⁴ | R⁹ | R¹⁰ |
|---|---|---|---|---|---|---|
| A-1 | H | H | H | H | CH₃ | CH₃ |
| A-2 | H | H | H | H | CH₃ | C₂H₅ |
| A-3 | H | H | H | H | C₂H₅ | CH₃ |
| A-4 | H | H | H | H | C₂H₅ | C₂H₅ |
| A-5 | F | H | H | H | CH₃ | CH₃ |
| A-6 | F | H | H | H | CH₃ | C₂H₅ |
| A-7 | F | H | H | H | C₂H₅ | CH₃ |
| A-8 | F | H | H | H | C₂H₅ | C₂H₅ |
| A-9 | Cl | H | H | H | CH₃ | CH₃ |
| A-10 | Cl | H | H | H | CH₃ | C₂H₅ |
| A-11 | Cl | H | H | H | C₂H₅ | CH₃ |
| A-12 | Cl | H | H | H | C₂H₅ | C₂H₅ |
| A-13 | CH₃ | H | H | H | CH₃ | CH₃ |
| A-14 | CH₃ | H | H | H | CH₃ | C₂H₅ |
| A-15 | CH₃ | H | H | H | C₂H₅ | CH₃ |
| A-16 | CH₃ | H | H | H | C₂H₅ | C₂H₅ |
| A-17 | H | F | H | H | CH₃ | CH₃ |
| A-18 | H | F | H | H | CH₃ | C₂H₅ |
| A-19 | H | F | H | H | C₂H₅ | CH₃ |
| A-20 | H | F | H | H | C₂H₅ | C₂H₅ |
| A-21 | F | F | H | H | CH₃ | CH₃ |
| A-22 | F | F | H | H | CH₃ | C₂H₅ |
| A-23 | F | F | H | H | C₂H₅ | CH₃ |
| A-24 | F | F | H | H | C₂H₅ | C₂H₅ |
| A-25 | Cl | F | H | H | CH₃ | CH₃ |
| A-26 | Cl | F | H | H | CH₃ | C₂H₅ |
| A-27 | Cl | F | H | H | C₂H₅ | CH₃ |
| A-28 | Cl | F | H | H | C₂H₅ | C₂H₅ |
| A-29 | CH₃ | F | H | H | CH₃ | CH₃ |
| A-30 | CH₃ | F | H | H | CH₃ | C₂H₅ |
| A-31 | CH₃ | F | H | H | C₂H₅ | CH₃ |
| A-32 | CH₃ | F | H | H | C₂H₅ | C₂H₅ |
| A-33 | H | CH₃ | H | H | CH₃ | CH₃ |
| A-34 | H | CH₃ | H | H | CH₃ | C₂H₅ |
| A-35 | H | CH₃ | H | H | C₂H₅ | CH₃ |
| A-36 | H | CH₃ | H | H | C₂H₅ | C₂H₅ |
| A-37 | F | CH₃ | H | H | CH₃ | CH₃ |
| A-38 | F | CH₃ | H | H | CH₃ | C₂H₅ |
| A-39 | F | CH₃ | H | H | C₂H₅ | CH₃ |
| A-40 | F | CH₃ | H | H | C₂H₅ | C₂H₅ |
| A-41 | Cl | CH₃ | H | H | CH₃ | CH₃ |
| A-42 | Cl | CH₃ | H | H | CH₃ | C₂H₅ |
| A-43 | Cl | CH₃ | H | H | C₂H₅ | CH₃ |
| A-44 | Cl | CH₃ | H | H | C₂H₅ | C₂H₅ |
| A-45 | CH₃ | CH₃ | H | H | CH₃ | CH₃ |
| A-46 | CH₃ | CH₃ | H | H | CH₃ | C₂H₅ |
| A-47 | CH₃ | CH₃ | H | H | C₂H₅ | CH₃ |
| A-48 | CH₃ | CH₃ | H | H | C₂H₅ | C₂H₅ |
| A-49 | H | Cl | H | H | CH₃ | CH₃ |
| A-50 | H | Cl | H | H | CH₃ | C₂H₅ |
| A-51 | H | Cl | H | H | C₂H₅ | CH₃ |
| A-52 | H | Cl | H | H | C₂H₅ | C₂H₅ |
| A-53 | F | Cl | H | H | CH₃ | CH₃ |
| A-54 | F | Cl | H | H | CH₃ | C₂H₅ |
| A-55 | F | Cl | H | H | C₂H₅ | CH₃ |
| A-56 | F | Cl | H | H | C₂H₅ | C₂H₅ |
| A-57 | Cl | Cl | H | H | CH₃ | CH₃ |
| A-58 | Cl | Cl | H | H | CH₃ | C₂H₅ |
| A-59 | Cl | Cl | H | H | C₂H₅ | CH₃ |
| A-60 | Cl | Cl | H | H | C₂H₅ | C₂H₅ |
| A-61 | CH₃ | Cl | H | H | CH₃ | CH₃ |
| A-62 | CH₃ | Cl | H | H | CH₃ | C₂H₅ |
| A-63 | CH₃ | Cl | H | H | C₂H₅ | CH₃ |
| A-64 | CH₃ | Cl | H | H | C₂H₅ | C₂H₅ |
| A-65 | H | H | CH₃ | CH₃ | CH₃ | CH₃ |
| A-66 | H | H | CH₃ | CH₃ | CH₃ | C₂H₅ |
| A-67 | H | H | CH₃ | CH₃ | C₂H₅ | CH₃ |
| A-68 | H | H | CH₃ | CH₃ | C₂H₅ | C₂H₅ |
| A-69 | F | H | CH₃ | CH₃ | CH₃ | CH₃ |
| A-70 | F | H | CH₃ | CH₃ | CH₃ | C₂H₅ |
| A-71 | F | H | CH₃ | CH₃ | C₂H₅ | CH₃ |
| A-72 | F | H | CH₃ | CH₃ | C₂H₅ | C₂H₅ |
| A-73 | Cl | H | CH₃ | CH₃ | CH₃ | CH₃ |
| A-74 | Cl | H | CH₃ | CH₃ | CH₃ | C₂H₅ |
| A-75 | Cl | H | CH₃ | CH₃ | C₂H₅ | CH₃ |
| A-76 | Cl | H | CH₃ | CH₃ | C₂H₅ | C₂H₅ |
| A-77 | CH₃ | H | CH₃ | CH₃ | CH₃ | CH₃ |
| A-78 | CH₃ | H | CH₃ | CH₃ | CH₃ | C₂H₅ |
| A-79 | CH₃ | H | CH₃ | CH₃ | C₂H₅ | CH₃ |
| A-80 | CH₃ | H | CH₃ | CH₃ | C₂H₅ | C₂H₅ |
| A-81 | H | F | CH₃ | CH₃ | CH₃ | CH₃ |
| A-82 | H | F | CH₃ | CH₃ | CH₃ | C₂H₅ |
| A-83 | H | F | CH₃ | CH₃ | C₂H₅ | CH₃ |
| A-84 | H | F | CH₃ | CH₃ | C₂H₅ | C₂H₅ |
| A-85 | F | F | CH₃ | CH₃ | CH₃ | CH₃ |
| A-86 | F | F | CH₃ | CH₃ | CH₃ | C₂H₅ |
| A-87 | F | F | CH₃ | CH₃ | C₂H₅ | CH₃ |
| A-88 | F | F | CH₃ | CH₃ | C₂H₅ | C₂H₅ |
| A-89 | Cl | F | CH₃ | CH₃ | CH₃ | CH₃ |
| A-90 | Cl | F | CH₃ | CH₃ | CH₃ | C₂H₅ |
| A-91 | Cl | F | CH₃ | CH₃ | C₂H₅ | CH₃ |
| A-92 | Cl | F | CH₃ | CH₃ | C₂H₅ | C₂H₅ |
| A-93 | CH₃ | F | CH₃ | CH₃ | CH₃ | CH₃ |
| A-94 | CH₃ | F | CH₃ | CH₃ | CH₃ | C₂H₅ |
| A-95 | CH₃ | F | CH₃ | CH₃ | C₂H₅ | CH₃ |
| A-96 | CH₃ | F | CH₃ | CH₃ | C₂H₅ | C₂H₅ |
| A-97 | H | CH₃ | CH₃ | CH₃ | CH₃ | CH₃ |
| A-98 | H | CH₃ | CH₃ | CH₃ | CH₃ | C₂H₅ |
| A-99 | H | CH₃ | CH₃ | CH₃ | C₂H₅ | CH₃ |
| A-100 | H | CH₃ | CH₃ | CH₃ | C₂H₅ | C₂H₅ |
| A-101 | F | CH₃ | CH₃ | CH₃ | CH₃ | CH₃ |
| A-102 | F | CH₃ | CH₃ | CH₃ | CH₃ | C₂H₅ |
| A-103 | F | CH₃ | CH₃ | CH₃ | C₂H₅ | CH₃ |
| A-104 | F | CH₃ | CH₃ | CH₃ | C₂H₅ | C₂H₅ |
| A-105 | Cl | CH₃ | CH₃ | CH₃ | CH₃ | CH₃ |
| A-106 | Cl | CH₃ | CH₃ | CH₃ | CH₃ | C₂H₅ |
| A-107 | Cl | CH₃ | CH₃ | CH₃ | C₂H₅ | CH₃ |
| A-108 | Cl | CH₃ | CH₃ | CH₃ | C₂H₅ | C₂H₅ |
| A-109 | CH₃ | CH₃ | CH₃ | CH₃ | CH₃ | CH₃ |
| A-110 | CH₃ | CH₃ | CH₃ | CH₃ | CH₃ | C₂H₅ |
| A-111 | CH₃ | CH₃ | CH₃ | CH₃ | C₂H₅ | CH₃ |
| A-112 | CH₃ | CH₃ | CH₃ | CH₃ | C₂H₅ | C₂H₅ |
| A-113 | H | Cl | CH₃ | CH₃ | CH₃ | CH₃ |
| A-114 | H | Cl | CH₃ | CH₃ | CH₃ | C₂H₅ |
| A-115 | H | Cl | CH₃ | CH₃ | C₂H₅ | CH₃ |
| A-116 | H | Cl | CH₃ | CH₃ | C₂H₅ | C₂H₅ |
| A-117 | F | Cl | CH₃ | CH₃ | CH₃ | CH₃ |
| A-118 | F | Cl | CH₃ | CH₃ | CH₃ | C₂H₅ |
| A-119 | F | Cl | CH₃ | CH₃ | C₂H₅ | CH₃ |
| A-120 | F | Cl | CH₃ | CH₃ | C₂H₅ | C₂H₅ |
| A-121 | Cl | Cl | CH₃ | CH₃ | CH₃ | CH₃ |
| A-122 | Cl | Cl | CH₃ | CH₃ | CH₃ | C₂H₅ |
| A-123 | Cl | Cl | CH₃ | CH₃ | C₂H₅ | CH₃ |
| A-124 | Cl | Cl | CH₃ | CH₃ | C₂H₅ | C₂H₅ |
| A-125 | CH₃ | Cl | CH₃ | CH₃ | CH₃ | CH₃ |
| A-126 | CH₃ | Cl | CH₃ | CH₃ | CH₃ | C₂H₅ |
| A-127 | CH₃ | Cl | CH₃ | CH₃ | C₂H₅ | CH₃ |
| A-128 | CH₃ | Cl | CH₃ | CH₃ | C₂H₅ | C₂H₅ |
| A-129 | H | H | C₂H₅ | C₂H₅ | CH₃ | CH₃ |
| A-130 | H | H | C₂H₅ | C₂H₅ | CH₃ | C₂H₅ |
| A-131 | H | H | C₂H₅ | C₂H₅ | C₂H₅ | CH₃ |
| A-132 | H | H | C₂H₅ | C₂H₅ | C₂H₅ | C₂H₅ |
| A-133 | F | H | C₂H₅ | C₂H₅ | CH₃ | CH₃ |
| A-134 | F | H | C₂H₅ | C₂H₅ | CH₃ | C₂H₅ |
| A-135 | F | H | C₂H₅ | C₂H₅ | C₂H₅ | CH₃ |
| A-136 | F | H | C₂H₅ | C₂H₅ | C₂H₅ | C₂H₅ |
| A-137 | Cl | H | C₂H₅ | C₂H₅ | CH₃ | CH₃ |
| A-138 | Cl | H | C₂H₅ | C₂H₅ | CH₃ | C₂H₅ |
| A-139 | Cl | H | C₂H₅ | C₂H₅ | C₂H₅ | CH₃ |
| A-140 | Cl | H | C₂H₅ | C₂H₅ | C₂H₅ | C₂H₅ |
| A-141 | CH₃ | H | C₂H₅ | C₂H₅ | CH₃ | CH₃ |
| A-142 | CH₃ | H | C₂H₅ | C₂H₅ | CH₃ | C₂H₅ |
| A-143 | CH₃ | H | C₂H₅ | C₂H₅ | C₂H₅ | CH₃ |
| A-144 | CH₃ | H | C₂H₅ | C₂H₅ | C₂H₅ | C₂H₅ |
| A-145 | H | F | C₂H₅ | C₂H₅ | CH₃ | CH₃ |
| A-146 | H | F | C₂H₅ | C₂H₅ | CH₃ | C₂H₅ |

TABLE A-continued

| line | R¹ | R² | R³ | R⁴ | R⁹ | R¹⁰ |
|---|---|---|---|---|---|---|
| A-147 | H | F | C₂H₅ | C₂H₅ | C₂H₅ | CH₃ |
| A-148 | H | F | C₂H₅ | C₂H₅ | C₂H₅ | C₂H₅ |
| A-149 | F | F | C₂H₅ | C₂H₅ | CH₃ | CH₃ |
| A-150 | F | F | C₂H₅ | C₂H₅ | CH₃ | C₂H₅ |
| A-151 | F | F | C₂H₅ | C₂H₅ | C₂H₅ | CH₃ |
| A-152 | F | F | C₂H₅ | C₂H₅ | C₂H₅ | C₂H₅ |
| A-153 | Cl | F | C₂H₅ | C₂H₅ | CH₃ | CH₃ |
| A-154 | Cl | F | C₂H₅ | C₂H₅ | CH₃ | C₂H₅ |
| A-155 | Cl | F | C₂H₅ | C₂H₅ | C₂H₅ | CH₃ |
| A-156 | Cl | F | C₂H₅ | C₂H₅ | C₂H₅ | C₂H₅ |
| A-157 | CH₃ | F | C₂H₅ | C₂H₅ | CH₃ | CH₃ |
| A-158 | CH₃ | F | C₂H₅ | C₂H₅ | CH₃ | C₂H₅ |
| A-159 | CH₃ | F | C₂H₅ | C₂H₅ | C₂H₅ | CH₃ |
| A-160 | CH₃ | F | C₂H₅ | C₂H₅ | C₂H₅ | C₂H₅ |
| A-161 | H | CH₃ | C₂H₅ | C₂H₅ | CH₃ | CH₃ |
| A-162 | H | CH₃ | C₂H₅ | C₂H₅ | CH₃ | C₂H₅ |
| A-163 | H | CH₃ | C₂H₅ | C₂H₅ | C₂H₅ | CH₃ |
| A-164 | H | CH₃ | C₂H₅ | C₂H₅ | C₂H₅ | C₂H₅ |
| A-165 | F | CH₃ | C₂H₅ | C₂H₅ | CH₃ | CH₃ |
| A-166 | F | CH₃ | C₂H₅ | C₂H₅ | CH₃ | C₂H₅ |
| A-167 | F | CH₃ | C₂H₅ | C₂H₅ | C₂H₅ | CH₃ |
| A-168 | F | CH₃ | C₂H₅ | C₂H₅ | C₂H₅ | C₂H₅ |
| A-169 | Cl | CH₃ | C₂H₅ | C₂H₅ | CH₃ | CH₃ |
| A-170 | Cl | CH₃ | C₂H₅ | C₂H₅ | CH₃ | C₂H₅ |
| A-171 | Cl | CH₃ | C₂H₅ | C₂H₅ | C₂H₅ | CH₃ |
| A-172 | Cl | CH₃ | C₂H₅ | C₂H₅ | C₂H₅ | C₂H₅ |
| A-173 | CH₃ | CH₃ | C₂H₅ | C₂H₅ | CH₃ | CH₃ |
| A-174 | CH₃ | CH₃ | C₂H₅ | C₂H₅ | CH₃ | C₂H₅ |
| A-175 | CH₃ | CH₃ | C₂H₅ | C₂H₅ | C₂H₅ | CH₃ |
| A-176 | CH₃ | CH₃ | C₂H₅ | C₂H₅ | C₂H₅ | C₂H₅ |
| A-177 | H | Cl | C₂H₅ | C₂H₅ | CH₃ | CH₃ |
| A-178 | H | Cl | C₂H₅ | C₂H₅ | CH₃ | C₂H₅ |
| A-179 | H | Cl | C₂H₅ | C₂H₅ | C₂H₅ | CH₃ |
| A-180 | H | Cl | C₂H₅ | C₂H₅ | C₂H₅ | C₂H₅ |
| A-181 | F | Cl | C₂H₅ | C₂H₅ | CH₃ | CH₃ |
| A-182 | F | Cl | C₂H₅ | C₂H₅ | CH₃ | C₂H₅ |
| A-183 | F | Cl | C₂H₅ | C₂H₅ | C₂H₅ | CH₃ |
| A-184 | F | Cl | C₂H₅ | C₂H₅ | C₂H₅ | C₂H₅ |
| A-185 | Cl | Cl | C₂H₅ | C₂H₅ | CH₃ | CH₃ |
| A-186 | Cl | Cl | C₂H₅ | C₂H₅ | CH₃ | C₂H₅ |
| A-187 | Cl | Cl | C₂H₅ | C₂H₅ | C₂H₅ | CH₃ |
| A-188 | Cl | Cl | C₂H₅ | C₂H₅ | C₂H₅ | C₂H₅ |
| A-189 | CH₃ | Cl | C₂H₅ | C₂H₅ | CH₃ | CH₃ |
| A-190 | CH₃ | Cl | C₂H₅ | C₂H₅ | CH₃ | C₂H₅ |
| A-191 | CH₃ | Cl | C₂H₅ | C₂H₅ | C₂H₅ | CH₃ |
| A-192 | CH₃ | Cl | C₂H₅ | C₂H₅ | C₂H₅ | C₂H₅ |
| A-193 | H | H | CH₃ | C₂H₅ | CH₃ | CH₃ |
| A-194 | H | H | CH₃ | C₂H₅ | CH₃ | C₂H₅ |
| A-195 | H | H | CH₃ | C₂H₅ | C₂H₅ | CH₃ |
| A-196 | H | H | CH₃ | C₂H₅ | C₂H₅ | C₂H₅ |
| A-197 | F | H | CH₃ | C₂H₅ | CH₃ | CH₃ |
| A-198 | F | H | CH₃ | C₂H₅ | CH₃ | C₂H₅ |
| A-199 | F | H | CH₃ | C₂H₅ | C₂H₅ | CH₃ |
| A-200 | F | H | CH₃ | C₂H₅ | C₂H₅ | C₂H₅ |
| A-201 | Cl | H | CH₃ | C₂H₅ | CH₃ | CH₃ |
| A-202 | Cl | H | CH₃ | C₂H₅ | CH₃ | C₂H₅ |
| A-203 | Cl | H | CH₃ | C₂H₅ | C₂H₅ | CH₃ |
| A-204 | Cl | H | CH₃ | C₂H₅ | C₂H₅ | C₂H₅ |
| A-205 | CH₃ | H | CH₃ | C₂H₅ | CH₃ | CH₃ |
| A-206 | CH₃ | H | CH₃ | C₂H₅ | CH₃ | C₂H₅ |
| A-207 | CH₃ | H | CH₃ | C₂H₅ | C₂H₅ | CH₃ |
| A-208 | CH₃ | H | CH₃ | C₂H₅ | C₂H₅ | C₂H₅ |
| A-209 | H | F | CH₃ | C₂H₅ | CH₃ | CH₃ |
| A-210 | H | F | CH₃ | C₂H₅ | CH₃ | C₂H₅ |
| A-211 | H | F | CH₃ | C₂H₅ | C₂H₅ | CH₃ |
| A-212 | H | F | CH₃ | C₂H₅ | C₂H₅ | C₂H₅ |
| A-213 | F | F | CH₃ | C₂H₅ | CH₃ | CH₃ |
| A-214 | F | F | CH₃ | C₂H₅ | CH₃ | C₂H₅ |
| A-215 | F | F | CH₃ | C₂H₅ | C₂H₅ | CH₃ |
| A-216 | F | F | CH₃ | C₂H₅ | C₂H₅ | C₂H₅ |
| A-217 | Cl | F | CH₃ | C₂H₅ | CH₃ | CH₃ |
| A-218 | Cl | F | CH₃ | C₂H₅ | CH₃ | C₂H₅ |
| A-219 | Cl | F | CH₃ | C₂H₅ | C₂H₅ | CH₃ |
| A-220 | Cl | F | CH₃ | C₂H₅ | C₂H₅ | C₂H₅ |
| A-221 | CH₃ | F | CH₃ | C₂H₅ | CH₃ | CH₃ |
| A-222 | CH₃ | F | CH₃ | C₂H₅ | CH₃ | C₂H₅ |
| A-223 | CH₃ | F | CH₃ | C₂H₅ | C₂H₅ | CH₃ |
| A-224 | CH₃ | F | CH₃ | C₂H₅ | C₂H₅ | C₂H₅ |
| A-225 | H | CH₃ | CH₃ | C₂H₅ | CH₃ | CH₃ |
| A-226 | H | CH₃ | CH₃ | C₂H₅ | CH₃ | C₂H₅ |
| A-227 | H | CH₃ | CH₃ | C₂H₅ | C₂H₅ | CH₃ |
| A-228 | H | CH₃ | CH₃ | C₂H₅ | C₂H₅ | C₂H₅ |
| A-229 | F | CH₃ | CH₃ | C₂H₅ | CH₃ | CH₃ |
| A-230 | F | CH₃ | CH₃ | C₂H₅ | CH₃ | C₂H₅ |
| A-231 | F | CH₃ | CH₃ | C₂H₅ | C₂H₅ | CH₃ |
| A-232 | F | CH₃ | CH₃ | C₂H₅ | C₂H₅ | C₂H₅ |
| A-233 | Cl | CH₃ | CH₃ | C₂H₅ | CH₃ | CH₃ |
| A-234 | Cl | CH₃ | CH₃ | C₂H₅ | CH₃ | C₂H₅ |
| A-235 | Cl | CH₃ | CH₃ | C₂H₅ | C₂H₅ | CH₃ |
| A-236 | Cl | CH₃ | CH₃ | C₂H₅ | C₂H₅ | C₂H₅ |
| A-237 | CH₃ | CH₃ | CH₃ | C₂H₅ | CH₃ | CH₃ |
| A-238 | CH₃ | CH₃ | CH₃ | C₂H₅ | CH₃ | C₂H₅ |
| A-239 | CH₃ | CH₃ | CH₃ | C₂H₅ | C₂H₅ | CH₃ |
| A-240 | CH₃ | CH₃ | CH₃ | C₂H₅ | C₂H₅ | C₂H₅ |
| A-241 | H | Cl | CH₃ | C₂H₅ | CH₃ | CH₃ |
| A-242 | H | Cl | CH₃ | C₂H₅ | CH₃ | C₂H₅ |
| A-243 | H | Cl | CH₃ | C₂H₅ | C₂H₅ | CH₃ |
| A-244 | H | Cl | CH₃ | C₂H₅ | C₂H₅ | C₂H₅ |
| A-245 | F | Cl | CH₃ | C₂H₅ | CH₃ | CH₃ |
| A-246 | F | Cl | CH₃ | C₂H₅ | CH₃ | C₂H₅ |
| A-247 | F | Cl | CH₃ | C₂H₅ | C₂H₅ | CH₃ |
| A-248 | F | Cl | CH₃ | C₂H₅ | C₂H₅ | C₂H₅ |
| A-249 | Cl | Cl | CH₃ | C₂H₅ | CH₃ | CH₃ |
| A-250 | Cl | Cl | CH₃ | C₂H₅ | CH₃ | C₂H₅ |
| A-251 | Cl | Cl | CH₃ | C₂H₅ | C₂H₅ | CH₃ |
| A-252 | Cl | Cl | CH₃ | C₂H₅ | C₂H₅ | C₂H₅ |
| A-253 | CH₃ | Cl | CH₃ | C₂H₅ | CH₃ | CH₃ |
| A-254 | CH₃ | Cl | CH₃ | C₂H₅ | CH₃ | C₂H₅ |
| A-255 | CH₃ | Cl | CH₃ | C₂H₅ | C₂H₅ | CH₃ |
| A-256 | CH₃ | Cl | CH₃ | C₂H₅ | C₂H₅ | C₂H₅ |
| A-257 | H | H | H | H | CH₃ | CH₃ |
| A-258 | H | H | H | H | CH₃ | C₂H₅ |
| A-259 | H | H | H | H | C₂H₅ | CH₃ |
| A-260 | H | H | H | H | C₂H₅ | C₂H₅ |
| A-261 | F | H | H | H | CH₃ | CH₃ |
| A-262 | F | H | H | H | CH₃ | C₂H₅ |
| A-263 | F | H | H | H | C₂H₅ | CH₃ |
| A-264 | F | H | H | H | C₂H₅ | C₂H₅ |
| A-265 | Cl | H | H | H | CH₃ | CH₃ |
| A-266 | Cl | H | H | H | CH₃ | C₂H₅ |
| A-267 | Cl | H | H | H | C₂H₅ | CH₃ |
| A-268 | Cl | H | H | H | C₂H₅ | C₂H₅ |
| A-269 | CH₃ | H | H | H | CH₃ | CH₃ |
| A-270 | CH₃ | H | H | H | CH₃ | C₂H₅ |
| A-271 | CH₃ | H | H | H | C₂H₅ | CH₃ |
| A-272 | CH₃ | H | H | H | C₂H₅ | C₂H₅ |
| A-273 | H | F | H | H | CH₃ | CH₃ |
| A-274 | H | F | H | H | CH₃ | C₂H₅ |
| A-275 | H | F | H | H | C₂H₅ | CH₃ |
| A-276 | H | F | H | H | C₂H₅ | C₂H₅ |
| A-277 | F | F | H | H | CH₃ | CH₃ |
| A-278 | F | F | H | H | CH₃ | C₂H₅ |
| A-279 | F | F | H | H | C₂H₅ | CH₃ |
| A-280 | F | F | H | H | C₂H₅ | C₂H₅ |
| A-281 | Cl | F | H | H | CH₃ | CH₃ |
| A-282 | Cl | F | H | H | CH₃ | C₂H₅ |
| A-283 | Cl | F | H | H | C₂H₅ | CH₃ |
| A-284 | Cl | F | H | H | C₂H₅ | C₂H₅ |
| A-285 | CH₃ | F | H | H | CH₃ | CH₃ |
| A-286 | CH₃ | F | H | H | CH₃ | C₂H₅ |
| A-287 | CH₃ | F | H | H | C₂H₅ | CH₃ |
| A-288 | CH₃ | F | H | H | C₂H₅ | C₂H₅ |
| A-289 | H | CH₃ | H | H | CH₃ | CH₃ |
| A-290 | H | CH₃ | H | H | CH₃ | C₂H₅ |
| A-291 | H | CH₃ | H | H | C₂H₅ | CH₃ |
| A-292 | H | CH₃ | H | H | C₂H₅ | C₂H₅ |
| A-293 | F | CH₃ | H | H | CH₃ | CH₃ |
| A-294 | H | CH₃ | H | H | CH₃ | C₂H₅ |
| A-295 | H | CH₃ | H | H | C₂H₅ | CH₃ |
| A-296 | H | CH₃ | H | H | C₂H₅ | C₂H₅ |
| A-297 | Cl | CH₃ | H | H | CH₃ | CH₃ |
| A-298 | Cl | CH₃ | H | H | CH₃ | C₂H₅ |
| A-299 | Cl | CH₃ | H | H | C₂H₅ | CH₃ |
| A-300 | Cl | CH₃ | H | H | C₂H₅ | C₂H₅ |
| A-301 | CH₃ | CH₃ | H | H | CH₃ | CH₃ |
| A-302 | CH₃ | CH₃ | H | H | CH₃ | C₂H₅ |

TABLE A-continued

| line | R¹ | R² | R³ | R⁴ | R⁹ | R¹⁰ |
| --- | --- | --- | --- | --- | --- | --- |
| A-303 | CH₃ | CH₃ | H | H | C₂H₅ | CH₃ |
| A-304 | CH₃ | CH₃ | H | H | C₂H₅ | C₂H₅ |
| A-305 | H | Cl | H | H | CH₃ | CH₃ |
| A-306 | H | Cl | H | H | CH₃ | C₂H₅ |
| A-307 | H | Cl | H | H | C₂H₅ | CH₃ |
| A-308 | H | Cl | H | H | C₂H₅ | C₂H₅ |
| A-309 | F | Cl | H | H | CH₃ | CH₃ |
| A-310 | F | Cl | H | H | CH₃ | C₂H₅ |
| A-311 | F | Cl | H | H | C₂H₅ | CH₃ |
| A-312 | F | Cl | H | H | C₂H₅ | C₂H₅ |
| A-313 | Cl | Cl | H | H | CH₃ | CH₃ |
| A-314 | Cl | Cl | H | H | CH₃ | C₂H₅ |
| A-315 | Cl | Cl | H | H | C₂H₅ | CH₃ |
| A-316 | Cl | Cl | H | H | C₂H₅ | C₂H₅ |
| A-317 | CH₃ | Cl | H | H | CH₃ | CH₃ |
| A-318 | CH₃ | Cl | H | H | CH₃ | C₂H₅ |
| A-319 | CH₃ | Cl | H | H | C₂H₅ | CH₃ |
| A-320 | CH₃ | Cl | H | H | C₂H₅ | C₂H₅ |
| A-321 | H | H | CH₃ | CH₃ | CH₃ | CH₃ |
| A-322 | H | H | CH₃ | CH₃ | CH₃ | C₂H₅ |
| A-323 | H | H | CH₃ | CH₃ | C₂H₅ | CH₃ |
| A-324 | H | H | CH₃ | CH₃ | C₂H₅ | C₂H₅ |
| A-325 | F | H | CH₃ | CH₃ | CH₃ | CH₃ |
| A-326 | F | H | CH₃ | CH₃ | CH₃ | C₂H₅ |
| A-327 | F | H | CH₃ | CH₃ | C₂H₅ | CH₃ |
| A-328 | F | H | CH₃ | CH₃ | C₂H₅ | C₂H₅ |
| A-329 | Cl | H | CH₃ | CH₃ | CH₃ | CH₃ |
| A-330 | Cl | H | CH₃ | CH₃ | CH₃ | C₂H₅ |
| A-331 | Cl | H | CH₃ | CH₃ | C₂H₅ | CH₃ |
| A-332 | Cl | H | CH₃ | CH₃ | C₂H₅ | C₂H₅ |
| A-333 | CH₃ | H | CH₃ | CH₃ | CH₃ | CH₃ |
| A-334 | CH₃ | H | CH₃ | CH₃ | CH₃ | C₂H₅ |
| A-335 | CH₃ | H | CH₃ | CH₃ | C₂H₅ | CH₃ |
| A-336 | CH₃ | H | CH₃ | CH₃ | C₂H₅ | C₂H₅ |
| A-337 | H | F | CH₃ | CH₃ | CH₃ | CH₃ |
| A-338 | H | F | CH₃ | CH₃ | CH₃ | C₂H₅ |
| A-339 | H | F | CH₃ | CH₃ | C₂H₅ | CH₃ |
| A-340 | H | F | CH₃ | CH₃ | C₂H₅ | C₂H₅ |
| A-341 | F | F | CH₃ | CH₃ | CH₃ | CH₃ |
| A-342 | F | F | CH₃ | CH₃ | CH₃ | C₂H₅ |
| A-343 | F | F | CH₃ | CH₃ | C₂H₅ | CH₃ |
| A-344 | F | F | CH₃ | CH₃ | C₂H₅ | C₂H₅ |
| A-345 | Cl | F | CH₃ | CH₃ | CH₃ | CH₃ |
| A-346 | Cl | F | CH₃ | CH₃ | CH₃ | C₂H₅ |
| A-347 | Cl | F | CH₃ | CH₃ | C₂H₅ | CH₃ |
| A-348 | Cl | F | CH₃ | CH₃ | C₂H₅ | C₂H₅ |
| A-349 | CH₃ | F | CH₃ | CH₃ | CH₃ | CH₃ |
| A-350 | CH₃ | F | CH₃ | CH₃ | CH₃ | C₂H₅ |
| A-351 | CH₃ | F | CH₃ | CH₃ | C₂H₅ | CH₃ |
| A-352 | CH₃ | F | CH₃ | CH₃ | C₂H₅ | C₂H₅ |
| A-353 | H | CH₃ | CH₃ | CH₃ | CH₃ | CH₃ |
| A-354 | H | CH₃ | CH₃ | CH₃ | CH₃ | C₂H₅ |
| A-355 | H | CH₃ | CH₃ | CH₃ | C₂H₅ | CH₃ |
| A-356 | H | CH₃ | CH₃ | CH₃ | C₂H₅ | C₂H₅ |
| A-357 | F | CH₃ | CH₃ | CH₃ | CH₃ | CH₃ |
| A-358 | F | CH₃ | CH₃ | CH₃ | CH₃ | C₂H₅ |
| A-359 | F | CH₃ | CH₃ | CH₃ | C₂H₅ | CH₃ |
| A-360 | F | CH₃ | CH₃ | CH₃ | C₂H₅ | C₂H₅ |
| A-361 | Cl | CH₃ | CH₃ | CH₃ | CH₃ | CH₃ |
| A-362 | Cl | CH₃ | CH₃ | CH₃ | CH₃ | C₂H₅ |
| A-363 | Cl | CH₃ | CH₃ | CH₃ | C₂H₅ | CH₃ |
| A-364 | Cl | CH₃ | CH₃ | CH₃ | C₂H₅ | C₂H₅ |
| A-365 | CH₃ | CH₃ | CH₃ | CH₃ | CH₃ | CH₃ |
| A-366 | CH₃ | CH₃ | CH₃ | CH₃ | CH₃ | C₂H₅ |
| A-367 | CH₃ | CH₃ | CH₃ | CH₃ | C₂H₅ | CH₃ |
| A-368 | CH₃ | CH₃ | CH₃ | CH₃ | C₂H₅ | C₂H₅ |
| A-369 | H | Cl | CH₃ | CH₃ | CH₃ | CH₃ |
| A-370 | H | Cl | CH₃ | CH₃ | CH₃ | C₂H₅ |
| A-371 | H | Cl | CH₃ | CH₃ | C₂H₅ | CH₃ |
| A-372 | H | Cl | CH₃ | CH₃ | C₂H₅ | C₂H₅ |
| A-373 | F | Cl | CH₃ | CH₃ | CH₃ | CH₃ |
| A-374 | F | Cl | CH₃ | CH₃ | CH₃ | C₂H₅ |
| A-375 | F | Cl | CH₃ | CH₃ | C₂H₅ | CH₃ |
| A-376 | F | Cl | CH₃ | CH₃ | C₂H₅ | C₂H₅ |
| A-377 | Cl | Cl | CH₃ | CH₃ | CH₃ | CH₃ |
| A-378 | Cl | Cl | CH₃ | CH₃ | CH₃ | C₂H₅ |
| A-379 | Cl | Cl | CH₃ | CH₃ | C₂H₅ | CH₃ |
| A-380 | Cl | Cl | CH₃ | CH₃ | C₂H₅ | C₂H₅ |
| A-381 | CH₃ | Cl | CH₃ | CH₃ | CH₃ | CH₃ |
| A-382 | CH₃ | Cl | CH₃ | CH₃ | CH₃ | C₂H₅ |
| A-383 | CH₃ | Cl | CH₃ | CH₃ | C₂H₅ | CH₃ |
| A-384 | CH₃ | Cl | CH₃ | CH₃ | C₂H₅ | C₂H₅ |
| A-385 | H | H | C₂H₅ | C₂H₅ | CH₃ | CH₃ |
| A-386 | H | H | C₂H₅ | C₂H₅ | CH₃ | C₂H₅ |
| A-387 | H | H | C₂H₅ | C₂H₅ | C₂H₅ | CH₃ |
| A-388 | H | H | C₂H₅ | C₂H₅ | C₂H₅ | C₂H₅ |
| A-389 | F | H | C₂H₅ | C₂H₅ | CH₃ | CH₃ |
| A-390 | F | H | C₂H₅ | C₂H₅ | CH₃ | C₂H₅ |
| A-391 | F | H | C₂H₅ | C₂H₅ | C₂H₅ | CH₃ |
| A-392 | F | H | C₂H₅ | C₂H₅ | C₂H₅ | C₂H₅ |
| A-393 | Cl | H | C₂H₅ | C₂H₅ | CH₃ | CH₃ |
| A-394 | Cl | H | C₂H₅ | C₂H₅ | CH₃ | C₂H₅ |
| A-395 | Cl | H | C₂H₅ | C₂H₅ | C₂H₅ | CH₃ |
| A-396 | Cl | H | C₂H₅ | C₂H₅ | C₂H₅ | C₂H₅ |
| A-397 | CH₃ | H | C₂H₅ | C₂H₅ | CH₃ | CH₃ |
| A-398 | CH₃ | H | C₂H₅ | C₂H₅ | CH₃ | C₂H₅ |
| A-399 | CH₃ | H | C₂H₅ | C₂H₅ | C₂H₅ | CH₃ |
| A-400 | CH₃ | H | C₂H₅ | C₂H₅ | C₂H₅ | C₂H₅ |
| A-401 | H | F | C₂H₅ | C₂H₅ | CH₃ | CH₃ |
| A-402 | H | F | C₂H₅ | C₂H₅ | CH₃ | C₂H₅ |
| A-403 | H | F | C₂H₅ | C₂H₅ | C₂H₅ | CH₃ |
| A-404 | H | F | C₂H₅ | C₂H₅ | C₂H₅ | C₂H₅ |
| A-405 | F | F | C₂H₅ | C₂H₅ | CH₃ | CH₃ |
| A-406 | F | F | C₂H₅ | C₂H₅ | CH₃ | C₂H₅ |
| A-407 | F | F | C₂H₅ | C₂H₅ | C₂H₅ | CH₃ |
| A-408 | F | F | C₂H₅ | C₂H₅ | C₂H₅ | C₂H₅ |
| A-409 | Cl | F | C₂H₅ | C₂H₅ | CH₃ | CH₃ |
| A-410 | Cl | F | C₂H₅ | C₂H₅ | CH₃ | C₂H₅ |
| A-411 | Cl | F | C₂H₅ | C₂H₅ | C₂H₅ | CH₃ |
| A-412 | Cl | F | C₂H₅ | C₂H₅ | C₂H₅ | C₂H₅ |
| A-413 | CH₃ | F | C₂H₅ | C₂H₅ | CH₃ | CH₃ |
| A-414 | CH₃ | F | C₂H₅ | C₂H₅ | CH₃ | C₂H₅ |
| A-415 | CH₃ | F | C₂H₅ | C₂H₅ | C₂H₅ | CH₃ |
| A-416 | CH₃ | F | C₂H₅ | C₂H₅ | C₂H₅ | C₂H₅ |
| A-417 | H | CH₃ | C₂H₅ | C₂H₅ | CH₃ | CH₃ |
| A-418 | H | CH₃ | C₂H₅ | C₂H₅ | CH₃ | C₂H₅ |
| A-419 | H | CH₃ | C₂H₅ | C₂H₅ | C₂H₅ | CH₃ |
| A-420 | H | CH₃ | C₂H₅ | C₂H₅ | C₂H₅ | C₂H₅ |
| A-421 | F | CH₃ | C₂H₅ | C₂H₅ | CH₃ | CH₃ |
| A-422 | F | CH₃ | C₂H₅ | C₂H₅ | CH₃ | C₂H₅ |
| A-423 | F | CH₃ | C₂H₅ | C₂H₅ | C₂H₅ | CH₃ |
| A-424 | F | CH₃ | C₂H₅ | C₂H₅ | C₂H₅ | C₂H₅ |
| A-425 | Cl | CH₃ | C₂H₅ | C₂H₅ | CH₃ | CH₃ |
| A-426 | Cl | CH₃ | C₂H₅ | C₂H₅ | CH₃ | C₂H₅ |
| A-427 | Cl | CH₃ | C₂H₅ | C₂H₅ | C₂H₅ | CH₃ |
| A-428 | Cl | CH₃ | C₂H₅ | C₂H₅ | C₂H₅ | C₂H₅ |
| A-429 | CH₃ | CH₃ | C₂H₅ | C₂H₅ | CH₃ | CH₃ |
| A-430 | CH₃ | CH₃ | C₂H₅ | C₂H₅ | CH₃ | C₂H₅ |
| A-431 | CH₃ | CH₃ | C₂H₅ | C₂H₅ | C₂H₅ | CH₃ |
| A-432 | CH₃ | CH₃ | C₂H₅ | C₂H₅ | C₂H₅ | C₂H₅ |
| A-433 | H | Cl | C₂H₅ | C₂H₅ | CH₃ | CH₃ |
| A-434 | H | Cl | C₂H₅ | C₂H₅ | CH₃ | C₂H₅ |
| A-435 | H | Cl | C₂H₅ | C₂H₅ | C₂H₅ | CH₃ |
| A-436 | H | Cl | C₂H₅ | C₂H₅ | C₂H₅ | C₂H₅ |
| A-437 | F | Cl | C₂H₅ | C₂H₅ | CH₃ | CH₃ |
| A-438 | F | Cl | C₂H₅ | C₂H₅ | CH₃ | C₂H₅ |
| A-439 | F | Cl | C₂H₅ | C₂H₅ | C₂H₅ | CH₃ |
| A-440 | F | Cl | C₂H₅ | C₂H₅ | C₂H₅ | C₂H₅ |
| A-441 | Cl | Cl | C₂H₅ | C₂H₅ | CH₃ | CH₃ |
| A-442 | Cl | Cl | C₂H₅ | C₂H₅ | CH₃ | C₂H₅ |
| A-443 | Cl | Cl | C₂H₅ | C₂H₅ | C₂H₅ | CH₃ |
| A-444 | Cl | Cl | C₂H₅ | C₂H₅ | C₂H₅ | C₂H₅ |
| A-445 | CH₃ | Cl | C₂H₅ | C₂H₅ | CH₃ | CH₃ |
| A-446 | CH₃ | Cl | C₂H₅ | C₂H₅ | CH₃ | C₂H₅ |
| A-447 | CH₃ | Cl | C₂H₅ | C₂H₅ | C₂H₅ | CH₃ |
| A-448 | CH₃ | Cl | C₂H₅ | C₂H₅ | C₂H₅ | C₂H₅ |
| A-449 | H | H | CH₃ | C₂H₅ | CH₃ | CH₃ |
| A-450 | H | H | CH₃ | C₂H₅ | CH₃ | C₂H₅ |
| A-451 | H | H | CH₃ | C₂H₅ | C₂H₅ | CH₃ |
| A-452 | H | H | CH₃ | C₂H₅ | C₂H₅ | C₂H₅ |
| A-453 | F | H | CH₃ | C₂H₅ | CH₃ | CH₃ |
| A-454 | F | H | CH₃ | C₂H₅ | CH₃ | C₂H₅ |
| A-455 | F | H | CH₃ | C₂H₅ | C₂H₅ | CH₃ |
| A-456 | F | H | CH₃ | C₂H₅ | C₂H₅ | C₂H₅ |
| A-457 | Cl | H | CH₃ | C₂H₅ | CH₃ | CH₃ |
| A-458 | Cl | H | CH₃ | C₂H₅ | CH₃ | C₂H₅ |

TABLE A-continued

| line | R¹ | R² | R³ | R⁴ | R⁹ | R¹⁰ |
|---|---|---|---|---|---|---|
| A-459 | Cl | H | CH$_3$ | C$_2$H$_5$ | C$_2$H$_5$ | CH$_3$ |
| A-460 | Cl | H | CH$_3$ | C$_2$H$_5$ | C$_2$H$_5$ | C$_2$H$_5$ |
| A-461 | CH$_3$ | H | CH$_3$ | C$_2$H$_5$ | CH$_3$ | CH$_3$ |
| A-462 | CH$_3$ | H | CH$_3$ | C$_2$H$_5$ | CH$_3$ | C$_2$H$_5$ |
| A-463 | CH$_3$ | H | CH$_3$ | C$_2$H$_5$ | C$_2$H$_5$ | CH$_3$ |
| A-464 | CH$_3$ | H | CH$_3$ | C$_2$H$_5$ | C$_2$H$_5$ | C$_2$H$_5$ |
| A-465 | H | F | CH$_3$ | C$_2$H$_5$ | CH$_3$ | CH$_3$ |
| A-466 | H | F | CH$_3$ | C$_2$H$_5$ | CH$_3$ | C$_2$H$_5$ |
| A-467 | H | F | CH$_3$ | C$_2$H$_5$ | C$_2$H$_5$ | CH$_3$ |
| A-468 | H | F | CH$_3$ | C$_2$H$_5$ | C$_2$H$_5$ | C$_2$H$_5$ |
| A-469 | F | F | CH$_3$ | C$_2$H$_5$ | CH$_3$ | CH$_3$ |
| A-470 | F | F | CH$_3$ | C$_2$H$_5$ | CH$_3$ | C$_2$H$_5$ |
| A-471 | F | F | CH$_3$ | C$_2$H$_5$ | C$_2$H$_5$ | CH$_3$ |
| A-472 | F | F | CH$_3$ | C$_2$H$_5$ | C$_2$H$_5$ | C$_2$H$_5$ |
| A-473 | Cl | F | CH$_3$ | C$_2$H$_5$ | CH$_3$ | CH$_3$ |
| A-474 | Cl | F | CH$_3$ | C$_2$H$_5$ | CH$_3$ | C$_2$H$_5$ |
| A-475 | Cl | F | CH$_3$ | C$_2$H$_5$ | C$_2$H$_5$ | CH$_3$ |
| A-476 | Cl | F | CH$_3$ | C$_2$H$_5$ | C$_2$H$_5$ | C$_2$H$_5$ |
| A-477 | CH$_3$ | F | CH$_3$ | C$_2$H$_5$ | CH$_3$ | CH$_3$ |
| A-478 | CH$_3$ | F | CH$_3$ | C$_2$H$_5$ | CH$_3$ | C$_2$H$_5$ |
| A-479 | CH$_3$ | F | CH$_3$ | C$_2$H$_5$ | C$_2$H$_5$ | CH$_3$ |
| A-480 | CH$_3$ | F | CH$_3$ | C$_2$H$_5$ | C$_2$H$_5$ | C$_2$H$_5$ |
| A-481 | H | CH$_3$ | CH$_3$ | C$_2$H$_5$ | CH$_3$ | CH$_3$ |
| A-482 | H | CH$_3$ | CH$_3$ | C$_2$H$_5$ | CH$_3$ | C$_2$H$_5$ |
| A-483 | H | CH$_3$ | CH$_3$ | C$_2$H$_5$ | C$_2$H$_5$ | CH$_3$ |
| A-484 | H | CH$_3$ | CH$_3$ | C$_2$H$_5$ | C$_2$H$_5$ | C$_2$H$_5$ |
| A-485 | F | CH$_3$ | CH$_3$ | C$_2$H$_5$ | CH$_3$ | CH$_3$ |
| A-486 | F | CH$_3$ | CH$_3$ | C$_2$H$_5$ | CH$_3$ | C$_2$H$_5$ |
| A-487 | F | CH$_3$ | CH$_3$ | C$_2$H$_5$ | C$_2$H$_5$ | CH$_3$ |
| A-488 | F | CH$_3$ | CH$_3$ | C$_2$H$_5$ | C$_2$H$_5$ | C$_2$H$_5$ |
| A-489 | Cl | CH$_3$ | CH$_3$ | C$_2$H$_5$ | CH$_3$ | CH$_3$ |
| A-490 | Cl | CH$_3$ | CH$_3$ | C$_2$H$_5$ | CH$_3$ | C$_2$H$_5$ |
| A-491 | Cl | CH$_3$ | CH$_3$ | C$_2$H$_5$ | C$_2$H$_5$ | CH$_3$ |
| A-492 | Cl | CH$_3$ | CH$_3$ | C$_2$H$_5$ | C$_2$H$_5$ | C$_2$H$_5$ |
| A-493 | CH$_3$ | CH$_3$ | CH$_3$ | C$_2$H$_5$ | CH$_3$ | CH$_3$ |
| A-494 | CH$_3$ | CH$_3$ | CH$_3$ | C$_2$H$_5$ | CH$_3$ | C$_2$H$_5$ |
| A-495 | CH$_3$ | CH$_3$ | CH$_3$ | C$_2$H$_5$ | C$_2$H$_5$ | CH$_3$ |
| A-496 | CH$_3$ | CH$_3$ | CH$_3$ | C$_2$H$_5$ | C$_2$H$_5$ | C$_2$H$_5$ |
| A-497 | H | Cl | CH$_3$ | C$_2$H$_5$ | CH$_3$ | CH$_3$ |
| A-498 | H | Cl | CH$_3$ | C$_2$H$_5$ | CH$_3$ | C$_2$H$_5$ |
| A-499 | H | Cl | CH$_3$ | C$_2$H$_5$ | C$_2$H$_5$ | CH$_3$ |
| A-500 | H | Cl | CH$_3$ | C$_2$H$_5$ | C$_2$H$_5$ | C$_2$H$_5$ |
| A-501 | F | Cl | CH$_3$ | C$_2$H$_5$ | CH$_3$ | CH$_3$ |
| A-502 | F | Cl | CH$_3$ | C$_2$H$_5$ | CH$_3$ | C$_2$H$_5$ |
| A-503 | F | Cl | CH$_3$ | C$_2$H$_5$ | C$_2$H$_5$ | CH$_3$ |
| A-504 | F | Cl | CH$_3$ | C$_2$H$_5$ | C$_2$H$_5$ | C$_2$H$_5$ |
| A-505 | Cl | Cl | CH$_3$ | C$_2$H$_5$ | CH$_3$ | CH$_3$ |
| A-506 | Cl | Cl | CH$_3$ | C$_2$H$_5$ | CH$_3$ | C$_2$H$_5$ |
| A-507 | Cl | Cl | CH$_3$ | C$_2$H$_5$ | C$_2$H$_5$ | CH$_3$ |
| A-508 | Cl | Cl | CH$_3$ | C$_2$H$_5$ | C$_2$H$_5$ | C$_2$H$_5$ |
| A-509 | CH$_3$ | Cl | CH$_3$ | C$_2$H$_5$ | CH$_3$ | CH$_3$ |
| A-510 | CH$_3$ | Cl | CH$_3$ | C$_2$H$_5$ | CH$_3$ | C$_2$H$_5$ |
| A-511 | CH$_3$ | Cl | CH$_3$ | C$_2$H$_5$ | C$_2$H$_5$ | CH$_3$ |
| A-512 | CH$_3$ | Cl | CH$_3$ | C$_2$H$_5$ | C$_2$H$_5$ | C$_2$H$_5$ |
| A-513 | H | H | H | H | CH$_3$ | CH$_3$ |
| A-514 | H | H | H | H | CH$_3$ | C$_2$H$_5$ |
| A-515 | H | H | H | H | C$_2$H$_5$ | CH$_3$ |
| A-516 | H | H | H | H | C$_2$H$_5$ | C$_2$H$_5$ |
| A-517 | F | H | H | H | CH$_3$ | CH$_3$ |
| A-518 | F | H | H | H | CH$_3$ | C$_2$H$_5$ |
| A-519 | F | H | H | H | C$_2$H$_5$ | CH$_3$ |
| A-520 | F | H | H | H | C$_2$H$_5$ | C$_2$H$_5$ |
| A-521 | Cl | H | H | H | CH$_3$ | CH$_3$ |
| A-522 | Cl | H | H | H | CH$_3$ | C$_2$H$_5$ |
| A-523 | Cl | H | H | H | C$_2$H$_5$ | CH$_3$ |
| A-524 | Cl | H | H | H | C$_2$H$_5$ | C$_2$H$_5$ |
| A-525 | CH$_3$ | H | H | H | CH$_3$ | CH$_3$ |
| A-526 | CH$_3$ | H | H | H | CH$_3$ | C$_2$H$_5$ |
| A-527 | CH$_3$ | H | H | H | C$_2$H$_5$ | CH$_3$ |
| A-528 | CH$_3$ | H | H | H | C$_2$H$_5$ | C$_2$H$_5$ |
| A-529 | H | F | H | H | CH$_3$ | CH$_3$ |
| A-530 | H | F | H | H | CH$_3$ | C$_2$H$_5$ |
| A-531 | H | F | H | H | C$_2$H$_5$ | CH$_3$ |
| A-532 | H | F | H | H | C$_2$H$_5$ | C$_2$H$_5$ |
| A-533 | F | F | H | H | CH$_3$ | CH$_3$ |
| A-534 | F | F | H | H | CH$_3$ | C$_2$H$_5$ |
| A-535 | F | F | H | H | C$_2$H$_5$ | CH$_3$ |
| A-536 | F | F | H | H | C$_2$H$_5$ | C$_2$H$_5$ |
| A-537 | Cl | F | H | H | CH$_3$ | CH$_3$ |
| A-538 | Cl | F | H | H | CH$_3$ | C$_2$H$_5$ |
| A-539 | Cl | F | H | H | C$_2$H$_5$ | CH$_3$ |
| A-540 | Cl | F | H | H | C$_2$H$_5$ | C$_2$H$_5$ |
| A-541 | CH$_3$ | F | H | H | CH$_3$ | CH$_3$ |
| A-542 | CH$_3$ | F | H | H | CH$_3$ | C$_2$H$_5$ |
| A-543 | CH$_3$ | F | H | H | C$_2$H$_5$ | CH$_3$ |
| A-544 | CH$_3$ | F | H | H | C$_2$H$_5$ | C$_2$H$_5$ |
| A-545 | H | CH$_3$ | H | H | CH$_3$ | CH$_3$ |
| A-546 | H | CH$_3$ | H | H | CH$_3$ | C$_2$H$_5$ |
| A-547 | H | CH$_3$ | H | H | C$_2$H$_5$ | CH$_3$ |
| A-548 | H | CH$_3$ | H | H | C$_2$H$_5$ | C$_2$H$_5$ |
| A-549 | F | CH$_3$ | H | H | CH$_3$ | CH$_3$ |
| A-550 | F | CH$_3$ | H | H | CH$_3$ | C$_2$H$_5$ |
| A-551 | F | CH$_3$ | H | H | C$_2$H$_5$ | CH$_3$ |
| A-552 | F | CH$_3$ | H | H | C$_2$H$_5$ | C$_2$H$_5$ |
| A-553 | Cl | CH$_3$ | H | H | CH$_3$ | CH$_3$ |
| A-554 | Cl | CH$_3$ | H | H | CH$_3$ | C$_2$H$_5$ |
| A-555 | Cl | CH$_3$ | H | H | C$_2$H$_5$ | CH$_3$ |
| A-556 | Cl | CH$_3$ | H | H | C$_2$H$_5$ | C$_2$H$_5$ |
| A-557 | CH$_3$ | CH$_3$ | H | H | CH$_3$ | CH$_3$ |
| A-558 | CH$_3$ | CH$_3$ | H | H | CH$_3$ | C$_2$H$_5$ |
| A-559 | CH$_3$ | CH$_3$ | H | H | C$_2$H$_5$ | CH$_3$ |
| A-560 | CH$_3$ | CH$_3$ | H | H | C$_2$H$_5$ | C$_2$H$_5$ |
| A-561 | H | Cl | H | H | CH$_3$ | CH$_3$ |
| A-562 | H | Cl | H | H | CH$_3$ | C$_2$H$_5$ |
| A-563 | H | Cl | H | H | C$_2$H$_5$ | CH$_3$ |
| A-564 | H | Cl | H | H | C$_2$H$_5$ | C$_2$H$_5$ |
| A-565 | F | Cl | H | H | CH$_3$ | CH$_3$ |
| A-566 | F | Cl | H | H | CH$_3$ | C$_2$H$_5$ |
| A-567 | F | Cl | H | H | C$_2$H$_5$ | CH$_3$ |
| A-568 | F | Cl | H | H | C$_2$H$_5$ | C$_2$H$_5$ |
| A-569 | Cl | Cl | H | H | CH$_3$ | CH$_3$ |
| A-570 | Cl | Cl | H | H | CH$_3$ | C$_2$H$_5$ |
| A-571 | Cl | Cl | H | H | C$_2$H$_5$ | CH$_3$ |
| A-572 | Cl | Cl | H | H | C$_2$H$_5$ | C$_2$H$_5$ |
| A-573 | CH$_3$ | Cl | H | H | CH$_3$ | CH$_3$ |
| A-574 | CH$_3$ | Cl | H | H | CH$_3$ | C$_2$H$_5$ |
| A-575 | CH$_3$ | Cl | H | H | C$_2$H$_5$ | CH$_3$ |
| A-576 | CH$_3$ | Cl | H | H | C$_2$H$_5$ | C$_2$H$_5$ |
| A-577 | H | H | CH$_3$ | CH$_3$ | CH$_3$ | CH$_3$ |
| A-578 | H | H | CH$_3$ | CH$_3$ | CH$_3$ | C$_2$H$_5$ |
| A-579 | H | H | CH$_3$ | CH$_3$ | C$_2$H$_5$ | CH$_3$ |
| A-580 | H | H | CH$_3$ | CH$_3$ | C$_2$H$_5$ | C$_2$H$_5$ |
| A-581 | F | H | CH$_3$ | CH$_3$ | CH$_3$ | CH$_3$ |
| A-582 | F | H | CH$_3$ | CH$_3$ | CH$_3$ | C$_2$H$_5$ |
| A-583 | F | H | CH$_3$ | CH$_3$ | C$_2$H$_5$ | CH$_3$ |
| A-584 | F | H | CH$_3$ | CH$_3$ | C$_2$H$_5$ | C$_2$H$_5$ |
| A-585 | Cl | H | CH$_3$ | CH$_3$ | CH$_3$ | CH$_3$ |
| A-586 | Cl | H | CH$_3$ | CH$_3$ | CH$_3$ | C$_2$H$_5$ |
| A-587 | Cl | H | CH$_3$ | CH$_3$ | C$_2$H$_5$ | CH$_3$ |
| A-588 | Cl | H | CH$_3$ | CH$_3$ | C$_2$H$_5$ | C$_2$H$_5$ |
| A-589 | CH$_3$ | H | CH$_3$ | CH$_3$ | CH$_3$ | CH$_3$ |
| A-590 | CH$_3$ | H | CH$_3$ | CH$_3$ | CH$_3$ | C$_2$H$_5$ |
| A-591 | CH$_3$ | H | CH$_3$ | CH$_3$ | C$_2$H$_5$ | CH$_3$ |
| A-592 | CH$_3$ | H | CH$_3$ | CH$_3$ | C$_2$H$_5$ | C$_2$H$_5$ |
| A-593 | H | F | CH$_3$ | CH$_3$ | CH$_3$ | CH$_3$ |
| A-594 | H | F | CH$_3$ | CH$_3$ | CH$_3$ | C$_2$H$_5$ |
| A-595 | H | F | CH$_3$ | CH$_3$ | C$_2$H$_5$ | CH$_3$ |
| A-596 | H | F | CH$_3$ | CH$_3$ | C$_2$H$_5$ | C$_2$H$_5$ |
| A-597 | F | F | CH$_3$ | CH$_3$ | CH$_3$ | CH$_3$ |
| A-598 | F | F | CH$_3$ | CH$_3$ | CH$_3$ | C$_2$H$_5$ |
| A-599 | F | F | CH$_3$ | CH$_3$ | C$_2$H$_5$ | CH$_3$ |
| A-600 | F | F | CH$_3$ | CH$_3$ | C$_2$H$_5$ | C$_2$H$_5$ |
| A-601 | Cl | F | CH$_3$ | CH$_3$ | CH$_3$ | CH$_3$ |
| A-602 | Cl | F | CH$_3$ | CH$_3$ | CH$_3$ | C$_2$H$_5$ |
| A-603 | Cl | F | CH$_3$ | CH$_3$ | C$_2$H$_5$ | CH$_3$ |
| A-604 | Cl | F | CH$_3$ | CH$_3$ | C$_2$H$_5$ | C$_2$H$_5$ |
| A-605 | CH$_3$ | F | CH$_3$ | CH$_3$ | CH$_3$ | CH$_3$ |
| A-606 | CH$_3$ | F | CH$_3$ | CH$_3$ | CH$_3$ | C$_2$H$_5$ |
| A-607 | CH$_3$ | F | CH$_3$ | CH$_3$ | C$_2$H$_5$ | CH$_3$ |
| A-608 | CH$_3$ | F | CH$_3$ | CH$_3$ | C$_2$H$_5$ | C$_2$H$_5$ |
| A-609 | H | CH$_3$ | CH$_3$ | CH$_3$ | CH$_3$ | CH$_3$ |
| A-610 | H | CH$_3$ | CH$_3$ | CH$_3$ | CH$_3$ | C$_2$H$_5$ |
| A-611 | H | CH$_3$ | CH$_3$ | CH$_3$ | C$_2$H$_5$ | CH$_3$ |
| A-612 | H | CH$_3$ | CH$_3$ | CH$_3$ | C$_2$H$_5$ | C$_2$H$_5$ |
| A-613 | F | CH$_3$ | CH$_3$ | CH$_3$ | CH$_3$ | CH$_3$ |
| A-614 | F | CH$_3$ | CH$_3$ | CH$_3$ | CH$_3$ | C$_2$H$_5$ |

TABLE A-continued

| line | R¹ | R² | R³ | R⁴ | R⁹ | R¹⁰ |
| --- | --- | --- | --- | --- | --- | --- |
| A-615 | F | CH₃ | CH₃ | CH₃ | C₂H₅ | CH₃ |
| A-616 | F | CH₃ | CH₃ | CH₃ | C₂H₅ | C₂H₅ |
| A-617 | Cl | CH₃ | CH₃ | CH₃ | CH₃ | CH₃ |
| A-618 | Cl | CH₃ | CH₃ | CH₃ | CH₃ | C₂H₅ |
| A-619 | Cl | CH₃ | CH₃ | CH₃ | C₂H₅ | CH₃ |
| A-620 | Cl | CH₃ | CH₃ | CH₃ | C₂H₅ | C₂H₅ |
| A-621 | CH₃ | CH₃ | CH₃ | CH₃ | CH₃ | CH₃ |
| A-622 | CH₃ | CH₃ | CH₃ | CH₃ | CH₃ | C₂H₅ |
| A-623 | CH₃ | CH₃ | CH₃ | CH₃ | C₂H₅ | CH₃ |
| A-624 | CH₃ | CH₃ | CH₃ | CH₃ | C₂H₅ | C₂H₅ |
| A-625 | H | Cl | CH₃ | CH₃ | CH₃ | CH₃ |
| A-626 | H | Cl | CH₃ | CH₃ | CH₃ | C₂H₅ |
| A-627 | H | Cl | CH₃ | CH₃ | C₂H₅ | CH₃ |
| A-628 | H | Cl | CH₃ | CH₃ | C₂H₅ | C₂H₅ |
| A-629 | F | Cl | CH₃ | CH₃ | CH₃ | CH₃ |
| A-630 | F | Cl | CH₃ | CH₃ | CH₃ | C₂H₅ |
| A-631 | F | Cl | CH₃ | CH₃ | C₂H₅ | CH₃ |
| A-632 | F | Cl | CH₃ | CH₃ | C₂H₅ | C₂H₅ |
| A-633 | Cl | Cl | CH₃ | CH₃ | CH₃ | CH₃ |
| A-634 | Cl | Cl | CH₃ | CH₃ | CH₃ | C₂H₅ |
| A-635 | Cl | Cl | CH₃ | CH₃ | C₂H₅ | CH₃ |
| A-636 | Cl | Cl | CH₃ | CH₃ | C₂H₅ | C₂H₅ |
| A-637 | CH₃ | Cl | CH₃ | CH₃ | CH₃ | CH₃ |
| A-638 | CH₃ | Cl | CH₃ | CH₃ | CH₃ | C₂H₅ |
| A-639 | CH₃ | Cl | CH₃ | CH₃ | C₂H₅ | CH₃ |
| A-640 | CH₃ | Cl | CH₃ | CH₃ | C₂H₅ | C₂H₅ |
| A-641 | H | H | C₂H₅ | C₂H₅ | CH₃ | CH₃ |
| A-642 | H | H | C₂H₅ | C₂H₅ | CH₃ | C₂H₅ |
| A-643 | H | H | C₂H₅ | C₂H₅ | C₂H₅ | CH₃ |
| A-644 | H | H | C₂H₅ | C₂H₅ | C₂H₅ | C₂H₅ |
| A-645 | F | H | C₂H₅ | C₂H₅ | CH₃ | CH₃ |
| A-646 | F | H | C₂H₅ | C₂H₅ | CH₃ | C₂H₅ |
| A-647 | F | H | C₂H₅ | C₂H₅ | C₂H₅ | CH₃ |
| A-648 | F | H | C₂H₅ | C₂H₅ | C₂H₅ | C₂H₅ |
| A-649 | Cl | H | C₂H₅ | C₂H₅ | CH₃ | CH₃ |
| A-650 | Cl | H | C₂H₅ | C₂H₅ | CH₃ | C₂H₅ |
| A-651 | Cl | H | C₂H₅ | C₂H₅ | C₂H₅ | CH₃ |
| A-652 | Cl | H | C₂H₅ | C₂H₅ | C₂H₅ | C₂H₅ |
| A-653 | CH₃ | H | C₂H₅ | C₂H₅ | CH₃ | CH₃ |
| A-654 | CH₃ | H | C₂H₅ | C₂H₅ | CH₃ | C₂H₅ |
| A-655 | CH₃ | H | C₂H₅ | C₂H₅ | C₂H₅ | CH₃ |
| A-656 | CH₃ | H | C₂H₅ | C₂H₅ | C₂H₅ | C₂H₅ |
| A-657 | H | F | C₂H₅ | C₂H₅ | CH₃ | CH₃ |
| A-658 | H | F | C₂H₅ | C₂H₅ | CH₃ | C₂H₅ |
| A-659 | H | F | C₂H₅ | C₂H₅ | C₂H₅ | CH₃ |
| A-660 | H | F | C₂H₅ | C₂H₅ | C₂H₅ | C₂H₅ |
| A-661 | F | F | C₂H₅ | C₂H₅ | CH₃ | CH₃ |
| A-662 | F | F | C₂H₅ | C₂H₅ | CH₃ | C₂H₅ |
| A-663 | F | F | C₂H₅ | C₂H₅ | C₂H₅ | CH₃ |
| A-664 | F | F | C₂H₅ | C₂H₅ | C₂H₅ | C₂H₅ |
| A-665 | Cl | F | C₂H₅ | C₂H₅ | CH₃ | CH₃ |
| A-666 | Cl | F | C₂H₅ | C₂H₅ | CH₃ | C₂H₅ |
| A-667 | Cl | F | C₂H₅ | C₂H₅ | C₂H₅ | CH₃ |
| A-668 | Cl | F | C₂H₅ | C₂H₅ | C₂H₅ | C₂H₅ |
| A-669 | CH₃ | F | C₂H₅ | C₂H₅ | CH₃ | CH₃ |
| A-670 | CH₃ | F | C₂H₅ | C₂H₅ | CH₃ | C₂H₅ |
| A-671 | CH₃ | F | C₂H₅ | C₂H₅ | C₂H₅ | CH₃ |
| A-672 | CH₃ | F | C₂H₅ | C₂H₅ | C₂H₅ | C₂H₅ |
| A-673 | H | CH₃ | C₂H₅ | C₂H₅ | CH₃ | CH₃ |
| A-674 | H | CH₃ | C₂H₅ | C₂H₅ | CH₃ | C₂H₅ |
| A-675 | H | CH₃ | C₂H₅ | C₂H₅ | C₂H₅ | CH₃ |
| A-676 | H | CH₃ | C₂H₅ | C₂H₅ | C₂H₅ | C₂H₅ |
| A-677 | F | CH₃ | C₂H₅ | C₂H₅ | CH₃ | CH₃ |
| A-678 | F | CH₃ | C₂H₅ | C₂H₅ | CH₃ | C₂H₅ |
| A-679 | F | CH₃ | C₂H₅ | C₂H₅ | C₂H₅ | CH₃ |
| A-680 | F | CH₃ | C₂H₅ | C₂H₅ | C₂H₅ | C₂H₅ |
| A-681 | Cl | CH₃ | C₂H₅ | C₂H₅ | CH₃ | CH₃ |
| A-682 | Cl | CH₃ | C₂H₅ | C₂H₅ | CH₃ | C₂H₅ |
| A-683 | Cl | CH₃ | C₂H₅ | C₂H₅ | C₂H₅ | CH₃ |
| A-684 | Cl | CH₃ | C₂H₅ | C₂H₅ | C₂H₅ | C₂H₅ |
| A-685 | CH₃ | CH₃ | C₂H₅ | C₂H₅ | CH₃ | CH₃ |
| A-686 | CH₃ | CH₃ | C₂H₅ | C₂H₅ | CH₃ | C₂H₅ |
| A-687 | CH₃ | CH₃ | C₂H₅ | C₂H₅ | C₂H₅ | CH₃ |
| A-688 | CH₃ | CH₃ | C₂H₅ | C₂H₅ | C₂H₅ | C₂H₅ |
| A-689 | H | Cl | C₂H₅ | C₂H₅ | CH₃ | CH₃ |
| A-690 | H | Cl | C₂H₅ | C₂H₅ | CH₃ | C₂H₅ |
| A-691 | H | Cl | C₂H₅ | C₂H₅ | C₂H₅ | CH₃ |
| A-692 | H | Cl | C₂H₅ | C₂H₅ | C₂H₅ | C₂H₅ |
| A-693 | F | Cl | C₂H₅ | C₂H₅ | CH₃ | CH₃ |
| A-694 | F | Cl | C₂H₅ | C₂H₅ | CH₃ | C₂H₅ |
| A-695 | F | Cl | C₂H₅ | C₂H₅ | C₂H₅ | CH₃ |
| A-696 | F | Cl | C₂H₅ | C₂H₅ | C₂H₅ | C₂H₅ |
| A-697 | Cl | Cl | C₂H₅ | C₂H₅ | CH₃ | CH₃ |
| A-698 | Cl | Cl | C₂H₅ | C₂H₅ | CH₃ | C₂H₅ |
| A-699 | Cl | Cl | C₂H₅ | C₂H₅ | C₂H₅ | CH₃ |
| A-700 | Cl | Cl | C₂H₅ | C₂H₅ | C₂H₅ | C₂H₅ |
| A-701 | CH₃ | Cl | C₂H₅ | C₂H₅ | CH₃ | CH₃ |
| A-702 | CH₃ | Cl | C₂H₅ | C₂H₅ | CH₃ | C₂H₅ |
| A-703 | CH₃ | Cl | C₂H₅ | C₂H₅ | C₂H₅ | CH₃ |
| A-704 | CH₃ | Cl | C₂H₅ | C₂H₅ | C₂H₅ | C₂H₅ |
| A-705 | H | H | CH₃ | C₂H₅ | CH₃ | CH₃ |
| A-706 | H | H | CH₃ | C₂H₅ | CH₃ | C₂H₅ |
| A-707 | H | H | CH₃ | C₂H₅ | C₂H₅ | CH₃ |
| A-708 | H | H | CH₃ | C₂H₅ | C₂H₅ | C₂H₅ |
| A-709 | F | H | CH₃ | C₂H₅ | CH₃ | CH₃ |
| A-710 | F | H | CH₃ | C₂H₅ | CH₃ | C₂H₅ |
| A-711 | F | H | CH₃ | C₂H₅ | C₂H₅ | CH₃ |
| A-712 | F | H | CH₃ | C₂H₅ | C₂H₅ | C₂H₅ |
| A-713 | Cl | H | CH₃ | C₂H₅ | CH₃ | CH₃ |
| A-714 | Cl | H | CH₃ | C₂H₅ | CH₃ | C₂H₅ |
| A-715 | Cl | H | CH₃ | C₂H₅ | C₂H₅ | CH₃ |
| A-716 | Cl | H | CH₃ | C₂H₅ | C₂H₅ | C₂H₅ |
| A-717 | CH₃ | H | CH₃ | C₂H₅ | CH₃ | CH₃ |
| A-718 | CH₃ | H | CH₃ | C₂H₅ | CH₃ | C₂H₅ |
| A-719 | CH₃ | H | CH₃ | C₂H₅ | C₂H₅ | CH₃ |
| A-720 | CH₃ | H | CH₃ | C₂H₅ | C₂H₅ | C₂H₅ |
| A-721 | H | F | CH₃ | C₂H₅ | CH₃ | CH₃ |
| A-722 | H | F | CH₃ | C₂H₅ | CH₃ | C₂H₅ |
| A-723 | H | F | CH₃ | C₂H₅ | C₂H₅ | CH₃ |
| A-724 | H | F | CH₃ | C₂H₅ | C₂H₅ | C₂H₅ |
| A-725 | F | F | CH₃ | C₂H₅ | CH₃ | CH₃ |
| A-726 | F | F | CH₃ | C₂H₅ | CH₃ | C₂H₅ |
| A-727 | F | F | CH₃ | C₂H₅ | C₂H₅ | CH₃ |
| A-728 | F | F | CH₃ | C₂H₅ | C₂H₅ | C₂H₅ |
| A-729 | Cl | F | CH₃ | C₂H₅ | CH₃ | CH₃ |
| A-730 | Cl | F | CH₃ | C₂H₅ | CH₃ | C₂H₅ |
| A-731 | Cl | F | CH₃ | C₂H₅ | C₂H₅ | CH₃ |
| A-732 | Cl | F | CH₃ | C₂H₅ | C₂H₅ | C₂H₅ |
| A-733 | CH₃ | F | CH₃ | C₂H₅ | CH₃ | CH₃ |
| A-734 | CH₃ | F | CH₃ | C₂H₅ | CH₃ | C₂H₅ |
| A-735 | CH₃ | F | CH₃ | C₂H₅ | C₂H₅ | CH₃ |
| A-736 | CH₃ | F | CH₃ | C₂H₅ | C₂H₅ | C₂H₅ |
| A-737 | H | CH₃ | CH₃ | C₂H₅ | CH₃ | CH₃ |
| A-738 | H | CH₃ | CH₃ | C₂H₅ | CH₃ | C₂H₅ |
| A-739 | H | CH₃ | CH₃ | C₂H₅ | C₂H₅ | CH₃ |
| A-740 | H | CH₃ | CH₃ | C₂H₅ | C₂H₅ | C₂H₅ |
| A-741 | F | CH₃ | CH₃ | C₂H₅ | CH₃ | CH₃ |
| A-742 | F | CH₃ | CH₃ | C₂H₅ | CH₃ | C₂H₅ |
| A-743 | F | CH₃ | CH₃ | C₂H₅ | C₂H₅ | CH₃ |
| A-744 | F | CH₃ | CH₃ | C₂H₅ | C₂H₅ | C₂H₅ |
| A-745 | Cl | CH₃ | CH₃ | C₂H₅ | CH₃ | CH₃ |
| A-746 | Cl | CH₃ | CH₃ | C₂H₅ | CH₃ | C₂H₅ |
| A-747 | Cl | CH₃ | CH₃ | C₂H₅ | C₂H₅ | CH₃ |
| A-748 | Cl | CH₃ | CH₃ | C₂H₅ | C₂H₅ | C₂H₅ |
| A-749 | CH₃ | CH₃ | CH₃ | C₂H₅ | CH₃ | CH₃ |
| A-750 | CH₃ | CH₃ | CH₃ | C₂H₅ | CH₃ | C₂H₅ |
| A-751 | CH₃ | CH₃ | CH₃ | C₂H₅ | C₂H₅ | CH₃ |
| A-752 | CH₃ | CH₃ | CH₃ | C₂H₅ | C₂H₅ | C₂H₅ |
| A-753 | H | Cl | CH₃ | C₂H₅ | CH₃ | CH₃ |
| A-754 | H | Cl | CH₃ | C₂H₅ | CH₃ | C₂H₅ |
| A-755 | H | Cl | CH₃ | C₂H₅ | C₂H₅ | CH₃ |
| A-756 | H | Cl | CH₃ | C₂H₅ | C₂H₅ | C₂H₅ |
| A-757 | F | Cl | CH₃ | C₂H₅ | CH₃ | CH₃ |
| A-758 | F | Cl | CH₃ | C₂H₅ | CH₃ | C₂H₅ |
| A-759 | F | Cl | CH₃ | C₂H₅ | C₂H₅ | CH₃ |
| A-760 | F | Cl | CH₃ | C₂H₅ | C₂H₅ | C₂H₅ |
| A-761 | Cl | Cl | CH₃ | C₂H₅ | CH₃ | CH₃ |
| A-762 | Cl | Cl | CH₃ | C₂H₅ | CH₃ | C₂H₅ |
| A-763 | Cl | Cl | CH₃ | C₂H₅ | C₂H₅ | CH₃ |
| A-764 | Cl | Cl | CH₃ | C₂H₅ | C₂H₅ | C₂H₅ |
| A-765 | CH₃ | Cl | CH₃ | C₂H₅ | CH₃ | CH₃ |
| A-766 | CH₃ | Cl | CH₃ | C₂H₅ | CH₃ | C₂H₅ |
| A-767 | CH₃ | Cl | CH₃ | C₂H₅ | C₂H₅ | CH₃ |
| A-768 | CH₃ | Cl | CH₃ | C₂H₅ | C₂H₅ | C₂H₅ |
| A-769 | H | H | H | H | CH₃ | CH₃ |
| A-770 | H | H | H | H | CH₃ | C₂H₅ |

TABLE A-continued

| line | R¹ | R² | R³ | R⁴ | R⁹ | R¹⁰ |
|---|---|---|---|---|---|---|
| A-771 | H | H | H | H | C₂H₅ | CH₃ |
| A-772 | H | H | H | H | C₂H₅ | C₂H₅ |
| A-773 | F | H | H | H | CH₃ | CH₃ |
| A-774 | F | H | H | H | CH₃ | C₂H₅ |
| A-775 | F | H | H | H | C₂H₅ | CH₃ |
| A-776 | F | H | H | H | C₂H₅ | C₂H₅ |
| A-777 | Cl | H | H | H | CH₃ | CH₃ |
| A-778 | Cl | H | H | H | CH₃ | C₂H₅ |
| A-779 | Cl | H | H | H | C₂H₅ | CH₃ |
| A-780 | Cl | H | H | H | C₂H₅ | C₂H₅ |
| A-781 | CH₃ | H | H | H | CH₃ | CH₃ |
| A-782 | CH₃ | H | H | H | CH₃ | C₂H₅ |
| A-783 | CH₃ | H | H | H | C₂H₅ | CH₃ |
| A-784 | CH₃ | H | H | H | C₂H₅ | C₂H₅ |
| A-785 | H | F | H | H | CH₃ | CH₃ |
| A-786 | H | F | H | H | CH₃ | C₂H₅ |
| A-787 | H | F | H | H | C₂H₅ | CH₃ |
| A-788 | H | F | H | H | C₂H₅ | C₂H₅ |
| A-789 | F | F | H | H | CH₃ | CH₃ |
| A-790 | F | F | H | H | CH₃ | C₂H₅ |
| A-791 | F | F | H | H | C₂H₅ | CH₃ |
| A-792 | F | F | H | H | C₂H₅ | C₂H₅ |
| A-793 | Cl | F | H | H | CH₃ | CH₃ |
| A-794 | Cl | F | H | H | CH₃ | C₂H₅ |
| A-795 | Cl | F | H | H | C₂H₅ | CH₃ |
| A-796 | Cl | F | H | H | C₂H₅ | C₂H₅ |
| A-797 | CH₃ | F | H | H | CH₃ | CH₃ |
| A-798 | CH₃ | F | H | H | CH₃ | C₂H₅ |
| A-799 | CH₃ | F | H | H | C₂H₅ | CH₃ |
| A-800 | CH₃ | F | H | H | C₂H₅ | C₂H₅ |
| A-801 | H | CH₃ | H | H | CH₃ | CH₃ |
| A-802 | H | CH₃ | H | H | CH₃ | C₂H₅ |
| A-803 | H | CH₃ | H | H | C₂H₅ | CH₃ |
| A-804 | H | CH₃ | H | H | C₂H₅ | C₂H₅ |
| A-805 | F | CH₃ | H | H | CH₃ | CH₃ |
| A-806 | F | CH₃ | H | H | CH₃ | C₂H₅ |
| A-807 | F | CH₃ | H | H | C₂H₅ | CH₃ |
| A-808 | F | CH₃ | H | H | C₂H₅ | C₂H₅ |
| A-809 | Cl | CH₃ | H | H | CH₃ | CH₃ |
| A-810 | Cl | CH₃ | H | H | CH₃ | C₂H₅ |
| A-811 | Cl | CH₃ | H | H | C₂H₅ | CH₃ |
| A-812 | Cl | CH₃ | H | H | C₂H₅ | C₂H₅ |
| A-813 | CH₃ | CH₃ | H | H | CH₃ | CH₃ |
| A-814 | CH₃ | CH₃ | H | H | CH₃ | C₂H₅ |
| A-815 | CH₃ | CH₃ | H | H | C₂H₅ | CH₃ |
| A-816 | CH₃ | CH₃ | H | H | C₂H₅ | C₂H₅ |
| A-817 | H | Cl | H | H | CH₃ | CH₃ |
| A-818 | H | Cl | H | H | CH₃ | C₂H₅ |
| A-819 | H | Cl | H | H | C₂H₅ | CH₃ |
| A-820 | H | Cl | H | H | C₂H₅ | C₂H₅ |
| A-821 | F | Cl | H | H | CH₃ | CH₃ |
| A-822 | F | Cl | H | H | CH₃ | C₂H₅ |
| A-823 | F | Cl | H | H | C₂H₅ | CH₃ |
| A-824 | F | Cl | H | H | C₂H₅ | C₂H₅ |
| A-825 | Cl | Cl | H | H | CH₃ | CH₃ |
| A-826 | Cl | Cl | H | H | CH₃ | C₂H₅ |
| A-827 | Cl | Cl | H | H | C₂H₅ | CH₃ |
| A-828 | Cl | Cl | H | H | C₂H₅ | C₂H₅ |
| A-829 | CH₃ | Cl | H | H | CH₃ | CH₃ |
| A-830 | CH₃ | Cl | H | H | CH₃ | C₂H₅ |
| A-831 | CH₃ | Cl | H | H | C₂H₅ | CH₃ |
| A-832 | CH₃ | Cl | H | H | C₂H₅ | C₂H₅ |
| A-833 | H | H | CH₃ | CH₃ | CH₃ | CH₃ |
| A-834 | H | H | CH₃ | CH₃ | CH₃ | C₂H₅ |
| A-835 | H | H | CH₃ | CH₃ | C₂H₅ | CH₃ |
| A-836 | H | H | CH₃ | CH₃ | C₂H₅ | C₂H₅ |
| A-837 | F | H | CH₃ | CH₃ | CH₃ | CH₃ |
| A-838 | F | H | CH₃ | CH₃ | CH₃ | C₂H₅ |
| A-839 | F | H | CH₃ | CH₃ | C₂H₅ | CH₃ |
| A-840 | F | H | CH₃ | CH₃ | C₂H₅ | C₂H₅ |
| A-841 | Cl | H | CH₃ | CH₃ | CH₃ | CH₃ |
| A-842 | Cl | H | CH₃ | CH₃ | CH₃ | C₂H₅ |
| A-843 | Cl | H | CH₃ | CH₃ | C₂H₅ | CH₃ |
| A-844 | Cl | H | CH₃ | CH₃ | C₂H₅ | C₂H₅ |
| A-845 | CH₃ | H | CH₃ | CH₃ | CH₃ | CH₃ |
| A-846 | CH₃ | H | CH₃ | CH₃ | CH₃ | C₂H₅ |
| A-847 | CH₃ | H | CH₃ | CH₃ | C₂H₅ | CH₃ |
| A-848 | CH₃ | H | CH₃ | CH₃ | C₂H₅ | C₂H₅ |
| A-849 | H | F | CH₃ | CH₃ | CH₃ | CH₃ |
| A-850 | H | F | CH₃ | CH₃ | CH₃ | C₂H₅ |
| A-851 | H | F | CH₃ | CH₃ | C₂H₅ | CH₃ |
| A-852 | H | F | CH₃ | CH₃ | C₂H₅ | C₂H₅ |
| A-853 | F | F | CH₃ | CH₃ | CH₃ | CH₃ |
| A-854 | F | F | CH₃ | CH₃ | CH₃ | C₂H₅ |
| A-855 | F | F | CH₃ | CH₃ | C₂H₅ | CH₃ |
| A-856 | F | F | CH₃ | CH₃ | C₂H₅ | C₂H₅ |
| A-857 | Cl | F | CH₃ | CH₃ | CH₃ | CH₃ |
| A-858 | Cl | F | CH₃ | CH₃ | CH₃ | C₂H₅ |
| A-859 | Cl | F | CH₃ | CH₃ | C₂H₅ | CH₃ |
| A-860 | Cl | F | CH₃ | CH₃ | C₂H₅ | C₂H₅ |
| A-861 | CH₃ | F | CH₃ | CH₃ | CH₃ | CH₃ |
| A-862 | CH₃ | F | CH₃ | CH₃ | CH₃ | C₂H₅ |
| A-863 | CH₃ | F | CH₃ | CH₃ | C₂H₅ | CH₃ |
| A-864 | CH₃ | F | CH₃ | CH₃ | C₂H₅ | C₂H₅ |
| A-865 | H | CH₃ | CH₃ | CH₃ | CH₃ | CH₃ |
| A-866 | H | CH₃ | CH₃ | CH₃ | CH₃ | C₂H₅ |
| A-867 | H | CH₃ | CH₃ | CH₃ | C₂H₅ | CH₃ |
| A-868 | H | CH₃ | CH₃ | CH₃ | C₂H₅ | C₂H₅ |
| A-869 | F | CH₃ | CH₃ | CH₃ | CH₃ | CH₃ |
| A-870 | F | CH₃ | CH₃ | CH₃ | CH₃ | C₂H₅ |
| A-871 | F | CH₃ | CH₃ | CH₃ | C₂H₅ | CH₃ |
| A-872 | F | CH₃ | CH₃ | CH₃ | C₂H₅ | C₂H₅ |
| A-873 | Cl | CH₃ | CH₃ | CH₃ | CH₃ | CH₃ |
| A-874 | Cl | CH₃ | CH₃ | CH₃ | CH₃ | C₂H₅ |
| A-875 | Cl | CH₃ | CH₃ | CH₃ | C₂H₅ | CH₃ |
| A-876 | Cl | CH₃ | CH₃ | CH₃ | C₂H₅ | C₂H₅ |
| A-877 | CH₃ | CH₃ | CH₃ | CH₃ | CH₃ | CH₃ |
| A-878 | CH₃ | CH₃ | CH₃ | CH₃ | CH₃ | C₂H₅ |
| A-879 | CH₃ | CH₃ | CH₃ | CH₃ | C₂H₅ | CH₃ |
| A-880 | CH₃ | CH₃ | CH₃ | CH₃ | C₂H₅ | C₂H₅ |
| A-881 | H | Cl | CH₃ | CH₃ | CH₃ | CH₃ |
| A-882 | H | Cl | CH₃ | CH₃ | CH₃ | C₂H₅ |
| A-883 | H | Cl | CH₃ | CH₃ | C₂H₅ | CH₃ |
| A-884 | H | Cl | CH₃ | CH₃ | C₂H₅ | C₂H₅ |
| A-885 | F | Cl | CH₃ | CH₃ | CH₃ | CH₃ |
| A-886 | F | Cl | CH₃ | CH₃ | CH₃ | C₂H₅ |
| A-887 | F | Cl | CH₃ | CH₃ | C₂H₅ | CH₃ |
| A-888 | F | Cl | CH₃ | CH₃ | C₂H₅ | C₂H₅ |
| A-889 | Cl | Cl | CH₃ | CH₃ | CH₃ | CH₃ |
| A-890 | Cl | Cl | CH₃ | CH₃ | CH₃ | C₂H₅ |
| A-891 | Cl | Cl | CH₃ | CH₃ | C₂H₅ | CH₃ |
| A-892 | Cl | Cl | CH₃ | CH₃ | C₂H₅ | C₂H₅ |
| A-893 | CH₃ | Cl | CH₃ | CH₃ | CH₃ | CH₃ |
| A-894 | CH₃ | Cl | CH₃ | CH₃ | CH₃ | C₂H₅ |
| A-895 | CH₃ | Cl | CH₃ | CH₃ | C₂H₅ | CH₃ |
| A-896 | CH₃ | Cl | CH₃ | CH₃ | C₂H₅ | C₂H₅ |
| A-897 | H | H | C₂H₅ | C₂H₅ | CH₃ | CH₃ |
| A-898 | H | H | C₂H₅ | C₂H₅ | CH₃ | C₂H₅ |
| A-899 | H | H | C₂H₅ | C₂H₅ | C₂H₅ | CH₃ |
| A-900 | H | H | C₂H₅ | C₂H₅ | C₂H₅ | C₂H₅ |
| A-901 | F | H | C₂H₅ | C₂H₅ | CH₃ | CH₃ |
| A-902 | F | H | C₂H₅ | C₂H₅ | CH₃ | C₂H₅ |
| A-903 | F | H | C₂H₅ | C₂H₅ | C₂H₅ | CH₃ |
| A-904 | F | H | C₂H₅ | C₂H₅ | C₂H₅ | C₂H₅ |
| A-905 | Cl | H | C₂H₅ | C₂H₅ | CH₃ | CH₃ |
| A-906 | Cl | H | C₂H₅ | C₂H₅ | CH₃ | C₂H₅ |
| A-907 | Cl | H | C₂H₅ | C₂H₅ | C₂H₅ | CH₃ |
| A-908 | Cl | H | C₂H₅ | C₂H₅ | C₂H₅ | C₂H₅ |
| A-909 | CH₃ | H | C₂H₅ | C₂H₅ | CH₃ | CH₃ |
| A-910 | CH₃ | H | C₂H₅ | C₂H₅ | CH₃ | C₂H₅ |
| A-911 | CH₃ | H | C₂H₅ | C₂H₅ | C₂H₅ | CH₃ |
| A-912 | CH₃ | H | C₂H₅ | C₂H₅ | C₂H₅ | C₂H₅ |
| A-913 | H | F | C₂H₅ | C₂H₅ | CH₃ | CH₃ |
| A-914 | H | F | C₂H₅ | C₂H₅ | CH₃ | C₂H₅ |
| A-915 | H | F | C₂H₅ | C₂H₅ | C₂H₅ | CH₃ |
| A-916 | H | F | C₂H₅ | C₂H₅ | C₂H₅ | C₂H₅ |
| A-917 | F | F | C₂H₅ | C₂H₅ | CH₃ | CH₃ |
| A-918 | F | F | C₂H₅ | C₂H₅ | CH₃ | C₂H₅ |
| A-919 | F | F | C₂H₅ | C₂H₅ | C₂H₅ | CH₃ |
| A-920 | F | F | C₂H₅ | C₂H₅ | C₂H₅ | C₂H₅ |
| A-921 | Cl | F | C₂H₅ | C₂H₅ | CH₃ | CH₃ |
| A-922 | Cl | F | C₂H₅ | C₂H₅ | CH₃ | C₂H₅ |
| A-923 | Cl | F | C₂H₅ | C₂H₅ | C₂H₅ | CH₃ |
| A-924 | Cl | F | C₂H₅ | C₂H₅ | C₂H₅ | C₂H₅ |
| A-925 | CH₃ | F | C₂H₅ | C₂H₅ | CH₃ | CH₃ |
| A-926 | CH₃ | F | C₂H₅ | C₂H₅ | CH₃ | C₂H₅ |

TABLE A-continued

| line | R¹ | R² | R³ | R⁴ | R⁹ | R¹⁰ |
|---|---|---|---|---|---|---|
| A-927 | CH₃ | F | C₂H₅ | C₂H₅ | C₂H₅ | CH₃ |
| A-928 | CH₃ | F | C₂H₅ | C₂H₅ | C₂H₅ | C₂H₅ |
| A-929 | H | CH₃ | C₂H₅ | C₂H₅ | CH₃ | CH₃ |
| A-930 | H | CH₃ | C₂H₅ | C₂H₅ | CH₃ | C₂H₅ |
| A-931 | H | CH₃ | C₂H₅ | C₂H₅ | C₂H₅ | CH₃ |
| A-932 | H | CH₃ | C₂H₅ | C₂H₅ | C₂H₅ | C₂H₅ |
| A-933 | F | CH₃ | C₂H₅ | C₂H₅ | CH₃ | CH₃ |
| A-934 | F | CH₃ | C₂H₅ | C₂H₅ | CH₃ | C₂H₅ |
| A-935 | F | CH₃ | C₂H₅ | C₂H₅ | C₂H₅ | CH₃ |
| A-936 | F | CH₃ | C₂H₅ | C₂H₅ | C₂H₅ | C₂H₅ |
| A-937 | Cl | CH₃ | C₂H₅ | C₂H₅ | CH₃ | CH₃ |
| A-938 | Cl | CH₃ | C₂H₅ | C₂H₅ | CH₃ | C₂H₅ |
| A-939 | Cl | CH₃ | C₂H₅ | C₂H₅ | C₂H₅ | CH₃ |
| A-940 | Cl | CH₃ | C₂H₅ | C₂H₅ | C₂H₅ | C₂H₅ |
| A-941 | CH₃ | CH₃ | C₂H₅ | C₂H₅ | CH₃ | CH₃ |
| A-942 | CH₃ | CH₃ | C₂H₅ | C₂H₅ | CH₃ | C₂H₅ |
| A-943 | CH₃ | CH₃ | C₂H₅ | C₂H₅ | C₂H₅ | CH₃ |
| A-944 | CH₃ | CH₃ | C₂H₅ | C₂H₅ | C₂H₅ | C₂H₅ |
| A-945 | H | Cl | C₂H₅ | C₂H₅ | CH₃ | CH₃ |
| A-946 | H | Cl | C₂H₅ | C₂H₅ | CH₃ | C₂H₅ |
| A-947 | H | Cl | C₂H₅ | C₂H₅ | C₂H₅ | CH₃ |
| A-948 | H | Cl | C₂H₅ | C₂H₅ | C₂H₅ | C₂H₅ |
| A-949 | F | Cl | C₂H₅ | C₂H₅ | CH₃ | CH₃ |
| A-950 | F | Cl | C₂H₅ | C₂H₅ | CH₃ | C₂H₅ |
| A-951 | F | Cl | C₂H₅ | C₂H₅ | C₂H₅ | CH₃ |
| A-952 | F | Cl | C₂H₅ | C₂H₅ | C₂H₅ | C₂H₅ |
| A-953 | Cl | Cl | C₂H₅ | C₂H₅ | CH₃ | CH₃ |
| A-954 | Cl | Cl | C₂H₅ | C₂H₅ | CH₃ | C₂H₅ |
| A-955 | Cl | Cl | C₂H₅ | C₂H₅ | C₂H₅ | CH₃ |
| A-956 | Cl | Cl | C₂H₅ | C₂H₅ | C₂H₅ | C₂H₅ |
| A-957 | CH₃ | Cl | C₂H₅ | C₂H₅ | CH₃ | CH₃ |
| A-958 | CH₃ | Cl | C₂H₅ | C₂H₅ | CH₃ | C₂H₅ |
| A-959 | CH₃ | Cl | C₂H₅ | C₂H₅ | C₂H₅ | CH₃ |
| A-960 | CH₃ | Cl | C₂H₅ | C₂H₅ | C₂H₅ | C₂H₅ |
| A-961 | H | H | CH₃ | C₂H₅ | CH₃ | CH₃ |
| A-962 | H | H | CH₃ | C₂H₅ | CH₃ | C₂H₅ |
| A-963 | H | H | CH₃ | C₂H₅ | C₂H₅ | CH₃ |
| A-964 | H | H | CH₃ | C₂H₅ | C₂H₅ | C₂H₅ |
| A-965 | F | H | CH₃ | C₂H₅ | CH₃ | CH₃ |
| A-966 | F | H | CH₃ | C₂H₅ | CH₃ | C₂H₅ |
| A-967 | F | H | CH₃ | C₂H₅ | C₂H₅ | CH₃ |
| A-968 | F | H | CH₃ | C₂H₅ | C₂H₅ | C₂H₅ |
| A-969 | Cl | H | CH₃ | C₂H₅ | CH₃ | CH₃ |
| A-970 | Cl | H | CH₃ | C₂H₅ | CH₃ | C₂H₅ |
| A-971 | Cl | H | CH₃ | C₂H₅ | C₂H₅ | CH₃ |
| A-972 | Cl | H | CH₃ | C₂H₅ | C₂H₅ | C₂H₅ |
| A-973 | CH₃ | H | CH₃ | C₂H₅ | CH₃ | CH₃ |
| A-974 | CH₃ | H | CH₃ | C₂H₅ | CH₃ | C₂H₅ |
| A-975 | CH₃ | H | CH₃ | C₂H₅ | C₂H₅ | CH₃ |
| A-976 | CH₃ | H | CH₃ | C₂H₅ | C₂H₅ | C₂H₅ |
| A-977 | H | F | CH₃ | C₂H₅ | CH₃ | CH₃ |
| A-978 | H | F | CH₃ | C₂H₅ | CH₃ | C₂H₅ |
| A-979 | H | F | CH₃ | C₂H₅ | C₂H₅ | CH₃ |
| A-980 | H | F | CH₃ | C₂H₅ | C₂H₅ | C₂H₅ |
| A-981 | F | F | CH₃ | C₂H₅ | CH₃ | CH₃ |
| A-982 | F | F | CH₃ | C₂H₅ | CH₃ | C₂H₅ |
| A-983 | F | F | CH₃ | C₂H₅ | C₂H₅ | CH₃ |
| A-984 | F | F | CH₃ | C₂H₅ | C₂H₅ | C₂H₅ |
| A-985 | Cl | F | CH₃ | C₂H₅ | CH₃ | CH₃ |
| A-986 | Cl | F | CH₃ | C₂H₅ | CH₃ | C₂H₅ |
| A-987 | Cl | F | CH₃ | C₂H₅ | C₂H₅ | CH₃ |
| A-988 | Cl | F | CH₃ | C₂H₅ | C₂H₅ | C₂H₅ |
| A-989 | CH₃ | F | CH₃ | C₂H₅ | CH₃ | CH₃ |
| A-990 | CH₃ | F | CH₃ | C₂H₅ | CH₃ | C₂H₅ |
| A-991 | CH₃ | F | CH₃ | C₂H₅ | C₂H₅ | CH₃ |
| A-992 | CH₃ | F | CH₃ | C₂H₅ | C₂H₅ | C₂H₅ |
| A-993 | H | CH₃ | CH₃ | C₂H₅ | CH₃ | CH₃ |
| A-994 | H | CH₃ | CH₃ | C₂H₅ | CH₃ | C₂H₅ |
| A-995 | H | CH₃ | CH₃ | C₂H₅ | C₂H₅ | CH₃ |
| A-996 | H | CH₃ | CH₃ | C₂H₅ | C₂H₅ | C₂H₅ |
| A-997 | F | CH₃ | CH₃ | C₂H₅ | CH₃ | CH₃ |
| A-998 | F | CH₃ | CH₃ | C₂H₅ | CH₃ | C₂H₅ |
| A-999 | F | CH₃ | CH₃ | C₂H₅ | C₂H₅ | CH₃ |
| A-1000 | F | CH₃ | CH₃ | C₂H₅ | C₂H₅ | C₂H₅ |
| A-1001 | Cl | CH₃ | CH₃ | C₂H₅ | CH₃ | CH₃ |
| A-1002 | Cl | CH₃ | CH₃ | C₂H₅ | CH₃ | C₂H₅ |
| A-1003 | Cl | CH₃ | CH₃ | C₂H₅ | C₂H₅ | CH₃ |
| A-1004 | Cl | CH₃ | CH₃ | C₂H₅ | C₂H₅ | C₂H₅ |
| A-1005 | CH₃ | CH₃ | CH₃ | C₂H₅ | CH₃ | CH₃ |
| A-1006 | CH₃ | CH₃ | CH₃ | C₂H₅ | CH₃ | C₂H₅ |
| A-1007 | CH₃ | CH₃ | CH₃ | C₂H₅ | C₂H₅ | CH₃ |
| A-1008 | CH₃ | CH₃ | CH₃ | C₂H₅ | C₂H₅ | C₂H₅ |
| A-1009 | H | Cl | CH₃ | C₂H₅ | CH₃ | CH₃ |
| A-1010 | H | Cl | CH₃ | C₂H₅ | CH₃ | C₂H₅ |
| A-1011 | H | Cl | CH₃ | C₂H₅ | C₂H₅ | CH₃ |
| A-1012 | H | Cl | CH₃ | C₂H₅ | C₂H₅ | C₂H₅ |
| A-1013 | F | Cl | CH₃ | C₂H₅ | CH₃ | CH₃ |
| A-1014 | F | Cl | CH₃ | C₂H₅ | CH₃ | C₂H₅ |
| A-1015 | F | Cl | CH₃ | C₂H₅ | C₂H₅ | CH₃ |
| A-1016 | F | Cl | CH₃ | C₂H₅ | C₂H₅ | C₂H₅ |
| A-1017 | Cl | Cl | CH₃ | C₂H₅ | CH₃ | CH₃ |
| A-1018 | Cl | Cl | CH₃ | C₂H₅ | CH₃ | C₂H₅ |
| A-1019 | Cl | Cl | CH₃ | C₂H₅ | C₂H₅ | CH₃ |
| A-1020 | Cl | Cl | CH₃ | C₂H₅ | C₂H₅ | C₂H₅ |
| A-1021 | CH₃ | Cl | CH₃ | C₂H₅ | CH₃ | CH₃ |
| A-1022 | CH₃ | Cl | CH₃ | C₂H₅ | CH₃ | C₂H₅ |
| A-1023 | CH₃ | Cl | CH₃ | C₂H₅ | C₂H₅ | CH₃ |
| A-1024 | CH₃ | Cl | CH₃ | C₂H₅ | C₂H₅ | C₂H₅ |
| A-1025 | H | H | Cl | C₂H₅ | CH₃ | CH₃ |
| A-1026 | H | H | Cl | C₂H₅ | CH₃ | C₂H₅ |
| A-1027 | H | H | Cl | C₂H₅ | C₂H₅ | CH₃ |
| A-1028 | H | H | Cl | C₂H₅ | C₂H₅ | C₂H₅ |
| A-1029 | F | H | Cl | C₂H₅ | CH₃ | CH₃ |
| A-1030 | F | H | Cl | C₂H₅ | CH₃ | C₂H₅ |
| A-1031 | F | H | Cl | C₂H₅ | C₂H₅ | CH₃ |
| A-1032 | F | H | Cl | C₂H₅ | C₂H₅ | C₂H₅ |
| A-1033 | Cl | H | Cl | C₂H₅ | CH₃ | CH₃ |
| A-1034 | Cl | H | Cl | C₂H₅ | CH₃ | C₂H₅ |
| A-1035 | Cl | H | Cl | C₂H₅ | C₂H₅ | CH₃ |
| A-1036 | Cl | H | Cl | C₂H₅ | C₂H₅ | C₂H₅ |
| A-1037 | CH₃ | H | Cl | C₂H₅ | CH₃ | CH₃ |
| A-1038 | CH₃ | H | Cl | C₂H₅ | CH₃ | C₂H₅ |
| A-1039 | CH₃ | H | Cl | C₂H₅ | C₂H₅ | CH₃ |
| A-1040 | CH₃ | H | Cl | C₂H₅ | C₂H₅ | C₂H₅ |
| A-1041 | H | F | Cl | C₂H₅ | CH₃ | CH₃ |
| A-1042 | H | F | Cl | C₂H₅ | CH₃ | C₂H₅ |
| A-1043 | H | F | Cl | C₂H₅ | C₂H₅ | CH₃ |
| A-1044 | H | F | Cl | C₂H₅ | C₂H₅ | C₂H₅ |
| A-1045 | F | F | Cl | C₂H₅ | CH₃ | CH₃ |
| A-1046 | F | F | Cl | C₂H₅ | CH₃ | C₂H₅ |
| A-1047 | F | F | Cl | C₂H₅ | C₂H₅ | CH₃ |
| A-1048 | F | F | Cl | C₂H₅ | C₂H₅ | C₂H₅ |
| A-1049 | Cl | F | Cl | C₂H₅ | CH₃ | CH₃ |
| A-1050 | Cl | F | Cl | C₂H₅ | CH₃ | C₂H₅ |
| A-1051 | Cl | F | Cl | C₂H₅ | C₂H₅ | CH₃ |
| A-1052 | Cl | F | Cl | C₂H₅ | C₂H₅ | C₂H₅ |
| A-1053 | CH₃ | F | Cl | C₂H₅ | CH₃ | CH₃ |
| A-1054 | CH₃ | F | Cl | C₂H₅ | CH₃ | C₂H₅ |
| A-1055 | CH₃ | F | Cl | C₂H₅ | C₂H₅ | CH₃ |
| A-1056 | CH₃ | F | Cl | C₂H₅ | C₂H₅ | C₂H₅ |
| A-1057 | H | CH₃ | Cl | C₂H₅ | CH₃ | CH₃ |
| A-1058 | H | CH₃ | Cl | C₂H₅ | CH₃ | C₂H₅ |
| A-1059 | H | CH₃ | Cl | C₂H₅ | C₂H₅ | CH₃ |
| A-1060 | H | CH₃ | Cl | C₂H₅ | C₂H₅ | C₂H₅ |
| A-1061 | F | CH₃ | Cl | C₂H₅ | CH₃ | CH₃ |
| A-1062 | F | CH₃ | Cl | C₂H₅ | CH₃ | C₂H₅ |
| A-1063 | F | CH₃ | Cl | C₂H₅ | C₂H₅ | CH₃ |
| A-1064 | F | CH₃ | Cl | C₂H₅ | C₂H₅ | C₂H₅ |
| A-1065 | Cl | CH₃ | Cl | C₂H₅ | CH₃ | CH₃ |
| A-1066 | Cl | CH₃ | Cl | C₂H₅ | CH₃ | C₂H₅ |
| A-1067 | Cl | CH₃ | Cl | C₂H₅ | C₂H₅ | CH₃ |
| A-1068 | Cl | CH₃ | Cl | C₂H₅ | C₂H₅ | C₂H₅ |
| A-1069 | CH₃ | CH₃ | Cl | C₂H₅ | CH₃ | CH₃ |
| A-1070 | CH₃ | CH₃ | Cl | C₂H₅ | CH₃ | C₂H₅ |
| A-1071 | CH₃ | CH₃ | Cl | C₂H₅ | C₂H₅ | CH₃ |
| A-1072 | CH₃ | CH₃ | Cl | C₂H₅ | C₂H₅ | C₂H₅ |
| A-1073 | H | Cl | Cl | C₂H₅ | CH₃ | CH₃ |
| A-1074 | H | Cl | Cl | C₂H₅ | CH₃ | C₂H₅ |
| A-1075 | H | Cl | Cl | C₂H₅ | C₂H₅ | CH₃ |
| A-1076 | H | Cl | Cl | C₂H₅ | C₂H₅ | C₂H₅ |
| A-1077 | F | Cl | Cl | C₂H₅ | CH₃ | CH₃ |
| A-1078 | F | Cl | Cl | C₂H₅ | CH₃ | C₂H₅ |
| A-1079 | F | Cl | Cl | C₂H₅ | C₂H₅ | CH₃ |
| A-1080 | F | Cl | Cl | C₂H₅ | C₂H₅ | C₂H₅ |
| A-1081 | Cl | Cl | Cl | C₂H₅ | CH₃ | CH₃ |
| A-1082 | Cl | Cl | Cl | C₂H₅ | CH₃ | C₂F-1₅ |

TABLE A-continued

| line | R¹ | R² | R³ | R⁴ | R⁹ | R¹⁰ |
|---|---|---|---|---|---|---|
| A-1083 | Cl | Cl | Cl | Cl | C₂H₅ | CH₃ |
| A-1084 | Cl | Cl | Cl | Cl | C₂H₅ | C₂H₅ |
| A-1085 | H | H | Cl | Cl | CH₃ | CH₃ |
| A-1086 | H | H | Cl | Cl | CH₃ | C₂H₅ |
| A-1087 | H | H | Cl | Cl | C₂H₅ | CH₃ |
| A-1088 | H | H | Cl | Cl | C₂H₅ | C₂H₅ |
| A-1089 | F | H | Cl | Cl | CH₃ | CH₃ |
| A-1090 | F | H | Cl | Cl | CH₃ | C₂H₅ |
| A-1091 | F | H | Cl | Cl | C₂H₅ | CH₃ |
| A-1092 | F | H | Cl | Cl | C₂H₅ | C₂H₅ |
| A-1093 | Cl | H | Cl | Cl | CH₃ | CH₃ |
| A-1094 | Cl | H | Cl | Cl | CH₃ | C₂H₅ |
| A-1095 | Cl | H | Cl | Cl | C₂H₅ | CH₃ |
| A-1096 | Cl | H | Cl | Cl | C₂H₅ | C₂H₅ |
| A-1097 | CH₃ | H | Cl | Cl | CH₃ | CH₃ |
| A-1098 | CH₃ | H | Cl | Cl | CH₃ | C₂H₅ |
| A-1099 | CH₃ | H | Cl | Cl | C₂H₅ | CH₃ |
| A-1100 | CH₃ | H | Cl | Cl | C₂H₅ | C₂H₅ |
| A-1101 | H | F | Cl | Cl | CH₃ | CH₃ |
| A-1102 | H | F | Cl | Cl | CH₃ | C₂H₅ |
| A-1103 | H | F | Cl | Cl | C₂H₅ | CH₃ |
| A-1104 | H | F | Cl | Cl | C₂H₅ | C₂H₅ |
| A-1105 | F | F | Cl | Cl | CH₃ | CH₃ |
| A-1106 | F | F | Cl | Cl | CH₃ | C₂H₅ |
| A-1107 | F | F | Cl | Cl | C₂H₅ | CH₃ |
| A-1108 | F | F | Cl | Cl | C₂H₅ | C₂H₅ |
| A-1109 | Cl | F | Cl | Cl | CH₃ | CH₃ |
| A-1110 | Cl | F | Cl | Cl | CH₃ | C₂H₅ |
| A-1111 | Cl | F | Cl | Cl | C₂H₅ | CH₃ |
| A-1112 | Cl | F | Cl | Cl | C₂H₅ | C₂H₅ |
| A-1113 | CH₃ | F | Cl | Cl | CH₃ | CH₃ |
| A-1114 | CH₃ | F | Cl | Cl | CH₃ | C₂H₅ |
| A-1115 | CH₃ | F | Cl | Cl | C₂H₅ | CH₃ |
| A-1116 | CH₃ | F | Cl | Cl | C₂H₅ | C₂H₅ |
| A-1117 | H | CH₃ | Cl | Cl | CH₃ | CH₃ |
| A-1118 | H | CH₃ | Cl | Cl | CH₃ | C₂H₅ |
| A-1119 | H | CH₃ | Cl | Cl | C₂H₅ | CH₃ |
| A-1120 | H | CH₃ | Cl | Cl | C₂H₅ | C₂H₅ |
| A-1121 | F | CH₃ | Cl | Cl | CH₃ | CH₃ |
| A-1122 | F | CH₃ | Cl | Cl | CH₃ | C₂H₅ |
| A-1123 | F | CH₃ | Cl | Cl | C₂H₅ | CH₃ |
| A-1124 | F | CH₃ | Cl | Cl | C₂H₅ | C₂H₅ |
| A-1125 | Cl | CH₃ | Cl | Cl | CH₃ | CH₃ |
| A-1126 | Cl | CH₃ | Cl | Cl | CH₃ | C₂H₅ |
| A-1127 | Cl | CH₃ | Cl | Cl | C₂H₅ | CH₃ |
| A-1128 | Cl | CH₃ | Cl | Cl | C₂H₅ | C₂H₅ |
| A-1129 | CH₃ | CH₃ | Cl | Cl | CH₃ | CH₃ |
| A-1130 | CH₃ | CH₃ | Cl | Cl | CH₃ | C₂H₅ |
| A-1131 | CH₃ | CH₃ | Cl | Cl | C₂H₅ | CH₃ |
| A-1132 | CH₃ | CH₃ | Cl | Cl | C₂H₅ | C₂H₅ |
| A-1133 | H | Cl | Cl | Cl | CH₃ | CH₃ |
| A-1134 | H | Cl | Cl | Cl | CH₃ | C₂H₅ |
| A-1135 | H | Cl | Cl | Cl | C₂H₅ | CH₃ |
| A-1136 | H | Cl | Cl | Cl | C₂H₅ | C₂H₅ |
| A-1137 | F | Cl | Cl | Cl | CH₃ | CH₃ |
| A-1138 | F | Cl | Cl | Cl | CH₃ | C₂H₅ |
| A-1139 | F | Cl | Cl | Cl | C₂H₅ | CH₃ |
| A-1140 | F | Cl | Cl | Cl | C₂H₅ | C₂H₅ |
| A-1141 | Cl | Cl | Cl | Cl | CH₃ | CH₃ |
| A-1142 | Cl | Cl | Cl | Cl | CH₃ | C₂H₅ |
| A-1143 | Cl | Cl | Cl | Cl | C₂H₅ | CH₃ |
| A-1144 | Cl | Cl | Cl | Cl | C₂H₅ | C₂H₅ |
| A-1145 | CH₃ | Cl | Cl | Cl | CH₃ | CH₃ |
| A-1146 | CH₃ | Cl | Cl | Cl | CH₃ | C₂H₅ |
| A-1147 | CH₃ | Cl | Cl | Cl | C₂H₅ | CH₃ |
| A-1148 | CH₃ | Cl | Cl | Cl | C₂H₅ | C₂H₅ |
| A-1149 | H | H | Cl | Cl | CH₃ | CH₃ |
| A-1150 | H | H | Cl | Cl | CH₃ | C₂H₅ |
| A-1151 | H | H | Cl | Cl | C₂H₅ | CH₃ |
| A-1152 | H | H | Cl | Cl | C₂H₅ | C₂H₅ |
| A-1153 | F | H | Cl | Cl | CH₃ | CH₃ |
| A-1154 | F | H | Cl | Cl | CH₃ | C₂H₅ |
| A-1155 | F | H | Cl | Cl | C₂H₅ | CH₃ |
| A-1156 | F | H | Cl | Cl | C₂H₅ | C₂H₅ |
| A-1157 | Cl | H | Cl | Cl | CH₃ | CH₃ |
| A-1158 | Cl | H | Cl | Cl | CH₃ | C₂H₅ |
| A-1159 | Cl | H | Cl | Cl | C₂H₅ | CH₃ |
| A-1160 | Cl | H | Cl | Cl | C₂H₅ | C₂H₅ |
| A-1161 | CH₃ | H | Cl | Cl | CH₃ | CH₃ |
| A-1162 | CH₃ | H | Cl | Cl | CH₃ | C₂H₅ |
| A-1163 | CH₃ | H | Cl | Cl | C₂H₅ | CH₃ |
| A-1164 | CH₃ | H | Cl | Cl | C₂H₅ | C₂H₅ |
| A-1165 | H | F | Cl | Cl | CH₃ | CH₃ |
| A-1166 | H | F | Cl | Cl | CH₃ | C₂H₅ |
| A-1167 | H | F | Cl | Cl | C₂H₅ | CH₃ |
| A-1168 | H | F | Cl | Cl | C₂H₅ | C₂H₅ |
| A-1169 | F | F | Cl | Cl | CH₃ | CH₃ |
| A-1170 | F | F | Cl | Cl | CH₃ | C₂H₅ |
| A-1171 | F | F | Cl | Cl | C₂H₅ | CH₃ |
| A-1172 | F | F | Cl | Cl | C₂H₅ | C₂H₅ |
| A-1173 | Cl | F | Cl | Cl | CH₃ | CH₃ |
| A-1174 | Cl | F | Cl | Cl | CH₃ | C₂H₅ |
| A-1175 | Cl | F | Cl | Cl | C₂H₅ | CH₃ |
| A-1176 | Cl | F | Cl | Cl | C₂H₅ | C₂H₅ |
| A-1177 | CH₃ | F | Cl | Cl | CH₃ | CH₃ |
| A-1178 | CH₃ | F | Cl | Cl | CH₃ | C₂H₅ |
| A-1179 | CH₃ | F | Cl | Cl | C₂H₅ | CH₃ |
| A-1180 | CH₃ | F | Cl | Cl | C₂H₅ | C₂H₅ |
| A-1181 | H | CH₃ | Cl | Cl | CH₃ | CH₃ |
| A-1182 | H | CH₃ | Cl | Cl | CH₃ | C₂H₅ |
| A-1183 | H | CH₃ | Cl | Cl | C₂H₅ | CH₃ |
| A-1184 | H | CH₃ | Cl | Cl | C₂H₅ | C₂H₅ |
| A-1185 | F | CH₃ | Cl | Cl | CH₃ | CH₃ |
| A-1186 | F | CH₃ | Cl | Cl | CH₃ | C₂H₅ |
| A-1187 | F | CH₃ | Cl | Cl | C₂H₅ | CH₃ |
| A-1188 | F | CH₃ | Cl | Cl | C₂H₅ | C₂H₅ |
| A-1189 | Cl | CH₃ | Cl | Cl | CH₃ | CH₃ |
| A-1190 | Cl | CH₃ | Cl | Cl | CH₃ | C₂H₅ |
| A-1191 | Cl | CH₃ | Cl | Cl | C₂H₅ | CH₃ |
| A-1192 | Cl | CH₃ | Cl | Cl | C₂H₅ | C₂H₅ |
| A-1193 | CH₃ | CH₃ | Cl | Cl | CH₃ | CH₃ |
| A-1194 | CH₃ | CH₃ | Cl | Cl | CH₃ | C₂H₅ |
| A-1195 | CH₃ | CH₃ | Cl | Cl | C₂H₅ | CH₃ |
| A-1196 | CH₃ | CH₃ | Cl | Cl | C₂H₅ | C₂H₅ |
| A-1197 | H | Cl | Cl | Cl | CH₃ | CH₃ |
| A-1198 | H | Cl | Cl | Cl | CH₃ | C₂H₅ |
| A-1199 | H | Cl | Cl | Cl | C₂H₅ | CH₃ |
| A-1200 | H | Cl | Cl | Cl | C₂H₅ | C₂H₅ |
| A-1201 | F | Cl | Cl | Cl | CH₃ | CH₃ |
| A-1202 | F | Cl | Cl | Cl | CH₃ | C₂H₅ |
| A-1203 | F | Cl | Cl | Cl | C₂H₅ | CH₃ |
| A-1204 | F | Cl | Cl | Cl | C₂H₅ | C₂H₅ |
| A-1205 | Cl | Cl | Cl | Cl | CH₃ | CH₃ |
| A-1206 | Cl | Cl | Cl | Cl | CH₃ | C₂H₅ |
| A-1207 | Cl | Cl | Cl | Cl | C₂H₅ | CH₃ |
| A-1208 | Cl | Cl | Cl | Cl | C₂H₅ | C₂H₅ |
| A-1209 | CH₃ | Cl | Cl | Cl | CH₃ | CH₃ |
| A-1210 | CH₃ | Cl | Cl | Cl | CH₃ | C₂H₅ |
| A-1211 | CH₃ | Cl | Cl | Cl | C₂H₅ | CH₃ |
| A-1212 | CH₃ | Cl | Cl | Cl | C₂H₅ | C₂H₅ |
| A-1213 | H | H | Cl | Cl | CH₃ | CH₃ |
| A-1214 | H | H | Cl | Cl | CH₃ | C₂H₅ |
| A-1215 | H | H | Cl | Cl | C₂H₅ | CH₃ |
| A-1216 | H | H | Cl | Cl | C₂H₅ | C₂H₅ |
| A-1217 | F | H | Cl | Cl | CH₃ | CH₃ |
| A-1218 | F | H | Cl | Cl | CH₃ | C₂H₅ |
| A-1219 | F | H | Cl | Cl | C₂H₅ | CH₃ |
| A-1220 | F | H | Cl | Cl | C₂H₅ | C₂H₅ |
| A-1221 | Cl | H | Cl | Cl | CH₃ | CH₃ |
| A-1222 | Cl | H | Cl | Cl | CH₃ | C₂H₅ |
| A-1223 | Cl | H | Cl | Cl | C₂H₅ | CH₃ |
| A-1224 | Cl | H | Cl | Cl | C₂H₅ | C₂H₅ |
| A-1225 | CH₃ | H | Cl | Cl | CH₃ | CH₃ |
| A-1226 | CH₃ | H | Cl | Cl | CH₃ | C₂H₅ |
| A-1227 | CH₃ | H | Cl | Cl | C₂H₅ | CH₃ |
| A-1228 | CH₃ | H | Cl | Cl | C₂H₅ | C₂H₅ |
| A-1229 | H | F | Cl | Cl | CH₃ | CH₃ |
| A-1230 | H | F | Cl | Cl | CH₃ | C₂H₅ |
| A-1231 | H | F | Cl | Cl | C₂H₅ | CH₃ |
| A-1232 | H | F | Cl | Cl | C₂H₅ | C₂H₅ |
| A-1233 | F | F | Cl | Cl | CH₃ | CH₃ |
| A-1234 | F | F | Cl | Cl | CH₃ | C₂H₅ |
| A-1235 | F | F | Cl | Cl | C₂H₅ | CH₃ |
| A-1236 | F | F | Cl | Cl | C₂H₅ | C₂H₅ |
| A-1237 | Cl | F | Cl | Cl | CH₃ | CH₃ |
| A-1238 | Cl | F | Cl | Cl | CH₃ | C₂H₅ |

TABLE A-continued

| line | R¹ | R² | R³ | R⁴ | R⁹ | R¹⁰ |
|---|---|---|---|---|---|---|
| A-1239 | Cl | F | | C1 | C₂H₅ | CH₃ |
| A-1240 | Cl | F | | C1 | C₂H₅ | C₂H₅ |
| A-1241 | CH₃ | F | | C1 | CH₃ | CH₃ |
| A-1242 | CH₃ | F | | C1 | CH₃ | C₂H₅ |
| A-1243 | CH₃ | F | | C1 | C₂H₅ | CH₃ |
| A-1244 | CH₃ | F | | C1 | C₂H₅ | C₂H₅ |
| A-1245 | H | CH₃ | | C1 | CH₃ | CH₃ |
| A-1246 | H | CH₃ | | C1 | CH₃ | C₂H₅ |
| A-1247 | H | CH₃ | | C1 | C₂H₅ | CH₃ |
| A-1248 | H | CH₃ | | C1 | C₂H₅ | C₂H₅ |
| A-1249 | F | CH₃ | | C1 | CH₃ | CH₃ |
| A-1250 | F | CH₃ | | C1 | CH₃ | C₂H₅ |
| A-1251 | F | CH₃ | | C1 | C₂H₅ | CH₃ |
| A-1252 | F | CH₃ | | C1 | C₂H₅ | C₂H₅ |
| A-1253 | Cl | CH₃ | | C1 | CH₃ | CH₃ |
| A-1254 | Cl | CH₃ | | C1 | CH₃ | C₂H₅ |
| A-1255 | Cl | CH₃ | | C1 | C₂H₅ | CH₃ |
| A-1256 | Cl | CH₃ | | C1 | C₂H₅ | C₂H₅ |
| A-1257 | CH₃ | CH₃ | | C1 | CH₃ | CH₃ |
| A-1258 | CH₃ | CH₃ | | C1 | CH₃ | C₂H₅ |
| A-1259 | CH₃ | CH₃ | | C1 | C₂H₅ | CH₃ |
| A-1260 | CH₃ | CH₃ | | C1 | C₂H₅ | C₂H₅ |
| A-1261 | H | Cl | | C1 | CH₃ | CH₃ |
| A-1262 | H | Cl | | C1 | CH₃ | C₂H₅ |
| A-1263 | H | Cl | | C1 | C₂H₅ | CH₃ |
| A-1264 | H | Cl | | C1 | C₂H₅ | C₂H₅ |
| A-1265 | F | Cl | | C1 | CH₃ | CH₃ |
| A-1266 | F | Cl | | C1 | CH₃ | C₂H₅ |
| A-1267 | F | Cl | | C1 | C₂H₅ | CH₃ |
| A-1268 | F | Cl | | C1 | C₂H₅ | C₂H₅ |
| A-1269 | Cl | Cl | | C1 | CH₃ | CH₃ |
| A-1270 | Cl | Cl | | C1 | CH₃ | C₂H₅ |
| A-1271 | Cl | Cl | | C1 | C₂H₅ | CH₃ |
| A-1272 | Cl | Cl | | C1 | C₂H₅ | C₂H₅ |
| A-1273 | CH₃ | Cl | | C1 | CH₃ | CH₃ |
| A-1274 | CH₃ | Cl | | C1 | CH₃ | C₂H₅ |
| A-1275 | CH₃ | Cl | | C1 | C₂H₅ | CH₃ |
| A-1276 | CH₃ | Cl | | C1 | C₂H₅ | C₂H₅ |
| A-1277 | H | H | | C2 | CH₃ | CH₃ |
| A-1278 | H | H | | C2 | CH₃ | C₂H₅ |
| A-1279 | H | H | | C2 | C₂H₅ | CH₃ |
| A-1280 | H | H | | C2 | C₂H₅ | C₂H₅ |
| A-1281 | F | H | | C2 | CH₃ | CH₃ |
| A-1282 | F | H | | C2 | CH₃ | C₂H₅ |
| A-1283 | F | H | | C2 | C₂H₅ | CH₃ |
| A-1284 | F | H | | C2 | C₂H₅ | C₂H₅ |
| A-1285 | Cl | H | | C2 | CH₃ | CH₃ |
| A-1286 | Cl | H | | C2 | CH₃ | C₂H₅ |
| A-1287 | Cl | H | | C2 | C₂H₅ | CH₃ |
| A-1288 | Cl | H | | C2 | C₂H₅ | C₂H₅ |
| A-1289 | CH₃ | H | | C2 | CH₃ | CH₃ |
| A-1290 | CH₃ | H | | C2 | CH₃ | C₂H₅ |
| A-1291 | CH₃ | H | | C2 | C₂H₅ | CH₃ |
| A-1292 | CH₃ | H | | C2 | C₂H₅ | C₂H₅ |
| A-1293 | H | F | | C2 | CH₃ | CH₃ |
| A-1294 | H | F | | C2 | CH₃ | C₂H₅ |
| A-1295 | H | F | | C2 | C₂H₅ | CH₃ |
| A-1296 | H | F | | C2 | C₂H₅ | C₂H₅ |
| A-1297 | F | F | | C2 | CH₃ | CH₃ |
| A-1298 | F | F | | C2 | CH₃ | C₂H₅ |
| A-1299 | F | F | | C2 | C₂H₅ | CH₃ |
| A-1300 | F | F | | C2 | C₂H₅ | C₂H₅ |
| A-1301 | Cl | F | | C2 | CH₃ | CH₃ |
| A-1302 | Cl | F | | C2 | CH₃ | C₂H₅ |
| A-1303 | Cl | F | | C2 | C₂H₅ | CH₃ |
| A-1304 | Cl | F | | C2 | C₂H₅ | C₂H₅ |
| A-1305 | CH₃ | F | | C2 | CH₃ | CH₃ |
| A-1306 | CH₃ | F | | C2 | CH₃ | C₂H₅ |
| A-1307 | CH₃ | F | | C2 | C₂H₅ | CH₃ |
| A-1308 | CH₃ | F | | C2 | C₂H₅ | C₂H₅ |
| A-1309 | H | CH₃ | | C2 | CH₃ | CH₃ |
| A-1310 | H | CH₃ | | C2 | CH₃ | C₂H₅ |
| A-1311 | H | CH₃ | | C2 | C₂H₅ | CH₃ |
| A-1312 | H | CH₃ | | C2 | C₂H₅ | C₂H₅ |
| A-1313 | F | CH₃ | | C2 | CH₃ | CH₃ |
| A-1314 | F | CH₃ | | C2 | CH₃ | C₂H₅ |
| A-1315 | F | CH₃ | | C2 | C₂H₅ | CH₃ |
| A-1316 | F | CH₃ | | C2 | C₂H₅ | C₂H₅ |
| A-1317 | Cl | CH₃ | | C2 | CH₃ | CH₃ |
| A-1318 | Cl | CH₃ | | C2 | CH₃ | C₂H₅ |
| A-1319 | Cl | CH₃ | | C2 | C₂H₅ | CH₃ |
| A-1320 | Cl | CH₃ | | C2 | C₂H₅ | C₂H₅ |
| A-1321 | CH₃ | CH₃ | | C2 | CH₃ | CH₃ |
| A-1322 | CH₃ | CH₃ | | C2 | CH₃ | C₂H₅ |
| A-1323 | CH₃ | CH₃ | | C2 | C₂H₅ | CH₃ |
| A-1324 | CH₃ | CH₃ | | C2 | C₂H₅ | C₂H₅ |
| A-1325 | H | Cl | | C2 | CH₃ | CH₃ |
| A-1326 | H | Cl | | C2 | CH₃ | C₂H₅ |
| A-1327 | H | Cl | | C2 | C₂H₅ | CH₃ |
| A-1328 | H | Cl | | C2 | C₂H₅ | C₂H₅ |
| A-1329 | F | Cl | | C2 | CH₃ | CH₃ |
| A-1330 | F | Cl | | C2 | CH₃ | C₂H₅ |
| A-1331 | F | Cl | | C2 | C₂H₅ | CH₃ |
| A-1332 | F | Cl | | C2 | C₂H₅ | C₂H₅ |
| A-1333 | Cl | Cl | | C2 | CH₃ | CH₃ |
| A-1334 | Cl | Cl | | C2 | CH₃ | C₂H₅ |
| A-1335 | Cl | Cl | | C2 | C₂H₅ | CH₃ |
| A-1336 | Cl | Cl | | C2 | C₂H₅ | C₂H₅ |
| A-1337 | CH₃ | Cl | | C2 | CH₃ | CH₃ |
| A-1338 | CH₃ | Cl | | C2 | CH₃ | C₂H₅ |
| A-1339 | CH₃ | Cl | | C2 | C₂H₅ | CH₃ |
| A-1340 | CH₃ | Cl | | C2 | C₂H₅ | C₂H₅ |
| A-1341 | H | H | | C2 | CH₃ | CH₃ |
| A-1342 | H | H | | C2 | CH₃ | C₂H₅ |
| A-1343 | H | H | | C2 | C₂H₅ | CH₃ |
| A-1344 | H | H | | C2 | C₂H₅ | C₂H₅ |
| A-1345 | F | H | | C2 | CH₃ | CH₃ |
| A-1346 | F | H | | C2 | CH₃ | C₂H₅ |
| A-1347 | F | H | | C2 | C₂H₅ | CH₃ |
| A-1348 | F | H | | C2 | C₂H₅ | C₂H₅ |
| A-1349 | Cl | H | | C2 | CH₃ | CH₃ |
| A-1350 | Cl | H | | C2 | CH₃ | C₂H₅ |
| A-1351 | Cl | H | | C2 | C₂H₅ | CH₃ |
| A-1352 | Cl | H | | C2 | C₂H₅ | C₂H₅ |
| A-1353 | CH₃ | H | | C2 | CH₃ | CH₃ |
| A-1354 | CH₃ | H | | C2 | CH₃ | C₂H₅ |
| A-1355 | CH₃ | H | | C2 | C₂H₅ | CH₃ |
| A-1356 | CH₃ | H | | C2 | C₂H₅ | C₂H₅ |
| A-1357 | H | F | | C2 | CH₃ | CH₃ |
| A-1358 | H | F | | C2 | CH₃ | C₂H₅ |
| A-1359 | H | F | | C2 | C₂H₅ | CH₃ |
| A-1360 | H | F | | C2 | C₂H₅ | C₂H₅ |
| A-1361 | F | F | | C2 | CH₃ | CH₃ |
| A-1362 | F | F | | C2 | CH₃ | C₂H₅ |
| A-1363 | F | F | | C2 | C₂H₅ | CH₃ |
| A-1364 | F | F | | C2 | C₂H₅ | C₂H₅ |
| A-1365 | Cl | F | | C2 | CH₃ | CH₃ |
| A-1366 | Cl | F | | C2 | CH₃ | C₂H₅ |
| A-1367 | Cl | F | | C2 | C₂H₅ | CH₃ |
| A-1368 | Cl | F | | C2 | C₂H₅ | C₂H₅ |
| A-1369 | CH₃ | F | | C2 | CH₃ | CH₃ |
| A-1370 | CH₃ | F | | C2 | CH₃ | C₂H₅ |
| A-1371 | CH₃ | F | | C2 | C₂H₅ | CH₃ |
| A-1372 | CH₃ | F | | C2 | C₂H₅ | C₂H₅ |
| A-1373 | H | CH₃ | | C2 | CH₃ | CH₃ |
| A-1374 | H | CH₃ | | C2 | CH₃ | C₂H₅ |
| A-1375 | H | CH₃ | | C2 | C₂H₅ | CH₃ |
| A-1376 | H | CH₃ | | C2 | C₂H₅ | C₂H₅ |
| A-1377 | F | CH₃ | | C2 | CH₃ | CH₃ |
| A-1378 | F | CH₃ | | C2 | CH₃ | C₂H₅ |
| A-1379 | F | CH₃ | | C2 | C₂H₅ | CH₃ |
| A-1380 | F | CH₃ | | C2 | C₂H₅ | C₂H₅ |
| A-1381 | Cl | CH₃ | | C2 | CH₃ | CH₃ |
| A-1382 | Cl | CH₃ | | C2 | CH₃ | C₂H₅ |
| A-1383 | Cl | CH₃ | | C2 | C₂H₅ | CH₃ |
| A-1384 | Cl | CH₃ | | C2 | C₂H₅ | C₂H₅ |
| A-1385 | CH₃ | CH₃ | | C2 | CH₃ | CH₃ |
| A-1386 | CH₃ | CH₃ | | C2 | CH₃ | C₂H₅ |
| A-1387 | CH₃ | CH₃ | | C2 | C₂H₅ | CH₃ |
| A-1388 | CH₃ | CH₃ | | C2 | C₂H₅ | C₂H₅ |
| A-1389 | H | Cl | | C2 | CH₃ | CH₃ |
| A-1390 | H | Cl | | C2 | CH₃ | C₂H₅ |
| A-1391 | H | Cl | | C2 | C₂H₅ | CH₃ |
| A-1392 | H | Cl | | C2 | C₂H₅ | C₂H₅ |
| A-1393 | F | Cl | | C2 | CH₃ | CH₃ |
| A-1394 | F | Cl | | C2 | CH₃ | C₂H₅ |

TABLE A-continued

| line | R¹ | R² | R³ | R⁴ | R⁹ | R¹⁰ |
|---|---|---|---|---|---|---|
| A-1395 | F | Cl | | C2 | C₂H₅ | CH₃ |
| A-1396 | F | Cl | | C2 | C₂H₅ | C₂H₅ |
| A-1397 | Cl | Cl | | C2 | CH₃ | CH₃ |
| A-1398 | Cl | Cl | | C2 | CH₃ | C₂H₅ |
| A-1399 | Cl | Cl | | C2 | C₂H₅ | CH₃ |
| A-1400 | Cl | Cl | | C2 | C₂H₅ | C₂H₅ |
| A-1401 | CH₃ | Cl | | C2 | CH₃ | CH₃ |
| A-1402 | CH₃ | Cl | | C2 | CH₃ | C₂H₅ |
| A-1403 | CH₃ | Cl | | C2 | C₂H₅ | CH₃ |
| A-1404 | CH₃ | Cl | | C2 | C₂H₅ | C₂H₅ |
| A-1405 | H | H | | C2 | CH₃ | CH₃ |
| A-1406 | H | H | | C2 | CH₃ | C₂H₅ |
| A-1407 | H | H | | C2 | C₂H₅ | CH₃ |
| A-1408 | H | H | | C2 | C₂H₅ | C₂H₅ |
| A-1409 | F | H | | C2 | CH₃ | CH₃ |
| A-1410 | F | H | | C2 | CH₃ | C₂H₅ |
| A-1411 | F | H | | C2 | C₂H₅ | CH₃ |
| A-1412 | F | H | | C2 | C₂H₅ | C₂H₅ |
| A-1413 | Cl | H | | C2 | CH₃ | CH₃ |
| A-1414 | Cl | H | | C2 | CH₃ | C₂H₅ |
| A-1415 | Cl | H | | C2 | C₂H₅ | CH₃ |
| A-1416 | Cl | H | | C2 | C₂H₅ | C₂H₅ |
| A-1417 | CH₃ | H | | C2 | CH₃ | CH₃ |
| A-1418 | CH₃ | H | | C2 | CH₃ | C₂H₅ |
| A-1419 | CH₃ | H | | C2 | C₂H₅ | CH₃ |
| A-1420 | CH₃ | H | | C2 | C₂H₅ | C₂H₅ |
| A-1421 | H | F | | C2 | CH₃ | CH₃ |
| A-1422 | H | F | | C2 | CH₃ | C₂H₅ |
| A-1423 | H | F | | C2 | C₂H₅ | CH₃ |
| A-1424 | H | F | | C2 | C₂H₅ | C₂H₅ |
| A-1425 | F | F | | C2 | CH₃ | CH₃ |
| A-1426 | F | F | | C2 | CH₃ | C₂H₅ |
| A-1427 | F | F | | C2 | C₂H₅ | CH₃ |
| A-1428 | F | F | | C2 | C₂H₅ | C₂H₅ |
| A-1429 | Cl | F | | C2 | CH₃ | CH₃ |
| A-1430 | Cl | F | | C2 | CH₃ | C₂H₅ |
| A-1431 | Cl | F | | C2 | C₂H₅ | CH₃ |
| A-1432 | Cl | F | | C2 | C₂H₅ | C₂H₅ |
| A-1433 | CH₃ | F | | C2 | CH₃ | CH₃ |
| A-1434 | CH₃ | F | | C2 | CH₃ | C₂H₅ |
| A-1435 | CH₃ | F | | C2 | C₂H₅ | CH₃ |
| A-1436 | CH₃ | F | | C2 | C₂H₅ | C₂H₅ |
| A-1437 | H | CH₃ | | C2 | CH₃ | CH₃ |
| A-1438 | H | CH₃ | | C2 | CH₃ | C₂H₅ |
| A-1439 | H | CH₃ | | C2 | C₂H₅ | CH₃ |
| A-1440 | H | CH₃ | | C2 | C₂H₅ | C₂H₅ |
| A-1441 | F | CH₃ | | C2 | CH₃ | CH₃ |
| A-1442 | F | CH₃ | | C2 | CH₃ | C₂H₅ |
| A-1443 | F | CH₃ | | C2 | C₂H₅ | CH₃ |
| A-1444 | F | CH₃ | | C2 | C₂H₅ | C₂H₅ |
| A-1445 | Cl | CH₃ | | C2 | CH₃ | CH₃ |
| A-1446 | Cl | CH₃ | | C2 | CH₃ | C₂H₅ |
| A-1447 | Cl | CH₃ | | C2 | C₂H₅ | CH₃ |
| A-1448 | Cl | CH₃ | | C2 | C₂H₅ | C₂H₅ |
| A-1449 | CH₃ | CH₃ | | C2 | CH₃ | CH₃ |
| A-1450 | CH₃ | CH₃ | | C2 | CH₃ | C₂H₅ |
| A-1451 | CH₃ | CH₃ | | C2 | C₂H₅ | CH₃ |
| A-1452 | CH₃ | CH₃ | | C2 | C₂H₅ | C₂H₅ |
| A-1453 | H | Cl | | C2 | CH₃ | CH₃ |
| A-1454 | H | Cl | | C2 | CH₃ | C₂H₅ |
| A-1455 | H | Cl | | C2 | C₂H₅ | CH₃ |
| A-1456 | H | Cl | | C2 | C₂H₅ | C₂H₅ |
| A-1457 | F | Cl | | C2 | CH₃ | CH₃ |
| A-1458 | F | Cl | | C2 | CH₃ | C₂H₅ |
| A-1459 | F | Cl | | C2 | C₂H₅ | CH₃ |
| A-1460 | F | Cl | | C2 | C₂H₅ | C₂H₅ |
| A-1461 | Cl | Cl | | C2 | CH₃ | CH₃ |
| A-1462 | Cl | Cl | | C2 | CH₃ | C₂H₅ |
| A-1463 | Cl | Cl | | C2 | C₂H₅ | CH₃ |
| A-1464 | Cl | Cl | | C2 | C₂H₅ | C₂H₅ |
| A-1465 | CH₃ | Cl | | C2 | CH₃ | CH₃ |
| A-1466 | CH₃ | Cl | | C2 | CH₃ | C₂H₅ |
| A-1467 | CH₃ | Cl | | C2 | C₂H₅ | CH₃ |
| A-1468 | CH₃ | Cl | | C2 | C₂H₅ | C₂H₅ |
| A-1469 | H | H | | C2 | CH₃ | CH₃ |
| A-1470 | H | H | | C2 | CH₃ | C₂H₅ |
| A-1471 | H | H | | C2 | C₂H₅ | CH₃ |
| A-1472 | H | H | | C2 | C₂H₅ | C₂H₅ |
| A-1473 | F | H | | C2 | CH₃ | CH₃ |
| A-1474 | F | H | | C2 | CH₃ | C₂H₅ |
| A-1475 | F | H | | C2 | C₂H₅ | CH₃ |
| A-1476 | F | H | | C2 | C₂H₅ | C₂H₅ |
| A-1477 | Cl | H | | C2 | CH₃ | CH₃ |
| A-1478 | Cl | H | | C2 | CH₃ | C₂H₅ |
| A-1479 | Cl | H | | C2 | C₂H₅ | CH₃ |
| A-1480 | Cl | H | | C2 | C₂H₅ | C₂H₅ |
| A-1481 | CH₃ | H | | C2 | CH₃ | CH₃ |
| A-1482 | CH₃ | H | | C2 | CH₃ | C₂H₅ |
| A-1483 | CH₃ | H | | C2 | C₂H₅ | CH₃ |
| A-1484 | CH₃ | H | | C2 | C₂H₅ | C₂H₅ |
| A-1485 | H | F | | C2 | CH₃ | CH₃ |
| A-1486 | H | F | | C2 | CH₃ | C₂H₅ |
| A-1487 | H | F | | C2 | C₂H₅ | CH₃ |
| A-1488 | H | F | | C2 | C₂H₅ | C₂H₅ |
| A-1489 | F | F | | C2 | CH₃ | CH₃ |
| A-1490 | F | F | | C2 | CH₃ | C₂H₅ |
| A-1491 | F | F | | C2 | C₂H₅ | CH₃ |
| A-1492 | F | F | | C2 | C₂H₅ | C₂H₅ |
| A-1493 | Cl | F | | C2 | CH₃ | CH₃ |
| A-1494 | Cl | F | | C2 | CH₃ | C₂H₅ |
| A-1495 | Cl | F | | C2 | C₂H₅ | CH₃ |
| A-1496 | Cl | F | | C2 | C₂H₅ | C₂H₅ |
| A-1497 | CH₃ | F | | C2 | CH₃ | CH₃ |
| A-1498 | CH₃ | F | | C2 | CH₃ | C₂H₅ |
| A-1499 | CH₃ | F | | C2 | C₂H₅ | CH₃ |
| A-1500 | CH₃ | F | | C2 | C₂H₅ | C₂H₅ |
| A-1501 | H | CH₃ | | C2 | CH₃ | CH₃ |
| A-1502 | H | CH₃ | | C2 | CH₃ | C₂H₅ |
| A-1503 | H | CH₃ | | C2 | C₂H₅ | CH₃ |
| A-1504 | H | CH₃ | | C2 | C₂H₅ | C₂H₅ |
| A-1505 | F | CH₃ | | C2 | CH₃ | CH₃ |
| A-1506 | F | CH₃ | | C2 | CH₃ | C₂H₅ |
| A-1507 | F | CH₃ | | C2 | C₂H₅ | CH₃ |
| A-1508 | F | CH₃ | | C2 | C₂H₅ | C₂H₅ |
| A-1509 | Cl | CH₃ | | C2 | CH₃ | CH₃ |
| A-1510 | Cl | CH₃ | | C2 | CH₃ | C₂H₅ |
| A-1511 | Cl | CH₃ | | C2 | C₂H₅ | CH₃ |
| A-1512 | Cl | CH₃ | | C2 | C₂H₅ | C₂H₅ |
| A-1513 | CH₃ | CH₃ | | C2 | CH₃ | CH₃ |
| A-1514 | CH₃ | CH₃ | | C2 | CH₃ | C₂H₅ |
| A-1515 | CH₃ | CH₃ | | C2 | C₂H₅ | CH₃ |
| A-1516 | CH₃ | CH₃ | | C2 | C₂H₅ | C₂H₅ |
| A-1517 | H | Cl | | C2 | CH₃ | CH₃ |
| A-1518 | H | Cl | | C2 | CH₃ | C₂H₅ |
| A-1519 | H | Cl | | C2 | C₂H₅ | CH₃ |
| A-1520 | H | Cl | | C2 | C₂H₅ | C₂H₅ |
| A-1521 | F | Cl | | C2 | CH₃ | CH₃ |
| A-1522 | F | Cl | | C2 | CH₃ | C₂H₅ |
| A-1523 | F | Cl | | C2 | C₂H₅ | CH₃ |
| A-1524 | F | Cl | | C2 | C₂H₅ | C₂H₅ |
| A-1525 | Cl | Cl | | C2 | CH₃ | CH₃ |
| A-1526 | Cl | Cl | | C2 | CH₃ | C₂H₅ |
| A-1527 | Cl | Cl | | C2 | C₂H₅ | CH₃ |
| A-1528 | Cl | Cl | | C2 | C₂H₅ | C₂H₅ |
| A-1529 | CH₃ | Cl | | C2 | CH₃ | CH₃ |
| A-1530 | CH₃ | Cl | | C2 | CH₃ | C₂H₅ |
| A-1531 | CH₃ | Cl | | C2 | C₂H₅ | CH₃ |
| A-1532 | CH₃ | Cl | | C2 | C₂H₅ | C₂H₅ |

Particular embodiments of the compounds II are the following compounds II*, In this formula, the substituents R⁹, R¹⁰, R⁷⁸ and o are independently as defined or preferably defined herein:

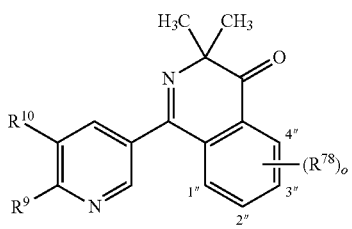

II*

Each of the groups mentioned for a substituent in the tables is furthermore per se, independently of the combination in which it is mentioned, a particularly preferred aspect of the substituent in question.

Particularly preferred embodiments of combinations of $R^9$ and $R^{10}$ according to the invention are as compiled in Table A*-1 to A*-9, wherein lines of A*-1 to A*-9 are also in any combination with one another a preferred embodiment of the present invention.

Table A*1 Compounds of formula II* in which o is 0 and the meaning for the combination of $R^9$ and $R^{10}$ for each individual compound corresponds in each case to one line of Table A*.

Table A*2 Compounds of formula II* in which o is 1, $R^{78}$ is 1"-F and the meaning for the combination of $R^9$ and $R^{10}$ for each individual compound corresponds in each case to one line of Table A*.

Table A*3 Compounds of formula II* in which o is 1, $R^{78}$ is 2"-F and the meaning for the combination of $R^9$ and $R^{10}$ for each individual compound corresponds in each case to one line of Table A*.

Table A*4 Compounds of formula II* in which o is 1, $R^{78}$ is 3"-F and the meaning for the combination of $R^9$ and $R^{10}$ for each individual compound corresponds in each case to one line of Table A*.

Table A*5 Compounds of formula II* in which o is 1, $R^{78}$ is 4"-F and the meaning for the combination of $R^9$ and $R^{10}$ for each individual compound corresponds in each case to one line of Table A*.

Table A*6 Compounds of formula II* in which o is 1, $R^{78}$ is 1"-Cl and the meaning for the combination of $R^9$ and $R^{10}$ for each individual compound corresponds in each case to one line of Table A*.

Table A*7 Compounds of formula II* in which o is 1, $R^{78}$ is 2"-Cl and the meaning for the combination of $R^9$ and $R^{10}$ for each individual compound corresponds in each case to one line of Table A*.

Table A*8 Compounds of formula I* in which o is 1, $R^{78}$ is 3"-Cl and the meaning for the combination of $R^9$ and $R^{10}$ for each individual compound corresponds in each case to one line of Table A*.

Table A*9 Compounds of formula I* in which o is 1, $R^{78}$ is 4"-Cl and the meaning for the combination $R^9$ and $R^{10}$ for each individual compound corresponds in each case to one line of Table A*.

TABLE A*

| line | $R^9$ | $R^{10}$ |
|---|---|---|
| A*-1 | H | H |
| A*-2 | H | $CH_3$ |
| A*-3 | H | $C_2H_5$ |
| A*-4 | H | F |
| A*-5 | H | Cl |
| A*-6 | H | Br |

TABLE A*-continued

| line | $R^9$ | $R^{10}$ |
|---|---|---|
| A*-7 | H | CN |
| A*-8 | H | $OCH_3$ |
| A*-9 | H | $OCHF_2$ |
| A*-10 | H | $CHF_2$ |
| A*-11 | H | $CF_3$ |
| A*-12 | H | $S-CH_3$ |
| A*-13 | H | $SO-CH_3$ |
| A*-14 | H | $SO_2-CH_3$ |
| A*-15 | H | $CO-NH_2$ |
| A*-16 | H | $CO-NH(CH_3)$ |
| A*-17 | H | $CO-N(CH_3)_2$ |
| A*-18 | $CH_3$ | H |
| A*-19 | $CH_3$ | $CH_3$ |
| A*-20 | $CH_3$ | $C_2H_5$ |
| A*-21 | $CH_3$ | F |
| A*-22 | $CH_3$ | Cl |
| A*-23 | $CH_3$ | Br |
| A*-24 | $CH_3$ | CN |
| A*-25 | $CH_3$ | $OCH_3$ |
| A*-26 | $CH_3$ | $OCHF_2$ |
| A*-27 | $CH_3$ | $CHF_2$ |
| A*-28 | $CH_3$ | $CF_3$ |
| A*-29 | $CH_3$ | $S-CH_3$ |
| A*-30 | $CH_3$ | $SO-CH_3$ |
| A*-31 | $CH_3$ | $SO_2-CH_3$ |
| A*-32 | $CH_3$ | $CO-NH_2$ |
| A*-33 | $CH_3$ | $CO-NH(CH_3)$ |
| A*-34 | $CH_3$ | $CO-N(CH_3)_2$ |
| A*-35 | $C_2H_5$ | H |
| A*-36 | $C_2H_5$ | $CH_3$ |
| A*-37 | $C_2H_5$ | $C_2H_5$ |
| A*-38 | $C_2H_5$ | F |
| A*-39 | $C_2H_5$ | Cl |
| A*-40 | $C_2H_5$ | Br |
| A*-41 | $C_2H_5$ | CN |
| A*-42 | $C_2H_5$ | $OCH_3$ |
| A*-43 | $C_2H_5$ | $OCHF_2$ |
| A*-44 | $C_2H_5$ | $CHF_2$ |
| A*-45 | $C_2H_5$ | $CF_3$ |
| A*-46 | $C_2H_5$ | $S-CH_3$ |
| A*-47 | $C_2H_5$ | $SO-CH_3$ |
| A*-48 | $C_2H_5$ | $SO_2-CH_3$ |
| A*-49 | $C_2H_5$ | $CO-NH_2$ |
| A*-50 | $C_2H_5$ | $CO-NH(CH_3)$ |
| A*-51 | $C_2H_5$ | $CO-N(CH_3)_2$ |
| A*-52 | F | H |
| A*-53 | F | $CH_3$ |
| A*-54 | F | $C_2H_5$ |
| A*-55 | F | F |
| A*-56 | F | Cl |
| A*-57 | F | Br |
| A*-58 | F | CN |
| A*-59 | F | $OCH_3$ |
| A*-60 | F | $OCHF_2$ |
| A*-61 | F | $CHF_2$ |
| A*-62 | F | $CF_3$ |
| A*-63 | F | $S-CH_3$ |
| A*-64 | F | $SO-CH_3$ |
| A*-65 | F | $SO_2-CH_3$ |
| A*-66 | F | $CO-NH_2$ |
| A*-67 | F | $CO-NH(CH_3)$ |
| A*-68 | F | $CO-N(CH_3)_2$ |
| A*-69 | Cl | H |
| A*-70 | Cl | $CH_3$ |
| A*-71 | Cl | $C_2H_5$ |
| A*-72 | Cl | F |
| A*-73 | Cl | Cl |
| A*-74 | Cl | Br |
| A*-75 | Cl | CN |
| A*-76 | Cl | $OCH_3$ |
| A*-77 | Cl | $OCHF_2$ |
| A*-78 | Cl | $CHF_2$ |
| A*-79 | Cl | $CF_3$ |
| A*-80 | Cl | $S-CH_3$ |
| A*-81 | Cl | $SO-CH_3$ |
| A*-82 | Cl | $SO_2-CH_3$ |
| A*-83 | Cl | $CO-NH_2$ |
| A*-84 | Cl | $CO-NH(CH_3)$ |

TABLE A*-continued

| line | R⁹ | R¹⁰ |
|---|---|---|
| A*-85 | Cl | CO—N(CH₃)₂ |
| A*-86 | Br | H |
| A*-87 | Br | CH₃ |
| A*-88 | Br | C₂H₅ |
| A*-89 | Br | F |
| A*-90 | Br | Cl |
| A*-91 | Br | Br |
| A*-92 | Br | CN |
| A*-93 | Br | OCH₃ |
| A*-94 | Br | OCHF₂ |
| A*-95 | Br | CHF₂ |
| A*-96 | Br | CF₃ |
| A*-97 | Br | S—CH₃ |
| A*-98 | Br | SO—CH₃ |
| A*-99 | Br | SO₂—CH₃ |
| A*-100 | Br | CO—NH₂ |
| A*-101 | Br | CO—NH(CH₃) |
| A*-102 | Br | CO—N(CH₃)₂ |
| A*-103 | CN | H |
| A*-104 | CN | CH₃ |
| A*-105 | CN | C₂H₅ |
| A*-106 | CN | F |
| A*-107 | CN | Cl |
| A*-108 | CN | Br |
| A*-109 | CN | CN |
| A*-110 | CN | OCH₃ |
| A*-111 | CN | OCHF₂ |
| A*-112 | CN | CHF₂ |
| A*-113 | CN | CF₃ |
| A*-114 | CN | S—CH₃ |
| A*-115 | CN | SO—CH₃ |
| A*-116 | CN | SO₂—CH₃ |
| A*-117 | CN | CO—NH₂ |
| A*-118 | CN | CO—NH(CH₃) |
| A*-119 | CN | CO—N(CH₃)₂ |
| A*-120 | OCH₃ | H |
| A*-121 | OCH₃ | CH₃ |
| A*-122 | OCH₃ | C₂H₅ |
| A*-123 | OCH₃ | F |
| A*-124 | OCH₃ | Cl |
| A*-125 | OCH₃ | Br |
| A*-126 | OCH₃ | CN |
| A*-127 | OCH₃ | OCH₃ |
| A*-128 | OCH₃ | OCHF₂ |
| A*-129 | OCH₃ | CHF₂ |
| A*-130 | OCH₃ | CF₃ |
| A*-131 | OCH₃ | S—CH₃ |
| A*-132 | OCH₃ | SO—CH₃ |
| A*-133 | OCH₃ | SO₂—CH₃ |
| A*-134 | OCH₃ | CO—NH₂ |
| A*-135 | OCH₃ | CO—NH(CH₃) |
| A*-136 | OCH₃ | CO—N(CH₃)₂ |
| A*-137 | OCHF₂ | H |
| A*-138 | OCHF₂ | CH₃ |
| A*-139 | OCHF₂ | C₂H₅ |
| A*-140 | OCHF₂ | F |
| A*-141 | OCHF₂ | Cl |
| A*-142 | OCHF₂ | Br |
| A*-143 | OCHF₂ | CN |
| A*-144 | OCHF₂ | OCH₃ |
| A*-145 | OCHF₂ | OCHF₂ |
| A*-146 | OCHF₂ | CHF₂ |
| A*-147 | OCHF₂ | CF₃ |
| A*-148 | OCHF₂ | S—CH₃ |
| A*-149 | OCHF₂ | SO—CH₃ |
| A*-150 | OCHF₂ | SO₂—CH₃ |
| A*-151 | OCHF₂ | CO—NH₂ |
| A*-152 | OCHF₂ | CO—NH(CH₃) |
| A*-153 | OCHF₂ | CO—N(CH₃)₂ |
| A*-154 | CHF₂ | H |
| A*-155 | CHF₂ | CH₃ |
| A*-156 | CHF₂ | C₂H₅ |
| A*-157 | CHF₂ | F |
| A*-158 | CHF₂ | Cl |
| A*-159 | CHF₂ | Br |
| A*-160 | CHF₂ | CN |
| A*-161 | CHF₂ | OCH₃ |
| A*-162 | CHF₂ | OCHF₂ |
| A*-163 | CHF₂ | CHF₂ |
| A*-164 | CHF₂ | CF₃ |
| A*-165 | CHF₂ | S—CH₃ |
| A*-166 | CHF₂ | SO—CH₃ |
| A*-167 | CHF₂ | SO₂—CH₃ |
| A*-168 | CHF₂ | CO—NH₂ |
| A*-169 | CHF₂ | CO—NH(CH₃) |
| A*-170 | CHF₂ | CO—N(CH₃)₂ |
| A*-171 | CF₃ | H |
| A*-172 | CF₃ | CH₃ |
| A*-173 | CF₃ | C₂H₅ |
| A*-174 | CF₃ | F |
| A*-175 | CF₃ | Cl |
| A*-176 | CF₃ | Br |
| A*-177 | CF₃ | CN |
| A*-178 | CF₃ | OCH₃ |
| A*-179 | CF₃ | OCHF₂ |
| A*-180 | CF₃ | CHF₂ |
| A*-181 | CF₃ | CF₃ |
| A*-182 | CF₃ | S—CH₃ |
| A*-183 | CF₃ | SO—CH₃ |
| A*-184 | CF₃ | SO₂—CH₃ |
| A*-185 | CF₃ | CO—NH₂ |
| A*-186 | CF₃ | CO—NH(CH₃) |
| A*-187 | CF₃ | CO—N(CH₃)₂ |
| A*-188 | S—CH₃ | H |
| A*-189 | S—CH₃ | CH₃ |
| A*-190 | S—CH₃ | C₂H₅ |
| A*-191 | S—CH₃ | F |
| A*-192 | S—CH₃ | Cl |
| A*-193 | S—CH₃ | Br |
| A*-194 | S—CH₃ | CN |
| A*-195 | S—CH₃ | OCH₃ |
| A*-196 | S—CH₃ | OCHF₂ |
| A*-197 | S—CH₃ | CHF₂ |
| A*-198 | S—CH₃ | CF₃ |
| A*-199 | S—CH₃ | S—CH₃ |
| A*-200 | S—CH₃ | SO—CH₃ |
| A*-201 | S—CH₃ | SO₂—CH₃ |
| A*-202 | S—CH₃ | CO—NH₂ |
| A*-203 | S—CH₃ | CO—NH(CH₃) |
| A*-204 | S—CH₃ | CO—N(CH₃)₂ |
| A*-205 | SO—CH₃ | H |
| A*-206 | SO—CH₃ | CH₃ |
| A*-207 | SO—CH₃ | C₂H₅ |
| A*-208 | SO—CH₃ | F |
| A*-209 | SO—CH₃ | Cl |
| A*-210 | SO—CH₃ | Br |
| A*-211 | SO—CH₃ | CN |
| A*-212 | SO—CH₃ | OCH₃ |
| A*-213 | SO—CH₃ | OCHF₂ |
| A*-214 | SO—CH₃ | CHF₂ |
| A*-215 | SO—CH₃ | CF₃ |
| A*-216 | SO—CH₃ | S—CH₃ |
| A*-217 | SO—CH₃ | SO—CH₃ |
| A*-218 | SO—CH₃ | SO₂—CH₃ |
| A*-219 | SO—CH₃ | CO—NH₂ |
| A*-220 | SO—CH₃ | CO—NH(CH₃) |
| A*-221 | SO—CH₃ | CO—N(CH₃)₂ |
| A*-222 | SO₂—CH₃ | H |
| A*-223 | SO₂—CH₃ | CH₃ |
| A*-224 | SO₂—CH₃ | C₂H₅ |
| A*-225 | SO₂—CH₃ | F |
| A*-226 | SO₂—CH₃ | Cl |
| A*-227 | SO₂—CH₃ | Br |
| A*-228 | SO₂—CH₃ | CN |
| A*-229 | SO₂—CH₃ | OCH₃ |
| A*-230 | SO₂—CH₃ | OCHF₂ |
| A*-231 | SO₂—CH₃ | CHF₂ |
| A*-232 | SO₂—CH₃ | CF₃ |
| A*-233 | SO₂—CH₃ | S—CH₃ |
| A*-234 | SO₂—CH₃ | SO—CH₃ |
| A*-235 | SO₂—CH₃ | SO₂—CH₃ |
| A*-236 | SO₂—CH₃ | CO—NH₂ |
| A*-237 | SO₂—CH₃ | CO—NH(CH₃) |
| A*-238 | SO₂—CH₃ | CO—N(CH₃)₂ |
| A*-239 | CO—NH₂ | H |
| A*-240 | CO—NH₂ | CH₃ |

TABLE A*-continued

| line | $R^9$ | $R^{10}$ |
|---|---|---|
| A*-241 | CO—NH$_2$ | C$_2$H$_5$ |
| A*-242 | CO—NH$_2$ | F |
| A*-243 | CO—NH$_2$ | Cl |
| A*-244 | CO—NH$_2$ | Br |
| A*-245 | CO—NH$_2$ | CN |
| A*-246 | CO—NH$_2$ | OCH$_3$ |
| A*-247 | CO—NH$_2$ | OCHF$_2$ |
| A*-248 | CO—NH$_2$ | CHF$_2$ |
| A*-249 | CO—NH$_2$ | CF$_3$ |
| A*-250 | CO—NH$_2$ | S—CH$_3$ |
| A*-251 | CO—NH$_2$ | SO—CH$_3$ |
| A*-252 | CO—NH$_2$ | SO$_2$—CH$_3$ |
| A*-253 | CO—NH$_2$ | CO—NH$_2$ |
| A*-254 | CO—NH$_2$ | CO—NH(CH$_3$) |
| A*-255 | CO—NH$_2$ | CO—N(CH$_3$)$_2$ |
| A*-256 | CO—NH(CH$_3$) | H |
| A*-257 | CO—NH(CH$_3$) | CH$_3$ |
| A*-258 | CO—NH(CH$_3$) | C$_2$H$_5$ |
| A*-259 | CO—NH(CH$_3$) | F |
| A*-260 | CO—NH(CH$_3$) | Cl |
| A*-261 | CO—NH(CH$_3$) | Br |
| A*-262 | CO—NH(CH$_3$) | CN |
| A*-263 | CO—NH(CH$_3$) | OCH$_3$ |
| A*-264 | CO—NH(CH$_3$) | OCHF$_2$ |
| A*-265 | CO—NH(CH$_3$) | CHF$_2$ |
| A*-266 | CO—NH(CH$_3$) | CF$_3$ |
| A*-267 | CO—NH(CH$_3$) | S—CH$_3$ |
| A*-268 | CO—NH(CH$_3$) | SO—CH$_3$ |
| A*-269 | CO—NH(CH$_3$) | SO$_2$—CH$_3$ |
| A*-270 | CO—NH(CH$_3$) | CO—NH$_2$ |
| A*-271 | CO—NH(CH$_3$) | CO—NH(CH$_3$) |
| A*-272 | CO—NH(CH$_3$) | CO—N(CH$_3$)$_2$ |
| A*-273 | CO—N(CH$_3$)$_2$ | H |
| A*-274 | CO—N(CH$_3$)$_2$ | CH$_3$ |
| A*-275 | CO—N(CH$_3$)$_2$ | C$_2$H$_5$ |
| A*-276 | CO—N(CH$_3$)$_2$ | F |
| A*-277 | CO—N(CH$_3$)$_2$ | Cl |
| A*-278 | CO—N(CH$_3$)$_2$ | Br |
| A*-279 | CO—N(CH$_3$)$_2$ | CN |
| A*-280 | CO—N(CH$_3$)$_2$ | OCH$_3$ |
| A*-281 | CO—N(CH$_3$)$_2$ | OCHF$_2$ |
| A*-282 | CO—N(CH$_3$)$_2$ | CHF$_2$ |
| A*-283 | CO—N(CH$_3$)$_2$ | CF$_3$ |
| A*-284 | CO—N(CH$_3$)$_2$ | S—CH$_3$ |
| A*-285 | CO—N(CH$_3$)$_2$ | SO—CH$_3$ |
| A*-286 | CO—N(CH$_3$)$_2$ | SO$_2$—CH$_3$ |
| A*-287 | CO—N(CH$_3$)$_2$ | CO—NH$_2$ |
| A*-288 | CO—N(CH$_3$)$_2$ | CO—NH(CH$_3$) |
| A*-289 | CO—N(CH$_3$)$_2$ | CO—N(CH$_3$)$_2$ |

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethyl propyl, 1-ethyl-1-methyl propyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-halogenalkyl" refers to an alkyl group having 1 or 6 carbon atoms as defined above, wherein some or all of the hydrogen atoms in these groups may be replaced by halogen atoms as mentioned above. Examples are "$C_1$-$C_2$-halogenalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein some or all of the hydrogen atoms in these groups may be replaced by OH groups.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methylpropoxy, 2-methylpropoxy or 1,1-dimethylethoxy.

The term "$C_1$-$C_6$-halogenalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-halogenalkoxy" groups, such as OCH$_2$F, OCHF$_2$, OCF$_3$, OCH$_2$Cl, OCHCl$_2$, OCCl$_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-tri-fluoroethoxy, 2-chloro-2-fluoroethoxy, 2-chloro-2,2-difluoroethoxy, 2,2-dichloro-2-fluoroethoxy, 2,2,2-trichloroethoxy, OC$_2$F$_5$, 2-fluoropropoxy, 3-fluoropropoxy, 2,2-difluoropropoxy, 2,3-difluoropropoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, OCH$_2$—C$_2$F$_5$, OCF$_2$—C$_2$F$_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "$C_2$-$C_6$-alkenyloxy" refers to a straight-chain or branched alkenyl group having 2 to 6 carbon atoms which is bonded via an oxygen, at any position in the alkenyl group. Examples are "$C_2$-$C_4$-alkenyloxy" groups.

The term "C$_2$-C$_6$-alkynyloxy" refers to a straight-chain or branched alkynyl group having 2 to 6 carbon atoms which is bonded via an oxygen, at any position in the alkynyl group. Examples are "C$_2$-C$_4$-alkynyloxy" groups.

The term "C$_3$-C$_6$-cycloalkyl" refers to monocyclic saturated hydrocarbon radicals having 3 to 6 carbon ring members, such as cyclopropyl, cyclobutyl, cyclopentyl, cyclohexyl. Accordingly, a saturated three-, four-, five-, six-, seven-, eight-, nine or ten-membered carbocyclyl or carbocycle is a "C$_3$-C$_{10}$-cycloalkyl".

The term "C$_3$-C$_6$-cycloalkenyl" refers to a monocyclic partially unsaturated 3-, 4-5- or 6-membered carbocycle having 3 to 6 carbon ring members and at least one double bond, such as cyclopentenyl, cyclopentadienyl, cyclohexadienyl. Accordingly, a partially unsaturated three-, four-, five-, six-, seven-, eight-, nine or ten-membered carbocyclyl or carbocycle is a "C$_3$-C$_{10}$-cycloalkenyl".

The term "C$_3$-C$_8$-cycloalkyl-C$_1$-C$_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "C$_1$-C$_6$-alkylthio" as used herein refers to straight-chain or branched alkyl groups having 1 to 6 carbon atoms (as defined above) bonded via a sulfur atom. Accordingly, the term "C$_1$-C$_6$-halogenalkylthio" as used herein refers to straight-chain or branched halogenalkyl group having 1 to 6 carbon atoms (as defined above) bonded through a sulfur atom, at any position in the halogenalkyl group.

The term "C(=O)—C$_1$-C$_6$-alkyl" refers to a radical which is attached through the carbon atom of the group C(=O) as indicated by the number valence of the carbon atom. The number of valence of carbon is 4, that of nitrogen is 3. Likewise the following terms are to be construed: NH(C$_1$-C$_4$-alkyl), N(C$_1$-C$_4$-alkyl)$_2$, NH(C$_3$-C$_6$-cycloalkyl), N(C$_3$-C$_6$-cycloalkyl)$_2$, C(=O)—NH(C$_1$-C$_6$-alkyl), C(=O)—N(C$_1$-C$_6$-alkyl)$_2$.

The term "saturated or partially unsaturated three-, four-, five-, six-, seven-, eight-, nine or ten-membered heterocyclyl or heterocycle, wherein the heterocyclyl or heterocycle contains 1, 2, 3 or 4 heteroatoms selected from N, O and S" is to be understood as meaning both saturated and partially unsaturated heterocycles, wherein the ring member atoms of the heterocycle include besides carbon atoms 1, 2, 3 or 4 heteroatoms independently selected from the group of O, N and S. For example:

a 3- or 4-membered saturated heterocycle which contains 1 or 2 heteroatoms from the group consisting of O, N and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of O, N and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydro-azepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "substituted" refers to substituted with 1, 2, 3 or up to the maximum possible number of substituents.

The term "5- or 6-membered heteroaryl" refers to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

$R^1$ according to the invention is in each case independently selected from hydrogen, halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; and wherein $R^x$ is $C_1$-$C_4$-alkyl, $C_1$-$C_4$-halogenalkyl, unsubstituted aryl or aryl that is substituted by one, two, three, four or five substituents $R^{x1}$ independently selected from $C_1$-$C_4$-alkyl;

wherein the aliphatic moieties of $R^1$ are unsubstituted or substituted with identical or different groups $R^{1a}$ which independently of one another are selected from:

$R^{1a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or unsubstituted or substituted with $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heteroaryl and aryl moieties of $R^1$ are unsubstituted or substituted with identical or different groups $R^{1b}$ which independently of one another are selected from:

$R^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

For every $R^1$ that is present in the inventive compounds, the following embodiments and preferences apply independently of the meaning of any other $R^1$ that may be present in the ring.

According to a further embodiment, $R^1$ is in each case independently selected from H, halogen or CN.

According to a further embodiment, $R^1$ is in each case independently selected from H, Cl or CN.

According to a further specific embodiment, $R^1$ is hydrogen.

According to a further specific embodiment, $R^1$ is CN.

According to one specific embodiment, $R^1$ is halogen, in particular Br, F or C, more specifically F or C, especially Cl.

According to a further specific embodiment, $R^1$ is OH.

According to a further specific embodiment $R^1$ is $NH_2$, $NH(C_1$-$C_4$-alkyl), $N(C_1$-$C_4$-alkyl)$_2$ or $NH$—$SO_2$—$R^x$, wherein $R^x$ is $C_1$-$C_4$-alkyl, $C_1$-$C_4$-halogenalkyl, unsubstituted aryl or aryl that is substituted by one, two, three, four or five substituents $R^{x1}$ independently selected from $C_1$-$C_4$-alkyl.

According to a further specific embodiment, $R^1$ is $C_1$-$C_6$-alkyl, in particular $C_1$-$C_4$-alkyl, such as $CH_3$.

According to a further specific embodiment, $R^1$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $R^1$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $R^1$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$.

According to a further specific embodiment, $R^1$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^1$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment $R^1$ is $C_3$-$C_6$-cycloalkyl, in particular cyclopropyl.

In a further specific embodiment, $R^1$ is $C_3$-$C_6$-cycloalkyl, for example cyclopropyl, substituted by one, two, three or up to the maximum possible number of identical or different groups $R^{1b}$ as defined and preferably herein.

According to a specific embodiment $R^1$ is $C_3$-$C_6$-halogencycloalkyl. In a special embodiment $R^1$ is fully or partially halogenated cyclopropyl.

According to still a further specific embodiment, $R^1$ is unsubstituted aryl or aryl that is substituted by one, two, three or four $R^{1b}$, as defined herein. In particular, $R^1$ is unsubstituted phenyl or phenyl that is substituted by one, two, three or four $R^{1b}$, as defined herein.

According to still a further specific embodiment, $R^1$ is unsubstituted 5- or 6-membered heteroaryl. According to still a further embodiment, $R^1$ is 5- or 6-membered heteroaryl that is substituted by one, two or three $R^{1b}$, as defined herein.

According to one further embodiment $R^1$ is in each case independently selected from hydrogen, halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl; wherein the aliphatic moieties of $R^1$ are not further substituted or carry one, two, three, four or five identical or different groups $R^{1a}$ as defined below and wherein the cycloalkyl moieties of $R^1$ are not further substituted or carry one, two, three, four or five identical or different groups $R^{1b}$ as defined below.

According to a further embodiment, $R^1$ is independently selected from hydrogen, halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from F, C, Br, CN, OH, $C_1$-$C_4$-alkyl, $C_1$-$C_4$-halogenalkyl, $C_1$-$C_4$-alkoxy and $C_1$-$C_4$-halogenalkoxy.

$R^{1a}$ are the possible substituents for the aliphatic moieties of $R^1$.

$R^{1a}$ according to the invention is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or unsubstituted or substituted with $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $R^{1a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $R^{1a}$ is independently selected from F, C, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $R^{1a}$ is independently selected from halogen, such as F, Cl, Br and I, more specifically F, Cl and Br.

According to a further embodiment, $R^{1a}$ is independently selected from OH, $C_3$-$C_6$-cycloalkyl, $C_3$-$C_6$-halogencycloalkyl and $C_1$-$C_2$-halogenalkoxy. Specifically, $R^{1a}$ is independently selected from OH, cyclopropyl and $C_1$-$C_2$-halogenalkoxy.

$R^{1b}$ are the possible substituents for the cycloalkyl, heteroaryl and aryl moieties of $R^1$.

$R^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $R^{1b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{1b}$ is independently selected from F, Cl, OH, CN, $CH_3$, $OCH_3$, cyclopropyl, 1-F-cyclopropyl, 1-Cl-cyclopropyl and halogenmethoxy.

According to a further embodiment thereof $R^{1b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{1b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

Particularly preferred embodiments of $R^1$ according to the invention are in Table P1 below, wherein each line of lines P1-1 to P1-16 corresponds to one particular embodiment of the invention. Thereby, for every $R^1$ that is present in the inventive compounds, these specific embodiments and preferences apply independently of the meaning of any other $R^1$ that may be present in the ring:

TABLE P1

"Ts" in the table stands for the tosylgroup $SO_2$-(p-$CH_3$)phenyl.

| No. | $R^1$ |
|---|---|
| P1-1 | H |
| P1-2 | Cl |
| P1-3 | F |
| P1-4 | Br |

TABLE P1-continued

"Ts" in the table stands for the tosylgroup $SO_2$-(p-$CH_3$)phenyl.

| No. | $R^1$ |
|---|---|
| P1-5 | OH |
| P1-6 | CN |
| P1-7 | $NO_2$ |
| P1-8 | $CH_3$ |
| P1-9 | —$CH_2CH_3$ |
| P1-10 | $CF_3$ |
| P1-11 | $CHF_2$ |
| P1-12 | $OCH_3$ |
| P1-13 | $OCH_2CH_3$ |
| P1-14 | $OCF_3$ |
| P1-15 | $OCHF_2$ |
| P1-16 | —NH-Ts |

$R^2$ according to the invention is is in each case independently selected from hydrogen, halogen, OH, CN, $NO_2$, SH, $NH_2$, $NH(C_1$-$C_4$-alkyl), $N(C_1$-$C_4$-alkyl$)_2$, NH—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; and wherein $R^x$ is $C_1$-$C_4$-alkyl, $C_1$-$C_4$-halogenalkyl, unsubstituted aryl or aryl that is substituted by one, two, three, four or five substituents $R^{x2}$ independently selected from $C_1$-$C_4$-alkyl; wherein the aliphatic moieties of $R^2$ are unsubstituted or substituted with identical or different groups $R^{2a}$ which independently of one another are selected from:

$R^{2a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or unsubstituted or substituted with $R^{22a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heteroaryl and aryl moieties of $R^2$ are unsubstituted or substituted with identical or different groups $R^{2b}$ which independently of one another are selected from:

$R^{2b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

For every $R^2$ that is present in the inventive compounds, the following embodiments and preferences apply independently of the meaning of the other $R^2$ that may be present in the ring.

According to a further embodiment, $R^1$ is in each case independently selected from H, halogen or CN.

According to a further embodiment, $R^1$ is in each case independently selected from H, Cl or CN.

According to a further specific embodiment, $R^1$ is hydrogen.

According to a further specific embodiment, $R^1$ is CN.

According to one specific embodiment, $R^2$ is halogen, in particular Br, F or C, more specifically F or Cl especially Cl According to a further specific embodiment, $R^2$ is OH.

According to a further specific embodiment $R^2$ is $NH_2$, $NH(C_1$-$C_4$-alkyl), $N(C_1$-$C_4$-alkyl$)_2$ or NH—$SO_2$—$R^x$, wherein $R^x$ is $C_1$-$C_4$-alkyl, $C_1$-$C_4$-halogenalkyl, unsubstituted aryl or aryl that is substituted by one, two, three, four or five substituents $R^{x2}$ independently selected from $C_1$-$C_4$-alkyl.

According to a further specific embodiment, $R^2$ is $C_1$-$C_6$-alkyl, in particular $C_1$-$C_4$-alkyl, such as $CH_3$.

According to a further specific embodiment, $R^2$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $R^2$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $R^2$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$.

According to a further specific embodiment, $R^2$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^2$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment $R^2$ is $C_3$-$C_6$-cycloalkyl, in particular cyclopropyl.

In a further specific embodiment, $R^2$ is $C_3$-$C_6$-cycloalkyl, for example cyclopropyl, substituted by one, two, three or up to the maximum possible number of identical or different groups $R^{2b}$ as defined and preferably herein.

According to a specific embodiment $R^2$ is $C_3$-$C_6$-halogencycloalkyl. In a special embodiment $R^2$ is fully or partially halogenated cyclopropyl.

According to still a further specific embodiment, $R^2$ is unsubstituted aryl or aryl that is substituted by one, two, three or four $R^{2b}$, as defined herein. In particular, $R^2$ is unsubstituted phenyl or phenyl that is substituted by one, two, three or four $R^{2b}$, as defined herein.

According to still a further embodiment, $R^2$ is unsubstituted 5- or 6-membered heteroaryl. According to still a further embodiment, $R^2$ is 5- or 6-membered heteroaryl that is substituted by one, two or three $R^{2b}$, as defined herein.

According to one further embodiment $R^2$ is in each case independently selected from hydrogen, halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl; wherein the aliphatic moieties of $R^2$ are not further substituted or carry one, two, three, four or five identical or different groups $R^{2a}$ as defined below and wherein the cycloalkyl moieties of $R^2$ are not further substituted or carry one, two, three, four or five identical or different groups $R^{2b}$ as defined below.

According to a further embodiment, $R^2$ is independently selected from hydrogen, halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from F, C, Br, CN, OH, $C_1$-$C_4$-alkyl, $C_1$-$C_4$-halogenalkyl, $C_1$-$C_4$-alkoxy and $C_1$-$C_4$-halogenalkoxy.

$R^{2a}$ are the possible substituents for the aliphatic moieties of $R^2$.

$R^{2a}$ according to the invention is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or unsubstituted or substituted with $R^{22a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $R^{2a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $R^{2a}$ is independently selected from F, C, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $R^{2a}$ is independently selected from halogen, such as F, Cl, Br and I, more specifically F, Cl and Br.

According to a further embodiment, $R^{2a}$ is independently selected from OH, $C_3$-$C_6$-cycloalkyl, $C_3$-$C_6$-halogencycloalkyl and $C_1$-$C_2$-halogenalkoxy. Specifically, $R^{2a}$ is independently selected from OH, cyclopropyl and $C_1$-$C_2$-halogenalkoxy.

$R^{2b}$ are the possible substituents for the cycloalkyl, heteroaryl and aryl moieties of $R^2$.

$R^{2b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $R^{2b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{2b}$ is independently selected from F, C, OH, CN, $CH_3$, $OCH_3$, cyclopropyl, 1-F-cyclopropyl, 1-Cl-cyclopropyl and halogenmethoxy.

According to a further embodiment thereof $R^{2b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{2b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

Particularly preferred embodiments of $R^2$ according to the invention are in Table P2 below, wherein each line of lines P2-1 to P2-16 corresponds to one particular embodiment of the invention. Thereby, for every $R^2$ that is present in the inventive compounds, these specific embodiments and preferences apply independently of the meaning of any other $R^2$ that may be present in the ring:

TABLE P2

"Ts" in the table stands for the tosylgroup $SO_2$-(p-$CH_3$)phenyl.

| No. | $R_2$ |
|---|---|
| P2-1 | H |
| P2-2 | Cl |
| P2-3 | F |
| P2-4 | Br |
| P2-5 | OH |
| P2-6 | CN |
| P2-7 | $NO_2$ |
| P2-8 | $CH_3$ |
| P2-9 | $CH_2CH_3$ |
| P2-10 | $CF_3$ |
| P2-11 | $CHF_2$ |
| P2-12 | $OCH_3$ |
| P2-13 | $OCH_2CH_3$ |
| P2-14 | $OCF_3$ |
| P2-15 | $OCHF_2$ |
| P2-16 | NH-Ts |

$R^3$,$R^4$ are independently selected from hydrogen, halogen, OH, CN, $NO_2$, SH, $C_1$-$C_6$-alkylthio, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, a saturated or partially unsaturated three-, four-, five-, six-, seven-, eight-, nine-, or ten-membered carbocycle or heterocycle, wherein in each case one or two $CH_2$ groups of the carbo- and heterocycle may be replaced by a group independently selected from C(=O) and C(=S), five- or six-membered heteroaryl and aryl; wherein the heterocycle and the heteroaryl contain independently one, two, three or four heteroatoms selected from N, O and S; wherein the aliphatic moieties of $R^3$ and $R^4$ are independently unsubstituted or substituted with identical or different groups $R^{3a}$ or $R^{4a}$, respectively, which independently of one another are selected from:

$R^{3a}, R^{4a}$ halogen, OH, CN, $NO_2$, SH, $NH_2$, $NH(C_1-C_4$-alkyl), $N(C_1-C_4$-alkyl)$_2$, $NH(C(=O)C_1-C_4$-alkyl), $N(C(=O)C_1-C_4$-alkyl)$_2$, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, aryl and phenoxy, wherein the aryl and phenyl groups are independently unsubstituted or substituted with substituents selected from the group consisting of halogen, OH, CN, $NO_2$, SH, $NH_2$, $NH(C_1-C_4$-alkyl), $N(C_1-C_4$-alkyl)$_2$, $NH(C(=O)C_1-C_4$-alkyl), $N(C(=O)C_1-C_4$-alkyl)$_2$, $NH-SO_2-R^x$, $C_1-C_6$-alkylthio, $C_1-C_4$-alkyl, $C_1-C_4$-halogenalkyl, $C_1-C_4$-alkoxy and $C_1-C_4$-halogenalkoxy;

wherein the carbocyclic, heterocyclic, heteroaryl and aryl moieties of $R^3$ and $R^4$ are independently unsubstituted or substituted with identical or different groups $R^{3b}$ or $R^{4b}$ respectively, which independently of one another are selected from:

$R^{3b}, R^{4b}$ halogen, OH, CN, $NO_2$, SH, $NH_2$, $NH(C_1-C_4$-alkyl), $N(C_1-C_4$-alkyl)$_2$, $NH(C(=O)C_1-C_4$-alkyl), $N(C(=O)C_1-C_4$-alkyl)$_2$, $NH-SO_2-R^x$, $C_1-C_4$-alkyl, $C_1-C_4$-alkoxy, $C_1-C_4$-halogenalkyl, $C_3-C_6$-cycloalkyl, $C_3-C_6$-halogencycloalkyl, $C_1-C_4$-halogenalkoxy, $C_1-C_6$-alkylthio, $C_1-C_6$-halogenalkylthio, $C_1-C_4$-alkoxy-$C_1-C_4$-alkyl, phenyl and phenoxy, wherein the phenyl groups are unsubstituted or substituted with substituents selected from the group consisting of halogen, OH, $C_1-C_4$-alkyl, $C_1-C_4$-halogenalkyl, $C_1-C_4$-alkoxy and $C_1-C_4$-halogenalkoxy;

and wherein $R^x$ is as defined above;

or $R^3$, $R^4$ together with the carbon atom to which they are bound (marked with * in formula I) form a saturated or partially unsaturated three-, four-, five-, six-, seven-, eight-, nine-, or ten-membered carbocycle or heterocycle; wherein the heterocycle contains one, two, three or four heteroatoms selected from N, O and S, wherein the heteroatom N may carry one substituent $R^N$ selected from $C_1-C_4$-alkyl, $C_1-C_4$-halogenalkyl and $SO_2Ph$, wherein Ph is unsubstituted phenyl or phenyl that is substituted by one, two or three substituents selected from $C_1-C_4$-alkyl, and wherein the heteroatom S may be in the form of its oxide SO or $SO_2$, and wherein the carbocycle or heterocycle is unsubstituted or carries one, two, three or four substituents $R^{34}$ independently selected from halogen, OH, CN, $NO_2$, SH, $NH_2$, $C_1-C_6$-alkyl, $C_1-C_6$-halogenalkyl, $C_1-C_6$-alkoxy, $C_1-C_6$-halogenalkoxy, $C_1-C_6$-alkylthio, $C_1-C_6$-halogenalkylthio, $C_1-C_4$-alkoxy-$C_1-C_4$-alkyl, phenyl and phenoxy, wherein the phenyl groups are unsubstituted or substituted with substituents $R^{34a}$ selected from the group consisting of halogen, OH, $C_1-C_4$-alkyl, $C_1-C_4$-halogenalkyl, $C_1-C_4$-alkoxy and $C_1-C_4$-halogenalkoxy; and wherein in each case one or two $CH_2$ groups of the heterocycle may be replaced by a group independently selected from C(=O) and C(=S).

According to one embodiment, $R^3$ is selected from hydrogen, halogen, OH, CN, SH, $C_1-C_6$-alkylthio, $NH_2$, $NH(C_1-C_4$-alkyl), $N(C_1-C_4$-alkyl)$_2$, $NH-SO_2-R^x$, $C_1-C_6$-alkyl, $C_2-C_6$-alkenyl, $C_2-C_6$-alkynyl, $C_1-C_6$-alkoxy and $C_1-C_6$-halogenalkoxy, in particular hydrogen, halogen, OH, CN, $C_1-C_4$-alkylthio, $C_1-C_6$-alkyl, $C_2-C_6$-alkenyl, $C_2-C_6$-alkynyl, $C_1-C_6$-alkoxy and $C_1-C_6$-halogenalkoxy, wherein $R^x$ is defined below; and wherein the aliphatic moieties of $R^4$ are unsubstituted or substituted with identical or different groups $R^{3a}$ as defined below.

According to a further embodiment, $R^3$ is selected from halogen, OH, CN, SH, $C_1-C_6$-alkylthio, $NH_2$, $NH(C_1-C_4$-alkyl), $N(C_1-C_4$-alkyl)$_2$, $NH-SO_2-R^x$, $C_1-C_6$-alkyl, $C_2-C_6$-alkenyl, $C_2-C_6$-alkynyl, $C_1-C_6$-alkoxy and $C_1-C_6$-halogenalkoxy, in particular halogen, OH, CN, $C_1-C_4$-alkylthio, $C_1-C_6$-alkyl, $C_2-C_6$-alkenyl, $C_2-C_6$-alkynyl, $C_1-C_6$-alkoxy and $C_1-C_6$-halogenalkoxy, wherein $R^x$ is defined below; and wherein the aliphatic moieties of $R^4$ are unsubstituted or substituted with identical or different groups $R^{3a}$ as defined below.

According to one particular embodiment, $R^3$ is hydrogen.

According to a further particular embodiment, $R^3$ is hydrogen or $C_1-C_6$-alkyl, such as hydrogen, methyl, ethyl, n-propyl, i-propyl, n-butyl, i-butyl, tert-butyl, n-pentyl or i-pentyl.

According to a further particular embodiment, $R^3$ is hydrogen or $CH_3$.

According to a further particular embodiment, $R^3$ is $C_1-C_6$-alkyl, such as methyl, ethyl, n-propyl, i-propyl, n-butyl, i-butyl, tert-butyl, n-pentyl or i-pentyl.

According to a further particular embodiment, $R^3$ is hydrogen or $C_1-C_6$-halogenalkyl, in particular hydrogen or $C_1-C_4$-halogenalkyl, more specifically hydrogen or $C_1-C_2$-halogenalkyl, such as H, $CF_3$, $CCl_3$, $FCH_2$, $ClCH_2$, $F_2CH$, $Cl_2CH$, $CF_3CH_2$, $CCl_3CH_2$ or $CF_2CHF_2$.

According to a further particular embodiment, $R^3$ is $C_1-C_6$-halogenalkyl, in particular $C_1-C_4$-halogenalkyl, more specifically $C_1-C_2$-halogenalkyl, such as $CF_3$, $CCl_3$, $FCH_2$, $ClCH_2$, $F_2CH$, $Cl_2CH$, $CF_3CH_2$, $CCl_3CH_2$ or $CF_2CHF_2$.

According to a further particular embodiment, $R^3$ is hydrogen or phenyl-$C_1-C_6$-alkyl, such as hydrogen or phenyl-$CH_2$, wherein the phenyl moiety in each case is unsubstituted or substituted by one, two or three identical or different groups $R^{3b}$ which independently of one another are selected from halogen, $C_1-C_2$-alkyl, $C_1-C_2$-alkoxy, $C_1-C_2$-halogenalkyl and $C_1-C_2$-halogenalkoxy, in particular selected from F, Cl, Br, methyl, $OCH_3$, $CF_3$ and $OCF_3$.

According to a further particular embodiment, $R^3$ is phenyl-$C_1-C_6$-alkyl, such as phenyl-$CH_2$, wherein the phenyl moiety in each case is unsubstituted or substituted by one, two or three identical or different groups $R^{3b}$ which independently of one another are selected from halogen, $C_1-C_2$-alkyl, $C_1-C_2$-alkoxy, $C_1-C_2$-halogenalkyl and $C_1-C_2$-halogenalkoxy, in particular F, Cl, Br, methyl, $OCH_3$, $CF_3$ and $OCF_3$.

According to a further particular embodiment, $R^3$ is hydrogen or aryl, in particular H or phenyl, wherein the aryl or phenyl moiety in each case is unsubstituted or carries one, two or three identical or different groups $R^{3b}$ which independently of one another are selected from halogen, $C_1-C_2$-alkyl, $C_1-C_2$-alkoxy, $C_1-C_2$-halogenalkyl and $C_1-C_2$-halogenalkoxy, in particular F, Cl, Br, methyl, $OCH_3$, $CF_3$ and $OCF_3$. In one embodiment, $R^3$ is H or unsubstituted phenyl. In another embodiment, $R^3$ is H or phenyl, that is substituted by one, two or three, in particular one, halogen, in particular selected from F, Cl and Br, more specifically selected from F and Cl.

According to a further particular embodiment, $R^4$ is aryl, in particular phenyl, wherein the aryl or phenyl moiety in each case is unsubstituted or carries one, two or three identical or different groups $R^{3b}$ which independently of one another are selected from halogen, $C_1-C_2$-alkyl, $C_1-C_2$-alkoxy, $C_1-C_2$-halogenalkyl and $C_1-C_2$-halogenalkoxy, in particular F, Cl, Br, methyl, $OCH_3$, $CF_3$ and $OCF_3$. In one embodiment, $R^3$ is unsubstituted phenyl. In another embodiment, $R^3$ is phenyl, that is substituted by one, two or three, in particular one, halogen, in particular selected from F, Cl and Br, more specifically selected from F and Cl.

According to a further embodiment, $R^3$ is hydrogen or a partially unsaturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{3b}$ as defined below. According to one embodiment thereof, the carbocycle or heterocycle is unsubstituted.

According to a further embodiment, $R^3$ is a partially unsaturated three-, four-, five-, six-, seven-eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{3b}$ as defined below. According to one embodiment thereof, the carbocycle or heterocycle is unsubstituted.

According to still a further embodiment, $R^3$ is hydrogen or a saturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{3b}$ as defined below. According to one embodiment thereof, the carbocycle or heterocycle is unsubstituted.

According to still a further embodiment, $R^3$ is a saturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{3b}$ as defined below. According to one embodiment thereof, the carbocycle or heterocycle is unsubstituted.

According to a further embodiment, $R^3$ is hydrogen or a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{3b}$ as defined below. According to one embodiment thereof, the heterocycle is unsubstituted.

According to a further embodiment, $R^3$ is a partially unsaturated three-, four-, five-, six-, seven-eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{3b}$ as defined below. According to one embodiment thereof, the heterocycle is unsubstituted.

According to a further embodiment, $R^3$ is hydrogen or a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{3a}$ as defined below. According to one embodiment thereof, the heterocycle is unsubstituted.

According to a further embodiment, $R^3$ is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{3b}$ as defined below. According to one embodiment thereof, the heterocycle is unsubstituted.

According to a further embodiment, in the embodiments of $R^3$ described above, the heterocycle contains preferably one, two or three, more specifically one or two heteroatoms selected from N, O and S. More specifically, the hetereocycle contains one heteroatom selected from N, O and S. In particular, the heterocycle contains one or two, in particular one O.

According to one particular embodiment, $R^3$ is hydrogen or a 4-membered saturated heterocycle which contains 1 or 2 heteroatoms, in particular 1 heteroatom, from the group consisting of N, O and S, as ring members. In one embodiment, the heterocycle contains one O as heteroatom. For example, the formed heterocycle is oxetane. According to one embodiment thereof, the heterocycle is unsubstituted, i.e. it does not carry any substituent $R^{3b}$. According to a further embodiment, it carries one, two, three or four $R^{3b}$ According to a further particular embodiment, $R^3$ is hydrogen or a 5-membered saturated heterocycle which contains 1, 2 or 3, in particular 1 or 2, heteroatoms from the group consisting of N, O and S, as ring members. In one embodiment, the heterocycle contains one O as heteroatom. According to one embodiment thereof, the heterocycle is unsubstituted, i.e. it does not carry any substituent $R^{3b}$. According to a further embodiment, it carries one, two, three or four $R^{3b}$.

According to a further particular embodiment, $R^3$ is a 5-membered saturated heterocycle which contains 1, 2 or 3, in particular 1 or 2, heteroatoms from the group consisting of N, O and S, as ring members. In one embodiment, the heterocycle contains one O as heteroatom. According to one embodiment thereof, the heterocycle is unsubstituted, i.e. it does not carry any substituent $R^{3b}$. According to a further embodiment, it carries one, two, three or four $R^{3b}$ According to a further particular embodiment, $R^3$ is hydrogen or a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $R^{3b}$. According to a further embodiment, it carries one, two, three or four $R^{3b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $R^{3b}$. According to a further embodiment, it carries one, two, three or four $R^{3b}$.

According to a further particular embodiment, $R^3$ is a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $R^{3b}$. According to a further embodiment, it carries one, two, three or four $R^{3b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $R^{3b}$. According to a further embodiment, it carries one, two, three or four $R^{3b}$ According to a further embodiment, $R^3$ is hydrogen or a partially unsaturated three-, four-, five-six-, seven-, eight-, nine-, or ten-membered carbocycle, in particular three-, four-, five- or six-membered, wherein the carbocycle is unsubstituted or carries one, two, three or four substituents $R^{3b}$ as defined below. According to one embodiment thereof, the carbocycle is unsubstituted.

According to a further embodiment, $R^3$ is a partially unsaturated three-, four-, five-, six-, seven-eight-, nine-, or ten-membered carbocycle, in particular three-, four-, five- or six-membered, wherein the carbocycle is unsubstituted or carries one, two, three or four substituents $R^{3b}$ as defined below. According to one embodiment thereof, the carbocycle is unsubstituted.

According to a further embodiment, $R^3$ is hydrogen or a saturated three-, four-, five-, six-, seven-, eight-, nine-, or ten-membered carbocycle, in particular three-, four-, five- or six-membered, wherein the carbocycle is unsubstituted or carries one, two, three or four substituents $R^{3b}$ as defined below. According to one embodiment thereof, the carbocycle is unsubstituted.

According to a further embodiment, $R^3$ is a saturated three-, four-, five-, six-, seven-, eight-, nine-, or ten-membered carbocycle, in particular three-, four-, five- or six-membered, wherein the carbocycle is unsubstituted or carries one, two, three or four substituents $R^{3b}$ as defined below. According to one embodiment thereof, the carbocycle is unsubstituted.

According to one particular embodiment, $R^3$ is hydrogen or a 3-membered saturated carbocycle. According to one embodiment thereof, the carbocycle is unsubstituted, i.e. it does not carry any substituent $R^{4a}$. According to a further embodiment, it carries one, two, three or four $R^{3b}$ According to one particular embodiment, $R^3$ is a 3-membered saturated carbocycle. According to one embodiment thereof, the carbocycle is unsubstituted, i.e. it does not carry any substituent $R^{3b}$. According to a further embodiment, it carries one, two, three or four $R^{3b}$ According to one particular embodiment, $R^3$ is hydrogen or a 4-membered saturated carbocycle. According to one embodiment thereof, the carbocycle is unsubstituted, i.e. it does not carry any substituent $R^{3b}$. According to a further embodiment, it carries one, two, three or four $R^{3b}$ According to one particular embodiment, $R^3$ is a 4-membered saturated carbocycle. According to one embodiment thereof, the carbocycle is unsubstituted, i.e. it does not carry any substituent $R^{3b}$. According to a further embodiment, it carries one, two, three or four $R^{3b}$ According to one particular embodiment, $R^3$ is hydrogen or a 5-membered saturated carbocycle. According to one embodiment thereof, the carbocycle is unsubstituted, i.e. it does not carry any substituent $R^{3b}$. According to a further embodiment, it carries one, two, three or four $R^{3b}$ According to one particular embodiment, $R^3$ is a 5-membered saturated carbocycle. According to one embodiment thereof, the carbocycle is unsubstituted, i.e. it does not carry any substituent $R^{3b}$. According to a further embodiment, it carries one, two, three or four $R^{3b}$ According to one particular embodiment, $R^3$ is hydrogen or a 6-membered saturated carbocycle. According to one embodiment thereof, the carbocycle is unsubstituted, i.e. it does not carry any substituent $R^{3b}$. According to a further embodiment, it carries one, two, three or four $R^{3b}$ According to one particular embodiment, $R^3$ is a 6-membered saturated carbocycle. According to one embodiment thereof, the carbocycle is unsubstituted, i.e. it does not carry any substituent $R^{3b}$. According to a further embodiment, it carries one, two, three or four $R^{3b}$ According to a further particular embodiment, $R^3$ is selected from hydrogen, $C_1$-$C_6$-alkyl, $C_1$-$C_6$-halogenalkyl, phenyl-$C_1$-$C_6$-alkyl, halogenphenyl-$C_1$-$C_6$-alkyl, phenyl, halogenphenyl and three-, four-, five- or six-membered carbocycle, wherein the carbocycle is unsubstituted or carries one, two, three or four substituents $R^{3b}$ as defined below. According to one embodiment thereof, the carbocycle is unsubstituted. In a particular embodiment, $R^3$ is selected from hydrogen, $C_1$-$C_6$-alkyl, $C_1$-$C_6$-halogenalkyl, phenyl-$CH_2$, halogenphenyl-$CH_2$, phenyl, halogenphenyl and three-, four-, five- or six-membered carbocycle, wherein the carbocycle is unsubstituted or carries one, two, three or four substituents $R^{3b}$ as defined below.

According to a further particular embodiment, $R^3$ is selected from $C_1$-$C_6$-alkyl, $C_1$-$C_6$-halogenalkyl, phenyl-$C_1$-$C_6$-alkyl, halogenphenyl-$C_1$-$C_6$-alkyl, phenyl, halogenphenyl and three-, four-, five- or six-membered carbocycle, wherein the carbocycle is unsubstituted or carries one, two, three or four substituents $R^{3b}$ as defined below. According to one embodiment thereof, the carbocycle is unsubstituted. In a particular embodiment, $R^3$ is selected from $C_1$-$C_6$-alkyl, $C_1$-$C_6$-halogenalkyl, phenyl-$CH_2$, halogenphenyl-$CH_2$, phenyl, halogenphenyl and three-, four-, five- or six-membered carbocycle, wherein the carbocycle is unsubstituted or carries one, two, three or four substituents $R^{3b}$ as defined below.

Particularly preferred embodiments of $R^3$ according to the invention are in Table P3 below, wherein each line of lines P3-1 to P3-33 corresponds to one particular embodiment of the invention. The connection point to the carbon atom, to which $R^3$ is bound is marked with "#" in the drawings.

TABLE P3

| No. | $R^3$ |
|---|---|
| P3-1 | H |
| P3-2 | $CH_3$ |
| P3-3 | $C_2H_5$ |
| P3-4 | $CH_2CH_2CH_3$ |
| P3-5 | $CH(CH_3)_2$ |
| P3-6 | $CH_2CH_2CH_2CH_3$ |
| P3-7 | $CH_2CH(CH_3)_2$ |
| P3-8 | $C(CH_3)_3$ |
| P3-9 | $CH_2CH_2CH_2CH_2CH_3$ |
| P3-10 | $CH_2CH_2CH(CH_3)_2$ |
| P3-11 | $CF_3$ |
| P3-12 | $CHF_2$ |
| P3-13 | $CHCl_2$ |
| P3-14 | $CH_2F$ |
| P3-15 | $CH_2Cl$ |
| P3-16 | $CH_2CF_3$ |
| P3-17 | $CH_2CCl_3$ |
| P3-18 | $CF_2CHF_2$ |
| P3-19 | $C_6H_5$ |
| P3-20 | 4-Cl—$C_6H_4$ |
| P3-21 | 4-F—$C_6H_4$ |
| P3-22 | $CH_2$—$C_6H_5$ |
| P3-23 | 3-pyridyl |
| P3-24 | 2-pyridyl |
| P3-25 | 4-pyridyl |
| P3-26 | 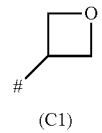 (C1) |
| P3-27 | 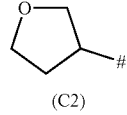 (C2) |

TABLE P3-continued

| No. | R³ |
|---|---|
| P3-28 | 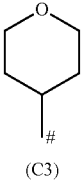 (C3) |
| P3-29 |  (C4) |
| P3-30 | 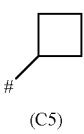 (C5) |
| P3-31 | 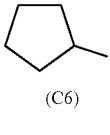 (C6) |
| P3-32 | 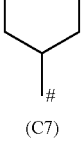 (C7) |
| P3-33 |  (C8) |

According to one embodiment, $R^4$ is selected from hydrogen, halogen, OH, CN, SH, $C_1$-$C_6$-alkylthio, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy and $C_1$-$C_6$-halogenalkoxy, in particular hydrogen, halogen, OH, CN, $C_1$-$C_4$-alkylthio, $C_1$-$C_6$-alkyl, $C_2$-$C_6$-alkenyl, $C_2$-$C_6$-alkynyl, $C_1$-$C_6$-alkoxy and $C_1$-$C_6$-halogenalkoxy, wherein $R^x$ is defined below; and wherein the aliphatic moieties of $R^4$ are unsubstituted or substituted with identical or different groups $R^{4a}$ as defined below.

According to a further embodiment, $R^4$ is selected from halogen, OH, CN, SH, $C_1$-$C_6$-alkylthio, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy and $C_1$-$C_6$-halogenalkoxy, in particular halogen, OH, CN, $C_1$-$C_4$-alkylthio, $C_1$-$C_6$-alkyl, $C_2$-$C_6$-alkenyl, $C_2$-$C_6$-alkynyl, $C_1$-$C_6$-alkoxy and $C_1$-$C_6$-halogenalkoxy, wherein $R^x$ is defined below; and wherein the aliphatic moieties of $R^4$ are unsubstituted or substituted with identical or different groups $R^{4a}$ as defined below.

According to one particular embodiment, $R^4$ is hydrogen.

According to a further particular embodiment, $R^4$ is hydrogen or $C_1$-$C_6$-alkyl, such as hydrogen, methyl, ethyl, n-propyl, i-propyl, n-butyl, i-butyl, tert-butyl, n-pentyl or i-pentyl.

According to a further particular embodiment, $R^3$ is hydrogen or $CH_3$.

According to a further particular embodiment, $R^4$ is $C_1$-$C_6$-alkyl, such as methyl, ethyl, n-propyl, i-propyl, n-butyl, i-butyl, tert-butyl, n-pentyl or i-pentyl.

According to a further particular embodiment, $R^4$ is hydrogen or $C_1$-$C_6$-halogenalkyl, in particular hydrogen or $C_1$-$C_4$-halogenalkyl, more specifically hydrogen or $C_1$-$C_2$-halogenalkyl, such as H, $CF_3$, $CCl_3$, $FCH_2$, $ClCH_2$, $F_2CH$, $Cl_2CH$, $CF_3CH_2$, $CCl_3CH_2$ or $CF_2CHF_2$.

According to a further particular embodiment, $R^4$ is $C_1$-$C_6$-halogenalkyl, in particular $C_1$-$C_4$-halogenalkyl, more specifically $C_1$-$C_2$-halogenalkyl, such as $CF_3$, $CCl_3$, $FCH_2$, $ClCH_2$, $F_2CH$, $Cl_2CH$, $CF_3CH_2$, $CCl_3CH_2$ or $CF_2CHF_2$.

According to a further particular embodiment, $R^4$ is hydrogen or phenyl-$C_1$-$C_6$-alkyl, such as hydrogen or phenyl-$CH_2$, wherein the phenyl moiety in each case is unsubstituted or substituted by one, two or three identical or different groups $R^{4b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular selected from F, C, Br, methyl, $OCH_3$, $CF_3$ and $OCF_3$.

According to a further particular embodiment, $R^4$ is phenyl-$C_1$-$C_6$-alkyl, such as phenyl-$CH_2$, wherein the phenyl moiety in each case is unsubstituted or substituted by one, two or three identical or different groups $R^{4b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, C, Br, methyl, $OCH_3$, $CF_3$ and $OCF_3$.

According to a further particular embodiment, $R^4$ is hydrogen or aryl, in particular H or phenyl, wherein the aryl or phenyl moiety in each case is unsubstituted or carries one, two or three identical or different groups $R^{4b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, C, Br, methyl, $OCH_3$, $CF_3$ and $OCF_3$. In one embodiment, $R^4$ is H or unsubstituted phenyl. In another embodiment, $R^4$ is H or phenyl, that is substituted by one, two or three, in particular one, halogen, in particular selected from F, Cl and Br, more specifically selected from F and C.

According to a further particular embodiment, $R^4$ is aryl, in particular phenyl, wherein the aryl or phenyl moiety in each case is unsubstituted or carries one, two or three identical or different groups $R^{4b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, C, Br, methyl, $OCH_3$, $CF_3$ and $OCF_3$. In one embodiment, $R^4$ is unsubstituted phenyl. In another embodiment, $R^4$ is phenyl, that is substituted by one, two or three, in particular one, halogen, in particular selected from F, Cl and Br, more specifically selected from F and Cl.

According to a further embodiment, $R^4$ is hydrogen or a partially unsaturated three-, four-, five-six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{4b}$ as defined below. According to one embodiment thereof, the carbocycle or heterocycle is unsubstituted.

According to a further embodiment, $R^4$ is a partially unsaturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{4b}$ as defined below. According to one embodiment thereof, the carbocycle or heterocycle is unsubstituted.

According to still a further embodiment, $R^4$ is hydrogen or a saturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{4b}$ as defined below. According to one embodiment thereof, the carbocycle or heterocycle is unsubstituted.

According to still a further embodiment, $R^4$ is a saturated three-, four-, five-, six-, seven-, eight-nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $R^{4b}$ as defined below. According to one embodiment thereof, the carbocycle or heterocycle is unsubstituted.

According to a further embodiment, $R^4$ is hydrogen or a partially unsaturated three-, four-, five-six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{4b}$ as defined below. According to one embodiment thereof, the heterocycle is unsubstituted.

According to a further embodiment, $R^4$ is a partially unsaturated three-, four-, five-, six-, seven-eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{4b}$ as defined below. According to one embodiment thereof, the heterocycle is unsubstituted.

According to a further embodiment, $R^4$ is hydrogen or a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{4a}$ as defined below. According to one embodiment thereof, the heterocycle is unsubstituted.

According to a further embodiment, $R^4$ is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or carries one, two, three or four substituents $R^{4b}$ as defined below. According to one embodiment thereof, the heterocycle is unsubstituted.

According to a further embodiment, in the embodiments of $R^4$ described above, the heterocycle contains preferably one, two or three, more specifically one or two heteroatoms selected from N, O and S. More specifically, the heterocycle contains one heteroatom selected from N, O and S. In particular, the heterocycle contains one or two, in particular one O.

According to one particular embodiment, $R^4$ is hydrogen or a 4-membered saturated heterocycle which contains 1 or 2 heteroatoms, in particular 1 heteroatom, from the group consisting of N, O and S, as ring members. In one embodiment, the heterocycle contains one O as heteroatom. For example, the formed heterocycle is oxetane. According to one embodiment thereof, the heterocycle is unsubstituted, i.e. it does not carry any substituent $R^{4b}$. According to a further embodiment, it carries one, two, three or four $R^{4b}$.

According to one particular embodiment, $R^4$ is a 4-membered saturated heterocycle which contains 1 or 2 heteroatoms, in particular 1 heteroatom, from the group consisting of N, O and S, as ring members. In one embodiment, the heterocycle contains one O as heteroatom. For example, the formed heterocycle is oxetane. According to one embodiment thereof, the heterocycle is unsubstituted, i.e. it does not carry any substituent $R^{4b}$. According to a further embodiment, it carries one, two, three or four $R^{4b}$.

According to a further particular embodiment, $R^4$ is hydrogen or a 5-membered saturated heterocycle which contains 1, 2 or 3, in particular 1 or 2, heteroatoms from the group consisting of N, O and S, as ring members. In one embodiment, the heterocycle contains one O as heteroatom. According to one embodiment thereof, the heterocycle is unsubstituted, i.e. it does not carry any substituent $R^{4b}$. According to a further embodiment, it carries one, two, three or four $R^{4b}$.

According to a further particular embodiment, $R^4$ is a 5-membered saturated heterocycle which contains 1, 2 or 3, in particular 1 or 2, heteroatoms from the group consisting of N, O and S, as ring members. In one embodiment, the heterocycle contains one O as heteroatom. According to one embodiment thereof, the heterocycle is unsubstituted, i.e. it does not carry any substituent $R^{4b}$. According to a further embodiment, it carries one, two, three or four $R^{4b}$.

According to a further particular embodiment, $R^4$ is hydrogen or a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $R^{4b}$. According to a further embodiment, it carries one, two, three or four $R^{4b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $R^{4b}$. According to a further embodiment, it carries one, two, three or four $R^{4b}$.

According to a further particular embodiment, $R^4$ is a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $R^{4b}$. According to a further embodiment, it carries one, two, three or four $R^{4b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $R^{4b}$. According to a further embodiment, it carries one, two, three or four $R^{4b}$.

According to a further embodiment, $R^4$ is hydrogen or a partially unsaturated three-, four-, five-, six-, seven-, eight-, nine-, or ten-membered carbocycle, in particular three-, four-, five- or six-membered, wherein the carbocycle is unsubstituted or carries one, two, three or four substituents $R^{4b}$ as defined below. According to one embodiment thereof, the carbocycle is unsubstituted.

According to a further embodiment, $R^4$ is a partially unsaturated three-, four-, five-, six-, seven-, eight-, nine-, or ten-membered carbocycle, in particular three-, four-, five- or six-membered, wherein the carbocycle is unsubstituted or carries one, two, three or four substituents $R^{4b}$ as defined below. According to one embodiment thereof, the carbocycle is unsubstituted.

According to a further embodiment, $R^4$ is hydrogen or a saturated three-, four-, five-, six-, seven-, eight-, nine-, or ten-membered carbocycle, in particular three-, four-, five- or six-membered, wherein the carbocycle is unsubstituted or carries one, two, three or four substituents $R^{4b}$ as defined below. According to one embodiment thereof, the carbocycle is unsubstituted.

According to a further embodiment, $R^4$ is a saturated three-, four-, five-, six-, seven-, eight-, nine-, or ten-membered carbocycle, in particular three-, four-, five- or six-membered, wherein the carbocycle is unsubstituted or carries one, two, three or four substituents $R^{4b}$ as defined below. According to one embodiment thereof, the carbocycle is unsubstituted.

According to one particular embodiment, $R^4$ is hydrogen or a 3-membered saturated carbocycle. According to one embodiment thereof, the carbocycle is unsubstituted, i.e. it does not carry any substituent $R^{4a}$. According to a further embodiment, it carries one, two, three or four $R^{4b}$.

According to one particular embodiment, $R^4$ is a 3-membered saturated carbocycle. According to one embodiment thereof, the carbocycle is unsubstituted, i.e. it does not carry any substituent $R^{4b}$. According to a further embodiment, it carries one, two, three or four $R^{4b}$.

According to one particular embodiment, $R^4$ is hydrogen or a 4-membered saturated carbocycle. According to one embodiment thereof, the carbocycle is unsubstituted, i.e. it does not carry any substituent $R^{4b}$. According to a further embodiment, it carries one, two, three or four $R^{4b}$.

According to one particular embodiment, $R^4$ is a 4-membered saturated carbocycle. According to one embodiment thereof, the carbocycle is unsubstituted, i.e. it does not carry any substituent $R^{4b}$. According to a further embodiment, it carries one, two, three or four $R^{4b}$.

According to one particular embodiment, $R^4$ is hydrogen or a 5-membered saturated carbocycle. According to one embodiment thereof, the carbocycle is unsubstituted, i.e. it does not carry any substituent $R^{4b}$. According to a further embodiment, it carries one, two, three or four $R^{4b}$.

According to one particular embodiment, $R^4$ is a 5-membered saturated carbocycle. According to one embodiment thereof, the carbocycle is unsubstituted, i.e. it does not carry any substituent $R^{4b}$. According to a further embodiment, it carries one, two, three or four $R^{4b}$.

According to one particular embodiment, $R^4$ is hydrogen or a 6-membered saturated carbocycle. According to one embodiment thereof, the carbocycle is unsubstituted, i.e. it does not carry any substituent $R^{4b}$. According to a further embodiment, it carries one, two, three or four $R^{4b}$ According to one particular embodiment, $R^4$ is a 6-membered saturated carbocycle. According to one embodiment thereof, the carbocycle is unsubstituted, i.e. it does not carry any substituent $R^{4b}$. According to a further embodiment, it carries one, two, three or four $R^{4b}$.

According to a further particular embodiment, $R^4$ is selected from hydrogen, $C_1$-$C_6$-alkyl, $C_1$-$C_6$ halogenalkyl, phenyl-$C_1$-$C_6$-alkyl, halogenphenyl-$C_1$-$C_6$-alkyl, phenyl, halogenphenyl and three-, four-, five- or six-membered carbocycle, wherein the carbocycle is unsubstituted or carries one, two, three or four substituents $R^{4b}$ as defined below. According to one embodiment thereof, the carbocycle is unsubstituted. In a particular embodiment, $R^4$ is selected from hydrogen, $C_1$-$C_6$-alkyl, $C_1$-$C_6$-halogenalkyl, phenyl-$CH_2$, halogenphenyl-$CH_2$, phenyl, halogenphenyl and three-, four-, five- or six-membered carbocycle, wherein the carbocycle is unsubstituted or carries one, two, three or four substituents $R^{4b}$ as defined below.

According to a further particular embodiment, $R^4$ is selected from $C_1$-$C_6$-alkyl, $C_1$-$C_6$-halogenalkyl, phenyl-$C_1$-$C_6$-alkyl, halogenphenyl-$C_1$-$C_6$-alkyl, phenyl, halogenphenyl and three-, four-, five- or six-membered carbocycle, wherein the carbocycle is unsubstituted or carries one, two, three or four substituents $R^{4b}$ as defined below. According to one embodiment thereof, the carbocycle is unsubstituted. In a particular embodiment, $R^4$ is selected from $C_1$-$C_6$-alkyl, $C_1$-$C_6$-halogenalkyl, phenyl-$CH_2$, halogenphenyl-$CH_2$, phenyl, halogenphenyl and three-, four-, five- or six-membered carbocycle, wherein the carbocycle is unsubstituted or carries one, two, three or four substituents $R^{4b}$ as defined below.

Particularly preferred embodiments of $R^4$ according to the invention are in Table P4 below, wherein each line of lines P4-1 to P4-33 corresponds to one particular embodiment of the invention, wherein P4-1 to P4-33 are also in any combination with one another a preferred embodiment of the present invention. The connection point to the carbon atom, to which $R^4$ is bound is marked with "#" in the drawings.

TABLE P4

| No. | $R^4$ |
| --- | --- |
| P4-1 | H |
| P4-2 | $CH_3$ |
| P4-3 | $C_2H_5$ |
| P4-4 | $CH_2CH_2CH_3$ |
| P4-5 | $CH(CH_3)_2$ |
| P4-6 | $CH_2CH_2CH_2CH_3$ |
| P4-7 | $CH_2CH(CH_3)_2$ |
| P4-8 | $C(CH_3)_3$ |
| P4-9 | $CH_2CH_2CH_2CH_2CH_3$ |
| P4-10 | $CH_2CH_2CH(CH_3)_2$ |
| P4-11 | $CF_3$ |
| P4-12 | $CHF_2$ |
| P4-13 | $CHCl_2$ |
| P4-14 | $CH_2F$ |
| P4-15 | $CH_2Cl$ |
| P4-16 | $CH_2CF_3$ |
| P4-17 | $CH_2CCl_3$ |
| P4-18 | $CF_2CHF_2$ |
| P4-19 | $C_6H_5$ |
| P4-20 | 4-Cl—$C_6H_4$ |
| P4-21 | 4-F—$C_6H_4$ |
| P4-22 | $CH_2$—$C_6H_5$ |
| P4-23 | 3-pyridyl |
| P4-24 | 2-pyridyl |
| P4-25 | 4-pyridyl |
| P4-26 | C1 |
| P4-27 | C2 |
| P4-28 | C3 |
| P4-29 | C4 |
| P4-30 | C5 |
| P4-31 | C6 |
| P4-32 | C7 |
| P4-33 | C8 |

According to a further embodiment, $R^3$ and $R^4$ together with the carbon atom to which they are bound (marked with * in formula I) form a saturated or partially unsaturated three-, four-, five-, six-, seven-, eight-, nine-, or ten-membered carbocycle or heterocycle; wherein the heterocycle contains one, two, three or four heteroatoms selected from N, O and S, wherein the heteroatom N may carry one substituent $R^N$ selected from $C_1$-$C_4$-alkyl, $C_1$-$C_4$-halogenalkyl and $SO_2Ph$, wherein Ph is unsubstituted phenyl or phenyl that is substituted by one, two or three substituents selected from $C_1$-$C_4$-alkyl, and wherein the heteroatom S may be in the form of its oxide SO or $SO_2$, and wherein the carbocycle or heterocycle is unsubstituted or carries one, two, three or four substituents $R^{34}$ independently selected from halogen, OH, CN, $NO_2$, SH, $NH_2$, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_1$-$C_4$-alkoxy-$C_1$-$C_4$-alkyl, phenyl and phenoxy, wherein the phenyl groups are unsubstituted or substituted with substituents $R^{34a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein in each case one or two $CH_2$ groups of the carbo- or heterocycle may be replaced by a group independently selected from $C(=O)$ and $C(=S)$.

According to one embodiment, $R^3$ and $R^4$ together with the carbon atom to which they are bound (marked with * in formula I) form a saturated or partially unsaturated three-, four-, five-, six-, seven-, eight-, nine-, or ten-membered heterocycle that is unsubstituted or substituted.

According to a further embodiment, the heterocycle formed by $R^3$ and $R^4$ is saturated.

According to a further embodiment, the heterocycle formed by $R^3$ and $R^4$ is a saturated unsubstituted or substituted heterocycle, wherein the heterocycle contains one, two or three, more particularly one or two, specifically one, heteroatom(s) selected from NH, $NR^N$, O, S, $S(=O)$ and $S(=O)_2$, wherein $R^N$ is defined and preferably defined above. According to one embodiment, this saturated heterocycle is unsubstituted. According to a further embodiment, the saturated heterocycle carries one, two, three or four substituents $R^{34}$. In one further particular embodiment, said heterocycle is four- or six-membered.

According to a further embodiment, the unsubstituted or substituted and saturated or partially unsaturated heterocycle is three-, four-, five- or six-membered and contains one, two or three, more particularly one or two, heteroatoms selected from NH, $NR^N$, O, S, $S(=O)$ and $S(=O)_2$, wherein $R^N$ is as defined above or preferably selected from $C_1$-$C_2$-alkyl, $C_1$-$C_2$-halogenalkyl and $SO_2Ph$, wherein Ph is unsubstituted phenyl or phenyl that is substituted by one $C_1$-$C_2$-alkyl. In one further particular embodiment, said heterocycle is four- or six-membered.

According to a further embodiment, the heterocycle formed by $R^3$ and $R^4$ contains one, two or three, more specifically one or two, heteroatoms selected from NH and $NR^N$, wherein $R^N$ is as defined and preferably defined below, more particularly selected from $C_1$-$C_2$-alkyl, $C_1$-$C_2$-halogenalkyl and $SO_2Ph$, wherein Ph is unsubstituted phenyl or phenyl that is substituted by one methyl. In one embodiment thereof, it contains one or two heteroatoms NH, in particular one NH. In another embodiment, it contains one or two heteroatoms $NR^N$, in particular one $NR^N$ wherein $R^N$ n each case is as defined and preferably defined above.

According to a further embodiment, the heterocycle formed by $R^3$ and $R^4$ contains one, two or three, more specifically one or two, in particular one, heteroatom(s) selected from S, $S(=O)$ and $S(=O)_2$. In one embodiment thereof, it contains one or two heteroatoms S, in particular one S. In another embodiment, it contains one or two heteroatoms $S(=O)$, in particular one $S(=O)$. In still another embodiment, it contains one or two heteroatoms $S(=O)_2$, in particular one $S(=O)_2$.

According to a further embodiment, the heterocycle formed by $R^3$ and $R^4$ contains one or two heteroatoms O. In one embodiment thereof, it contains one heteroatom O. In another embodiment, it contains two heteroatoms O.

According to a further embodiment, the heterocycle formed by $R^3$ and $R^4$ is unsubstituted, i.e. it does not carry any substituent $R^{34}$. According to a further embodiment, it carries one, two, three or four $R^{34}$ According to one particular embodiment, $R^3$ and $R^4$ together form a 4-membered saturated heterocycle which contains 1 or 2 heteroatoms, in particular 1 heteroatom, from the group consisting of NH, $NR^N$, O, S, $S(=O)$ and $S(=O)_2$, as ring members, wherein $R^N$ is defined and preferably defined above. In one embodiment, the heterocycle contains one 0 as heteroatom. For example, the formed heterocycle is oxetane. According to one embodiment thereof, the heterocycle is unsubstituted, i.e. it does not carry any substituent $R^{34}$. According to a further embodiment, it carries one, two, three or four $R^{34}$ According to a further particular embodiment, $R^3$ and $R^4$ together form a 5-membered saturated heterocycle which contains 1, 2 or 3, in particular 1 or 2, heteroatoms from the group consisting of NH, $NR^N$, O, S, $S(=O)$ and $S(=O)_2$, as ring members, wherein $R^N$ is as defined and preferably defined above. According to one embodiment thereof, the heterocycle is unsubstituted, i.e. it does not carry any substituent $R^{34}$. According to a further embodiment, it carries one, two, three or four $R^{34}$ According to a further particular embodiment, $R^3$ and $R^4$ together form a 6-membered saturated heterocycle which contains 1, 2 or 3, in particular 1 or 2, heteroatoms from the group consisting of NH, $NR^N$, O, S, $S(=O)$ and $S(=O)_2$, as ring members, wherein $R^N$ is as defined and preferably defined below. According to one embodiment thereof, the heterocycle is unsubstituted, i.e. it does not carry any substituent $R^{34}$. According to a further embodiment, it carries one, two, three or four $R^{34}$. According to one specific embodiment thereof, said 6-membered saturated heterocycle contains 1 or 2 heteroatoms selected from NH and $NR^N$. According to a further specific embodiment thereof, said 6-membered saturated heterocycle contains 1 or 2 heteroatoms O. According to a further specific embodiment thereof, said 6-membered saturated heterocycle contains 1 or 2 heteroatoms selected from S, $S(=O)$ and $S(=O)_2$. According to one embodiment thereof, the respective 6-membered heterocycle is unsubstituted, i.e. it does not carry any substituent $R^{34}$. According to a further embodiment, it carries one, two, three or four $R^{34}$.

According to one further embodiment $R^3$ together with $R^4$ and with the carbon atom to which they are bound form a saturated three-, four-, five-, six-, seven-, eight-, nine-, or ten-membered, in particular three-, four-, five- or six-membered carbocycle, more specifically five- or six-membered carbocycle, that is unsubstituted or carries one, two, three or four substituents $R^{34}$ as defined below. According to one embodiment thereof, $R^3$ and $R^4$ form a cyclopropyl, that is unsubstituted or carries one, two, three or four substituents $R^{34}$ as defined below. According to a further embodiment thereof, $R^3$ and $R^4$ form a cyclobutyl, that is unsubstituted or carries one, two, three or four substituents $R^{34}$ as defined below. According to still a further embodiment thereof, $R^3$ and $R^4$ form a cyclopentyl, that is unsubstituted or carries one, two, three or four substituents $R^{34}$ as defined below. According to still a further embodiment thereof, $R^3$ and $R^4$ form a cyclohexyl, that is unsubstituted or carries one, two, three or four substituents $R^{34}$ as defined below. According to still a further embodiment thereof, $R^3$ and $R^4$ form a cycloheptyl, that is unsubstituted or carries one, two, three or four substituents $R^{34}$ as defined below.

$R^{34}$ are the possible substituents for the carbo- or heterocycle formed by $R^3$ and $R^4$ and are independently selected from halogen, OH, CN, $NO_2$, SH, $NH_2$, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_1$-$C_4$-alkoxy-$C_1$-$C_4$-alkyl, phenyl and phenoxy, wherein the phenyl groups are unsubstituted or substituted with substituents $R^{34a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein in each case one or two $CH_2$ groups of the carbo- or heterocycle may be replaced by a group independently selected from $C(=O)$ and $C(=S)$.

In one preferred embodiment, $R^{34}$ is in each case independently selected from halogen, OH, CN, SH, $C_1$-$C_6$-alkyl, $C_1$-$C_6$-halogenalkyl, $C_1$-$C_6$-alkoxy, $C_1$-$C_6$-halogenalkoxy and $C_1$-$C_6$-alkylthio. In one further preferred embodiment, $R^{34}$ is in each case independently selected from halogen, $C_1$-$C_6$-alkyl and $C_1$-$C_6$-halogenalkyl. In one further particular embodiment, $R^{34}$ is in each case independently selected from $C_1$-$C_6$-alkyl, such as methyl and ethyl.

$R^N$ is the substituent of the heteroatom $NR^N$ that is contained in the heterocycle formed by $R^3$ and $R^4$ in some of the inventive compounds. $R^N$ is selected from $C_1$-$C_4$-alkyl, $C_1$-$C_4$-halogenalkyl and $SO_2Ph$, wherein Ph is unsubstituted phenyl or phenyl that is substituted by one, two or three substituents selected from $C_1$-$C_4$-alkyl. In one preferred embodiment, $R^N$ is in each case independently selected from $C_1$-$C_2$-alkyl, $C_1$-$C_2$-halogenalkyl and $SO_2Ph$, wherein Ph is unsubstituted phenyl or phenyl that is substituted by one methyl substituents. In one particular embodiment, $R^N$ is in each case independently selected from $C_1$-$C_2$-alkyl, more particularly methyl. In one particular embodiment, $R^N$ is in each case independently selected from $SO_2Ph$, wherein Ph is unsubstituted phenyl or phenyl that is substituted by one methyl.

Particularly preferred embodiments of combinations of $R^3$ and $R^4$ according to the invention are in Table P34 below, wherein each line of lines P34-1 to P34-256 corresponds to one particular embodiment of the invention, wherein P34-1 to P34-256 are also in any combination with one another a preferred embodiment of the present invention. The carbon atom, to which $R^3$ and $R^4$ are bound is marked with * in the drawings. "Ts" in the drawings stands for the tosyl-group $SO_2$-(p-$CH_3$)phenyl. The abbreviations of the cycles (C1 to C8) are explained in Table P3 above

TABLE P34

| No. | $R^3$ | $R^4$ |
|---|---|---|
| P34-1 | H | H |
| P34-2 | $CH_3$ | H |
| P34-3 | $C_2H_5$ | H |
| P34-4 | $CH_3$ | $CH_3$ |
| P34-5 | $C_2H_5$ | $CH_3$ |
| P34-6 | $C_2H_5$ | $C_2H_5$ |
| P34-7 | C1 | H |
| P34-8 | C2 | H |
| P34-9 | C3 | H |
| P34-10 | C4 | H |
| P34-11 | C5 | H |
| P34-12 | C6 | H |
| P34-13 | C7 | H |
| P34-14 | C8 | H |
| P34-15 | C1 | $CH_3$ |
| P34-16 | C2 | $CH_3$ |
| P34-17 | C3 | $CH_3$ |
| P34-18 | C4 | $CH_3$ |
| P34-19 | C5 | $CH_3$ |
| P34-20 | C6 | $CH_3$ |
| P34-21 | C7 | $CH_3$ |
| P34-22 | C8 | $CH_3$ |
| P34-23 | C1 | $C_2H_5$ |
| P34-24 | C2 | $C_2H_5$ |
| P34-25 | C3 | $C_2H_5$ |
| P34-26 | C4 | $C_2H_5$ |
| P34-27 | C5 | $C_2H_5$ |
| P34-28 | C6 | $C_2H_5$ |
| P34-29 | C7 | $C_2H_5$ |
| P34-30 | C8 | $C_2H_5$ |
| P34-31 | C1 | $CH(CH_3)_2$ |
| P34-32 | C2 | $CH(CH_3)_2$ |
| P34-33 | C3 | $CH(CH_3)_2$ |
| P34-34 | C4 | $CH(CH_3)_2$ |
| P34-35 | C5 | $CH(CH_3)_2$ |
| P34-36 | C6 | $CH(CH_3)_2$ |
| P34-37 | C7 | $CH(CH_3)_2$ |
| P34-38 | C8 | $CH(CH_3)_2$ |
| P34-39 | C1 | $CH_2CH_2CH_3$ |
| P34-40 | C2 | $CH_2CH_2CH_3$ |
| P34-41 | C3 | $CH_2CH_2CH_3$ |
| P34-42 | C4 | $CH_2CH_2CH_3$ |
| P34-43 | C5 | $CH_2CH_2CH_3$ |
| P34-44 | C6 | $CH_2CH_2CH_3$ |
| P34-45 | C7 | $CH_2CH_2CH_3$ |
| P34-46 | C1 | $CH(CH_3)_2$ |
| P34-47 | C2 | $CH(CH_3)_2$ |
| P34-48 | C3 | $CH(CH_3)_2$ |
| P34-49 | C4 | $CH(CH_3)_2$ |
| P34-50 | C5 | $CH(CH_3)_2$ |
| P34-51 | C6 | $CH(CH_3)_2$ |
| P34-52 | C7 | $CH(CH_3)_2$ |
| P34-53 | C8 | $CH(CH_3)_2$ |
| P34-54 | C1 | $CH_2CH_2CH_2CH_3$ |
| P34-55 | C2 | $CH_2CH_2CH_2CH_3$ |
| P34-56 | C3 | $CH_2CH_2CH_2CH_3$ |
| P34-57 | C4 | $CH_2CH_2CH_2CH_3$ |
| P34-58 | C5 | $CH_2CH_2CH_2CH_3$ |
| P34-59 | C6 | $CH_2CH_2CH_2CH_3$ |
| P34-60 | C7 | $CH_2CH_2CH_2CH_3$ |
| P34-61 | C8 | $CH_2CH_2CH_2CH_3$ |
| P34-62 | C1 | $CH_2CH(CH_3)_2$ |
| P34-63 | C2 | $CH_2CH(CH_3)_2$ |
| P34-64 | C3 | $CH_2CH(CH_3)_2$ |
| P34-65 | C4 | $CH_2CH(CH_3)_2$ |
| P34-66 | C5 | $CH_2CH(CH_3)_2$ |
| P34-67 | C6 | $CH_2CH(CH_3)_2$ |
| P34-68 | C7 | $CH_2CH(CH_3)_2$ |
| P34-69 | C8 | $CH_2CH(CH_3)_2$ |
| P34-70 | C1 | $C(CH_3)_3$ |
| P34-71 | C2 | $C(CH_3)_3$ |
| P34-72 | C3 | $C(CH_3)_3$ |
| P34-73 | C4 | $C(CH_3)_3$ |
| P34-74 | C5 | $C(CH_3)_3$ |
| P34-75 | C6 | $C(CH_3)_3$ |
| P34-76 | C7 | $C(CH_3)_3$ |
| P34-77 | C8 | $C(CH_3)_3$ |
| P34-78 | C1 | $CH_2CH_2CH_2CH_2CH_3$ |
| P34-79 | C2 | $CH_2CH_2CH_2CH_2CH_3$ |
| P34-80 | C3 | $CH_2CH_2CH_2CH_2CH_3$ |
| P34-81 | C4 | $CH_2CH_2CH_2CH_2CH_3$ |
| P34-82 | C5 | $CH_2CH_2CH_2CH_2CH_3$ |
| P34-83 | C6 | $CH_2CH_2CH_2CH_2CH_3$ |
| P34-84 | C7 | $CH_2CH_2CH_2CH_2CH_3$ |
| P34-85 | C8 | $CH_2CH_2CH_2CH_2CH_3$ |
| P34-86 | C1 | $CH_2CH_2CH(CH_3)_2$ |
| P34-87 | C2 | $CH_2CH_2CH(CH_3)_2$ |
| P34-88 | C3 | $CH_2CH_2CH(CH_3)_2$ |
| P34-89 | C4 | $CH_2CH_2CH(CH_3)_2$ |
| P34-90 | C5 | $CH_2CH_2CH(CH_3)_2$ |
| P34-91 | C6 | $CH_2CH_2CH(CH_3)_2$ |
| P34-92 | C7 | $CH_2CH_2CH(CH_3)_2$ |
| P34-93 | C8 | $CH_2CH_2CH(CH_3)_2$ |
| P34-94 | C1 | $CF_3$ |
| P34-95 | C2 | $CF_3$ |
| P34-96 | C3 | $CF_3$ |

TABLE P34-continued

| No. | R³ | R⁴ |
|---|---|---|
| P34-97 | C4 | CF₃ |
| P34-98 | C5 | CF₃ |
| P34-99 | C6 | CF₃ |
| P34-100 | C7 | CF₃ |
| P34-101 | C8 | CF₃ |
| P34-102 | C1 | CHF₂ |
| P34-103 | C2 | CHF₂ |
| P34-104 | C3 | CHF₂ |
| P34-105 | C4 | CHF₂ |
| P34-106 | C5 | CHF₂ |
| P34-107 | C6 | CHF₂ |
| P34-108 | C7 | CHF₂ |
| P34-109 | C8 | CHF₂ |
| P34-110 | C1 | CHCl₂ |
| P34-111 | C2 | CHCl₂ |
| P34-112 | C3 | CHCl₂ |
| P34-113 | C4 | CHCl₂ |
| P34-114 | C5 | CHCl₂ |
| P34-115 | C6 | CHCl₂ |
| P34-116 | C7 | CHCl₂ |
| P34-117 | C8 | CHCl₂ |
| P34-118 | C1 | CH₂F |
| P34-119 | C2 | CH₂F |
| P34-120 | C3 | CH₂F |
| P34-121 | C4 | CH₂F |
| P34-122 | C5 | CH₂F |
| P34-123 | C6 | CH₂F |
| P34-124 | C7 | CH₂F |
| P34-125 | C8 | CH₂F |
| P34-126 | C1 | CH₂Cl |
| P34-127 | C2 | CH₂Cl |
| P34-128 | C3 | CH₂Cl |
| P34-129 | C4 | CH₂Cl |
| P34-130 | C5 | CH₂Cl |
| P34-131 | C6 | CH₂Cl |
| P34-132 | C7 | CH₂Cl |
| P34-133 | C8 | CH₂Cl |
| P34-134 | C1 | CH₂CF₃ |
| P34-135 | C2 | CH₂CF₃ |
| P34-136 | C3 | CH₂CF₃ |
| P34-137 | C4 | CH₂CF₃ |
| P34-138 | C5 | CH₂CF₃ |
| P34-139 | C6 | CH₂CF₃ |
| P34-140 | C7 | CH₂CF₃ |
| P34-141 | C8 | CH₂CF₃ |
| P34-142 | C1 | CH₂CCl₃ |
| P34-143 | C2 | CH₂CCl₃ |
| P34-144 | C3 | CH₂CCl₃ |
| P34-145 | C4 | CH₂CCl₃ |
| P34-146 | C5 | CH₂CCl₃ |
| P34-147 | C6 | CH₂CCl₃ |
| P34-148 | C7 | CH₂CCl₃ |
| P34-149 | C8 | CH₂CCl₃ |
| P34-150 | C1 | C₆H₅ |
| P34-151 | C2 | C₆H₅ |
| P34-152 | C3 | C₆H₅ |
| P34-153 | C4 | C₆H₅ |
| P34-154 | C5 | C₆H₅ |
| P34-155 | C6 | C₆H₅ |
| P34-156 | C7 | C₆H₅ |
| P34-157 | C8 | C₆H₅ |
| P34-158 | C1 | 4-Cl—C₆H₄ |
| P34-159 | C2 | 4-Cl—C₆H₄ |
| P34-160 | C3 | 4-Cl—C₆H₄ |
| P34-161 | C4 | 4-Cl—C₆H₄ |
| P34-162 | C5 | 4-Cl—C₆H₄ |
| P34-163 | C6 | 4-Cl—C₆H₄ |
| P34-164 | C7 | 4-Cl—C₆H₄ |
| P34-165 | C8 | 4-Cl—C₆H₄ |
| P34-166 | C1 | 4-F—C₆H₄ |
| P34-167 | C2 | 4-F—C₆H₄ |
| P34-168 | C3 | 4-F—C₆H₄ |
| P34-169 | C4 | 4-F—C₆H₄ |
| P34-170 | C5 | 4-F—C₆H₄ |
| P34-171 | C6 | 4-F—C₆H₄ |
| P34-172 | C7 | 4-F—C₆H₄ |
| P34-173 | C8 | 4-F—C₆H₄ |
| P34-174 | C1 | CH₂—C₆H₅ |
| P34-175 | C2 | CH₂—C₆H₅ |
| P34-176 | C3 | CH₂—C₆H₅ |
| P34-177 | C4 | CH₂—C₆H₅ |
| P34-178 | C5 | CH₂—C₆H₅ |
| P34-179 | C6 | CH₂—C₆H₅ |
| P34-180 | C7 | CH₂—C₆H₅ |
| P34-181 | C8 | CH₂—C₆H₅ |
| P34-182 | C1 | 3-pyridyl |
| P34-183 | C2 | 3-pyridyl |
| P34-184 | C3 | 3-pyridyl |
| P34-185 | C4 | 3-pyridyl |
| P34-186 | C5 | 3-pyridyl |
| P34-187 | C6 | 3-pyridyl |
| P34-188 | C7 | 3-pyridyl |
| P34-189 | C8 | 3-pyridyl |
| P34-190 | C1 | 4-pyridyl |
| P34-191 | C2 | 4-pyridyl |
| P34-192 | C3 | 4-pyridyl |
| P34-193 | C4 | 4-pyridyl |
| P34-194 | C5 | 4-pyridyl |
| P34-195 | C6 | 4-pyridyl |
| P34-196 | C7 | 4-pyridyl |
| P34-197 | C8 | 4-pyridyl |
| P34-198 | C1 | C1 |
| P34-199 | C2 | C1 |
| P34-200 | C3 | C1 |
| P34-201 | C4 | C1 |
| P34-202 | C5 | C1 |
| P34-203 | C6 | C1 |
| P34-204 | C7 | C1 |
| P34-205 | C8 | C1 |
| P34-206 | C2 | C2 |
| P34-207 | C3 | C2 |
| P34-208 | C4 | C2 |
| P34-209 | C5 | C2 |
| P34-210 | C6 | C2 |
| P34-211 | C7 | C2 |
| P34-212 | C8 | C2 |
| P34-213 | C3 | C3 |
| P34-214 | C4 | C3 |
| P34-215 | C5 | C3 |
| P34-216 | C6 | C3 |
| P34-217 | C7 | C3 |
| P34-218 | C8 | C3 |
| P34-219 | C4 | C4 |
| P34-220 | C5 | C4 |
| P34-221 | C6 | C4 |
| P34-222 | C7 | C4 |
| P34-223 | C8 | C4 |
| P34-224 | C5 | C5 |
| P34-225 | C6 | C5 |
| P34-226 | C7 | C5 |
| P34-227 | C8 | C5 |
| P34-228 | C6 | C6 |
| P34-229 | C7 | C6 |
| P34-230 | C8 | C6 |
| P34-231 | C7 | C7 |
| P34-232 | C8 | C7 |
| P34-233 | C8 | C8 |
| P34-234 | | 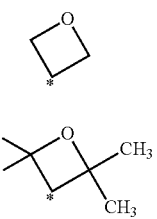 |
| P34-235 | | 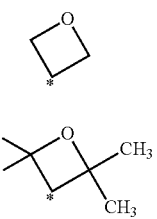 |
| P34-236 | | 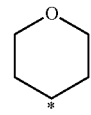 |

TABLE P34-continued

| No. | R³ | R⁴ |
|---|---|---|
| P34-237 | | 2,2,6,6-tetramethyltetrahydropyran-yl |
| P34-238 | | piperidin-4-yl |
| P34-239 | | N-methylpiperidin-4-yl |
| P34-240 | | 1,2,2,6,6-pentamethylpiperidin-4-yl |
| P34-241 | | N-tosylpiperidin-4-yl |
| P34-242 | | 2,2,6,6-tetramethyl-N-tosylpiperidin-4-yl |
| P34-243 | | tetrahydrothiopyran-4-yl |
| P34-244 | | 2,2,6,6-tetramethyltetrahydrothiopyran-4-yl |
| P34-245 | | 1-oxo-tetrahydrothiopyran-4-yl |
| P34-246 | | 1-oxo-2,2,6,6-tetramethyltetrahydrothiopyran-4-yl |
| P34-247 | | 1,1-dioxo-tetrahydrothiopyran-4-yl |
| P34-248 | | 1,1-dioxo-2,2,6,6-tetramethyltetrahydrothiopyran-4-yl |
| P34-249 | | 1,3-dioxan-5-yl |
| P34-250 | | 1,3-dioxan-2-yl |
| P34-251 | | tetrahydropyran-2-yl |
| P34-252 | | N-methylpiperidin-2-yl |
| P34-253 | | cyclobutyl |
| P34-254 | | cyclopentyl |
| P34-255 | | cyclohexyl |
| P34-256 | | cycloheptyl |

$R^x$ in the substituent $NH-SO_2R^x$ is in each case independently selected from $C_1$-$C_4$-alkyl, $C_1$-$C_4$-halogenalkyl, unsubstituted aryl and aryl that is substituted by one, two, three, four or five substituents $R^{x1}$ independently selected from $C_1$-$C_4$-alkyl. In particular, $R^x$ is in each case independently selected from $C_1$-$C_4$-alkyl and phenyl that is substituted by one, two or three $R^{x1}$ independently selected from $C_1$-$C_2$-alkyl, more specifically $R^x$ is in each case independently selected from $C_1$-$C_4$-alkyl and phenyl that is substituted by one H₃, more specifically $SO_2$—$R^x$ is the tosyl group ("Ts").

$R^3$ are the possible substituents for the the aliphatic moieties of $R^3$ and the $R^{3a}$ are in each case independently selected from halogen, OH, CN, $NO_2$, SH, $N_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl), $OC_1$—$C_6$-alkoxy, $OC_3$—$C_6$-cycloalkyl, $OC_3$—$C_6$-halogencycloalkyl, $OC_1$—$C_4$-halogenalkoxy, $C_1$-$C_6$-alkylthio, aryl and phenoxy, wherein the aryl and phenyl groups are independently unsubstituted or substituted with substituents selected from the group consisting of halogen, OH, N, $NO_2$, SH, $N_2$,$NH(C_1$-$C_4$-alkyl), $N(C_1$-$C_4$-alkyl), $NH(C(=O)C_1$-$C_4$-alkyl), $N(C(=O)C_1$-$C_4$-alkyl)$_2$, $NH$—$SO_2$—$R^x$, $OC_1$—$C_6$-alkylthio, $OC_1$—$C_4$-alkyl, $C_1$-$C_4$-halogenalkyl, $OC_1$—$C_4$-alkoxy and $OC_1$-4-halogenalkoxy.

In one preferred embodiment, $R^{3a}$ is in each case independently selected from halogen, OH, ON, $OC_1$—$C_6$-alkoxy, $OC_1$—$C_6$-halogenalkoxy, phenyl and halogenphenyl, wherein the halogenphenyl carries one, two or three halogen selected from the group consisting of F, Cl. In one further preferred embodiment, $R^{3a}$ is in each case independently selected from halogen, phenyl and halogenphenyl, wherein the halogenphenyl carries one, two or three halogen selected from the group consisting of F, Cl and Br, in particular selected from F and Cl.

$R^{3b}$ are the possible substituents for the carbocycle, heterocycle, heteroaryl and aryl moieties and are independently selected from halogen, OH, CN, $NO_2$, SH, NH, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, $C_1$-$C_6$-alkylthio, $C_1$-$C_6$-halogenalkylthio, $C_1$-$C_4$-alkoxy-$C_1$-$C_4$-alkyl, phenyl and phenoxy, wherein the phenyl groups are unsubstituted or substituted with substituents selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment, $R^{3b}$ is in each case independently selected from halogen, OH, CN, SH, $C_1$-$C_6$-alkyl, $C_1$-$C_6$-halogenalkyl, $C_1$-$C_6$-alkoxy, $C_1$-$C_6$-halogenalkoxy and $C_1$-$C_6$-alkylthio. In one further preferred embodiment, $R^{3b}$ is in each case independently selected from halogen, $C_1$-$C_6$-alkyl and $C_1$-$C_6$-halogenalkyl. In one further particular embodiment, $R^{3b}$ is in each case independently selected from $C_1$-$C_6$-alkyl, such as methyl and ethyl. In one further particular embodiment, $R^{3b}$ is in each case independently selected from halogen, such as F, Cl and Br.

$R^{4a}$ are the possible substituents for the the aliphatic moieties of $R^4$ and the $R^{4a}$ are in each case independently selected from halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $C_1$-$C_4$-alkoxy, $C_3$-$C_6$-cycloalkyl, $C_3$-$C_6$-halogencycloalkyl, $C_1$-$C_4$-halogenalkoxy, $C_1$-$C_6$-alkylthio, aryl and phenoxy, wherein the aryl and phenyl groups are independently unsubstituted or substituted with substituents selected from the group consisting of halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy and $C_1$-$C_4$-halogenalkoxy.

In one preferred embodiment, $R^{4a}$ is in each case independently selected from halogen, OH, CN, $C_1$-$C_6$-alkoxy, $C_1$-$C_6$-halogenalkoxy, phenyl and halogenphenyl, wherein the halogenphenyl carries one, two or three halogen selected from the group consisting of F, Cl and Br. In one further preferred embodiment, $R^{4a}$ is in each case independently selected from halogen, phenyl and halogenphenyl, wherein the halogenphenyl carries one, two or three halogen selected from the group consisting of F, Cl and Br, in particular selected from F and C.

$R^{4b}$ are the possible substituents for the carbocycle, heterocycle, heteroaryl and aryl moieties and are independently selected from halogen, OH, CN, $NO_2$, SH, NH, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, $C_1$-$C_6$-alkylthio, $C_1$-$C_6$-halogenalkylthio, $C_1$-$C_4$-alkoxy-$C_1$-$C_4$-alkyl, phenyl and phenoxy, wherein the phenyl groups are unsubstituted or substituted with substituents selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment, $R^{4b}$ is in each case independently selected from halogen, OH, CN, SH, $C_1$-$C_6$-alkyl, $C_1$-$C_6$-halogenalkyl, $C_1$-$C_6$-alkoxy, $C_1$-$C_6$-halogenalkoxy and $C_1$-$C_6$-alkylthio. In one further preferred embodiment, $R^{4b}$ is in each case independently selected from halogen, $C_1$-$C_6$-alkyl and $C_1$-$C_6$-halogenalkyl. In one further particular embodiment, $R^{4b}$ is in each case independently selected from $C_1$-$C_6$-alkyl, such as methyl and ethyl. In one further particular embodiment, $R^{4b}$ is in each case independently selected from halogen, such as F, Cl and Br.

$R^5$ according to the invention is a halogen and is selected from F, Cl, Br and I.

According to further embodiment, $R^5$ is F.

According to still further embodiment, $R^5$ is Cl.

According to still further embodiment, $R^5$ is Br.

According to still further embodiment, $R^5$ is I.

$R^6$ according to the invention is hydrogen or a halogen,

According to one specific embodiment, $R^6$ is hydrogen.

According to one further specific embodiment, $R^6$ is hydrogen or halogen, in particular H, Br, F, I or Cl, according to one embodiment it is H or F, according to a further embodiment, it is H or Cl.

According to one specific embodiment, $R^6$ is halogen, in particular Br, F or C, according to one embodiment it is F, according to a further embodiment, it is Cl.

Particularly preferred embodiments of the combination of $R^5$ and $R^6$ according to the invention are in Table P56 below, wherein each line of lines P56-1 to P56-20 corresponds to one particular embodiment of the invention, wherein P56-1 to P56-20 are also in any combination with one another a preferred embodiment of the present invention.

TABLE P56

| No. | $R^5$ | $R^6$ |
|---|---|---|
| P56-1 | F | H |
| P56-2 | Cl | H |
| P56-3 | Br | H |
| P56-4 | I | H |
| P56-5 | F | F |
| P56-6 | Cl | F |
| P56-7 | Br | F |
| P56-8 | I | F |
| P56-9 | F | Cl |
| P56-10 | Cl | Cl |
| P56-11 | Br | Cl |
| P56-12 | I | Cl |
| P56-13 | F | Br |
| P56-14 | Cl | Br |
| P56-15 | Br | Br |
| P56-16 | I | Br |
| P56-17 | F | I |
| P56-18 | Cl | I |
| P56-19 | Br | I |
| P56-20 | I | I |

$R^7$ and $R^8$ together with the carbon atoms to which they are bound form a ring A as shown in structure I-A below

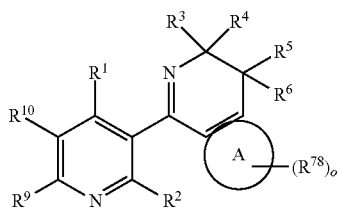

I-A

Wherein the ring A is a phenyl ring or five- or six-membered heteroaryl; wherein the ring A contains one, two or three heteroatoms selected from N, O and S, and wherein the ring A is substituted with $(R^{78})_o$, wherein o is 0, 1, 2 or 3; and $R^{78}$ are independently selected from halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $CH(=O)$, $C(=O)C_1$-$C_6$-alkyl, $C(=O)NH$ $(C_1$-$C_6$-alkyl), $CR'=NOR''$, $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, $C_2$-$C_6$-alkenyloxy, $C_2$-$C_6$-alkynyloxy, $C_3$-$C_6$-cycloalkyl, $C_3$-$C_6$-cycloalkenyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; wherein R and R'' are independently selected from $C_1$-$C_4$-alkyl, $C_2$-$C_6$-alkenyl, $C_2$-$C_6$-alkynyl, $C_3$-$C_6$-cycloalkyl, saturated or partially unsaturated three-, four-, five-, six-, seven-, eight-, nine-, or ten-membered heterocycle, five- or six-membered heteroaryl or aryl; wherein the heterocycle or heteroaryl contains one, two or three heteroatoms selected from N, O and S, and wherein R' and/or R'' are independently unsubstituted or substituted with R''' independently selected from halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl; and wherein $R^x$ is defined above; and wherein the aliphatic moieties of $R^{78}$ are unsubstituted or substituted with identical or different groups $R^{78a}$ which independently of one another are selected from:

$R^{78a}$ halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heterorayl, phenyl and phenoxy group is unsubstituted or unsubstituted or substituted with $R^{78aa}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; wherein the alicyclic, phenyl, heterocyclic and heteroaryl moieties of $R^{78}$ are unsubstituted or substituted with identical or different groups $R^{78b}$ which independently of one another are selected from:

$R^{78b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment, $R^7$ and $R^8$ together with the carbon atoms to which they are bound form a phenyl ring; wherein the phenyl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to further embodiment, $R^7$ and $R^8$ together with the carbon atoms to which they are bound form a five- or six-membered heteroaryl; wherein the heteroaryl contains one or two heteroatoms selected from N, O and S, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to a further embodiment, $R^7$ and $R^8$ together with the carbon atoms to which they are bound form a five- or six-membered heteroaryl; wherein the heteroaryl contains one or two heteroatoms N, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to a further embodiment, $R^7$ and $R^8$ together with the carbon atoms to which they are bound form a five- or six-membered heteroaryl; wherein the heteroaryl contains one or two heteroatoms selected from S and O, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to a further embodiment, $R^7$ and $R^8$ together with the carbon atoms to which they are bound form a five- or six-membered heteroaryl; wherein the heteroaryl contains one heteroatom S, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to a further embodiment, $R^7$ and $R^8$ together with the carbon atoms to which they are bound form a five- or six-membered heteroaryl; wherein the heteroaryl contains one heteroatom O, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to one embodiment, $R^7$ and $R^8$ together with the carbon atoms to which they are bound form a five-membered heteroaryl; wherein the heteroaryl contains one or two heteroatoms selected from N, O and S, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to one embodiment, $R^7$ and $R^8$ together with the carbon atoms to which they are bound form a five-membered heteroaryl; wherein the heteroaryl contains one or two heteroatoms N, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to one embodiment, $R^7$ and $R^8$ together with the carbon atoms to which they are bound form a five-membered heteroaryl; wherein the heteroaryl contains one or two heteroatoms selected from O and S, and wherein the heteroaryl carries zero, one or two substituents $(R^{78})_o$, as defined and preferably defined herein, wherein o is 0, 1 or 2.

According to one specific embodiment, o is 0. According to a further embodiment, o is 1 or 2. Particular embodiments thereof are listed in Table P78.

According to one embodiment, $R^7$ and $R^8$ together with the carbon atoms to which they are bound form a five-membered heteroaryl; wherein the heteroaryl contains one heteroatom S, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2.

According to one embodiment, $R^7$ and $R^8$ together with the carbon atoms to which they are bound form a five-membered heteroaryl; wherein the heteroaryl contains one heteroatom O, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to a further embodiment, $R^7$ and $R^8$ together with the carbon atoms to which they are bound form a six-membered heteroaryl; wherein the heteroaryl contains one or two heteroatoms selected from N, O and S, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to a further embodiment, $R^7$ and $R^8$ together with the carbon atoms to which they are bound form a six-membered heteroaryl; wherein the heteroaryl contains one or two heteroatoms N, and wherein the heteroaryl carries zero, one or two substituents $(R^{78})_o$, as defined and preferably defined herein, wherein o is 0, 1 or 2. According to one specific embodiment, o is 0. According to a further embodiment, o is 1 or 2. Particular embodiments thereof are listed in Table P78.

According to the invention, there can be zero, one, two or three $R^{78}$ present, namely for o is 0, 1, 2 or 3.

According to one embodiment, o is 0.
According to a further embodiment, o is 1.
According to a further embodiment, o is 2 or 3. According to one specific embodiment thereof, o is 2, according to a further specific embodiment, o is 3.

For every $R^{78}$ that is present in the inventive compounds, the following embodiments and preferences apply independently of the meaning of any other $R^{78}$ that may be present in the ring. Furthermore, the particular embodiments and preferences given herein for $R^{78}$ apply independently for each of o=1, o=2 and o=3.

According to one specific embodiment, $R^{78}$ is halogen, in particular F, Cl, Br or I, more specifically F, Cl or Br, in particular F or Cl.

According to a further specific embodiment, $R^{78}$ is OH.
According to a further specific embodiment, $R^{78}$ is CN.
According to a further specific embodiment, $R^{78}$ is $C_1$-$C_6$-alkyl, in particular $C_1$-$C_4$-alkyl, such as $CH_3$. or $C_2H_5$, in particular $CH_3$.

According to a further specific embodiment, $R^{78}$ is $C_1$-$C_6$-halogenalkyl, in particular $C_1$-$C_4$-halogenalkyl, such as $CF_3$, $CHF_2$, $CH_2F$, $CCl_3$, $CHCl_2$ and $CH_2Cl$.

According to still a further embodiment, $R^{78}$ is $C_2$-$C_6$-alkenyl, in particular $C_2$-$C_4$-alkenyl, such as CH=$CH_2$.

According to still a further embodiment, $R^{78}$ is $C_3$-$C_6$-cycloalkyl-$C_2$-$C_6$-alkenyl, in particular $C_3$-$C_6$-cycloalkyl-$C_2$-$C_4$-alkenyl, more specifically $C_3$-$C_6$-cycloalkyl-$C_2$-$C_3$-alkenyl, such as $C_3H_5$—CH=$CH_2$.

According to a further specific embodiment, $R^{78}$ is $C_2$-$C_6$-halogenalkenyl, in particular $C_2$-$C_4$-halogenalkenyl, more specifically $C_2$-$C_3$-halogenalkenyl.

According to still a further embodiment, $R^{78}$ is $C_2$-$C_6$-alkynyl, in particular $C_2$-$C_4$-alkynyl, more specifically $C_2$-$C_3$-alkynyl, such as C≡CH.

According to still a further embodiment, $R^{78}$ is $C_2$-$C_6$-halogenalkynyl, in particular $C_2$-$C_4$-halogenalkynyl, more specifically $C_2$-$C_3$-halogenalkynyl.

According to a further specific embodiment, $R^{78}$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^{78}$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$, $OCH_2Cl$ and $OCF_2CHF_2$, in particular $OCF_3$, $OCHF_2$ and $OCF_2CHF_2$.

According to still a further specific embodiment, $R^{78}$ is unsubstituted phenyl or phenyl that is substituted by one, two, three or four $R^{78b}$, as defined and preferably herein. In particular, $R^{78}$ is unsubstituted phenyl or phenyl that is substituted by one, two, three or four $R^{78b}$, as defined herein. In one embodiment $R^{78}$ is unsubstituted phenyl.

According to one further embodiment, $R^{78}$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy, $C_3$-$C_6$-cycloalkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein the aliphatic moieties of $R^{78}$ are unsubstituted or substituted with identical or different groups $R^{78a}$ as defined and preferably defined herein, and wherein the heterocyclic, alicyclic, phenyl and heteroaryl moieties of $R^{78}$ are unsubstituted or substituted with identical or different groups $R^{78b}$ as defined and preferably defined herein.

According to one further embodiment, $R^{78}$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein the aliphatic moieties of $R^{78}$ are unsubstituted or substituted with identical or different groups $R^{78a}$ as defined and preferably defined herein, and wherein the heterocyclic, alicyclic, phenyl and heteroaryl moieties of $R^{78}$ are unsubstituted or substituted with identical or different groups $R^{78b}$ as defined and preferably defined herein. According to one specific embodiment, the aliphatic and cyclic moieties of $R^{78}$ are not further substituted, according to another embodiment, the aliphatic moieties of $R^{78}$ carry one, two, three or four identical or different groups $R^{78a}$ as defined and preferably defined herein.

According to a further embodiment, $R^{78}$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy and $C_3$-$C_6$-cycloalkyl, wherein the aliphatic moieties of $R^{78}$ are unsubstituted or substituted with identical or different groups $R^{78a}$ as defined and preferably defined herein, and wherein the cycloalkyl moieties of $R^{78}$ are unsubstituted or substituted with identical or different groups $R^{78b}$ as defined and preferably defined herein.

According to a further embodiment, $R^{78}$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy and $C_3$-$C_6$-cycloalkyl, wherein the aliphatic moieties of $R^{78}$ are unsubstituted or substituted with identical or different groups $R^{78a}$ as defined and preferably defined herein, and wherein the cycloalkyl moieties of $R^{78}$ are unsubstituted or substituted with identical or different groups $R^{78b}$ as defined and preferably defined herein. According to one specific embodiment, the aliphatic and cyclic moieties of $R^{78}$ are not further substituted, according to another embodiment, the aliphatic moieties of $R^{78}$ carry one, two, three or four identical or different groups $R^{78a}$ as defined and preferably defined herein.

According to still a further embodiment, $R^{78}$ is in each case independently selected from halogen, $C_1$-$C_6$-alkyl and $C_1$-$C_6$-alkoxy, wherein the aliphatic moieties of $R^{78}$ are unsubstituted or substituted with identical or different groups $R^{78a}$ defined and preferably defined herein.

According to still a further embodiment, $R^{78}$ is in each case independently selected from halogen, $C_1$-$C_6$-alkyl, $C_1$-$C_6$-alkoxy and $C_1$-$C_6$-halogenalkoxy, wherein the aliphatic moieties of $R^{78}$ are unsubstituted or substituted with identical or different groups $R^{78a}$ defined and preferably defined herein. According to one specific embodiment, the aliphatic and cyclic moieties of $R^{78}$ are not further substituted, according to another embodiment, the aliphatic moieties of $R^{78}$ carry one, two, three or four identical or different groups $R^{78a}$ as defined and preferably defined herein.

$R^{78a}$ are the possible substituents for the aliphatic moieties of $R^{78}$. $R^{78a}$ is independently selected from halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heterorayl, phenyl and phenoxy group is unsubstituted or unsubstituted or substituted with $R^{78aa}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

According to one embodiment $R^{78a}$ is independently selected from halogen, $C_1$-$C_6$-alkoxy, $C_3$-$C_6$-cycloalkyl, $C_3$-$C_6$-halogencycloalkyl and $C_1$-$C_4$-halogenalkoxy. Specifically, $R^{78a}$ is independently selected from F, C, Br, I, $C_1$-$C_2$-alkoxy, cyclopropyl, 1-F-cyclopropyl, 1-Cl-cyclopropyl and $C_1$-$C_2$-halogenalkoxy.

According to a further embodiment, $R^{78a}$ is independently halogen, in particular selected from F, Cl, Br and I, more specifically F, Cl and Br.

$R^{78b}$ are the possible substituents for the cycloalkyl, heterocyclyl, heteroaryl and phenyl moieties of $R^{78}$. $R^{78b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment thereof $R^{78b}$ is independently selected from halogen, CN, $C_1$-$C_4$-alkyl, $C_1$-$C_4$-alkoxy, $C_1$-$C_4$-halogenalkyl and $C_1$-$C_4$-halogenalkoxy, in particular halogen, $C_1$-$C_4$-alkyl and $C_1$-$C_4$-alkoxy. Specifically, $R^{78b}$ is independently selected from F, Cl, CN, $CH_3$, $OCH_3$ and halogenmethoxy.

Particularly preferred embodiments of $R^7$ and $R^8$, optionally substituted by $(R^{78})_o$, according to the invention are in Table P78 below, wherein each line of lines P78-1 to P78-42 corresponds to one particular embodiment of the invention, wherein P78-1 to P78-42 are also in any combination with one another a preferred embodiment of the present invention. Thereby, the positions of the phenyl or heteroaryls marked with "#" represents the connection points (carbon atoms 5' and 6' in formula I) with the remaining skeleton of the compounds of formula I:

TABLE P78

| No. | $R^7 + R^8$ |
|---|---|
| P78-1 | phenyl (#5', #6') |
| P78-2 | phenyl-(R$^{78}$)$_o$ (#5', #6') |
| P78-3 | thiophene (#5', #6', S) |
| P78-4 | thiophene (#, #, S) |
| P78-5 | thiophene (#5', #6', S) |
| P78-6 | thiophene-(R$^{78}$)$_o$ (#5', #6', S) |
| P78-7 | thiophene-(R$^{78}$)$_o$ (#, #, S) |
| P78-8 | thiophene-(R$^{78}$)$_o$ (#5', #6', S) |
| P78-9 | furan (#5', #6', O) |
| P78-10 | furan (#, #, O) |
| P78-11 | furan (#5', #6', O) |

TABLE P78-continued

| No. | R⁷ + R⁸ |
|---|---|
| P78-12 | furan (#6', #5', O) (R⁷⁸)ₒ |
| P78-13 | furan (#, #, O) (R⁷⁸)ₒ |
| P78-14 | furan (#6', #5', O) (R⁷⁸)ₒ |
| P78-15 | pyrrole (#6', #5', NH) |
| P78-16 | pyrrole (#, #, NH) |
| P78-17 | pyrrole (#6', #5', NH) |
| P78-18 | N-methyl pyrrole (#6', #5', N-CH₃) |
| P78-19 | N-methyl pyrrole (#, #, N-CH₃) |
| P78-20 | N-methyl pyrrole (#6', #5', N-CH₃) |
| P78-21 | pyrrole (#6', #5', NH) (R⁷⁸)ₒ |
| P78-22 | pyrrole (#, NH) (R⁷⁸)ₒ |
| P78-23 | pyrrole (#6', #5', NH) (R⁷⁸)ₒ |

TABLE P78-continued

| No. | R⁷ + R⁸ |
|---|---|
| P78-24 | N-methyl pyrrole (#6', #5', N-CH₃) (R⁷⁸)ₒ |
| P78-25 | N-methyl pyrrole (#, N-CH₃) (R⁷⁸)ₒ |
| P78-26 | N-methyl pyrrole (#6', #5', N-CH₃) (R⁷⁸)ₒ |
| P78-27 | pyrazole (#6', #5', NH, N) |
| P78-28 | pyrazole (#6', #5', N, NH) |
| P78-29 | N-methyl pyrazole (#6', #5', N-CH₃, N) |
| P78-30 | N-methyl pyrazole (#6', #5', N, N-CH₃) |
| P78-31 | pyrazole (#6', #5', NH, N) (R⁷⁸)ₒ |
| P78-32 | pyrazole (#6', #5', N, NH) (R⁷⁸)ₒ |
| P78-33 | N-methyl pyrazole (#6', #5', N-CH₃, N) (R⁷⁸)ₒ |

TABLE P78-continued
| No. | R⁷ + R⁸ |
|---|---|
| P78-34 | 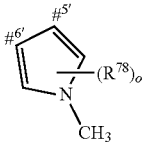 |
| P78-35 | 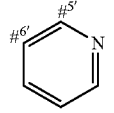 |
| P78-36 | 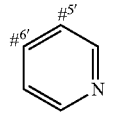 |
| P78-37 | 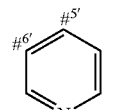 |
| P78-38 | 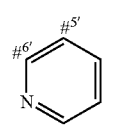 |
| P78-39 | 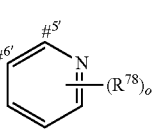 |
| P78-40 | 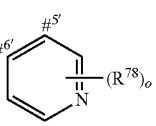 |
| P78-41 | 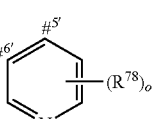 |
| P78-42 | 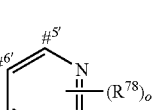 |
Preferred embodiments of the present invention are the following compounds I.A, I.B, I.C, I.D, I.E, I.F, I.G, I.H, I.I, I.J, I.K and I.Ka. In these formulae, the substituents $R^1$, $R^2$, $R^3$, $R^4$, $R^5$, $R^6$, $R^9$, $R^{10}$, $R^{78}$ and o are independently as defined or preferably defined herein:
I.A
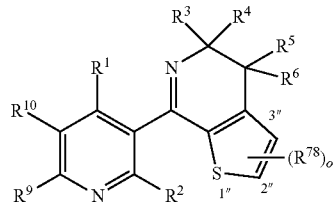
I.B
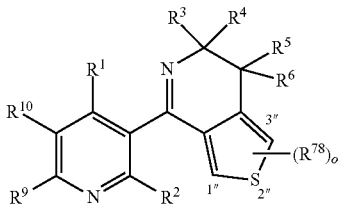
I.C
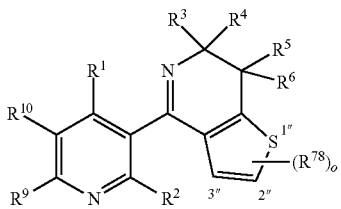
I.D
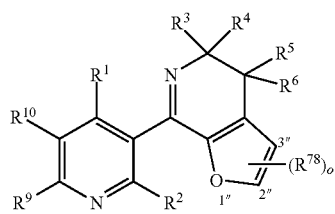
I.E
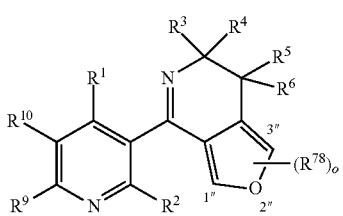
I.F
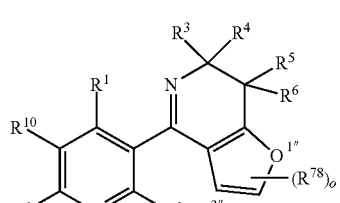
I.G
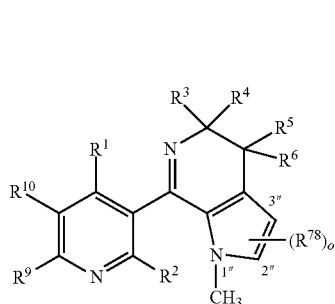

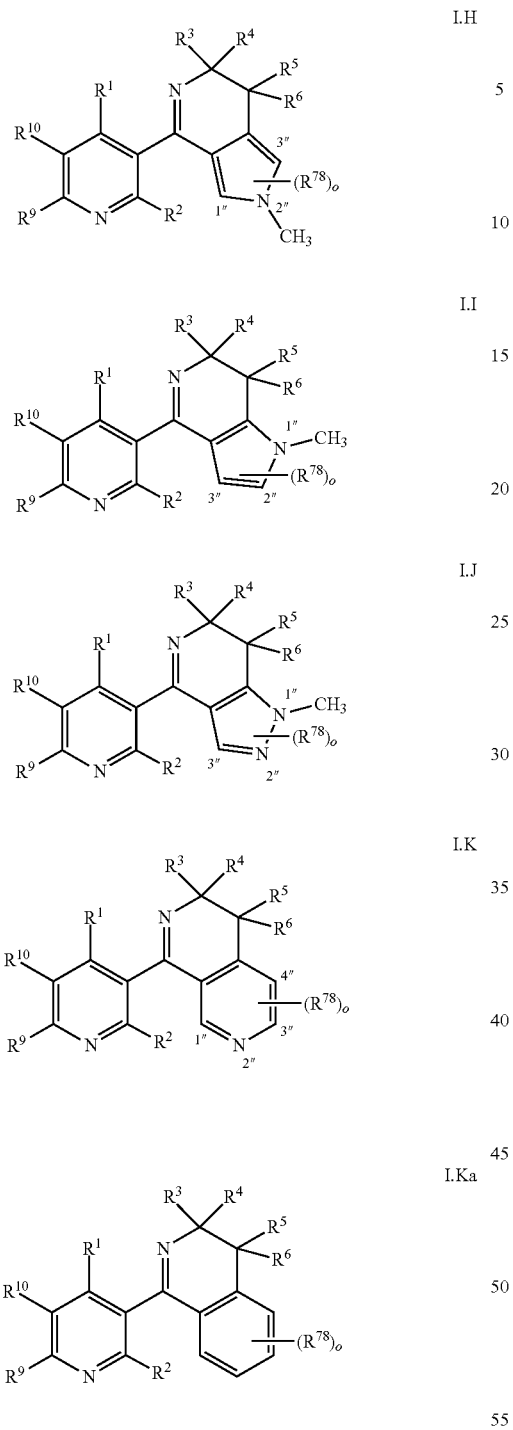
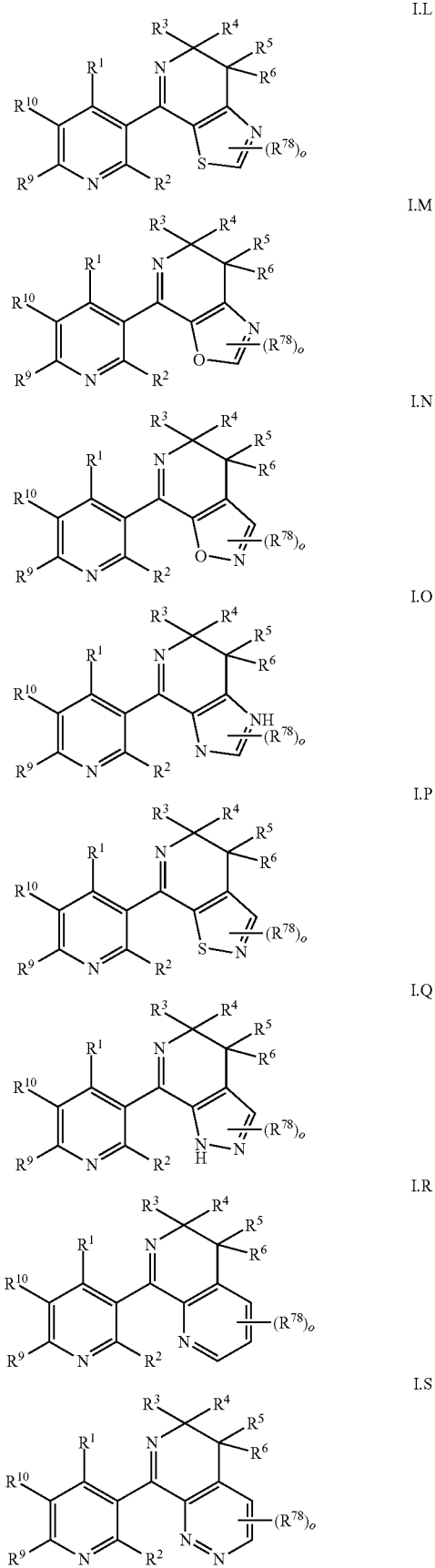

According to one embodiment, o in each of the formulae I.A, I.B, I.C, I.D, I.E, I.F, I.G, I.H, I.I, I.J I.K and I.Ka, respectively, is 0, i.e. the heteroaryl or phenyl group is not substituted. These compounds are named I.A.1, I.B.1, I.C.1, I.D.1, I.E.1, I.F.1, I.G.1, I.H.1, I.I.1, I.J.1 and I.K.1, I.Ka.1 respectively.

Further preferred compounds I are the following compounds I.L, I.M, I.N, I.O, I.P, I.Q, I.R, I.S, I.T and I.U. In these formulae, the substituents $R^1$, $R^2$, $R^3$, $R^4$, $R^5$, $R^6$, $R^9$, $R^{10}$, $R^{78}$ and o are independently as defined or preferably defined herein:

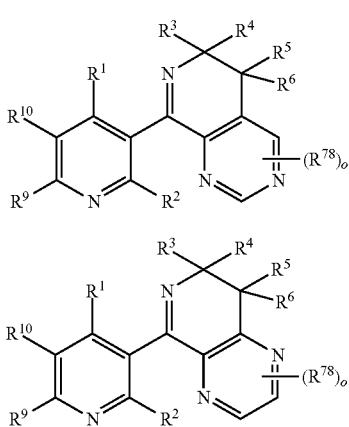

According to one embodiment, o in each of the formulae I.L, I.M, I.N, I.O, I.P, I.Q, I.R, I.S, I.T and I.U, respectively, is 0, i.e. the heteroaryl is not substituted. These compounds are named I.L.1, I.M.1, I.N.1, I.O.1, I.P.1, I.Q.1, I.R.1, I.S.1, I.T.1 and I.U.1, respectively.

In particular with a view to their use, according to one embodiment, preference is given to the compounds of the formulae I.A, I.B, I.C, I.D, I.E, I.F, I.G, I.H, I.I, I.J, I.K and I.Ka that are compiled in the Tables 1a to 60a, Tables 1b to 60b, Tables 1c to 60c, Tables 1d to 60d, Tables 1e to 56e, Tables 1f to 64f, Tables 1g to 60g, Tables 1h to 60h, Tables 1i to 60i, Tables 1j to 32j, Tables 1k to 88k, Tables 1Ka to 88Ka. Each of the groups mentioned for a substituent in the tables is furthermore per se, independently of the combination in which it is mentioned, a particularly preferred aspect of the substituent in question.

Table 1a Compounds of formula I.A in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2a Compounds of formula I.A in which o is 1, $R^{78}$ is 2"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3a Compounds of formula I.A in which o is 1, $R^{78}$ is 2"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4a Compounds of formula I.A in which o is 1, $R^{78}$ is 2"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5a Compounds of formula I.A in which o is 1, $R^{78}$ is 2"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6a Compounds of formula I.A in which o is 1, $R^{78}$ is 2"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7a Compounds of formula I.A in which o is 1, $R^{78}$ is 2"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8a Compounds of formula I.A in which o is 1, $R^{78}$ is 2"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9a Compounds of formula I.A in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10a Compounds of formula I.A in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11a Compounds of formula I.A in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12a Compounds of formula I.A in which o is 1, $R^{78}$ is 3"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13a Compounds of formula I.A in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14a Compounds of formula I.A in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15a Compounds of formula I.A in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B Table 16a Compounds of formula I.A in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17a Compounds of formula I.A in which o is 1, $R^{78}$ is 2"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18a Compounds of formula I.A in which o is 1, $R^{78}$ is 2"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19a Compounds of formula I.A in which o is 1, $R^{78}$ is 2"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20a Compounds of formula I.A in which o is 1, $R^{78}$ is 2"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21a Compounds of formula I.A in which o is 1, $R^{78}$ is 2"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22a Compounds of formula I.A in which o is 1, $R^{78}$ is 2"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23a Compounds of formula I.A in which o is 1, $R^{78}$ is 2"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24a Compounds of formula I.A in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25a Compounds of formula I.A in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26a Compounds of formula I.A in which o is 1, $R^{78}$ is 3"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27a Compounds of formula I.A in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28a Compounds of formula I.A in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29a Compounds of formula I.A in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30a Compounds of formula I.A in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31a Compounds of formula I.A in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32a Compounds of formula I.A in which o is 1, $R^{78}$ is 2"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33a Compounds of formula I.A in which o is 1, $R^{78}$ is 2"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34a Compounds of formula I.A in which o is 1, $R^{78}$ is 2"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35a Compounds of formula I.A in which o is 1, $R^{78}$ is 2"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36a Compounds of formula I.A in which o is 1, $R^{78}$ is 2"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37a Compounds of formula I.A in which o is 1, $R^{78}$ is 2"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38a Compounds of formula I.A in which o is 1, $R^{78}$ is 2"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39a Compounds of formula I.A in which o is 1, $R^{78}$ is 3-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40a Compounds of formula I.A in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41a Compounds of formula I.A in which o is 1, $R^{78}$ is 3"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42a Compounds of formula I.A in which o is 1, $R^{78}$ is 3"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43a Compounds of formula I.A in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44a Compounds of formula I.A in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45a Compounds of formula I.A in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46a Compounds of the formula I.A in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47a Compounds of the formula I.A in which o is 1, $R^{78}$ is 2"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48a Compounds of the formula I.A in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49a Compounds of the formula I.A in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50a Compounds of the formula I.A in which o is 1, $R^{78}$ is 2"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51a Compounds of the formula I.A in which o is 1, $R^{78}$ is 2"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52a Compounds of the formula I.A in which o is 1, $R^{78}$ is 2"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53a Compounds of the formula I.A in which o is 1, $R^{78}$ is 2"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54a Compounds of the formula I.A in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55a Compounds of the formula I.A in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56a Compounds of the formula I.A in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57a Compounds of the formula I.A in which o is 1, $R^{78}$ is 3"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58a Compounds of the formula I.A in which o is 1, $R^{78}$ is 3"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59a Compounds of the formula I.A in which o is 1, $R^{78}$ is 3"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60a Compounds of the formula I.A in which o is 1, $R^{78}$ is 3"-CH$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1b Compounds of formula I.B in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2b Compounds of formula I.B in which o is 1, $R^{78}$ is 1"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3b Compounds of formula I.B in which o is 1, $R^{78}$ is 1"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4b Compounds of formula I.B in which o is 1, $R^{78}$ is 1"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5b Compounds of formula I.B in which o is 1, $R^{78}$ is 1"-CH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6b Compounds of formula I.B in which o is 1, $R^{78}$ is 1"-OCH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7b Compounds of formula I.B in which o is 1, $R^{78}$ is 1"-OCHF$_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8b Compounds of formula I.B in which o is 1, $R^{78}$ is 1"-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9b Compounds of formula I.B in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10b Compounds of formula I.B in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11b Compounds of formula I.B in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12b Compounds of formula I.B in which o is 1, $R^{78}$ is 3"-CH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13b Compounds of formula I.B in which o is 1, $R^{78}$ is 3"-OCH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14b Compounds of formula I.B in which o is 1, $R^{78}$ is 3"-OCHF$_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15b Compounds of formula I.B in which o is 1, $R^{78}$ is 3"-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16b Compounds of formula I.B in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17b Compounds of formula I.B in which o is 1, $R^{78}$ is 1"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18b Compounds of formula I.B in which o is 1, $R^{78}$ is 1"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19b Compounds of formula I.B in which o is 1, $R^{78}$ is 1"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20b Compounds of formula I.B in which o is 1, $R^{78}$ is 1"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21b Compounds of formula I.B in which o is 1, $R^{78}$ is 1"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22b Compounds of formula I.B in which o is 1, $R^{78}$ is 1"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23b Compounds of formula I.B in which o is 1, $R^{78}$ is 1"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24b Compounds of formula I.B in which o is 1, $R^{78}$ is 3"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25b Compounds of formula I.B in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26b Compounds of formula I.B in which o is 1, $R^{78}$ is 3"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27b Compounds of formula I.B in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28b Compounds of formula I.B in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29b Compounds of formula I.B in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30b Compounds of formula I.B in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31b Compounds of formula I.B in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32b Compounds of formula I.B in which o is 1, $R^{78}$ is 1"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33b Compounds of formula I.B in which o is 1, $R^{78}$ is 1"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34b Compounds of formula I.B in which o is 1, $R^{78}$ is 1"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35b Compounds of formula I.B in which o is 1, $R^{78}$ is 1"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36b Compounds of formula I.B in which o is 1, $R^{78}$ is 1"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37b Compounds of formula I.B in which o is 1, $R^{78}$ is 1"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38b Compounds of formula I.B in which o is 1, $R^{78}$ is 1"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39b Compounds of formula I.B in which o is 1, $R^{78}$ is 3"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40b Compounds of formula I.B in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41b Compounds of formula I.B in which o is 1, $R^{78}$ is 3"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42b Compounds of formula I.B in which o is 1, $R^{78}$ is 3"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43b Compounds of formula I.B in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44b Compounds of formula I.B in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45b Compounds of formula I.B in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46b Compounds of the formula I.B in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47b Compounds of the formula I.B in which o is 1, $R^{78}$ is 1"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48b Compounds of the formula I.B in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49b Compounds of the formula I.B in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50b Compounds of the formula I.B in which o is 1, $R^{78}$ is 1"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51b Compounds of the formula I.B in which o is 1, $R^{78}$ is 1"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52b Compounds of the formula I.B in which o is 1, $R^{78}$ is 1"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53b Compounds of the formula I.B in which o is 1, $R^{78}$ is 1"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54b Compounds of the formula I.B in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55b Compounds of the formula I.B in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56b Compounds of the formula I.B in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57b Compounds of the formula I.B in which o is 1, $R^{78}$ is 3"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58b Compounds of the formula I.B in which o is 1, $R^{78}$ is 3"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59b Compounds of the formula I.B in which o is 1, $R^{78}$ is 3"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60b Compounds of the formula I.B in which o is 1, $R^{78}$ is 3"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1c Compounds of formula I.C in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2c Compounds of formula I.C in which o is 1, $R^{78}$ is 2"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3c Compounds of formula I.C in which o is 1, $R^{78}$ is 2"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4c Compounds of formula I.C in which o is 1, $R^{78}$ is 2"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5c Compounds of formula I.C in which o is 1, $R^{78}$ is 2"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6c Compounds of formula I.C in which o is 1, $R^{78}$ is 2"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7c Compounds of formula I.C in which o is 1, $R^{78}$ is 2"-$OCHF_2$, $R^5$ is F, $R^6$ is F and the meaning for the combination of $R^1$, $R^2$, $R^3$, $R^4$, $R^5$, $R^6$, $R^9$ and $R^{10}$ for each individual compound corresponds in each case to one line of Table B.

Table 8c Compounds of formula I.C in which o is 1, $R^{78}$ is 2"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9c Compounds of formula I.C in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10c Compounds of formula I.C in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11c Compounds of formula I.C in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12c Compounds of formula I.C in which o is 1, $R^{78}$ is 3"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13c Compounds of formula I.C in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14c Compounds of formula I.C in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15c Compounds of formula I.C in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16c Compounds of formula I.C in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17c Compounds of formula I.C in which o is 1, $R^{78}$ is 2"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18c Compounds of formula I.C in which o is 1, $R^{78}$ is 2"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19c Compounds of formula I.C in which o is 1, $R^{78}$ is 2"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20c Compounds of formula I.C in which o is 1, $R^{78}$ is 2"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21c Compounds of formula I.C in which o is 1, $R^{78}$ is 2"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22c Compounds of formula I.C in which o is 1, $R^{78}$ is 2"-$OCHF_2$, $R^5$ is Cl, $R^6$ is Cl and the meaning for the combination of $R^1$, $R^2$, $R^3$, $R^4$, $R^5$, $R^6$, $R^9$ and $R^{10}$ for each individual compound corresponds in each case to one line of Table B.

Table 23c Compounds of formula I.C in which o is 1, $R^{78}$ is 2"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24c Compounds of formula I.C in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25c Compounds of formula I.C in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26c Compounds of formula I.C in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27c Compounds of formula I.C in which o is 1, $R^{78}$ is 3-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28c Compounds of formula I.C in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29c Compounds of formula I.C in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30c Compounds of formula I.C in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31c Compounds of formula I.C in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32c Compounds of formula I.C in which o is 1, $R^{78}$ is 2"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33c Compounds of formula I.C in which o is 1, $R^{78}$ is 2"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34c Compounds of formula I.C in which o is 1, $R^{78}$ is 2"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35c Compounds of formula I.C in which o is 1, $R^{78}$ is 2"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36c Compounds of formula I.C in which o is 1, $R^{78}$ is 2"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37c Compounds of formula I.C in which o is 1, $R^{78}$ is 2"-$OCHF_2$, $R^5$ is Cl, $R^6$ is F and the meaning for the combination of $R^1$, $R^2$, $R^3$, $R^4$, $R^5$, $R^6$, $R^9$ and $R^{10}$ for each individual compound corresponds in each case to one line of Table B.

Table 38c Compounds of formula I.C in which o is 1, $R^{78}$ is 2"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39c Compounds of formula I.C in which o is 1, $R^{78}$ is 3"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40c Compounds of formula I.C in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41c Compounds of formula I.C in which o is 1, $R^{78}$ is 3"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42c Compounds of formula I.C in which o is 1, $R^{78}$ is 3-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43c Compounds of formula I.C in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44c Compounds of formula I.C in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45c Compounds of formula I.C in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46c Compounds of the formula I.C in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47c Compounds of the formula I.C in which o is 1, $R^{78}$ is 2"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48c Compounds of the formula I.C in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49c Compounds of formula I.C in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50c Compounds of formula I.C in which o is 1, $R^{78}$ is 2"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51c Compounds of formula I.C in which o is 1, $R^{78}$ is 2"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52c Compounds of formula I.C in which o is 1, $R^{78}$ is 2"-$OCHF_2$, $R^5$ is Br, $R^6$ is Br and the meaning for the combination of $R^1$, $R^2$, $R^3$, $R^4$, $R^5$, $R^6$, $R^9$ and $R^{10}$ for each individual compound corresponds in each case to one line of Table B.

Table 53c Compounds of formula I.C in which o is 1, $R^{78}$ is 2"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54c Compounds of the formula I.C in which o is 1, $R^{78}$ is 3-F, $R^5$ is Br, R6 is Br and the meaning for the combination of $R^1$, $R^2$, $R^3$, $R^4$, $R^9$ and $R^{10}$ for each individual compound corresponds in each case to one line of Table B.

Table 55c Compounds of formula I.C in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56c Compounds of formula I.C in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57c Compounds of formula I.C in which o is 1, $R^{78}$ is 3-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58c Compounds of the formula I.C in which o is 1, $R^{78}$ is 3"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59c Compounds of the formula I.C in which o is 1, $R^{78}$ is 3-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60c Compounds of the formula I.C in which o is 1, $R^{78}$ is 3-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1d Compounds of formula I.D in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2d Compounds of formula I.D in which o is 1, $R^{78}$ is 2"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3d Compounds of formula I.D in which o is 1, $R^{78}$ is 2"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4d Compounds of formula I.D in which o is 1, $R^{78}$ is 2"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5d Compounds of formula I.D in which o is 1, $R^{78}$ is 2"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6d Compounds of formula I.D in which o is 1, $R^{78}$ is 2"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7d Compounds of formula I.D in which o is 1, $R^{78}$ is 2"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8d Compounds of formula I.D in which o is 1, $R^{78}$ is 2"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9d Compounds of formula I.D in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10d Compounds of formula I.D in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11d Compounds of formula I.D in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12d Compounds of formula I.D in which o is 1, $R^{78}$ is 3-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13d Compounds of formula I.D in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14d Compounds of formula I.D in which o is 1, $R^{78}$ is 3"-OCHF$_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15d Compounds of formula I.D in which o is 1, $R^{78}$ is 3-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16d Compounds of formula I.D in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17d Compounds of formula I.D in which o is 1, $R^{78}$ is 2"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18d Compounds of formula I.D in which o is 1, $R^{78}$ is 2"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19d Compounds of formula I.D in which o is 1, $R^{78}$ is 2"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20d Compounds of formula I.D in which o is 1, $R^{78}$ is 2"-CH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21d Compounds of formula I.D in which o is 1, $R^{78}$ is 2"-OCH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22d Compounds of formula I.D in which o is 1, $R^{78}$ is 2"-OCHF$_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23d Compounds of formula I.D in which o is 1, $R^{78}$ is 2"-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24d Compounds of formula I.D in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25d Compounds of formula I.D in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26d Compounds of formula I.D in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27d Compounds of formula I.D in which o is 1, $R^{78}$ is 3-CH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28d Compounds of formula I.D in which o is 1, $R^{78}$ is 3"-OCH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29d Compounds of formula I.D in which o is 1, $R^{78}$ is 3-OCHF$_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30d Compounds of formula I.D in which o is 1, $R^{78}$ is 3"-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31d Compounds of formula I.D in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32d Compounds of formula I.D in which o is 1, $R^{78}$ is 2"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33d Compounds of formula I.D in which o is 1, $R^{78}$ is 2"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34d Compounds of formula I.D in which o is 1, $R^{78}$ is 2"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35d Compounds of formula I.D in which o is 1, $R^{78}$ is 2"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36d Compounds of formula I.D in which o is 1, $R^{78}$ is 2"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37d Compounds of formula I.D in which o is 1, $R^{78}$ is 2"-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38d Compounds of formula I.D in which o is 1, $R^{78}$ is 2"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39d Compounds of formula I.D in which o is 1, $R^{78}$ is 3"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40d Compounds of formula I.D in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41d Compounds of formula I.D in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42d Compounds of formula I.D in which o is 1, $R^{78}$ is 3-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43d Compounds of formula I.D in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44d Compounds of formula I.D in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45d Compounds of formula I.D in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46d Compounds of the formula I.D in which o is 0, $R^5$ is Br, R6 is Br and the meaning for the combination of $R^1$, $R^2$, $R^3$, $R^4$, $R^9$ and $R^{10}$ for each individual compound corresponds in each case to one line of Table B.

Table 47d Compounds of the formula I.D in which o is 1, $R^{78}$ is 2"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48d Compounds of the formula I.D in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49d Compounds of the formula I.D in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50d Compounds of the formula I.D in which o is 1, $R^{78}$ is 2"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51d Compounds of the formula I.D in which o is 1, $R^{78}$ is 2"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52d Compounds of the formula I.D in which o is 1, $R^{78}$ is 2"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53d Compounds of the formula I.D in which o is 1, $R^{78}$ is 2"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54d Compounds of the formula I.D in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55d Compounds of the formula I.D in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56d Compounds of the formula I.D in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57d Compounds of the formula I.D in which o is 1, $R^{78}$ is 3-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58d Compounds of the formula I.D in which o is 1, $R^{78}$ is 3"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59d Compounds of the formula I.D in which o is 1, $R^{78}$ is 3-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60d Compounds of the formula I.D in which o is 1, $R^{78}$ is 3-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1e Compounds of formula I.E in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2e Compounds of formula I.E in which o is 1, $R^{78}$ is 1"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3e Compounds of formula I.E in which o is 1, $R^{78}$ is 1"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4e Compounds of formula I.E in which o is 1, $R^{78}$ is 1"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5e Compounds of formula I.E in which o is 1, $R^{78}$ is 1"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6e Compounds of formula I.E in which o is 1, $R^{78}$ is 1"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7e Compounds of formula I.E in which o is 1, $R^{78}$ is 1"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8e Compounds of formula I.E in which o is 1, $R^{78}$ is 1"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9e Compounds of formula I.E in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10e Compounds of formula I.E in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11e Compounds of formula I.E in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12e Compounds of formula I.E in which o is 1, $R^{78}$ is 3-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13e Compounds of formula I.E in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14e Compounds of formula I.E in which o is 1, $R^{78}$ is 3-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15e Compounds of formula I.E in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 16e Compounds of formula I.E in which o is 1, $R^{78}$ is 1"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17e Compounds of formula I.E in which o is 1, $R^{78}$ is 1"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18e Compounds of formula I.E in which o is 1, $R^{78}$ is 1"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19e Compounds of formula I.E in which o is 1, $R^{78}$ is 1"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20e Compounds of formula I.E in which o is 1, $R^{78}$ is 1"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21e Compounds of formula I.E in which o is 1, $R^{78}$ is 1"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22e Compounds of formula I.E in which o is 1, $R^{78}$ is 1"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23e Compounds of formula I.E in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24e Compounds of formula I.E in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25e Compounds of formula I.E in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26e Compounds of formula I.E in which o is 1, $R^{78}$ is 3-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27e Compounds of formula I.E in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28e Compounds of formula I.E in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29e Compounds of formula I.E in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 30e Compounds of formula I.E in which o is 1, $R^{78}$ is 1"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 31e Compounds of formula I.E in which o is 1, $R^{78}$ is 1"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32e Compounds of formula I.E in which o is 1, $R^{78}$ is 1"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33e Compounds of formula I.E in which o is 1, $R^{78}$ is 1"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34e Compounds of formula I.E in which o is 1, $R^{78}$ is 1"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35e Compounds of formula I.E in which o is 1, $R^{78}$ is 1"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36e Compounds of formula I.E in which o is 1, $R^{78}$ is 1"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37e Compounds of formula I.E in which o is 1, $R^{78}$ is 3"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38e Compounds of formula I.E in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39e Compounds of formula I.E in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40e Compounds of formula I.E in which o is 1, $R^{78}$ is 3-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41e Compounds of formula I.E in which o is 1, $R^{78}$ is 3"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42e Compounds of formula I.E in which o is 1, $R^{78}$ is 3-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43e Compounds of the formula I.E in which o is 0, $R^5$ is Br, R6 is Br and the meaning for the combination of $R^1$, $R^2$, $R^3$, $R^4$, $R^9$ and $R^{10}$ for each individual compound corresponds in each case to one line of Table B.

Table 44e Compounds of the formula I.E in which o is 1, $R^{78}$ is 1"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 45e Compounds of the formula I.E in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 46e Compounds of the formula I.E in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47e Compounds of the formula I.E in which o is 1, $R^{78}$ is 1"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48e Compounds of the formula I.E in which o is 1, $R^{78}$ is 1"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49e Compounds of the formula I.E in which o is 1, $R^{78}$ is 1"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50e Compounds of the formula I.E in which o is 1, $R^{78}$ is 1"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51e Compounds of the formula I.E in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52e Compounds of the formula I.E in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53e Compounds of the formula I.E in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54e Compounds of the formula I.E in which o is 1, $R^{78}$ is 3-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55e Compounds of the formula I.E in which o is 1, $R^{78}$ is 3"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56e Compounds of the formula I.E in which o is 1, $R^{78}$ is 3"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1f Compounds of formula I.E in which o is 1, $R^{78}$ is 3"-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2f Compounds of formula I.F in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3f Compounds of formula I.F in which o is 1, $R^{78}$ is 2"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4f Compounds of formula I.F in which o is 1, $R^{78}$ is 2"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5f Compounds of formula I.F in which o is 1, $R^{78}$ is 2"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6f Compounds of formula I.F in which o is 1, $R^{78}$ is 2"-CH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7f Compounds of formula I.F in which o is 1, $R^{78}$ is 2"-OCH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8f Compounds of formula I.F in which o is 1, $R^{78}$ is 2"-OCHF$_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9f Compounds of formula I.F in which o is 1, $R^{78}$ is 2"-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10f Compounds of formula I.F in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11f Compounds of formula I.F in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12f Compounds of formula I.F in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13f Compounds of formula I.F in which o is 1, $R^{78}$ is 3-CH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14f Compounds of formula I.F in which o is 1, $R^{78}$ is 3"-OCH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15f Compounds of formula I.F in which o is 1, $R^{78}$ is 3"-OCHF$_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16f Compounds of formula I.F in which o is 1, $R^{78}$ is 3-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 17f Compounds of formula I.E in which o is 1, $R^{78}$ is 3-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18f Compounds of formula I.F in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19f Compounds of formula I.F in which o is 1, $R^{78}$ is 2"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20f Compounds of formula I.F in which o is 1, $R^{78}$ is 2"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21f Compounds of formula I.F in which o is 1, $R^{78}$ is 2"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22f Compounds of formula I.F in which o is 1, $R^{78}$ is 2"-CH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23f Compounds of formula I.F in which o is 1, $R^{78}$ is 2"-OCH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24f Compounds of formula I.F in which o is 1, $R^{78}$ is 2"-OCHF$_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25f Compounds of formula I.F in which o is 1, $R^{78}$ is 2"-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26f Compounds of formula I.F in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27f Compounds of formula I.F in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28f Compounds of formula I.F in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29f Compounds of formula I.F in which o is 1, $R^{78}$ is 3-CH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30f Compounds of formula I.F in which o is 1, $R^{78}$ is 3"-OCH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31f Compounds of formula I.F in which o is 1, $R^{78}$ is 3"-OCHF$_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 32f Compounds of formula I.F in which o is 1, $R^{78}$ is 3"-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 33f Compounds of formula I.E in which o is 1, $R^{78}$ is 3"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34f Compounds of formula I.F in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35f Compounds of formula I.F in which o is 1, $R^{78}$ is 2"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36f Compounds of formula I.F in which o is 1, $R^{78}$ is 2"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37f Compounds of formula I.F in which o is 1, $R^{78}$ is 2"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38f Compounds of formula I.F in which o is 1, $R^{78}$ is 2"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39f Compounds of formula I.F in which o is 1, $R^{78}$ is 2"-OCH$_3$, $R^5$ is Cl, $R^6$ is F and the meaning for the Table 40f Compounds of formula I.F in which o is 1, $R^{78}$ is 2"-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41f Compounds of formula I.F in which o is 1, $R^{78}$ is 2"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42f Compounds of formula I.F in which o is 1, $R^{78}$ is 3-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43f Compounds of formula I.F in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44f Compounds of formula I.F in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45f Compounds of formula I.F in which o is 1, $R^{78}$ is 3"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46f Compounds of formula I.F in which o is 1, $R^{78}$ is 3"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 47f Compounds of formula I.F in which o is 1, $R^{78}$ is 3"-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 48f Compounds of formula I.F in which o is 1, $R^{78}$ is 3"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 49f Compounds of the formula I.E in which o is 1, $R^{78}$ is 3"-CH$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50f Compounds of the formula I.F in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51f Compounds of the formula I.F in which o is 1, $R^{78}$ is 2"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52f Compounds of the formula I.F in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53f Compounds of the formula I.F in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54f Compounds of the formula I.F in which o is 1, $R^{78}$ is 2"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55f Compounds of the formula I.F in which o is 1, $R^{78}$ is 2"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56f Compounds of the formula I.F in which o is 1, $R^{78}$ is 2"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57f Compounds of the formula I.F in which o is 1, $R^{78}$ is 2"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58f Compounds of the formula I.F in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59f Compounds of the formula I.F in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60f Compounds of the formula I.F in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 61f Compounds of the formula I.F in which o is 1, $R^{78}$ is 3-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 62f Compounds of the formula I.F in which o is 1, $R^{78}$ is 3-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 63f Compounds of the formula I.F in which o is 1, $R^{78}$ is 3"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 64f Compounds of the formula I.F in which o is 1, $R^{78}$ is 3"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1g Compounds of formula I.G in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2g Compounds of formula I.G in which o is 1, $R^{78}$ is 2"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3g Compounds of formula I.G in which o is 1, $R^{78}$ is 2"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4g Compounds of formula I.G in which o is 1, $R^{78}$ is 2"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5g Compounds of formula I.G in which o is 1, $R^{78}$ is 2"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6g Compounds of formula I.G in which o is 1, $R^{78}$ is 2"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7g Compounds of formula I.G in which o is 1, $R^{78}$ is 2"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8g Compounds of formula I.G in which o is 1, $R^{78}$ is 2"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9g Compounds of formula I.G in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10g Compounds of formula I.G in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11g Compounds of formula I.G in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12g Compounds of formula I.G in which o is 1, $R^{78}$ is 3-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13g Compounds of formula I.G in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14g Compounds of formula I.G in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15g Compounds of formula I.G in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16g Compounds of formula I.G in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17g Compounds of formula I.G in which o is 1, $R^{78}$ is 2"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18g Compounds of formula I.G in which o is 1, $R^{78}$ is 2"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19g Compounds of formula I.G in which o is 1, $R^{78}$ is 2"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20g Compounds of formula I.G in which o is 1, $R^{78}$ is 2"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21g Compounds of formula I.G in which o is 1, $R^{78}$ is 2"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22g Compounds of formula I.G in which o is 1, $R^{78}$ is 2"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23g Compounds of formula I.G in which o is 1, $R^{78}$ is 2"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24g Compounds of formula I.G in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25g Compounds of formula I.G in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26g Compounds of formula I.G in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27g Compounds of formula I.G in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28g Compounds of formula I.G in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29g Compounds of formula I.G in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30g Compounds of formula I.G in which o is 1, $R^{78}$ is 3"-$C_6H_5$ and the meaning for the combination of $R^1$, $R^2$, $R^3$, $R^4$, $R^9$ and $R^{10}$ for each individual compound corresponds in each case to one line of Table B.

Table 31g Compounds of formula I.G in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32g Compounds of formula I.G in which o is 1, $R^{78}$ is 2"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33g Compounds of formula I.G in which o is 1, $R^{78}$ is 2"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34g Compounds of formula I.G in which o is 1, $R^{78}$ is 2"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35g Compounds of formula I.G in which o is 1, $R^{78}$ is 2"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36g Compounds of formula I.G in which o is 1, $R^{78}$ is 2"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37g Compounds of formula I.G in which o is 1, $R^{78}$ is 2"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38g Compounds of formula I.G in which o is 1, $R^{78}$ is 2"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39g Compounds of formula I.G in which o is 1, $R^{78}$ is 3-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40g Compounds of formula I.G in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41g Compounds of formula I.G in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42g Compounds of formula I.G in which o is 1, $R^{78}$ is 3"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43g Compounds of formula I.G in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44g Compounds of formula I.G in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45g Compounds of formula I.G in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46g Compounds of the formula I.G in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47g Compounds of the formula I.G in which o is 1, $R^{78}$ is 2"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48g Compounds of the formula I.G in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49g Compounds of the formula I.G in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50g Compounds of the formula I.G in which o is 1, $R^{78}$ is 2"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51g Compounds of the formula I.G in which o is 1, $R^{78}$ is 2"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52g Compounds of the formula I.G in which o is 1, $R^{78}$ is 2"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53g Compounds of the formula I.G in which o is 1, $R^{78}$ is 2"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54g Compounds of the formula I.G in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55g Compounds of the formula I.G in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56g Compounds of the formula I.G in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57g Compounds of the formula I.G in which o is 1, $R^{78}$ is 3-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58g Compounds of the formula I.G in which o is 1, $R^{78}$ is 3-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59g Compounds of the formula I.G in which o is 1, $R^{78}$ is 3"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60g Compounds of the formula I.G in which o is 1, $R^{78}$ is 3"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1h Compounds of formula I.H in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2h Compounds of formula I.H in which o is 1, $R^{78}$ is 1"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3h Compounds of formula I.H in which o is 1, $R^{78}$ is 1"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4h Compounds of formula I.H in which o is 1, $R^{78}$ is 1"-Br, $R^5$ is F, $R^6$ is F and the meaning for the combination of $R^1$, $R^2$, $R^3$, $R^4$, $R^5$, $R^6$, $R^9$ and $R^{10}$ for each individual compound corresponds in each case to one line of Table B.

Table 5h Compounds of formula I.H in which o is 1, $R^{78}$ is 1"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6h Compounds of formula I.H in which o is 1, $R^{78}$ is 1"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7h Compounds of formula I.H in which o is 1, $R^{78}$ is 1"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8h Compounds of formula I.H in which o is 1, $R^{78}$ is 1"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9h Compounds of formula I.H in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10h Compounds of formula I.H in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11h Compounds of formula I.H in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12h Compounds of formula I.H in which o is 1, $R^{78}$ is 3-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13h Compounds of formula I.H in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14h Compounds of formula I.H in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15h Compounds of formula I.H in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ 6 for each individual compound corresponds in each case to one line of Table B.

Table 16h Compounds of formula I.H in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17h Compounds of formula I.H in which o is 1, $R^{78}$ is 1"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18h Compounds of formula I.H in which o is 1, $R^{78}$ is 1"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19h Compounds of formula I.H in which o is 1, $R^{78}$ is 1"-Br, $R^5$ is Cl, $R^6$ is Cl and the meaning for the combination of $R^1$, $R^2$, $R^3$, $R^4$, $R^5$, $R^6$, $R^9$ and $R^{10}$ for each individual compound corresponds in each case to one line of Table B.

Table 20h Compounds of formula I.H in which o is 1, $R^{78}$ is 1"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 21h Compounds of formula I.H in which o is 1, $R^{78}$ is 1"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22h Compounds of formula I.H in which o is 1, $R^{78}$ is 1"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23h Compounds of formula I.H in which o is 1, $R^{78}$ is 1"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24h Compounds of formula I.H in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25h Compounds of formula I.H in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26h Compounds of formula I.H in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27h Compounds of formula I.H in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28h Compounds of formula I.H in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29h Compounds of formula I.H in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30h Compounds of formula I.H in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ 6 for each individual compound corresponds in each case to one line of Table B.

Table 31h Compounds of formula I.H in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32h Compounds of formula I.H in which o is 1, $R^{78}$ is 1"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33h Compounds of formula I.H in which o is 1, $R^{78}$ is 1"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34h Compounds of formula I.H in which o is 1, $R^{78}$ is 1"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35h Compounds of formula I.H in which o is 1, $R^{78}$ is 1"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 36h Compounds of formula I.H in which o is 1, $R^{78}$ is 1"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37h Compounds of formula I.H in which o is 1, $R^{78}$ is 1"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38h Compounds of formula I.H in which o is 1, $R^{78}$ is 1"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39h Compounds of formula I.H in which o is 1, $R^{78}$ is 3-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40h Compounds of formula I.H in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 41h Compounds of formula I.H in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42h Compounds of formula I.H in which o is 1, $R^{78}$ is 3"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43h Compounds of formula I.H in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44h Compounds of formula I.H in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45h Compounds of formula I.H in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ 6 for each individual compound corresponds in each case to one line of Table B.

Table 46h Compounds of the formula I.H in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47h Compounds of the formula I.H in which o is 1, $R^{78}$ is 1"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48h Compounds of the formula I.H in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49h Compounds of the formula I.H in which o is 1, $R^{78}$ is 1"-Br, $R^5$ is Br, $R^6$ is Br and the meaning for the combination of $R^1$, $R^2$, $R^3$, $R^4$, $R^5$, $R^6$, $R^9$ and $R^{10}$ for each individual compound corresponds in each case to one line of Table B.

Table 50h Compounds of the formula I.H in which o is 1, $R^{78}$ is 1"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 51h Compounds of the formula I.H in which o is 1, $R^{78}$ is 1"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52h Compounds of the formula I.H in which o is 1, $R^{78}$ is 1"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53h Compounds of the formula I.H in which o is 1, $R^{78}$ is 1"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54h Compounds of the formula I.H in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55h Compounds of the formula I.H in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 56h Compounds of the formula I.H in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57h Compounds of the formula I.H in which o is 1, $R^{78}$ is 3"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58h Compounds of the formula I.H in which o is 1, $R^{78}$ is 3"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59h Compounds of the formula I.H in which o is 1, $R^{78}$ is 3-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60h Compounds of the formula I.H in which o is 1, $R^{78}$ is 3"-$C_6H_5$, $R^5$ is Br, $R^6$ is Br and the meaning for the combination of $R^1$, $R^2$, $R^3$, $R^4$, $R^9$ and $R^{10}$ 6 for each individual compound corresponds in each case to one line of Table B.

Table 1i Compounds of formula I.I in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2i Compounds of formula I.I in which o is 1, $R^{78}$ is 2"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3i Compounds of formula I.I in which o is 1, $R^{78}$ is 2"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4i Compounds of formula I.I in which o is 1, $R^{78}$ is 2"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5i Compounds of formula I.I in which o is 1, $R^{78}$ is 2"-$CH_3$, $R^5$ is F, $R^6$ is F and the meaning for the combination of $R^1$, $R^2$, $R^3$, $R^4$, $R^9$ and $R^{10}$ 6 for each individual compound corresponds in each case to one line of Table B.

Table 6i Compounds of formula I.I in which o is 1, $R^{78}$ is 2"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7i Compounds of formula I.I in which o is 1, $R^{78}$ is 2"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8i Compounds of formula I.I in which o is 1, $R^{78}$ is 2"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9i Compounds of formula I.I in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10i Compounds of formula I.I in which o is 1, $R^{78}$ is 3-Cl, $R^5$ is F, $R^6$ is F and the meaning for the combination of $R^1$, $R^2$, $R^3$, $R^4$, $R^5$, $R^6$, $R^9$ and $R^{10}$ for each individual compound corresponds in each case to one line of Table B.

Table 11i Compounds of formula I.I in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12i Compounds of formula I.I in which o is 1, $R^{78}$ is 3"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13i Compounds of formula I.I in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14i Compounds of formula I.I in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15i Compounds of formula I.I in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16i Compounds of formula I.I in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17i Compounds of formula I.I in which o is 1, $R^{78}$ is 2"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 18i Compounds of formula I.I in which o is 1, $R^{78}$ is 2"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 19i Compounds of formula I.I in which o is 1, $R^{78}$ is 2"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 20i Compounds of formula I.I in which o is 1, $R^{78}$ is 2"-$CH_3$, $R^5$ is Cl, $R^6$ is Cl and the meaning for the combination of $R^1$, $R^2$, $R^3$, $R^4$, $R^9$ and $R^{10}$ 6 for each individual compound corresponds in each case to one line of Table B.

Table 21i Compounds of formula I.I in which o is 1, $R^{78}$ is 2"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 22i Compounds of formula I.I in which o is 1, $R^{78}$ is 2"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 23i Compounds of formula I.I in which o is 1, $R^{78}$ is 2"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24i Compounds of formula I.I in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25i Compounds of formula I.I in which o is 1, $R^{78}$ is 3-Cl, $R^5$ is Cl, $R^6$ is Cl and the meaning for the combination of $R^1$, $R^2$, $R^3$, $R^4$, $R^5$, $R^6$, $R^9$ and $R^{10}$ for each individual compound corresponds in each case to one line of Table B.

Table 26i Compounds of formula I.I in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27i Compounds of formula I.I in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28i Compounds of formula I.I in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29i Compounds of formula I.I in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30i Compounds of formula I.I in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31i Compounds of formula I.I in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 32i Compounds of formula I.I in which o is 1, $R^{78}$ is 2"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 33i Compounds of formula I.I in which o is 1, $R^{78}$ is 2"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 34i Compounds of formula I.I in which o is 1, $R^{78}$ is 2"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 35i Compounds of formula I.I in which o is 1, $R^{78}$ is 2"-$CH_3$, $R^5$ is Cl, $R^6$ is F and the meaning for the combination of $R^1$, $R^2$, $R^3$, $R^4$, $R^9$ and $R^{10}$ 6 for each individual compound corresponds in each case to one line of Table B.

Table 36i Compounds of formula I.I in which o is 1, $R^{78}$ is 2"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 37i Compounds of formula I.I in which o is 1, $R^{78}$ is 2"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 38i Compounds of formula I.I in which o is 1, $R^{78}$ is 2"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 39i Compounds of formula I.I in which o is 1, $R^{78}$ is 3-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 40i Compounds of formula I.I in which o is 1, $R^{78}$ is 3-Cl, $R^5$ is Cl, $R^6$ is F and the meaning for the combination of $R^1$, $R^2$, $R^3$, $R^4$, $R^5$, $R^6$, $R^9$ and $R^{10}$ for each individual compound corresponds in each case to one line of Table B.

Table 41i Compounds of formula I.I in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 42i Compounds of formula I.I in which o is 1, $R^{78}$ is 3"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 43i Compounds of formula I.I in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 44i Compounds of formula I.I in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 45i Compounds of formula I.I in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46i Compounds of the formula I.I in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 47i Compounds of the formula I.I in which o is 1, $R^{78}$ is 2"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 48i Compounds of the formula I.I in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 49i Compounds of the formula I.I in which o is 1, $R^{78}$ is 2"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 50i Compounds of the formula I.I in which o is 1, $R^{78}$ is 2"-$CH_3$, $R^5$ is Br, $R^6$ is Br and the meaning for the combination of $R^1$, $R^2$, $R^3$, $R^4$, $R^9$ and $R^{10}$ 6 for each individual compound corresponds in each case to one line of Table B.

Table 51i Compounds of the formula I.I in which o is 1, $R^{78}$ is 2"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 52i Compounds of the formula I.I in which o is 1, $R^{78}$ is 2"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 53i Compounds of the formula I.I in which o is 1, $R^{78}$ is 2"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 54i Compounds of the formula I.I in which o is 1, $R^{78}$ is 3-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 55i Compounds of the formula I.I in which o is 1, $R^{78}$ is 3-Br, $R^5$ is Br, $R^6$ is Br and the meaning for the combination of $R^1$, $R^2$, $R^3$, $R^4$, $R^5$, $R^6$, $R^9$ and $R^{10}$ for each individual compound corresponds in each case to one line of Table B.

Table 56i Compounds of the formula I.I in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 57i Compounds of the formula I.I in which o is 1, $R^{78}$ is 3"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 58i Compounds of the formula I.I in which o is 1, $R^{78}$ is 3"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 59i Compounds of the formula I.I in which o is 1, $R^{78}$ is 3-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 60i Compounds of the formula I.I in which o is 1, $R^{78}$ is 3"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1j Compounds of formula I.J in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2j Compounds of formula I.J in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3j Compounds of formula I.J in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4j Compounds of formula I.J in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5j Compounds of formula I.J in which o is 1, $R^{78}$ is 3-CH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6j Compounds of formula I.J in which o is 1, $R^{78}$ is 3-OCH$_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7j Compounds of formula I.J in which o is 1, $R^{78}$ is 3-OCHF$_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8j Compounds of formula I.J in which o is 1, $R^{78}$ is 3-C$_6$H$_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9j Compounds of formula I.J in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 10j Compounds of formula I.J in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 11j Compounds of formula I.J in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 12j Compounds of formula I.J in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 13j Compounds of formula I.J in which o is 1, $R^{78}$ is 3"-CH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 14j Compounds of formula I.J in which o is 1, $R^{78}$ is 3"-OCH$_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 15j Compounds of formula I.J in which o is 1, $R^{78}$ is 3"-OCHF$_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 16j Compounds of formula I.J in which o is 1, $R^{78}$ is 3"-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 17j Compounds of formula I.J in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 18j Compounds of formula I.J in which o is 1, $R^{78}$ is 3-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 19j Compounds of formula I.J in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 20j Compounds of formula I.J in which o is 1, $R^{78}$ is 3-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 21j Compounds of formula I.J in which o is 1, $R^{78}$ is 3"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 22j Compounds of formula I.J in which o is 1, $R^{78}$ is 3"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 23j Compounds of formula I.J in which o is 1, $R^{78}$ is 3-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 24j Compounds of formula I.J in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 25j Compounds of the formula I.J in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 26j Compounds of the formula I.J in which o is 1, $R^{78}$ is 3"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 27j Compounds of the formula I.J in which o is 1, $R^{78}$ is 3"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 28j Compounds of the formula I.J in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 29j Compounds of the formula I.J in which o is 1, $R^{78}$ is 3-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 30j Compounds of the formula I.J in which o is 1, $R^{78}$ is 3-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 31j Compounds of the formula I.J in which o is 1, $R^{78}$ is 3"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 32j Compounds of the formula I.J in which o is 1, $R^{78}$ is 3"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1k Compounds of formula I.K in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2k Compounds of formula I.K in which o is 1, $R^{78}$ is 1"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3k Compounds of formula I.K in which o is 1, $R^{78}$ is 1"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4k Compounds of formula I.K in which o is 1, $R^{78}$ is 1"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5k Compounds of formula I.K in which o is 1, $R^{78}$ is 1"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6k Compounds of formula I.K in which o is 1, $R^{78}$ is 1"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7k Compounds of formula I.K in which o is 1, $R^{78}$ is 1"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8k Compounds of formula I.K in which o is 1, $R^{78}$ is 1"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9k Compounds of formula I.K in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10k Compounds of formula I.K in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11k Compounds of formula I.K in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12k Compounds of formula I.K in which o is 1, $R^{78}$ is 3"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13k Compounds of formula I.K in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14k Compounds of formula I.K in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15k Compounds of formula I.K in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16k Compounds of formula I.K in which o is 1, $R^{78}$ is 4"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 17k Compounds of formula I.K in which o is 1, $R^{78}$ is 4"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 18k Compounds of formula I.K in which o is 1, $R^{78}$ is 4"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 19k Compounds of formula I.K in which o is 1, $R^{78}$ is 4"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 20k Compounds of formula I.K in which o is 1, $R^{78}$ is 4"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 21k Compounds of formula I.K in which o is 1, $R^{78}$ is 4"-$OCHF_2$ and the meaning for the combination of $R^1$, $R^2$, $R^3$, $R^4$, $R^9$ and $R^{10}$ for each individual compound corresponds in each case to one line of Table B.

Table 22k Compounds of formula I.K in which o is 1, $R^{78}$ is 4"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 23k Compounds of formula I.K in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24k Compounds of formula I.K in which o is 1, $R^{78}$ is 1"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25k Compounds of formula I.K in which o is 1, $R^{78}$ is 1"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26k Compounds of formula I.K in which o is 1, $R^{78}$ is 1"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27k Compounds of formula I.K in which o is 1, $R^{78}$ is 1"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28k Compounds of formula I.K in which o is 1, $R^{78}$ is 1"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29k Compounds of formula I.K in which o is 1, $R^{78}$ is 1"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30k Compounds of formula I.K in which o is 1, $R^{78}$ is 1"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31k Compounds of formula I.K in which o is 1, $R^{78}$ is 3"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 32k Compounds of formula I.K in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 33k Compounds of formula I.K in which o is 1, $R^{78}$ is 3"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 34k Compounds of formula I.K in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 35k Compounds of formula I.K in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 36k Compounds of formula I.K in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 37k Compounds of formula I.K in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 38k Compounds of formula I.K in which o is 1, $R^{78}$ is 4"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 39k Compounds of formula I.K in which o is 1, $R^{78}$ is 4"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 40k Compounds of formula I.K in which o is 1, $R^{78}$ is 4"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 41k Compounds of formula I.K in which o is 1, $R^{78}$ is 4"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 42k Compounds of formula I.K in which o is 1, $R^{78}$ is 4"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 43k Compounds of formula I.K in which o is 1, $R^{78}$ is 4"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 44k Compounds of formula I.K in which o is 1, $R^{78}$ is 4"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 45k Compounds of formula I.K in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46k Compounds of formula I.K in which o is 1, $R^{78}$ is 1"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 47k Compounds of formula I.K in which o is 1, $R^{78}$ is 1"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 48k Compounds of formula I.K in which o is 1, $R^{78}$ is 1"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 49k Compounds of formula I.K in which o is 1, $R^{78}$ is 1"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 50k Compounds of formula I.K in which o is 1, $R^{78}$ is 1"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 51k Compounds of formula I.K in which o is 1, $R^{78}$ is 1"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 52k Compounds of formula I.K in which o is 1, $R^{78}$ is 1"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 53k Compounds of formula I.K in which o is 1, $R^{78}$ is 3"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 54k Compounds of formula I.K in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 55k Compounds of formula I.K in which o is 1, $R^{78}$ is 3"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 56k Compounds of formula I.K in which o is 1, $R^{78}$ is 3"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 57k Compounds of formula I.K in which o is 1, $R^{78}$ is 3"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 58k Compounds of formula I.K in which o is 1, $R^{78}$ is 3-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 59k Compounds of formula I.K in which o is 1, $R^{78}$ is 3"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 60k Compounds of formula I.K in which o is 1, $R^{78}$ is 4"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 61k Compounds of formula I.K in which o is 1, $R^{78}$ is 4"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 62k Compounds of formula I.K in which o is 1, $R^{78}$ is 4"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 63k Compounds of formula I.K in which o is 1, $R^{78}$ is 4"-$CH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 64k Compounds of formula I.K in which o is 1, $R^{78}$ is 4"-$OCH_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 65k Compounds of formula I.K in which o is 1, $R^{78}$ is 4"-$OCHF_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 66k Compounds of formula I.K in which o is 1, $R^{78}$ is 4"-$C_6H_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 67k Compounds of the formula I.K in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 68k Compounds of the formula I.K in which o is 1, $R^{78}$ is 1"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 69k Compounds of the formula I.K in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 70k Compounds of the formula I.K in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 71k Compounds of the formula I.K in which o is 1, $R^{78}$ is 1"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 72k Compounds of the formula I.K in which o is 1, $R^{78}$ is 1"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 73k Compounds of the formula I.K in which o is 1, $R^{78}$ is 1"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 74k Compounds of the formula I.K in which o is 1, $R^{78}$ is 1"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 75k Compounds of the formula I.K in which o is 1, $R^{78}$ is 3"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 76k Compounds of the formula I.K in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 77k Compounds of the formula I.K in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 78k Compounds of the formula I.K in which o is 1, $R^{78}$ is 3-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 79k Compounds of the formula I.K in which o is 1, $R^{78}$ is 3-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 80k Compounds of the formula I.K in which o is 1, $R^{78}$ is 3"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 81k Compounds of the formula I.K in which o is 1, $R^{78}$ is 3"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 82k Compounds of the formula I.K in which o is 1, $R^{78}$ is 4"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 83k Compounds of the formula I.K in which o is 1, $R^{78}$ is 4"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 84k Compounds of the formula I.K in which o is 1, $R^{78}$ is 4"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 85k Compounds of the formula I.K in which o is 1, $R^{78}$ is 4"-$CH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 86k Compounds of the formula I.K in which o is 1, $R^{78}$ is 4"-$OCH_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 87k Compounds of the formula I.K in which o is 1, $R^{78}$ is 4"-$OCHF_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 88k Compounds of the formula I.K in which o is 1, $R^{78}$ is 4"-$C_6H_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 1ka Compounds of formula I.Ka in which o is 0, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 2ka Compounds of formula I.Ka in which o is 1, $R^{78}$ is 1"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 3ka Compounds of formula I.Ka in which o is 1, $R^{78}$ is 1"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 4ka Compounds of formula I.Ka in which o is 1, $R^{78}$ is 1"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 5ka Compounds of formula I.Ka in which o is 1, $R^{78}$ is 1"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 6ka Compounds of formula I.Ka in which o is 1, $R^{78}$ is 1"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 7ka Compounds of formula I.Ka in which o is 1, $R^{78}$ is 1"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 8ka Compounds of formula I.Ka in which o is 1, $R^{78}$ is 1"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 9ka Compounds of formula I.Ka in which o is 1, $R^{78}$ is 3-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 10ka Compounds of formula I.Ka in which o is 1, $R^{78}$ is 3-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 11ka Compounds of formula I.Ka in which o is 1, $R^{78}$ is 3-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 12ka Compounds of formula I.Ka in which o is 1, $R^{78}$ is 3"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 13ka Compounds of formula I.Ka in which o is 1, $R^{78}$ is 3"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 14ka Compounds of formula I.Ka in which o is 1, $R^{78}$ is 3"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 15ka Compounds of formula I.Ka in which o is 1, $R^{78}$ is 3"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 16ka Compounds of formula I.Ka in which o is 1, $R^{78}$ is 4"-F, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 17ka Compounds of formula I.Ka in which o is 1, $R^{78}$ is 4"-Cl, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 18ka Compounds of formula I.Ka in which o is 1, $R^{78}$ is 4"-Br, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 19ka Compounds of formula I.Ka in which o is 1, $R^{78}$ is 4"-$CH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 20ka Compounds of formula I.Ka in which o is 1, $R^{78}$ is 4"-$OCH_3$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 21ka Compounds of formula I.Ka in which o is 1, $R^{78}$ is 4"-$OCHF_2$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 22ka Compounds of formula I.Ka in which o is 1, $R^{78}$ is 4"-$C_6H_5$, $R^5$ is F, $R^6$ is F and the meaning for the combination of $R^1$, $R^2$, $R^3$, $R^4$, $R^9$ and $R^{10}$ for each individual compound corresponds in each case to one line of Table B.

Table 23ka Compounds of formula I.Ka in which o is 0, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 24ka Compounds of formula I.Ka in which o is 1, $R^{78}$ is 1"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 25ka Compounds of formula I.Ka in which o is 1, $R^{78}$ is 1"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 26ka Compounds of formula I.Ka in which o is 1, $R^{78}$ is 1"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 27ka Compounds of formula I.Ka in which o is 1, $R^{78}$ is 1"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 28ka Compounds of formula I.Ka in which o is 1, $R^{78}$ is 1"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 29ka Compounds of formula I.Ka in which o is 1, $R^{78}$ is 1"-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 30ka Compounds of formula I.Ka in which o is 1, $R^{78}$ is 1"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 31ka Compounds of formula I.Ka in which o is 1, $R^{78}$ is 3-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 32ka Compounds of formula I.Ka in which o is 1, $R^{78}$ is 3-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 33ka Compounds of formula I.Ka in which o is 1, $R^{78}$ is 3-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 34ka Compounds of formula I.Ka in which o is 1, $R^{78}$ is 3"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 35ka Compounds of formula I.Ka in which o is 1, $R^{78}$ is 3"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 36ka Compounds of formula I.Ka in which o is 1, $R^{78}$ is 3-$OCHF_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 37ka Compounds of formula I.Ka in which o is 1, $R^{78}$ is 3"-$C_6H_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 38ka Compounds of formula I.Ka in which o is 1, $R^{78}$ is 4"-F, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 39ka Compounds of formula I.Ka in which o is 1, $R^{78}$ is 4"-Cl, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 40ka Compounds of formula I.Ka in which o is 1, $R^{78}$ is 4"-Br, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 41ka Compounds of formula I.Ka in which o is 1, $R^{78}$ is 4"-$CH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 42ka Compounds of formula I.Ka in which o is 1, $R^{78}$ is 4"-$OCH_3$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 43ka Compounds of formula I.Ka in which o is 1, $R^{78}$ is 4"-OCHF$_2$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 44ka Compounds of formula I.Ka in which o is 1, $R^{78}$ is 4"-C$_6$H$_5$, $R^5$ is Cl, $R^6$ is Cl and the meaning for the combination of $R^1$, $R^2$, $R^3$, $R^4$, $R^9$ and $R^{10}$ for each individual compound corresponds in each case to one line of Table B.

Table 45ka Compounds of formula I.Ka in which o is 0, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 46ka Compounds of formula I.Ka in which o is 1, $R^{78}$ is 1"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 47ka Compounds of formula I.Ka in which o is 1, $R^{78}$ is 1"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 48ka Compounds of formula I.Ka in which o is 1, $R^{78}$ is 1"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 49ka Compounds of formula I.Ka in which o is 1, $R^{78}$ is 1"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 50ka Compounds of formula I.Ka in which o is 1, $R^{78}$ is 1"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 51ka Compounds of formula I.Ka in which o is 1, $R^{78}$ is 1"-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 52ka Compounds of formula I.Ka in which o is 1, $R^{78}$ is 1"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 53ka Compounds of formula I.Ka in which o is 1, $R^{78}$ is 3"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 54ka Compounds of formula I.Ka in which o is 1, $R^{78}$ is 3-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 55ka Compounds of formula I.Ka in which o is 1, $R^{78}$ is 3"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 56ka Compounds of formula I.Ka in which o is 1, $R^{78}$ is 3"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 57ka Compounds of formula I.Ka in which o is 1, $R^{78}$ is 3"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 58ka Compounds of formula I.Ka in which o is 1, $R^{78}$ is 3-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 59ka Compounds of formula I.Ka in which o is 1, $R^{78}$ is 3"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 60ka Compounds of formula I.Ka in which o is 1, $R^{78}$ is 4"-F, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 61ka Compounds of formula I.Ka in which o is 1, $R^{78}$ is 4"-Cl, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 62ka Compounds of formula I.Ka in which o is 1, $R^{78}$ is 4"-Br, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 63ka Compounds of formula I.Ka in which o is 1, $R^{78}$ is 4"-CH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 64ka Compounds of formula I.Ka in which o is 1, $R^{78}$ is 4"-OCH$_3$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 65ka Compounds of formula I.Ka in which o is 1, $R^{78}$ is 4"-OCHF$_2$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 66ka Compounds of formula I.Ka in which o is 1, $R^{78}$ is 4"-C$_6$H$_5$, $R^5$ is Cl, $R^6$ is F and the meaning for the combination of $R^1$, $R^2$, $R^3$, $R^4$, $R^9$ and $R^{10}$ for each individual compound corresponds in each case to one line of Table B.

Table 67ka Compounds of the formula I.Ka in which o is 0, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 68ka Compounds of the formula I.Ka in which o is 1, $R^{78}$ is 1"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 69ka Compounds of the formula I.Ka in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 70ka Compounds of the formula I.Ka in which o is 1, $R^{78}$ is 1"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 71ka Compounds of the formula I.Ka in which o is 1, $R^{78}$ is 1"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 72ka Compounds of the formula I.Ka in which o is 1, $R^{78}$ is 1"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 73ka Compounds of the formula I.Ka in which o is 1, $R^{78}$ is 1"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 74ka Compounds of the formula I.Ka in which o is 1, $R^{78}$ is 1"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 75ka Compounds of the formula I.Ka in which o is 1, $R^{78}$ is 3"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 76ka Compounds of the formula I.Ka in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 77ka Compounds of the formula I.Ka in which o is 1, $R^{78}$ is 3-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 78ka Compounds of the formula I.Ka in which o is 1, $R^{78}$ is 3"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 79ka Compounds of the formula I.Ka in which o is 1, $R^{78}$ is 3-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 80ka Compounds of the formula I.Ka in which o is 1, $R^{78}$ is 3-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 81ka Compounds of the formula I.Ka in which o is 1, $R^{78}$ is 3-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 82ka Compounds of the formula I.Ka in which o is 1, $R^{78}$ is 4"-F, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 83ka Compounds of the formula I.Ka in which o is 1, $R^{78}$ is 4"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 84ka Compounds of the formula I.Ka in which o is 1, $R^{78}$ is 4"-Br, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 85ka Compounds of the formula I.Ka in which o is 1, $R^{78}$ is 4"-CH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 86ka Compounds of the formula I.Ka in which o is 1, $R^{78}$ is 4"-OCH$_3$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 87ka Compounds of the formula I.Ka in which o is 1, $R^{78}$ is 4"-OCHF$_2$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

Table 88ka Compounds of the formula I.Ka in which o is 1, $R^{78}$ is 4"-C$_6$H$_5$, $R^5$ is Br, $R^6$ is Br and the meaning for the combination of $R^1$, $R^2$, $R^3$, $R^4$, $R^9$ and $R^{10}$ for each individual compound corresponds in each case to one line of Table B.

In the Table B the following abbreviations are used:

TABLE B

| line | $R^1$ | $R^2$ | $R^3$ | $R^4$ | $R^9$ | $R^{10}$ |
|---|---|---|---|---|---|---|
| B-1 | H | H | H | H | CH$_3$ | CH$_3$ |
| B-2 | H | H | H | H | CH$_3$ | C$_2$H$_5$ |
| B-3 | H | H | H | H | C$_2$H$_5$ | CH$_3$ |
| B-4 | H | H | H | H | C$_2$H$_5$ | C$_2$H$_5$ |
| B-5 | F | H | H | H | CH$_3$ | CH$_3$ |
| B-6 | F | H | H | H | CH$_3$ | C$_2$H$_5$ |
| B-7 | F | H | H | H | C$_2$H$_5$ | CH$_3$ |
| B-8 | F | H | H | H | C$_2$H$_5$ | C$_2$H$_5$ |
| B-9 | Cl | H | H | H | CH$_3$ | CH$_3$ |
| B-10 | Cl | H | H | H | CH$_3$ | C$_2$H$_5$ |
| B-11 | Cl | H | H | H | C$_2$H$_5$ | CH$_3$ |
| B-12 | Cl | H | H | H | C$_2$H$_5$ | C$_2$H$_5$ |
| B-13 | CH$_3$ | H | H | H | CH$_3$ | CH$_3$ |
| B-14 | CH$_3$ | H | H | H | CH$_3$ | C$_2$H$_5$ |
| B-15 | CH$_3$ | H | H | H | C$_2$H$_5$ | CH$_3$ |
| B-16 | CH$_3$ | H | H | H | C$_2$H$_5$ | C$_2$H$_5$ |
| B-17 | H | F | H | H | CH$_3$ | CH$_3$ |
| B-18 | H | F | H | H | CH$_3$ | C$_2$H$_5$ |
| B-19 | H | F | H | H | C$_2$H$_5$ | CH$_3$ |
| B-20 | H | F | H | H | C$_2$H$_5$ | C$_2$H$_5$ |
| B-21 | F | F | H | H | CH$_3$ | CH$_3$ |
| B-22 | F | F | H | H | CH$_3$ | C$_2$H$_5$ |
| B-23 | F | F | H | H | C$_2$H$_5$ | CH$_3$ |
| B-24 | F | F | H | H | C$_2$H$_5$ | C$_2$H$_5$ |
| B-25 | Cl | F | H | H | CH$_3$ | CH$_3$ |
| B-26 | Cl | F | H | H | CH$_3$ | C$_2$H$_5$ |
| B-27 | Cl | F | H | H | C$_2$H$_5$ | CH$_3$ |
| B-28 | Cl | F | H | H | C$_2$H$_5$ | C$_2$H$_5$ |

TABLE B-continued

| line | R¹ | R² | R³ | R⁴ | R⁹ | R¹⁰ |
|---|---|---|---|---|---|---|
| B-29 | CH₃ | F | H | H | CH₃ | CH₃ |
| B-30 | CH₃ | F | H | H | CH₃ | C₂H₅ |
| B-31 | CH₃ | F | H | H | C₂H₅ | CH₃ |
| B-32 | CH₃ | F | H | H | C₂H₅ | C₂H₅ |
| B-33 | H | CH₃ | H | H | CH₃ | CH₃ |
| B-34 | H | CH₃ | H | H | CH₃ | C₂H₅ |
| B-35 | H | CH₃ | H | H | C₂H₅ | CH₃ |
| B-36 | H | CH₃ | H | H | C₂H₅ | C₂H₅ |
| B-37 | F | CH₃ | H | H | CH₃ | CH₃ |
| B-38 | F | CH₃ | H | H | CH₃ | C₂H₅ |
| B-39 | F | CH₃ | H | H | C₂H₅ | CH₃ |
| B-40 | F | CH₃ | H | H | C₂H₅ | C₂H₅ |
| B-41 | Cl | CH₃ | H | H | CH₃ | CH₃ |
| B-42 | Cl | CH₃ | H | H | CH₃ | C₂H₅ |
| B-43 | Cl | CH₃ | H | H | C₂H₅ | CH₃ |
| B-44 | Cl | CH₃ | H | H | C₂H₅ | C₂H₅ |
| B-45 | CH₃ | CH₃ | H | H | CH₃ | CH₃ |
| B-46 | CH₃ | CH₃ | H | H | CH₃ | C₂H₅ |
| B-47 | CH₃ | CH₃ | H | H | C₂H₅ | CH₃ |
| B-48 | CH₃ | CH₃ | H | H | C₂H₅ | C₂H₅ |
| B-49 | H | Cl | H | H | CH₃ | CH₃ |
| B-50 | H | Cl | H | H | CH₃ | C₂H₅ |
| B-51 | H | Cl | H | H | C₂H₅ | CH₃ |
| B-52 | H | Cl | H | H | C₂H₅ | C₂H₅ |
| B-53 | F | Cl | H | H | CH₃ | CH₃ |
| B-54 | F | Cl | H | H | CH₃ | C₂H₅ |
| B-55 | F | Cl | H | H | C₂H₅ | CH₃ |
| B-56 | F | Cl | H | H | C₂H₅ | C₂H₅ |
| B-57 | Cl | Cl | H | H | CH₃ | CH₃ |
| B-58 | Cl | Cl | H | H | CH₃ | C₂H₅ |
| B-59 | Cl | Cl | H | H | C₂H₅ | CH₃ |
| B-60 | Cl | Cl | H | H | C₂H₅ | C₂H₅ |
| B-61 | CH₃ | Cl | H | H | CH₃ | CH₃ |
| B-62 | CH₃ | Cl | H | H | CH₃ | C₂H₅ |
| B-63 | CH₃ | Cl | H | H | C₂H₅ | CH₃ |
| B-64 | CH₃ | Cl | H | H | C₂H₅ | C₂H₅ |
| B-65 | H | H | CH₃ | CH₃ | CH₃ | CH₃ |
| B-66 | H | H | CH₃ | CH₃ | CH₃ | C₂H₅ |
| B-67 | H | H | CH₃ | CH₃ | C₂H₅ | CH₃ |
| B-68 | H | H | CH₃ | CH₃ | C₂H₅ | C₂H₅ |
| B-69 | F | H | CH₃ | CH₃ | CH₃ | CH₃ |
| B-70 | F | H | CH₃ | CH₃ | CH₃ | C₂H₅ |
| B-71 | F | H | CH₃ | CH₃ | C₂H₅ | CH₃ |
| B-72 | F | H | CH₃ | CH₃ | C₂H₅ | C₂H₅ |
| B-73 | Cl | H | CH₃ | CH₃ | CH₃ | CH₃ |
| B-74 | Cl | H | CH₃ | CH₃ | CH₃ | C₂H₅ |
| B-75 | Cl | H | CH₃ | CH₃ | C₂H₅ | CH₃ |
| B-76 | Cl | H | CH₃ | CH₃ | C₂H₅ | C₂H₅ |
| B-77 | CH₃ | H | CH₃ | CH₃ | CH₃ | CH₃ |
| B-78 | CH₃ | H | CH₃ | CH₃ | CH₃ | C₂H₅ |
| B-79 | CH₃ | H | CH₃ | CH₃ | C₂H₅ | CH₃ |
| B-80 | CH₃ | H | CH₃ | CH₃ | C₂H₅ | C₂H₅ |
| B-81 | H | F | CH₃ | CH₃ | CH₃ | CH₃ |
| B-82 | H | F | CH₃ | CH₃ | CH₃ | C₂H₅ |
| B-83 | H | F | CH₃ | CH₃ | C₂H₅ | CH₃ |
| B-84 | H | F | CH₃ | CH₃ | C₂H₅ | C₂H₅ |
| B-85 | F | F | CH₃ | CH₃ | CH₃ | CH₃ |
| B-86 | F | F | CH₃ | CH₃ | CH₃ | C₂H₅ |
| B-87 | F | F | CH₃ | CH₃ | C₂H₅ | CH₃ |
| B-88 | F | F | CH₃ | CH₃ | C₂H₅ | C₂H₅ |
| B-89 | Cl | F | CH₃ | CH₃ | CH₃ | CH₃ |
| B-90 | Cl | F | CH₃ | CH₃ | CH₃ | C₂H₅ |
| B-91 | Cl | F | CH₃ | CH₃ | C₂H₅ | CH₃ |
| B-92 | Cl | F | CH₃ | CH₃ | C₂H₅ | C₂H₅ |
| B-93 | CH₃ | F | CH₃ | CH₃ | CH₃ | CH₃ |
| B-94 | CH₃ | F | CH₃ | CH₃ | CH₃ | C₂H₅ |
| B-95 | CH₃ | F | CH₃ | CH₃ | C₂H₅ | CH₃ |
| B-96 | CH₃ | F | CH₃ | CH₃ | C₂H₅ | C₂H₅ |
| B-97 | H | CH₃ | CH₃ | CH₃ | CH₃ | CH₃ |
| B-98 | H | CH₃ | CH₃ | CH₃ | CH₃ | C₂H₅ |
| B-99 | H | CH₃ | CH₃ | CH₃ | C₂H₅ | CH₃ |
| B-100 | H | CH₃ | CH₃ | CH₃ | C₂H₅ | C₂H₅ |
| B-101 | F | CH₃ | CH₃ | CH₃ | CH₃ | CH₃ |
| B-102 | F | CH₃ | CH₃ | CH₃ | CH₃ | C₂H₅ |
| B-103 | F | CH₃ | CH₃ | CH₃ | C₂H₅ | CH₃ |
| B-104 | F | CH₃ | CH₃ | CH₃ | C₂H₅ | C₂H₅ |
| B-105 | Cl | CH₃ | CH₃ | CH₃ | CH₃ | CH₃ |
| B-106 | Cl | CH₃ | CH₃ | CH₃ | CH₃ | C₂H₅ |
| B-107 | Cl | CH₃ | CH₃ | CH₃ | C₂H₅ | CH₃ |
| B-108 | Cl | CH₃ | CH₃ | CH₃ | C₂H₅ | C₂H₅ |
| B-109 | CH₃ | CH₃ | CH₃ | CH₃ | CH₃ | CH₃ |
| B-110 | CH₃ | CH₃ | CH₃ | CH₃ | CH₃ | C₂H₅ |
| B-111 | CH₃ | CH₃ | CH₃ | CH₃ | C₂H₅ | CH₃ |
| B-112 | CH₃ | CH₃ | CH₃ | CH₃ | C₂H₅ | C₂H₅ |
| B-113 | H | Cl | CH₃ | CH₃ | CH₃ | CH₃ |
| B-114 | H | Cl | CH₃ | CH₃ | CH₃ | C₂H₅ |
| B-115 | H | Cl | CH₃ | CH₃ | C₂H₅ | CH₃ |
| B-116 | H | Cl | CH₃ | CH₃ | C₂H₅ | C₂H₅ |
| B-117 | F | Cl | CH₃ | CH₃ | CH₃ | CH₃ |
| B-118 | F | Cl | CH₃ | CH₃ | CH₃ | C₂H₅ |
| B-119 | F | Cl | CH₃ | CH₃ | C₂H₅ | CH₃ |
| B-120 | F | Cl | CH₃ | CH₃ | C₂H₅ | C₂H₅ |
| B-121 | Cl | Cl | CH₃ | CH₃ | CH₃ | CH₃ |
| B-122 | Cl | Cl | CH₃ | CH₃ | CH₃ | C₂H₅ |
| B-123 | Cl | Cl | CH₃ | CH₃ | C₂H₅ | CH₃ |
| B-124 | Cl | Cl | CH₃ | CH₃ | C₂H₅ | C₂H₅ |
| B-125 | CH₃ | Cl | CH₃ | CH₃ | CH₃ | CH₃ |
| B-126 | CH₃ | Cl | CH₃ | CH₃ | CH₃ | C₂H₅ |
| B-127 | CH₃ | Cl | CH₃ | CH₃ | C₂H₅ | CH₃ |
| B-128 | CH₃ | Cl | CH₃ | CH₃ | C₂H₅ | C₂H₅ |
| B-129 | H | H | C₂H₅ | C₂H₅ | CH₃ | CH₃ |
| B-130 | H | H | C₂H₅ | C₂H₅ | CH₃ | C₂H₅ |
| B-131 | H | H | C₂H₅ | C₂H₅ | C₂H₅ | CH₃ |
| B-132 | H | H | C₂H₅ | C₂H₅ | C₂H₅ | C₂H₅ |
| B-133 | F | H | C₂H₅ | C₂H₅ | CH₃ | CH₃ |
| B-134 | F | H | C₂H₅ | C₂H₅ | CH₃ | C₂H₅ |
| B-135 | F | H | C₂H₅ | C₂H₅ | C₂H₅ | CH₃ |
| B-136 | F | H | C₂H₅ | C₂H₅ | C₂H₅ | C₂H₅ |
| B-137 | Cl | H | C₂H₅ | C₂H₅ | CH₃ | CH₃ |
| B-138 | Cl | H | C₂H₅ | C₂H₅ | CH₃ | C₂H₅ |
| B-139 | Cl | H | C₂H₅ | C₂H₅ | C₂H₅ | CH₃ |
| B-140 | Cl | H | C₂H₅ | C₂H₅ | C₂H₅ | C₂H₅ |
| B-141 | CH₃ | H | C₂H₅ | C₂H₅ | CH₃ | CH₃ |
| B-142 | CH₃ | H | C₂H₅ | C₂H₅ | CH₃ | C₂H₅ |
| B-143 | CH₃ | H | C₂H₅ | C₂H₅ | C₂H₅ | CH₃ |
| B-144 | CH₃ | H | C₂H₅ | C₂H₅ | C₂H₅ | C₂H₅ |
| B-145 | H | F | C₂H₅ | C₂H₅ | CH₃ | CH₃ |
| B-146 | H | F | C₂H₅ | C₂H₅ | CH₃ | C₂H₅ |
| B-147 | H | F | C₂H₅ | C₂H₅ | C₂H₅ | CH₃ |
| B-148 | H | F | C₂H₅ | C₂H₅ | C₂H₅ | C₂H₅ |
| B-149 | F | 2-F | C₂H₅ | C₂H₅ | CH₃ | CH₃ |
| B-150 | F | 2-F | C₂H₅ | C₂H₅ | CH₃ | C₂H₅ |
| B-151 | F | 2-F | C₂H₅ | C₂H₅ | C₂H₅ | CH₃ |
| B-152 | F | 2-F | C₂H₅ | C₂H₅ | C₂H₅ | C₂H₅ |
| B-153 | Cl | F | C₂H₅ | C₂H₅ | CH₃ | CH₃ |
| B-154 | Cl | F | C₂H₅ | C₂H₅ | CH₃ | C₂H₅ |
| B-155 | Cl | F | C₂H₅ | C₂H₅ | C₂H₅ | CH₃ |
| B-156 | Cl | F | C₂H₅ | C₂H₅ | C₂H₅ | C₂H₅ |
| B-157 | CH₃ | F | C₂H₅ | C₂H₅ | CH₃ | CH₃ |
| B-158 | CH₃ | F | C₂H₅ | C₂H₅ | CH₃ | C₂H₅ |
| B-159 | CH₃ | F | C₂H₅ | C₂H₅ | C₂H₅ | CH₃ |
| B-160 | CH₃ | F | C₂H₅ | C₂H₅ | C₂H₅ | C₂H₅ |
| B-161 | H | CH₃ | C₂H₅ | C₂H₅ | CH₃ | CH₃ |
| B-162 | H | CH₃ | C₂H₅ | C₂H₅ | CH3 | C₂H₅ |
| B-163 | H | CH₃ | C₂H₅ | C₂H₅ | C₂H₅ | CH₃ |
| B-164 | H | CH₃ | C₂H₅ | C₂H₅ | C₂H₅ | C₂H₅ |
| B-165 | F | CH₃ | C₂H₅ | C₂H₅ | CH₃ | CH₃ |
| B-166 | F | CH₃ | C₂H₅ | C₂H₅ | CH₃ | C₂H₅ |
| B-167 | F | CH₃ | C₂H₅ | C₂H₅ | C₂H₅ | CH₃ |
| B-168 | F | CH₃ | C₂H₅ | C₂H₅ | C₂H₅ | C₂H₅ |
| B-169 | Cl | CH₃ | C₂H₅ | C₂H₅ | CH₃ | CH₃ |
| B-170 | Cl | CH₃ | C₂H₅ | C₂H₅ | CH₃ | C₂H₅ |
| B-171 | Cl | CH₃ | C₂H₅ | C₂H₅ | C₂H₅ | CH₃ |
| B-172 | Cl | CH₃ | C₂H₅ | C₂H₅ | C₂H₅ | C₂H₅ |
| B-173 | CH₃ | CH₃ | C₂H₅ | C₂H₅ | CH₃ | CH₃ |
| B-174 | CH₃ | CH₃ | C₂H₅ | C₂H₅ | CH₃ | C₂H₅ |
| B-175 | CH₃ | CH₃ | C₂H₅ | C₂H₅ | C₂H₅ | CH₃ |
| B-176 | CH₃ | CH₃ | C₂H₅ | C₂H₅ | C₂H₅ | C₂H₅ |
| B-177 | H | Cl | C₂H₅ | C₂H₅ | CH₃ | CH₃ |
| B-178 | H | Cl | C₂H₅ | C₂H₅ | CH₃ | C₂H₅ |
| B-179 | H | Cl | C₂H₅ | C₂H₅ | C₂H₅ | CH₃ |
| B-180 | H | Cl | C₂H₅ | C₂H₅ | C₂H₅ | C₂H₅ |
| B-181 | F | Cl | C₂H₅ | C₂H₅ | CH₃ | CH₃ |
| B-182 | F | Cl | C₂H₅ | C₂H₅ | CH₃ | C₂H₅ |
| B-183 | F | Cl | C₂H₅ | C₂H₅ | C₂H₅ | CH₃ |
| B-184 | F | Cl | C₂H₅ | C₂H₅ | C₂H₅ | C₂H₅ |

TABLE B-continued

| line | R¹ | R² | R³ | R⁴ | R⁹ | R¹⁰ |
|---|---|---|---|---|---|---|
| B-185 | Cl | Cl | C₂H₅ | C₂H₅ | CH₃ | CH₃ |
| B-186 | Cl | Cl | C₂H₅ | C₂H₅ | CH₃ | C₂H₅ |
| B-187 | Cl | Cl | C₂H₅ | C₂H₅ | C₂H₅ | CH₃ |
| B-188 | Cl | Cl | C₂H₅ | C₂H₅ | C₂H₅ | C₂H₅ |
| B-189 | CH₃ | Cl | C₂H₅ | C₂H₅ | CH₃ | CH₃ |
| B-190 | CH₃ | Cl | C₂H₅ | C₂H₅ | CH₃ | C₂H₅ |
| B-191 | CH₃ | Cl | C₂H₅ | C₂H₅ | C₂H₅ | CH₃ |
| B-192 | CH₃ | Cl | C₂H₅ | C₂H₅ | C₂H₅ | C₂H₅ |
| B-193 | H | H | CH₃ | C₂H₅ | CH₃ | CH₃ |
| B-194 | H | H | CH₃ | C₂H₅ | CH₃ | C₂H₅ |
| B-195 | H | H | CH₃ | C₂H₅ | C₂H₅ | CH₃ |
| B-196 | H | H | CH₃ | C₂H₅ | C₂H₅ | C₂H₅ |
| B-197 | F | H | CH₃ | C₂H₅ | CH₃ | CH₃ |
| B-198 | F | H | CH₃ | C₂H₅ | CH₃ | C₂H₅ |
| B-199 | F | H | CH₃ | C₂H₅ | C₂H₅ | CH₃ |
| B-200 | F | H | CH₃ | C₂H₅ | C₂H₅ | C₂H₅ |
| B-201 | Cl | H | CH₃ | C₂H₅ | CH₃ | CH₃ |
| B-202 | Cl | H | CH₃ | C₂H₅ | CH₃ | C₂H₅ |
| B-203 | Cl | H | CH₃ | C₂H₅ | C₂H₅ | CH₃ |
| B-204 | Cl | H | CH₃ | C₂H₅ | C₂H₅ | C₂H₅ |
| B-205 | CH₃ | H | CH₃ | C₂H₅ | CH₃ | CH₃ |
| B-206 | CH₃ | H | CH₃ | C₂H₅ | CH₃ | C₂H₅ |
| B-207 | CH₃ | H | CH₃ | C₂H₅ | C₂H₅ | CH₃ |
| B-208 | CH₃ | H | CH₃ | C₂H₅ | C₂H₅ | C₂H₅ |
| B-209 | H | F | CH₃ | C₂H₅ | CH₃ | CH₃ |
| B-210 | H | F | CH₃ | C₂H₅ | CH₃ | C₂H₅ |
| B-211 | H | F | CH₃ | C₂H₅ | C₂H₅ | CH₃ |
| B-212 | H | F | CH₃ | C₂H₅ | C₂H₅ | C₂H₅ |
| B-213 | F | F | CH₃ | C₂H₅ | CH₃ | CH₃ |
| B-214 | F | F | CH₃ | C₂H₅ | CH₃ | C₂H₅ |
| B-215 | F | F | CH₃ | C₂H₅ | C₂H₅ | CH₃ |
| B-216 | F | F | CH₃ | C₂H₅ | C₂H₅ | C₂H₅ |
| B-217 | Cl | F | CH₃ | C₂H₅ | CH₃ | CH₃ |
| B-218 | Cl | F | CH₃ | C₂H₅ | CH₃ | C₂H₅ |
| B-219 | Cl | F | CH₃ | C₂H₅ | C₂H₅ | CH₃ |
| B-220 | Cl | F | CH₃ | C₂H₅ | C₂H₅ | C₂H₅ |
| B-221 | CH₃ | F | CH₃ | C₂H₅ | CH₃ | CH₃ |
| B-222 | CH₃ | F | CH₃ | C₂H₅ | CH₃ | C₂H₅ |
| B-223 | CH₃ | F | CH₃ | C₂H₅ | C₂H₅ | CH₃ |
| B-224 | CH₃ | F | CH₃ | C₂H₅ | C₂H₅ | C₂H₅ |
| B-225 | H | CH₃ | CH₃ | C₂H₅ | CH₃ | CH₃ |
| B-226 | H | CH₃ | CH₃ | C₂H₅ | CH₃ | C₂H₅ |
| B-227 | H | CH₃ | CH₃ | C₂H₅ | C₂H₅ | CH₃ |
| B-228 | H | CH₃ | CH₃ | C₂H₅ | C₂H₅ | C₂H₅ |
| B-229 | F | CH₃ | CH₃ | C₂H₅ | CH₃ | CH₃ |
| B-230 | F | CH₃ | CH₃ | C₂H₅ | CH₃ | C₂H₅ |
| B-231 | F | CH₃ | CH₃ | C₂H₅ | C₂H₅ | CH₃ |
| B-232 | F | CH₃ | CH₃ | C₂H₅ | C₂H₅ | C₂H₅ |
| B-233 | Cl | CH₃ | CH₃ | C₂H₅ | CH₃ | CH₃ |
| B-234 | Cl | CH₃ | CH₃ | C₂H₅ | CH₃ | C₂H₅ |
| B-235 | Cl | CH₃ | CH₃ | C₂H₅ | C₂H₅ | CH₃ |
| B-236 | Cl | CH₃ | CH₃ | C₂H₅ | C₂H₅ | C₂H₅ |
| B-237 | CH₃ | CH₃ | CH₃ | C₂H₅ | CH₃ | CH₃ |
| B-238 | CH₃ | CH₃ | CH₃ | C₂H₅ | CH₃ | C₂H₅ |
| B-239 | CH₃ | CH₃ | CH₃ | C₂H₅ | C₂H₅ | CH₃ |
| B-240 | CH₃ | CH₃ | CH₃ | C₂H₅ | C₂H₅ | C₂H₅ |
| B-241 | H | Cl | CH₃ | C₂H₅ | CH₃ | CH₃ |
| B-242 | H | Cl | CH₃ | C₂H₅ | CH₃ | C₂H₅ |
| B-243 | H | Cl | CH₃ | C₂H₅ | C₂H₅ | CH₃ |
| B-244 | H | Cl | CH₃ | C₂H₅ | C₂H₅ | C₂H₅ |
| B-245 | F | Cl | CH₃ | C₂H₅ | CH₃ | CH₃ |
| B-246 | F | Cl | CH₃ | C₂H₅ | CH₃ | C₂H₅ |
| B-247 | F | Cl | CH₃ | C₂H₅ | C₂H₅ | CH₃ |
| B-248 | F | Cl | CH₃ | C₂H₅ | C₂H₅ | C₂H₅ |
| B-249 | Cl | Cl | CH₃ | C₂H₅ | CH₃ | CH₃ |
| B-250 | Cl | Cl | CH₃ | C₂H₅ | CH₃ | C₂H₅ |
| B-251 | Cl | Cl | CH₃ | C₂H₅ | C₂H₅ | CH₃ |
| B-252 | Cl | Cl | CH₃ | C₂H₅ | C₂H₅ | C₂H₅ |
| B-253 | CH₃ | Cl | CH₃ | C₂H₅ | CH₃ | CH₃ |
| B-254 | CH₃ | Cl | CH₃ | C₂H₅ | CH₃ | C₂H₅ |
| B-255 | CH₃ | Cl | CH₃ | C₂H₅ | C₂H₅ | CH₃ |
| B-256 | CH₃ | Cl | CH₃ | C₂H₅ | C₂H₅ | C₂H₅ |
| B-257 | H | H | H | H | CH₃ | CH₃ |
| B-258 | H | H | H | H | CH₃ | C₂H₅ |
| B-259 | H | H | H | H | C₂H₅ | CH₃ |
| B-260 | H | H | H | H | C₂H₅ | C₂H₅ |
| B-261 | F | H | H | H | CH₃ | CH₃ |
| B-262 | F | H | H | H | CH₃ | C₂H₅ |
| B-263 | F | H | H | H | C₂H₅ | CH₃ |
| B-264 | F | H | H | H | C₂H₅ | C₂H₅ |
| B-265 | Cl | H | H | H | CH₃ | CH₃ |
| B-266 | Cl | H | H | H | CH₃ | C₂H₅ |
| B-267 | Cl | H | H | H | C₂H₅ | CH₃ |
| B-268 | Cl | H | H | H | C₂H₅ | C₂H₅ |
| B-269 | CH₃ | H | H | H | CH₃ | CH₃ |
| B-270 | CH₃ | H | H | H | CH₃ | C₂H₅ |
| B-271 | CH₃ | H | H | H | C₂H₅ | CH₃ |
| B-272 | CH₃ | H | H | H | C₂H₅ | C₂H₅ |
| B-273 | H | F | H | H | CH₃ | CH₃ |
| B-274 | H | F | H | H | CH₃ | C₂H₅ |
| B-275 | H | F | H | H | C₂H₅ | CH₃ |
| B-276 | H | F | H | H | C₂H₅ | C₂H₅ |
| B-277 | F | F | H | H | CH₃ | CH₃ |
| B-278 | F | F | H | H | CH₃ | C₂H₅ |
| B-279 | F | F | H | H | C₂H₅ | CH₃ |
| B-280 | F | F | H | H | C₂H₅ | C₂H₅ |
| B-281 | Cl | F | H | H | CH₃ | CH₃ |
| B-282 | Cl | F | H | H | CH₃ | C₂H₅ |
| B-283 | Cl | F | H | H | C₂H₅ | CH₃ |
| B-284 | Cl | F | H | H | C₂H₅ | C₂H₅ |
| B-285 | CH₃ | F | H | H | CH₃ | CH₃ |
| B-286 | CH₃ | F | H | H | CH₃ | C₂H₅ |
| B-287 | CH₃ | F | H | H | C₂H₅ | CH₃ |
| B-288 | CH₃ | F | H | H | C₂H₅ | C₂H₅ |
| B-289 | H | CH₃ | H | H | CH₃ | CH₃ |
| B-290 | H | CH₃ | H | H | CH₃ | C₂H₅ |
| B-291 | H | CH₃ | H | H | C₂H₅ | CH₃ |
| B-292 | H | CH₃ | H | H | C₂H₅ | C₂H₅ |
| B-293 | F | CH₃ | H | H | CH₃ | CH₃ |
| B-294 | H | CH₃ | H | H | CH₃ | C₂H₅ |
| B-295 | H | CH₃ | H | H | C₂H₅ | CH₃ |
| B-296 | H | CH₃ | H | H | C₂H₅ | C₂H₅ |
| B-297 | Cl | CH₃ | H | H | CH₃ | CH₃ |
| B-298 | Cl | CH₃ | H | H | CH₃ | C₂H₅ |
| B-299 | Cl | CH₃ | H | H | C₂H₅ | CH₃ |
| B-300 | Cl | CH₃ | H | H | C₂H₅ | C₂H₅ |
| B-301 | CH₃ | CH₃ | H | H | CH₃ | CH₃ |
| B-302 | CH₃ | CH₃ | H | H | CH₃ | C₂H₅ |
| B-303 | CH₃ | CH₃ | H | H | C₂H₅ | CH₃ |
| B-304 | CH₃ | CH₃ | H | H | C₂H₅ | C₂H₅ |
| B-305 | H | Cl | H | H | CH₃ | CH₃ |
| B-306 | H | Cl | H | H | CH₃ | C₂H₅ |
| B-307 | H | Cl | H | H | C₂H₅ | CH₃ |
| B-308 | H | Cl | H | H | C₂H₅ | C₂H₅ |
| B-309 | F | Cl | H | H | CH₃ | CH₃ |
| B-310 | F | Cl | H | H | CH₃ | C₂H₅ |
| B-311 | F | Cl | H | H | C₂H₅ | CH₃ |
| B-312 | F | Cl | H | H | C₂H₅ | C₂H₅ |
| B-313 | Cl | Cl | H | H | CH₃ | CH₃ |
| B-314 | Cl | Cl | H | H | CH₃ | C₂H₅ |
| B-315 | Cl | Cl | H | H | C₂H₅ | CH₃ |
| B-316 | Cl | Cl | H | H | C₂H₅ | C₂H₅ |
| B-317 | CH₃ | Cl | H | H | CH₃ | CH₃ |
| B-318 | CH₃ | Cl | H | H | CH₃ | C₂H₅ |
| B-319 | CH₃ | Cl | H | H | C₂H₅ | CH₃ |
| B-320 | CH₃ | Cl | H | H | C₂H₅ | C₂H₅ |
| B-321 | H | H | CH₃ | CH₃ | CH₃ | CH₃ |
| B-322 | H | H | CH₃ | CH₃ | CH₃ | C₂H₅ |
| B-323 | H | H | CH₃ | CH₃ | C₂H₅ | CH₃ |
| B-324 | H | H | CH₃ | CH₃ | C₂H₅ | C₂H₅ |
| B-325 | F | H | CH₃ | CH₃ | CH₃ | CH₃ |
| B-326 | F | H | CH₃ | CH₃ | CH₃ | C₂H₅ |
| B-327 | F | H | CH₃ | CH₃ | C₂H₅ | CH₃ |
| B-328 | F | H | CH₃ | CH₃ | C₂H₅ | C₂H₅ |
| B-329 | Cl | H | CH₃ | CH₃ | CH₃ | CH₃ |
| B-330 | Cl | H | CH₃ | CH₃ | CH₃ | C₂H₅ |
| B-331 | Cl | H | CH₃ | CH₃ | C₂H₅ | CH₃ |
| B-332 | Cl | H | CH₃ | CH₃ | C₂H₅ | C₂H₅ |
| B-333 | CH₃ | H | CH₃ | CH₃ | CH₃ | CH₃ |
| B-334 | CH₃ | H | CH₃ | CH₃ | CH₃ | C₂H₅ |
| B-335 | CH₃ | H | CH₃ | CH₃ | C₂H₅ | CH₃ |
| B-336 | CH₃ | H | CH₃ | CH₃ | C₂H₅ | C₂H₅ |
| B-337 | H | F | CH₃ | CH₃ | CH₃ | CH₃ |
| B-338 | H | F | CH₃ | CH₃ | CH₃ | C₂H₅ |
| B-339 | H | F | CH₃ | CH₃ | C₂H₅ | CH₃ |
| B-340 | H | F | CH₃ | CH₃ | C₂H₅ | C₂H₅ |

TABLE B-continued

| line | R$^1$ | R$^2$ | R$^3$ | R$^4$ | R$^9$ | R$^{10}$ |
|---|---|---|---|---|---|---|
| B-341 | F | F | CH$_3$ | CH$_3$ | CH$_3$ | CH$_3$ |
| B-342 | F | F | CH$_3$ | CH$_3$ | CH$_3$ | C$_2$H$_5$ |
| B-343 | F | F | CH$_3$ | CH$_3$ | C$_2$H$_5$ | CH$_3$ |
| B-344 | F | F | CH$_3$ | CH$_3$ | C$_2$H$_5$ | C$_2$H$_5$ |
| B-345 | Cl | F | CH$_3$ | CH$_3$ | CH$_3$ | CH$_3$ |
| B-346 | Cl | F | CH$_3$ | CH$_3$ | CH$_3$ | C$_2$H$_5$ |
| B-347 | Cl | F | CH$_3$ | CH$_3$ | C$_2$H$_5$ | CH$_3$ |
| B-348 | Cl | F | CH$_3$ | CH$_3$ | C$_2$H$_5$ | C$_2$H$_5$ |
| B-349 | CH$_3$ | F | CH$_3$ | CH$_3$ | CH$_3$ | CH$_3$ |
| B-350 | CH$_3$ | F | CH$_3$ | CH$_3$ | CH$_3$ | C$_2$H$_5$ |
| B-351 | CH$_3$ | F | CH$_3$ | CH$_3$ | C$_2$H$_5$ | CH$_3$ |
| B-352 | CH$_3$ | F | CH$_3$ | CH$_3$ | C$_2$H$_5$ | C$_2$H$_5$ |
| B-353 | H | CH$_3$ | CH$_3$ | CH$_3$ | CH$_3$ | CH$_3$ |
| B-354 | H | CH$_3$ | CH$_3$ | CH$_3$ | CH$_3$ | C$_2$H$_5$ |
| B-355 | H | CH$_3$ | CH$_3$ | CH$_3$ | C$_2$H$_5$ | CH$_3$ |
| B-356 | H | CH$_3$ | CH$_3$ | CH$_3$ | C$_2$H$_5$ | C$_2$H$_5$ |
| B-357 | F | CH$_3$ | CH$_3$ | CH$_3$ | CH$_3$ | CH$_3$ |
| B-358 | F | CH$_3$ | CH$_3$ | CH$_3$ | CH$_3$ | C$_2$H$_5$ |
| B-359 | F | CH$_3$ | CH$_3$ | CH$_3$ | C$_2$H$_5$ | CH$_3$ |
| B-360 | F | CH$_3$ | CH$_3$ | CH$_3$ | C$_2$H$_5$ | C$_2$H$_5$ |
| B-361 | Cl | CH$_3$ | CH$_3$ | CH$_3$ | CH$_3$ | CH$_3$ |
| B-362 | Cl | CH$_3$ | CH$_3$ | CH$_3$ | CH$_3$ | C$_2$H$_5$ |
| B-363 | Cl | CH$_3$ | CH$_3$ | CH$_3$ | C$_2$H$_5$ | CH$_3$ |
| B-364 | Cl | CH$_3$ | CH$_3$ | CH$_3$ | C$_2$H$_5$ | C$_2$H$_5$ |
| B-365 | CH$_3$ | CH$_3$ | CH$_3$ | CH$_3$ | CH$_3$ | CH$_3$ |
| B-366 | CH$_3$ | CH$_3$ | CH$_3$ | CH$_3$ | CH$_3$ | C$_2$H$_5$ |
| B-367 | CH$_3$ | CH$_3$ | CH$_3$ | CH$_3$ | C$_2$H$_5$ | CH$_3$ |
| B-368 | CH$_3$ | CH$_3$ | CH$_3$ | CH$_3$ | C$_2$H$_5$ | C$_2$H$_5$ |
| B-369 | H | Cl | CH$_3$ | CH$_3$ | CH$_3$ | CH$_3$ |
| B-370 | H | Cl | CH$_3$ | CH$_3$ | CH$_3$ | C$_2$H$_5$ |
| B-371 | H | Cl | CH$_3$ | CH$_3$ | C$_2$H$_5$ | CH$_3$ |
| B-372 | H | Cl | CH$_3$ | CH$_3$ | C$_2$H$_5$ | C$_2$H$_5$ |
| B-373 | F | Cl | CH$_3$ | CH$_3$ | CH$_3$ | CH$_3$ |
| B-374 | F | Cl | CH$_3$ | CH$_3$ | CH$_3$ | C$_2$H$_5$ |
| B-375 | F | Cl | CH$_3$ | CH$_3$ | C$_2$H$_5$ | CH$_3$ |
| B-376 | F | Cl | CH$_3$ | CH$_3$ | C$_2$H$_5$ | C$_2$H$_5$ |
| B-377 | Cl | Cl | CH$_3$ | CH$_3$ | CH$_3$ | CH$_3$ |
| B-378 | Cl | Cl | CH$_3$ | CH$_3$ | CH$_3$ | C$_2$H$_5$ |
| B-379 | Cl | Cl | CH$_3$ | CH$_3$ | C$_2$H$_5$ | CH$_3$ |
| B-380 | Cl | Cl | CH$_3$ | CH$_3$ | C$_2$H$_5$ | C$_2$H$_5$ |
| B-381 | CH$_3$ | Cl | CH$_3$ | CH$_3$ | CH$_3$ | CH$_3$ |
| B-382 | CH$_3$ | Cl | CH$_3$ | CH$_3$ | CH$_3$ | C$_2$H$_5$ |
| B-383 | CH$_3$ | Cl | CH$_3$ | CH$_3$ | C$_2$H$_5$ | CH$_3$ |
| B-384 | CH$_3$ | Cl | CH$_3$ | CH$_3$ | C$_2$H$_5$ | C$_2$H$_5$ |
| B-385 | H | H | C$_2$H$_5$ | C$_2$H$_5$ | CH$_3$ | CH$_3$ |
| B-386 | H | H | C$_2$H$_5$ | C$_2$H$_5$ | CH$_3$ | C$_2$H$_5$ |
| B-387 | H | H | C$_2$H$_5$ | C$_2$H$_5$ | C$_2$H$_5$ | CH$_3$ |
| B-388 | H | H | C$_2$H$_5$ | C$_2$H$_5$ | C$_2$H$_5$ | C$_2$H$_5$ |
| B-389 | F | H | C$_2$H$_5$ | C$_2$H$_5$ | CH$_3$ | CH$_3$ |
| B-390 | F | H | C$_2$H$_5$ | C$_2$H$_5$ | CH$_3$ | C$_2$H$_5$ |
| B-391 | F | H | C$_2$H$_5$ | C$_2$H$_5$ | C$_2$H$_5$ | CH$_3$ |
| B-392 | F | H | C$_2$H$_5$ | C$_2$H$_5$ | C$_2$H$_5$ | C$_2$H$_5$ |
| B-393 | Cl | H | C$_2$H$_5$ | C$_2$H$_5$ | CH$_3$ | CH$_3$ |
| B-394 | Cl | H | C$_2$H$_5$ | C$_2$H$_5$ | CH$_3$ | C$_2$H$_5$ |
| B-395 | Cl | H | C$_2$H$_5$ | C$_2$H$_5$ | C$_2$H$_5$ | CH$_3$ |
| B-396 | Cl | H | C$_2$H$_5$ | C$_2$H$_5$ | C$_2$H$_5$ | C$_2$H$_5$ |
| B-397 | CH$_3$ | H | C$_2$H$_5$ | C$_2$H$_5$ | CH$_3$ | CH$_3$ |
| B-398 | CH$_3$ | H | C$_2$H$_5$ | C$_2$H$_5$ | CH$_3$ | C$_2$H$_5$ |
| B-399 | CH$_3$ | H | C$_2$H$_5$ | C$_2$H$_5$ | C$_2$H$_5$ | CH$_3$ |
| B-400 | CH$_3$ | H | C$_2$H$_5$ | C$_2$H$_5$ | C$_2$H$_5$ | C$_2$H$_5$ |
| B-401 | H | F | C$_2$H$_5$ | C$_2$H$_5$ | CH$_3$ | CH$_3$ |
| B-402 | H | F | C$_2$H$_5$ | C$_2$H$_5$ | CH$_3$ | C$_2$H$_5$ |
| B-403 | H | F | C$_2$H$_5$ | C$_2$H$_5$ | C$_2$H$_5$ | CH$_3$ |
| B-404 | H | F | C$_2$H$_5$ | C$_2$H$_5$ | C$_2$H$_5$ | C$_2$H$_5$ |
| B-405 | F | F | C$_2$H$_5$ | C$_2$H$_5$ | CH$_3$ | CH$_3$ |
| B-406 | F | F | C$_2$H$_5$ | C$_2$H$_5$ | CH$_3$ | C$_2$H$_5$ |
| B-407 | F | F | C$_2$H$_5$ | C$_2$H$_5$ | C$_2$H$_5$ | CH$_3$ |
| B-408 | F | F | C$_2$H$_5$ | C$_2$H$_5$ | C$_2$H$_5$ | C$_2$H$_5$ |
| B-409 | Cl | F | C$_2$H$_5$ | C$_2$H$_5$ | CH$_3$ | CH$_3$ |
| B-410 | Cl | F | C$_2$H$_5$ | C$_2$H$_5$ | CH$_3$ | C$_2$H$_5$ |
| B-411 | Cl | F | C$_2$H$_5$ | C$_2$H$_5$ | C$_2$H$_5$ | CH$_3$ |
| B-412 | Cl | F | C$_2$H$_5$ | C$_2$H$_5$ | C$_2$H$_5$ | C$_2$H$_5$ |
| B-413 | CH$_3$ | F | C$_2$H$_5$ | C$_2$H$_5$ | CH$_3$ | CH$_3$ |
| B-414 | CH$_3$ | F | C$_2$H$_5$ | C$_2$H$_5$ | CH$_3$ | C$_2$H$_5$ |
| B-415 | CH$_3$ | F | C$_2$H$_5$ | C$_2$H$_5$ | C$_2$H$_5$ | CH$_3$ |
| B-416 | CH$_3$ | F | C$_2$H$_5$ | C$_2$H$_5$ | C$_2$H$_5$ | C$_2$H$_5$ |
| B-417 | H | CH$_3$ | C$_2$H$_5$ | C$_2$H$_5$ | CH$_3$ | CH$_3$ |
| B-418 | H | CH$_3$ | C$_2$H$_5$ | C$_2$H$_5$ | CH$_3$ | C$_2$H$_5$ |
| B-419 | H | CH$_3$ | C$_2$H$_5$ | C$_2$H$_5$ | C$_2$H$_5$ | CH$_3$ |
| B-420 | H | CH$_3$ | C$_2$H$_5$ | C$_2$H$_5$ | C$_2$H$_5$ | C$_2$H$_5$ |
| B-421 | F | CH$_3$ | C$_2$H$_5$ | C$_2$H$_5$ | CH$_3$ | CH$_3$ |
| B-422 | F | CH$_3$ | C$_2$H$_5$ | C$_2$H$_5$ | CH$_3$ | C$_2$H$_5$ |
| B-423 | F | CH$_3$ | C$_2$H$_5$ | C$_2$H$_5$ | C$_2$H$_5$ | CH$_3$ |
| B-424 | F | CH$_3$ | C$_2$H$_5$ | C$_2$H$_5$ | C$_2$H$_5$ | C$_2$H$_5$ |
| B-425 | Cl | CH$_3$ | C$_2$H$_5$ | C$_2$H$_5$ | CH$_3$ | CH$_3$ |
| B-426 | Cl | CH$_3$ | C$_2$H$_5$ | C$_2$H$_5$ | CH$_3$ | C$_2$H$_5$ |
| B-427 | Cl | CH$_3$ | C$_2$H$_5$ | C$_2$H$_5$ | C$_2$H$_5$ | CH$_3$ |
| B-428 | Cl | CH$_3$ | C$_2$H$_5$ | C$_2$H$_5$ | C$_2$H$_5$ | C$_2$H$_5$ |
| B-429 | CH$_3$ | CH$_3$ | C$_2$H$_5$ | C$_2$H$_5$ | CH$_3$ | CH$_3$ |
| B-430 | CH$_3$ | CH$_3$ | C$_2$H$_5$ | C$_2$H$_5$ | CH$_3$ | C$_2$H$_5$ |
| B-431 | CH$_3$ | CH$_3$ | C$_2$H$_5$ | C$_2$H$_5$ | C$_2$H$_5$ | CH$_3$ |
| B-432 | CH$_3$ | CH$_3$ | C$_2$H$_5$ | C$_2$H$_5$ | C$_2$H$_5$ | C$_2$H$_5$ |
| B-433 | H | Cl | C$_2$H$_5$ | C$_2$H$_5$ | CH$_3$ | CH$_3$ |
| B-434 | H | Cl | C$_2$H$_5$ | C$_2$H$_5$ | CH$_3$ | C$_2$H$_5$ |
| B-435 | H | Cl | C$_2$H$_5$ | C$_2$H$_5$ | C$_2$H$_5$ | CH$_3$ |
| B-436 | H | Cl | C$_2$H$_5$ | C$_2$H$_5$ | C$_2$H$_5$ | C$_2$H$_5$ |
| B-437 | F | Cl | C$_2$H$_5$ | C$_2$H$_5$ | CH$_3$ | CH$_3$ |
| B-438 | F | Cl | C$_2$H$_5$ | C$_2$H$_5$ | CH$_3$ | C$_2$H$_5$ |
| B-439 | F | Cl | C$_2$H$_5$ | C$_2$H$_5$ | C$_2$H$_5$ | CH$_3$ |
| B-440 | F | Cl | C$_2$H$_5$ | C$_2$H$_5$ | C$_2$H$_5$ | C$_2$H$_5$ |
| B-441 | Cl | Cl | C$_2$H$_5$ | C$_2$H$_5$ | CH$_3$ | CH$_3$ |
| B-442 | Cl | Cl | C$_2$H$_5$ | C$_2$H$_5$ | CH$_3$ | C$_2$H$_5$ |
| B-443 | Cl | Cl | C$_2$H$_5$ | C$_2$H$_5$ | C$_2$H$_5$ | CH$_3$ |
| B-444 | Cl | Cl | C$_2$H$_5$ | C$_2$H$_5$ | C$_2$H$_5$ | C$_2$H$_5$ |
| B-445 | CH$_3$ | Cl | C$_2$H$_5$ | C$_2$H$_5$ | CH$_3$ | CH$_3$ |
| B-446 | CH$_3$ | Cl | C$_2$H$_5$ | C$_2$H$_5$ | CH$_3$ | C$_2$H$_5$ |
| B-447 | CH$_3$ | Cl | C$_2$H$_5$ | C$_2$H$_5$ | C$_2$H$_5$ | CH$_3$ |
| B-448 | CH$_3$ | Cl | C$_2$H$_5$ | C$_2$H$_5$ | C$_2$H$_5$ | C$_2$H$_5$ |
| B-449 | H | H | CH$_3$ | C$_2$H$_5$ | CH$_3$ | CH$_3$ |
| B-450 | H | H | CH$_3$ | C$_2$H$_5$ | CH$_3$ | C$_2$H$_5$ |
| B-451 | H | H | CH$_3$ | C$_2$H$_5$ | C$_2$H$_5$ | CH$_3$ |
| B-452 | H | H | CH$_3$ | C$_2$H$_5$ | C$_2$H$_5$ | C$_2$H$_5$ |
| B-453 | F | H | CH$_3$ | C$_2$H$_5$ | CH$_3$ | CH$_3$ |
| B-454 | F | H | CH$_3$ | C$_2$H$_5$ | CH$_3$ | C$_2$H$_5$ |
| B-455 | F | H | CH$_3$ | C$_2$H$_5$ | C$_2$H$_5$ | CH$_3$ |
| B-456 | F | H | CH$_3$ | C$_2$H$_5$ | C$_2$H$_5$ | C$_2$H$_5$ |
| B-457 | Cl | H | CH$_3$ | C$_2$H$_5$ | CH$_3$ | CH$_3$ |
| B-458 | Cl | H | CH$_3$ | C$_2$H$_5$ | CH$_3$ | C$_2$H$_5$ |
| B-459 | Cl | H | CH$_3$ | C$_2$H$_5$ | C$_2$H$_5$ | CH$_3$ |
| B-460 | Cl | H | CH$_3$ | C$_2$H$_5$ | C$_2$H$_5$ | C$_2$H$_5$ |
| B-461 | CH$_3$ | H | CH$_3$ | C$_2$H$_5$ | CH$_3$ | CH$_3$ |
| B-462 | CH$_3$ | H | CH$_3$ | C$_2$H$_5$ | CH$_3$ | C$_2$H$_5$ |
| B-463 | CH$_3$ | H | CH$_3$ | C$_2$H$_5$ | C$_2$H$_5$ | CH$_3$ |
| B-464 | CH$_3$ | H | CH$_3$ | C$_2$H$_5$ | C$_2$H$_5$ | C$_2$H$_5$ |
| B-465 | H | F | CH$_3$ | C$_2$H$_5$ | CH$_3$ | CH$_3$ |
| B-466 | H | F | CH$_3$ | C$_2$H$_5$ | CH$_3$ | C$_2$H$_5$ |
| B-467 | H | F | CH$_3$ | C$_2$H$_5$ | C$_2$H$_5$ | CH$_3$ |
| B-468 | H | F | CH$_3$ | C$_2$H$_5$ | C$_2$H$_5$ | C$_2$H$_5$ |
| B-469 | F | F | CH$_3$ | C$_2$H$_5$ | CH$_3$ | CH$_3$ |
| B-470 | F | F | CH$_3$ | C$_2$H$_5$ | CH$_3$ | C$_2$H$_5$ |
| B-471 | F | F | CH$_3$ | C$_2$H$_5$ | C$_2$H$_5$ | CH$_3$ |
| B-472 | F | F | CH$_3$ | C$_2$H$_5$ | C$_2$H$_5$ | C$_2$H$_5$ |
| B-473 | Cl | F | CH$_3$ | C$_2$H$_5$ | CH$_3$ | CH$_3$ |
| B-474 | Cl | F | CH$_3$ | C$_2$H$_5$ | CH$_3$ | C$_2$H$_5$ |
| B-475 | Cl | F | CH$_3$ | C$_2$H$_5$ | C$_2$H$_5$ | CH$_3$ |
| B-476 | Cl | F | CH$_3$ | C$_2$H$_5$ | C$_2$H$_5$ | C$_2$H$_5$ |
| B-477 | CH$_3$ | F | CH$_3$ | C$_2$H$_5$ | CH$_3$ | CH$_3$ |
| B-478 | CH$_3$ | F | CH$_3$ | C$_2$H$_5$ | CH$_3$ | C$_2$H$_5$ |
| B-479 | CH$_3$ | F | CH$_3$ | C$_2$H$_5$ | C$_2$H$_5$ | CH$_3$ |
| B-480 | CH$_3$ | F | CH$_3$ | C$_2$H$_5$ | C$_2$H$_5$ | C$_2$H$_5$ |
| B-481 | H | CH$_3$ | CH$_3$ | C$_2$H$_5$ | CH$_3$ | CH$_3$ |
| B-482 | H | CH$_3$ | CH$_3$ | C$_2$H$_5$ | CH$_3$ | C$_2$H$_5$ |
| B-483 | H | CH$_3$ | CH$_3$ | C$_2$H$_5$ | C$_2$H$_5$ | CH$_3$ |
| B-484 | H | CH$_3$ | CH$_3$ | C$_2$H$_5$ | C$_2$H$_5$ | C$_2$H$_5$ |
| B-485 | F | CH$_3$ | CH$_3$ | C$_2$H$_5$ | CH$_3$ | CH$_3$ |
| B-486 | F | CH$_3$ | CH$_3$ | C$_2$H$_5$ | CH$_3$ | C$_2$H$_5$ |
| B-487 | F | CH$_3$ | CH$_3$ | C$_2$H$_5$ | C$_2$H$_5$ | CH$_3$ |
| B-488 | F | CH$_3$ | CH$_3$ | C$_2$H$_5$ | C$_2$H$_5$ | C$_2$H$_5$ |
| B-489 | Cl | CH$_3$ | CH$_3$ | C$_2$H$_5$ | CH$_3$ | CH$_3$ |
| B-490 | Cl | CH$_3$ | CH$_3$ | C$_2$H$_5$ | CH$_3$ | C$_2$H$_5$ |
| B-491 | Cl | CH$_3$ | CH$_3$ | C$_2$H$_5$ | C$_2$H$_5$ | CH$_3$ |
| B-492 | Cl | CH$_3$ | CH$_3$ | C$_2$H$_5$ | C$_2$H$_5$ | C$_2$H$_5$ |
| B-493 | CH$_3$ | CH$_3$ | CH$_3$ | C$_2$H$_5$ | CH$_3$ | CH$_3$ |
| B-494 | CH$_3$ | CH$_3$ | CH$_3$ | C$_2$H$_5$ | CH$_3$ | C$_2$H$_5$ |
| B-495 | CH$_3$ | CH$_3$ | CH$_3$ | C$_2$H$_5$ | C$_2$H$_5$ | CH$_3$ |
| B-496 | CH$_3$ | CH$_3$ | CH$_3$ | C$_2$H$_5$ | C$_2$H$_5$ | C$_2$H$_5$ |

TABLE B-continued

| line | R¹ | R² | R³ | R⁴ | R⁹ | R¹⁰ |
|---|---|---|---|---|---|---|
| B-497 | H | Cl | CH₃ | C₂H₅ | CH₃ | CH₃ |
| B-498 | H | Cl | CH₃ | C₂H₅ | CH₃ | C₂H₅ |
| B-499 | H | Cl | CH₃ | C₂H₅ | C₂H₅ | CH₃ |
| B-500 | H | Cl | CH₃ | C₂H₅ | C₂H₅ | C₂H₅ |
| B-501 | F | Cl | CH₃ | C₂H₅ | CH₃ | CH₃ |
| B-502 | F | Cl | CH₃ | C₂H₅ | CH₃ | C₂H₅ |
| B-503 | F | Cl | CH₃ | C₂H₅ | C₂H₅ | CH₃ |
| B-504 | F | Cl | CH₃ | C₂H₅ | C₂H₅ | C₂H₅ |
| B-505 | Cl | Cl | CH₃ | C₂H₅ | CH₃ | CH₃ |
| B-506 | Cl | Cl | CH₃ | C₂H₅ | CH₃ | C₂H₅ |
| B-507 | Cl | Cl | CH₃ | C₂H₅ | C₂H₅ | CH₃ |
| B-508 | Cl | Cl | CH₃ | C₂H₅ | C₂H₅ | C₂H₅ |
| B-509 | CH₃ | Cl | CH₃ | C₂H₅ | CH₃ | CH₃ |
| B-510 | CH₃ | Cl | CH₃ | C₂H₅ | CH₃ | C₂H₅ |
| B-511 | CH₃ | Cl | CH₃ | C₂H₅ | C₂H₅ | CH₃ |
| B-512 | CH₃ | Cl | CH₃ | C₂H₅ | C₂H₅ | C₂H₅ |
| B-513 | H | H | H | H | CH₃ | CH₃ |
| B-514 | H | H | H | H | CH₃ | C₂H₅ |
| B-515 | H | H | H | H | C₂H₅ | CH₃ |
| B-516 | H | H | H | H | C₂H₅ | C₂H₅ |
| B-517 | F | H | H | H | CH₃ | CH₃ |
| B-518 | F | H | H | H | CH₃ | C₂H₅ |
| B-519 | F | H | H | H | C₂H₅ | CH₃ |
| B-520 | F | H | H | H | C₂H₅ | C₂H₅ |
| B-521 | Cl | H | H | H | CH₃ | CH₃ |
| B-522 | Cl | H | H | H | CH₃ | C₂H₅ |
| B-523 | Cl | H | H | H | C₂H₅ | CH₃ |
| B-524 | Cl | H | H | H | C₂H₅ | C₂H₅ |
| B-525 | CH₃ | H | H | H | CH₃ | CH₃ |
| B-526 | CH₃ | H | H | H | CH₃ | C₂H₅ |
| B-527 | CH₃ | H | H | H | C₂H₅ | CH₃ |
| B-528 | CH₃ | H | H | H | C₂H₅ | C₂H₅ |
| B-529 | H | F | H | H | CH₃ | CH₃ |
| B-530 | H | F | H | H | CH₃ | C₂H₅ |
| B-531 | H | F | H | H | C₂H₅ | CH₃ |
| B-532 | H | F | H | H | C₂H₅ | C₂H₅ |
| B-533 | F | F | H | H | CH₃ | CH₃ |
| B-534 | F | F | H | H | CH₃ | C₂H₅ |
| B-535 | F | F | H | H | C₂H₅ | CH₃ |
| B-536 | F | F | H | H | C₂H₅ | C₂H₅ |
| B-537 | Cl | F | H | H | CH₃ | CH₃ |
| B-538 | Cl | F | H | H | CH₃ | C₂H₅ |
| B-539 | Cl | F | H | H | C₂H₅ | CH₃ |
| B-540 | Cl | F | H | H | C₂H₅ | C₂H₅ |
| B-541 | CH₃ | F | H | H | CH₃ | CH₃ |
| B-542 | CH₃ | F | H | H | CH₃ | C₂H₅ |
| B-543 | CH₃ | F | H | H | C₂H₅ | CH₃ |
| B-544 | CH₃ | F | H | H | C₂H₅ | C₂H₅ |
| B-545 | H | CH₃ | H | H | CH₃ | CH₃ |
| B-546 | H | CH₃ | H | H | CH₃ | C₂H₅ |
| B-547 | H | CH₃ | H | H | C₂H₅ | CH₃ |
| B-548 | H | CH₃ | H | H | C₂H₅ | C₂H₅ |
| B-549 | F | CH₃ | H | H | CH₃ | CH₃ |
| B-550 | F | CH₃ | H | H | CH₃ | C₂H₅ |
| B-551 | F | CH₃ | H | H | C₂H₅ | CH₃ |
| B-552 | F | CH₃ | H | H | C₂H₅ | C₂H₅ |
| B-553 | Cl | CH₃ | H | H | CH₃ | CH₃ |
| B-554 | Cl | CH₃ | H | H | CH₃ | C₂H₅ |
| B-555 | Cl | CH₃ | H | H | C₂H₅ | CH₃ |
| B-556 | Cl | CH₃ | H | H | C₂H₅ | C₂H₅ |
| B-557 | CH₃ | CH₃ | H | H | CH₃ | CH₃ |
| B-558 | CH₃ | CH₃ | H | H | CH₃ | C₂H₅ |
| B-559 | CH₃ | CH₃ | H | H | C₂H₅ | CH₃ |
| B-560 | CH₃ | CH₃ | H | H | C₂H₅ | C₂H₅ |
| B-561 | H | Cl | H | H | CH₃ | CH₃ |
| B-562 | H | Cl | H | H | CH₃ | C₂H₅ |
| B-563 | H | Cl | H | H | C₂H₅ | CH₃ |
| B-564 | H | Cl | H | H | C₂H₅ | C₂H₅ |
| B-565 | F | Cl | H | H | CH₃ | CH₃ |
| B-566 | F | Cl | H | H | CH₃ | C₂H₅ |
| B-567 | F | Cl | H | H | C₂H₅ | CH₃ |
| B-568 | F | Cl | H | H | C₂H₅ | C₂H₅ |
| B-569 | Cl | Cl | H | H | CH₃ | CH₃ |
| B-570 | Cl | Cl | H | H | CH₃ | C₂H₅ |
| B-571 | Cl | Cl | H | H | C₂H₅ | CH₃ |
| B-572 | Cl | Cl | H | H | C₂H₅ | C₂H₅ |
| B-573 | CH₃ | Cl | H | H | CH₃ | CH₃ |
| B-574 | CH₃ | Cl | H | H | CH₃ | C₂H₅ |
| B-575 | CH₃ | Cl | H | H | C₂H₅ | CH₃ |
| B-576 | CH₃ | Cl | H | H | C₂H₅ | C₂H₅ |
| B-577 | H | H | CH₃ | CH₃ | CH₃ | CH₃ |
| B-578 | H | H | CH₃ | CH₃ | CH₃ | C₂H₅ |
| B-579 | H | H | CH₃ | CH₃ | C₂H₅ | CH₃ |
| B-580 | H | H | CH₃ | CH₃ | C₂H₅ | C₂H₅ |
| B-581 | F | H | CH₃ | CH₃ | CH₃ | CH₃ |
| B-582 | F | H | CH₃ | CH₃ | CH₃ | C₂H₅ |
| B-583 | F | H | CH₃ | CH₃ | C₂H₅ | CH₃ |
| B-584 | F | H | CH₃ | CH₃ | C₂H₅ | C₂H₅ |
| B-585 | Cl | H | CH₃ | CH₃ | CH₃ | CH₃ |
| B-586 | Cl | H | CH₃ | CH₃ | CH₃ | C₂H₅ |
| B-587 | Cl | H | CH₃ | CH₃ | C₂H₅ | CH₃ |
| B-588 | Cl | H | CH₃ | CH₃ | C₂H₅ | C₂H₅ |
| B-589 | CH₃ | H | CH₃ | CH₃ | CH₃ | CH₃ |
| B-590 | CH₃ | H | CH₃ | CH₃ | CH₃ | C₂H₅ |
| B-591 | CH₃ | H | CH₃ | CH₃ | C₂H₅ | CH₃ |
| B-592 | CH₃ | H | CH₃ | CH₃ | C₂H₅ | C₂H₅ |
| B-593 | H | F | CH₃ | CH₃ | CH₃ | CH₃ |
| B-594 | H | F | CH₃ | CH₃ | CH₃ | C₂H₅ |
| B-595 | H | F | CH₃ | CH₃ | C₂H₅ | CH₃ |
| B-596 | H | F | CH₃ | CH₃ | C₂H₅ | C₂H₅ |
| B-597 | F | F | CH₃ | CH₃ | CH₃ | CH₃ |
| B-598 | F | F | CH₃ | CH₃ | CH₃ | C₂H₅ |
| B-599 | F | F | CH₃ | CH₃ | C₂H₅ | CH₃ |
| B-600 | F | F | CH₃ | CH₃ | C₂H₅ | C₂H₅ |
| B-601 | Cl | F | CH₃ | CH₃ | CH₃ | CH₃ |
| B-602 | Cl | F | CH₃ | CH₃ | CH₃ | C₂H₅ |
| B-603 | Cl | F | CH₃ | CH₃ | C₂H₅ | CH₃ |
| B-604 | Cl | F | CH₃ | CH₃ | C₂H₅ | C₂H₅ |
| B-605 | CH₃ | F | CH₃ | CH₃ | CH₃ | CH₃ |
| B-606 | CH₃ | F | CH₃ | CH₃ | CH₃ | C₂H₅ |
| B-607 | CH₃ | F | CH₃ | CH₃ | C₂H₅ | CH₃ |
| B-608 | CH₃ | F | CH₃ | CH₃ | C₂H₅ | C₂H₅ |
| B-609 | H | CH₃ | CH₃ | CH₃ | CH₃ | CH₃ |
| B-610 | H | CH₃ | CH₃ | CH₃ | CH₃ | C₂H₅ |
| B-611 | H | CH₃ | CH₃ | CH₃ | C₂H₅ | CH₃ |
| B-612 | H | CH₃ | CH₃ | CH₃ | C₂H₅ | C₂H₅ |
| B-613 | F | CH₃ | CH₃ | CH₃ | CH₃ | CH₃ |
| B-614 | F | CH₃ | CH₃ | CH₃ | CH₃ | C₂H₅ |
| B-615 | F | CH₃ | CH₃ | CH₃ | C₂H₅ | CH₃ |
| B-616 | F | CH₃ | CH₃ | CH₃ | C₂H₅ | C₂H₅ |
| B-617 | Cl | CH₃ | CH₃ | CH₃ | CH₃ | CH₃ |
| B-618 | Cl | CH₃ | CH₃ | CH₃ | CH₃ | C₂H₅ |
| B-619 | Cl | CH₃ | CH₃ | CH₃ | C₂H₅ | CH₃ |
| B-620 | Cl | CH₃ | CH₃ | CH₃ | C₂H₅ | C₂H₅ |
| B-621 | CH₃ | CH₃ | CH₃ | CH₃ | CH₃ | CH₃ |
| B-622 | CH₃ | CH₃ | CH₃ | CH₃ | CH₃ | C₂H₅ |
| B-623 | CH₃ | CH₃ | CH₃ | CH₃ | C₂H₅ | CH₃ |
| B-624 | CH₃ | CH₃ | CH₃ | CH₃ | C₂H₅ | C₂H₅ |
| B-625 | H | Cl | CH₃ | CH₃ | CH₃ | CH₃ |
| B-626 | H | Cl | CH₃ | CH₃ | CH₃ | C₂H₅ |
| B-627 | H | Cl | CH₃ | CH₃ | C₂H₅ | CH₃ |
| B-628 | H | Cl | CH₃ | CH₃ | C₂H₅ | C₂H₅ |
| B-629 | F | Cl | CH₃ | CH₃ | CH₃ | CH₃ |
| B-630 | F | Cl | CH₃ | CH₃ | CH₃ | C₂H₅ |
| B-631 | F | Cl | CH₃ | CH₃ | C₂H₅ | CH₃ |
| B-632 | F | Cl | CH₃ | CH₃ | C₂H₅ | C₂H₅ |
| B-633 | Cl | Cl | CH₃ | CH₃ | CH₃ | CH₃ |
| B-634 | Cl | Cl | CH₃ | CH₃ | CH₃ | C₂H₅ |
| B-635 | Cl | Cl | CH₃ | CH₃ | C₂H₅ | CH₃ |
| B-636 | Cl | Cl | CH₃ | CH₃ | C₂H₅ | C₂H₅ |
| B-637 | CH₃ | Cl | CH₃ | CH₃ | CH₃ | CH₃ |
| B-638 | CH₃ | Cl | CH₃ | CH₃ | CH₃ | C₂H₅ |
| B-639 | CH₃ | Cl | CH₃ | CH₃ | C₂H₅ | CH₃ |
| B-640 | CH₃ | Cl | CH₃ | CH₃ | C₂H₅ | C₂H₅ |
| B-641 | H | H | C₂H₅ | C₂H₅ | CH₃ | CH₃ |
| B-642 | H | H | C₂H₅ | C₂H₅ | CH₃ | C₂H₅ |
| B-643 | H | H | C₂H₅ | C₂H₅ | C₂H₅ | CH₃ |
| B-644 | H | H | C₂H₅ | C₂H₅ | C₂H₅ | C₂H₅ |
| B-645 | F | H | C₂H₅ | C₂H₅ | CH₃ | CH₃ |
| B-646 | F | H | C₂H₅ | C₂H₅ | CH₃ | C₂H₅ |
| B-647 | F | H | C₂H₅ | C₂H₅ | C₂H₅ | CH₃ |
| B-648 | F | H | C₂H₅ | C₂H₅ | C₂H₅ | C₂H₅ |
| B-649 | Cl | H | C₂H₅ | C₂H₅ | CH₃ | CH₃ |
| B-650 | Cl | H | C₂H₅ | C₂H₅ | CH₃ | C₂H₅ |
| B-651 | Cl | H | C₂H₅ | C₂H₅ | C₂H₅ | CH₃ |
| B-652 | Cl | H | C₂H₅ | C₂H₅ | C₂H₅ | C₂H₅ |

TABLE B-continued

| line | R$^1$ | R$^2$ | R$^3$ | R$^4$ | R$^9$ | R$^{10}$ |
|---|---|---|---|---|---|---|
| B-653 | CH$_3$ | H | C$_2$H$_5$ | C$_2$H$_5$ | CH$_3$ | CH$_3$ |
| B-654 | CH$_3$ | H | C$_2$H$_5$ | C$_2$H$_5$ | CH$_3$ | C$_2$H$_5$ |
| B-655 | CH$_3$ | H | C$_2$H$_5$ | C$_2$H$_5$ | C$_2$H$_5$ | CH$_3$ |
| B-656 | CH$_3$ | H | C$_2$H$_5$ | C$_2$H$_5$ | C$_2$H$_5$ | C$_2$H$_5$ |
| B-657 | H | F | C$_2$H$_5$ | C$_2$H$_5$ | CH$_3$ | CH$_3$ |
| B-658 | H | F | C$_2$H$_5$ | C$_2$H$_5$ | CH$_3$ | C$_2$H$_5$ |
| B-659 | H | F | C$_2$H$_5$ | C$_2$H$_5$ | C$_2$H$_5$ | CH$_3$ |
| B-660 | H | F | C$_2$H$_5$ | C$_2$H$_5$ | C$_2$H$_5$ | C$_2$H$_5$ |
| B-661 | F | F | C$_2$H$_5$ | C$_2$H$_5$ | CH$_3$ | CH$_3$ |
| B-662 | F | F | C$_2$H$_5$ | C$_2$H$_5$ | CH$_3$ | C$_2$H$_5$ |
| B-663 | F | F | C$_2$H$_5$ | C$_2$H$_5$ | C$_2$H$_5$ | CH$_3$ |
| B-664 | F | F | C$_2$H$_5$ | C$_2$H$_5$ | C$_2$H$_5$ | C$_2$H$_5$ |
| B-665 | Cl | F | C$_2$H$_5$ | C$_2$H$_5$ | CH$_3$ | CH$_3$ |
| B-666 | Cl | F | C$_2$H$_5$ | C$_2$H$_5$ | CH$_3$ | C$_2$H$_5$ |
| B-667 | Cl | F | C$_2$H$_5$ | C$_2$H$_5$ | C$_2$H$_5$ | CH$_3$ |
| B-668 | Cl | F | C$_2$H$_5$ | C$_2$H$_5$ | C$_2$H$_5$ | C$_2$H$_5$ |
| B-669 | CH$_3$ | F | C$_2$H$_5$ | C$_2$H$_5$ | CH$_3$ | CH$_3$ |
| B-670 | CH$_3$ | F | C$_2$H$_5$ | C$_2$H$_5$ | CH$_3$ | C$_2$H$_5$ |
| B-671 | CH$_3$ | F | C$_2$H$_5$ | C$_2$H$_5$ | C$_2$H$_5$ | CH$_3$ |
| B-672 | CH$_3$ | F | C$_2$H$_5$ | C$_2$H$_5$ | C$_2$H$_5$ | C$_2$H$_5$ |
| B-673 | H | CH$_3$ | C$_2$H$_5$ | C$_2$H$_5$ | CH$_3$ | CH$_3$ |
| B-674 | H | CH$_3$ | C$_2$H$_5$ | C$_2$H$_5$ | CH$_3$ | C$_2$H$_5$ |
| B-675 | H | CH$_3$ | C$_2$H$_5$ | C$_2$H$_5$ | C$_2$H$_5$ | CH$_3$ |
| B-676 | H | CH$_3$ | C$_2$H$_5$ | C$_2$H$_5$ | C$_2$H$_5$ | C$_2$H$_5$ |
| B-677 | F | CH$_3$ | C$_2$H$_5$ | C$_2$H$_5$ | CH$_3$ | CH$_3$ |
| B-678 | F | CH$_3$ | C$_2$H$_5$ | C$_2$H$_5$ | CH$_3$ | C$_2$H$_5$ |
| B-679 | F | CH$_3$ | C$_2$H$_5$ | C$_2$H$_5$ | C$_2$H$_5$ | CH$_3$ |
| B-680 | F | CH$_3$ | C$_2$H$_5$ | C$_2$H$_5$ | C$_2$H$_5$ | C$_2$H$_5$ |
| B-681 | Cl | CH$_3$ | C$_2$H$_5$ | C$_2$H$_5$ | CH$_3$ | CH$_3$ |
| B-682 | Cl | CH$_3$ | C$_2$H$_5$ | C$_2$H$_5$ | CH$_3$ | C$_2$H$_5$ |
| B-683 | Cl | CH$_3$ | C$_2$H$_5$ | C$_2$H$_5$ | C$_2$H$_5$ | CH$_3$ |
| B-684 | Cl | CH$_3$ | C$_2$H$_5$ | C$_2$H$_5$ | C$_2$H$_5$ | C$_2$H$_5$ |
| B-685 | CH$_3$ | CH$_3$ | C$_2$H$_5$ | C$_2$H$_5$ | CH$_3$ | CH$_3$ |
| B-686 | CH$_3$ | CH$_3$ | C$_2$H$_5$ | C$_2$H$_5$ | CH$_3$ | C$_2$H$_5$ |
| B-687 | CH$_3$ | CH$_3$ | C$_2$H$_5$ | C$_2$H$_5$ | C$_2$H$_5$ | CH$_3$ |
| B-688 | CH$_3$ | CH$_3$ | C$_2$H$_5$ | C$_2$H$_5$ | C$_2$H$_5$ | C$_2$H$_5$ |
| B-689 | H | Cl | C$_2$H$_5$ | C$_2$H$_5$ | CH$_3$ | CH$_3$ |
| B-690 | H | Cl | C$_2$H$_5$ | C$_2$H$_5$ | CH$_3$ | C$_2$H$_5$ |
| B-691 | H | Cl | C$_2$H$_5$ | C$_2$H$_5$ | C$_2$H$_5$ | CH$_3$ |
| B-692 | H | Cl | C$_2$H$_5$ | C$_2$H$_5$ | C$_2$H$_5$ | C$_2$H$_5$ |
| B-693 | F | Cl | C$_2$H$_5$ | C$_2$H$_5$ | CH$_3$ | CH$_3$ |
| B-694 | F | Cl | C$_2$H$_5$ | C$_2$H$_5$ | CH$_3$ | C$_2$H$_5$ |
| B-695 | F | Cl | C$_2$H$_5$ | C$_2$H$_5$ | C$_2$H$_5$ | CH$_3$ |
| B-696 | F | Cl | C$_2$H$_5$ | C$_2$H$_5$ | C$_2$H$_5$ | C$_2$H$_5$ |
| B-697 | Cl | Cl | C$_2$H$_5$ | C$_2$H$_5$ | CH$_3$ | CH$_3$ |
| B-698 | Cl | Cl | C$_2$H$_5$ | C$_2$H$_5$ | CH$_3$ | C$_2$H$_5$ |
| B-699 | Cl | Cl | C$_2$H$_5$ | C$_2$H$_5$ | C$_2$H$_5$ | CH$_3$ |
| B-700 | Cl | Cl | C$_2$H$_5$ | C$_2$H$_5$ | C$_2$H$_5$ | C$_2$H$_5$ |
| B-701 | CH$_3$ | Cl | C$_2$H$_5$ | C$_2$H$_5$ | CH$_3$ | CH$_3$ |
| B-702 | CH$_3$ | Cl | C$_2$H$_5$ | C$_2$H$_5$ | CH$_3$ | C$_2$H$_5$ |
| B-703 | CH$_3$ | Cl | C$_2$H$_5$ | C$_2$H$_5$ | C$_2$H$_5$ | CH$_3$ |
| B-704 | CH$_3$ | Cl | C$_2$H$_5$ | C$_2$H$_5$ | C$_2$H$_5$ | C$_2$H$_5$ |
| B-705 | H | H | CH$_3$ | C$_2$H$_5$ | CH$_3$ | CH$_3$ |
| B-706 | H | H | CH$_3$ | C$_2$H$_5$ | CH$_3$ | C$_2$H$_5$ |
| B-707 | H | H | CH$_3$ | C$_2$H$_5$ | C$_2$H$_5$ | CH$_3$ |
| B-708 | H | H | CH$_3$ | C$_2$H$_5$ | C$_2$H$_5$ | C$_2$H$_5$ |
| B-709 | F | H | CH$_3$ | C$_2$H$_5$ | CH$_3$ | CH$_3$ |
| B-710 | F | H | CH$_3$ | C$_2$H$_5$ | CH$_3$ | C$_2$H$_5$ |
| B-711 | F | H | CH$_3$ | C$_2$H$_5$ | C$_2$H$_5$ | CH$_3$ |
| B-712 | F | H | CH$_3$ | C$_2$H$_5$ | C$_2$H$_5$ | C$_2$H$_5$ |
| B-713 | Cl | H | CH$_3$ | C$_2$H$_5$ | CH$_3$ | CH$_3$ |
| B-714 | Cl | H | CH$_3$ | C$_2$H$_5$ | CH$_3$ | C$_2$H$_5$ |
| B-715 | Cl | H | CH$_3$ | C$_2$H$_5$ | C$_2$H$_5$ | CH$_3$ |
| B-716 | Cl | H | CH$_3$ | C$_2$H$_5$ | C$_2$H$_5$ | C$_2$H$_5$ |
| B-717 | CH$_3$ | H | CH$_3$ | C$_2$H$_5$ | CH$_3$ | CH$_3$ |
| B-718 | CH$_3$ | H | CH$_3$ | C$_2$H$_5$ | CH$_3$ | C$_2$H$_5$ |
| B-719 | CH$_3$ | H | CH$_3$ | C$_2$H$_5$ | C$_2$H$_5$ | CH$_3$ |
| B-720 | CH$_3$ | H | CH$_3$ | C$_2$H$_5$ | C$_2$H$_5$ | C$_2$H$_5$ |
| B-721 | H | F | CH$_3$ | C$_2$H$_5$ | CH$_3$ | CH$_3$ |
| B-722 | H | F | CH$_3$ | C$_2$H$_5$ | CH$_3$ | C$_2$H$_5$ |
| B-723 | H | F | CH$_3$ | C$_2$H$_5$ | C$_2$H$_5$ | CH$_3$ |
| B-724 | H | F | CH$_3$ | C$_2$H$_5$ | C$_2$H$_5$ | C$_2$H$_5$ |
| B-725 | F | F | CH$_3$ | C$_2$H$_5$ | CH$_3$ | CH$_3$ |
| B-726 | F | F | CH$_3$ | C$_2$H$_5$ | CH$_3$ | C$_2$H$_5$ |
| B-727 | F | F | CH$_3$ | C$_2$H$_5$ | C$_2$H$_5$ | CH$_3$ |
| B-728 | F | F | CH$_3$ | C$_2$H$_5$ | C$_2$H$_5$ | C$_2$H$_5$ |
| B-729 | Cl | F | CH$_3$ | C$_2$H$_5$ | CH$_3$ | CH$_3$ |
| B-730 | Cl | F | CH$_3$ | C$_2$H$_5$ | CH$_3$ | C$_2$H$_5$ |
| B-731 | Cl | F | CH$_3$ | C$_2$H$_5$ | C$_2$H$_5$ | CH$_3$ |
| B-732 | Cl | F | CH$_3$ | C$_2$H$_5$ | C$_2$H$_5$ | C$_2$H$_5$ |
| B-733 | CH$_3$ | F | CH$_3$ | C$_2$H$_5$ | CH$_3$ | CH$_3$ |
| B-734 | CH$_3$ | F | CH$_3$ | C$_2$H$_5$ | CH$_3$ | C$_2$H$_5$ |
| B-735 | CH$_3$ | F | CH$_3$ | C$_2$H$_5$ | C$_2$H$_5$ | CH$_3$ |
| B-736 | CH$_3$ | F | CH$_3$ | C$_2$H$_5$ | C$_2$H$_5$ | C$_2$H$_5$ |
| B-737 | H | CH$_3$ | CH$_3$ | C$_2$H$_5$ | CH$_3$ | CH$_3$ |
| B-738 | H | CH$_3$ | CH$_3$ | C$_2$H$_5$ | CH$_3$ | C$_2$H$_5$ |
| B-739 | H | CH$_3$ | CH$_3$ | C$_2$H$_5$ | C$_2$H$_5$ | CH$_3$ |
| B-740 | H | CH$_3$ | CH$_3$ | C$_2$H$_5$ | C$_2$H$_5$ | C$_2$H$_5$ |
| B-741 | F | CH$_3$ | CH$_3$ | C$_2$H$_5$ | CH$_3$ | CH$_3$ |
| B-742 | F | CH$_3$ | CH$_3$ | C$_2$H$_5$ | CH$_3$ | C$_2$H$_5$ |
| B-743 | F | CH$_3$ | CH$_3$ | C$_2$H$_5$ | C$_2$H$_5$ | CH$_3$ |
| B-744 | F | CH$_3$ | CH$_3$ | C$_2$H$_5$ | C$_2$H$_5$ | C$_2$H$_5$ |
| B-745 | Cl | CH$_3$ | CH$_3$ | C$_2$H$_5$ | CH$_3$ | CH$_3$ |
| B-746 | Cl | CH$_3$ | CH$_3$ | C$_2$H$_5$ | CH$_3$ | C$_2$H$_5$ |
| B-747 | Cl | CH$_3$ | CH$_3$ | C$_2$H$_5$ | C$_2$H$_5$ | CH$_3$ |
| B-748 | Cl | CH$_3$ | CH$_3$ | C$_2$H$_5$ | C$_2$H$_5$ | C$_2$H$_5$ |
| B-749 | CH$_3$ | CH$_3$ | CH$_3$ | C$_2$H$_5$ | CH$_3$ | CH$_3$ |
| B-750 | CH$_3$ | CH$_3$ | CH$_3$ | C$_2$H$_5$ | CH$_3$ | C$_2$H$_5$ |
| B-751 | CH$_3$ | CH$_3$ | CH$_3$ | C$_2$H$_5$ | C$_2$H$_5$ | CH$_3$ |
| B-752 | CH$_3$ | CH$_3$ | CH$_3$ | C$_2$H$_5$ | C$_2$H$_5$ | C$_2$H$_5$ |
| B-753 | H | Cl | CH$_3$ | C$_2$H$_5$ | CH$_3$ | CH$_3$ |
| B-754 | H | Cl | CH$_3$ | C$_2$H$_5$ | CH$_3$ | C$_2$H$_5$ |
| B-755 | H | Cl | CH$_3$ | C$_2$H$_5$ | C$_2$H$_5$ | CH$_3$ |
| B-756 | H | Cl | CH$_3$ | C$_2$H$_5$ | C$_2$H$_5$ | C$_2$H$_5$ |
| B-757 | F | Cl | CH$_3$ | C$_2$H$_5$ | CH$_3$ | CH$_3$ |
| B-758 | F | Cl | CH$_3$ | C$_2$H$_5$ | CH$_3$ | C$_2$H$_5$ |
| B-759 | F | Cl | CH$_3$ | C$_2$H$_5$ | C$_2$H$_5$ | CH$_3$ |
| B-760 | F | Cl | CH$_3$ | C$_2$H$_5$ | C$_2$H$_5$ | C$_2$H$_5$ |
| B-761 | Cl | Cl | CH$_3$ | C$_2$H$_5$ | CH$_3$ | CH$_3$ |
| B-762 | Cl | Cl | CH$_3$ | C$_2$H$_5$ | CH$_3$ | C$_2$H$_5$ |
| B-763 | Cl | Cl | CH$_3$ | C$_2$H$_5$ | C$_2$H$_5$ | CH$_3$ |
| B-764 | Cl | Cl | CH$_3$ | C$_2$H$_5$ | C$_2$H$_5$ | C$_2$H$_5$ |
| B-765 | CH$_3$ | Cl | CH$_3$ | C$_2$H$_5$ | CH$_3$ | CH$_3$ |
| B-766 | CH$_3$ | Cl | CH$_3$ | C$_2$H$_5$ | CH$_3$ | C$_2$H$_5$ |
| B-767 | CH$_3$ | Cl | CH$_3$ | C$_2$H$_5$ | C$_2$H$_5$ | CH$_3$ |
| B-768 | CH$_3$ | Cl | CH$_3$ | C$_2$H$_5$ | C$_2$H$_5$ | C$_2$H$_5$ |
| B-769 | H | H | H | H | CH$_3$ | CH$_3$ |
| B-770 | H | H | H | H | CH$_3$ | C$_2$H$_5$ |
| B-771 | H | H | H | H | C$_2$H$_5$ | CH$_3$ |
| B-772 | H | H | H | H | C$_2$H$_5$ | C$_2$H$_5$ |
| B-773 | F | H | H | H | CH$_3$ | CH$_3$ |
| B-774 | F | H | H | H | CH$_3$ | C$_2$H$_5$ |
| B-775 | F | H | H | H | C$_2$H$_5$ | CH$_3$ |
| B-776 | F | H | H | H | C$_2$H$_5$ | C$_2$H$_5$ |
| B-777 | Cl | H | H | H | CH$_3$ | CH$_3$ |
| B-778 | Cl | H | H | H | CH$_3$ | C$_2$H$_5$ |
| B-779 | Cl | H | H | H | C$_2$H$_5$ | CH$_3$ |
| B-780 | Cl | H | H | H | C$_2$H$_5$ | C$_2$H$_5$ |
| B-781 | CH$_3$ | H | H | H | CH$_3$ | CH$_3$ |
| B-782 | CH$_3$ | H | H | H | CH$_3$ | C$_2$H$_5$ |
| B-783 | CH$_3$ | H | H | H | C$_2$H$_5$ | CH$_3$ |
| B-784 | CH$_3$ | H | H | H | C$_2$H$_5$ | C$_2$H$_5$ |
| B-785 | H | F | H | H | CH$_3$ | CH$_3$ |
| B-786 | H | F | H | H | CH$_3$ | C$_2$H$_5$ |
| B-787 | H | F | H | H | C$_2$H$_5$ | CH$_3$ |
| B-788 | H | F | H | H | C$_2$H$_5$ | C$_2$H$_5$ |
| B-789 | F | F | H | H | CH$_3$ | CH$_3$ |
| B-790 | F | F | H | H | CH$_3$ | C$_2$H$_5$ |
| B-791 | F | F | H | H | C$_2$H$_5$ | CH$_3$ |
| B-792 | F | F | H | H | C$_2$H$_5$ | C$_2$H$_5$ |
| B-793 | Cl | F | H | H | CH$_3$ | CH$_3$ |
| B-794 | Cl | F | H | H | CH$_3$ | C$_2$H$_5$ |
| B-795 | Cl | F | H | H | C$_2$H$_5$ | CH$_3$ |
| B-796 | Cl | F | H | H | C$_2$H$_5$ | C$_2$H$_5$ |
| B-797 | CH$_3$ | F | H | H | CH$_3$ | CH$_3$ |
| B-798 | CH$_3$ | F | H | H | CH$_3$ | C$_2$H$_5$ |
| B-799 | CH$_3$ | F | H | H | C$_2$H$_5$ | CH$_3$ |
| B-800 | CH$_3$ | F | H | H | C$_2$H$_5$ | C$_2$H$_5$ |
| B-801 | H | CH$_3$ | H | H | CH$_3$ | CH$_3$ |
| B-802 | H | CH$_3$ | H | H | CH$_3$ | C$_2$H$_5$ |
| B-803 | H | CH$_3$ | H | H | C$_2$H$_5$ | CH$_3$ |
| B-804 | H | CH$_3$ | H | H | C$_2$H$_5$ | C$_2$H$_5$ |
| B-805 | F | CH$_3$ | H | H | CH$_3$ | CH$_3$ |
| B-806 | F | CH$_3$ | H | H | CH$_3$ | C$_2$H$_5$ |
| B-807 | F | CH$_3$ | H | H | C$_2$H$_5$ | CH$_3$ |
| B-808 | F | CH$_3$ | H | H | C$_2$H$_5$ | C$_2$H$_5$ |

TABLE B-continued

| line | R¹ | R² | R³ | R⁴ | R⁹ | R¹⁰ |
|---|---|---|---|---|---|---|
| B-809 | Cl | CH₃ | H | H | CH₃ | CH₃ |
| B-810 | Cl | CH₃ | H | H | CH₃ | C₂H₅ |
| B-811 | Cl | CH₃ | H | H | C₂H₅ | CH₃ |
| B-812 | Cl | CH₃ | H | H | C₂H₅ | C₂H₅ |
| B-813 | CH₃ | CH₃ | H | H | CH₃ | CH₃ |
| B-814 | CH₃ | CH₃ | H | H | CH₃ | C₂H₅ |
| B-815 | CH₃ | CH₃ | H | H | C₂H₅ | CH₃ |
| B-816 | CH₃ | CH₃ | H | H | C₂H₅ | C₂H₅ |
| B-817 | H | Cl | H | H | CH₃ | CH₃ |
| B-818 | H | Cl | H | H | CH₃ | C₂H₅ |
| B-819 | H | Cl | H | H | C₂H₅ | CH₃ |
| B-820 | H | Cl | H | H | C₂H₅ | C₂H₅ |
| B-821 | F | Cl | H | H | CH₃ | CH₃ |
| B-822 | F | Cl | H | H | CH₃ | C₂H₅ |
| B-823 | F | Cl | H | H | C₂H₅ | CH₃ |
| B-824 | F | Cl | H | H | C₂H₅ | C₂H₅ |
| B-825 | Cl | Cl | H | H | CH₃ | CH₃ |
| B-826 | Cl | Cl | H | H | CH₃ | C₂H₅ |
| B-827 | Cl | Cl | H | H | C₂H₅ | CH₃ |
| B-828 | Cl | Cl | H | H | C₂H₅ | C₂H₅ |
| B-829 | CH₃ | Cl | H | H | CH₃ | CH₃ |
| B-830 | CH₃ | Cl | H | H | CH₃ | C₂H₅ |
| B-831 | CH₃ | Cl | H | H | C₂H₅ | CH₃ |
| B-832 | CH₃ | Cl | H | H | C₂H₅ | C₂H₅ |
| B-833 | H | H | CH₃ | CH₃ | CH₃ | CH₃ |
| B-834 | H | H | CH₃ | CH₃ | CH₃ | C₂H₅ |
| B-835 | H | H | CH₃ | CH₃ | C₂H₅ | CH₃ |
| B-836 | H | H | CH₃ | CH₃ | C₂H₅ | C₂H₅ |
| B-837 | F | H | CH₃ | CH₃ | CH₃ | CH₃ |
| B-838 | F | H | CH₃ | CH₃ | CH₃ | C₂H₅ |
| B-839 | F | H | CH₃ | CH₃ | C₂H₅ | CH₃ |
| B-840 | F | H | CH₃ | CH₃ | C₂H₅ | C₂H₅ |
| B-841 | Cl | H | CH₃ | CH₃ | CH₃ | CH₃ |
| B-842 | Cl | H | CH₃ | CH₃ | CH₃ | C₂H₅ |
| B-843 | Cl | H | CH₃ | CH₃ | C₂H₅ | CH₃ |
| B-844 | Cl | H | CH₃ | CH₃ | C₂H₅ | C₂H₅ |
| B-845 | CH₃ | H | CH₃ | CH₃ | CH₃ | CH₃ |
| B-846 | CH₃ | H | CH₃ | CH₃ | CH₃ | C₂H₅ |
| B-847 | CH₃ | H | CH₃ | CH₃ | C₂H₅ | CH₃ |
| B-848 | CH₃ | H | CH₃ | CH₃ | C₂H₅ | C₂H₅ |
| B-849 | H | F | CH₃ | CH₃ | CH₃ | CH₃ |
| B-850 | H | F | CH₃ | CH₃ | CH₃ | C₂H₅ |
| B-851 | H | F | CH₃ | CH₃ | C₂H₅ | CH₃ |
| B-852 | H | F | CH₃ | CH₃ | C₂H₅ | C₂H₅ |
| B-853 | F | F | CH₃ | CH₃ | CH₃ | CH₃ |
| B-854 | F | F | CH₃ | CH₃ | CH₃ | C₂H₅ |
| B-855 | F | F | CH₃ | CH₃ | C₂H₅ | CH₃ |
| B-856 | F | F | CH₃ | CH₃ | C₂H₅ | C₂H₅ |
| B-857 | Cl | F | CH₃ | CH₃ | CH₃ | CH₃ |
| B-858 | Cl | F | CH₃ | CH₃ | CH₃ | C₂H₅ |
| B-859 | Cl | F | CH₃ | CH₃ | C₂H₅ | CH₃ |
| B-860 | Cl | F | CH₃ | CH₃ | C₂H₅ | C₂H₅ |
| B-861 | CH₃ | F | CH₃ | CH₃ | CH₃ | CH₃ |
| B-862 | CH₃ | F | CH₃ | CH₃ | CH₃ | C₂H₅ |
| B-863 | CH₃ | F | CH₃ | CH₃ | C₂H₅ | CH₃ |
| B-864 | CH₃ | F | CH₃ | CH₃ | C₂H₅ | C₂H₅ |
| B-865 | H | CH₃ | CH₃ | CH₃ | CH₃ | CH₃ |
| B-866 | H | CH₃ | CH₃ | CH₃ | CH₃ | C₂H₅ |
| B-867 | H | CH₃ | CH₃ | CH₃ | C₂H₅ | CH₃ |
| B-868 | H | CH₃ | CH₃ | CH₃ | C₂H₅ | C₂H₅ |
| B-869 | F | CH₃ | CH₃ | CH₃ | CH₃ | CH₃ |
| B-870 | F | CH₃ | CH₃ | CH₃ | CH₃ | C₂H₅ |
| B-871 | F | CH₃ | CH₃ | CH₃ | C₂H₅ | CH₃ |
| B-872 | F | CH₃ | CH₃ | CH₃ | C₂H₅ | C₂H₅ |
| B-873 | Cl | CH₃ | CH₃ | CH₃ | CH₃ | CH₃ |
| B-874 | Cl | CH₃ | CH₃ | CH₃ | CH₃ | C₂H₅ |
| B-875 | Cl | CH₃ | CH₃ | CH₃ | C₂H₅ | CH₃ |
| B-876 | Cl | CH₃ | CH₃ | CH₃ | C₂H₅ | C₂H₅ |
| B-877 | CH₃ | CH₃ | CH₃ | CH₃ | CH₃ | CH₃ |
| B-878 | CH₃ | CH₃ | CH₃ | CH₃ | CH₃ | C₂H₅ |
| B-879 | CH₃ | CH₃ | CH₃ | CH₃ | C₂H₅ | CH₃ |
| B-880 | CH₃ | CH₃ | CH₃ | CH₃ | C₂H₅ | C₂H₅ |
| B-881 | H | Cl | CH₃ | CH₃ | CH₃ | CH₃ |
| B-882 | H | Cl | CH₃ | CH₃ | CH₃ | C₂H₅ |
| B-883 | H | Cl | CH₃ | CH₃ | C₂H₅ | CH₃ |
| B-884 | H | Cl | CH₃ | CH₃ | C₂H₅ | C₂H₅ |
| B-885 | F | Cl | CH₃ | CH₃ | CH₃ | CH₃ |
| B-886 | F | Cl | CH₃ | CH₃ | CH₃ | C₂H₅ |
| B-887 | F | Cl | CH₃ | CH₃ | C₂H₅ | CH₃ |
| B-888 | F | Cl | CH₃ | CH₃ | C₂H₅ | C₂H₅ |
| B-889 | Cl | Cl | CH₃ | CH₃ | CH₃ | CH₃ |
| B-890 | Cl | Cl | CH₃ | CH₃ | CH₃ | C₂H₅ |
| B-891 | Cl | Cl | CH₃ | CH₃ | C₂H₅ | CH₃ |
| B-892 | Cl | Cl | CH₃ | CH₃ | C₂H₅ | C₂H₅ |
| B-893 | CH₃ | Cl | CH₃ | CH₃ | CH₃ | CH₃ |
| B-894 | CH₃ | Cl | CH₃ | CH₃ | CH₃ | C₂H₅ |
| B-895 | CH₃ | Cl | CH₃ | CH₃ | C₂H₅ | CH₃ |
| B-896 | CH₃ | Cl | CH₃ | CH₃ | C₂H₅ | C₂H₅ |
| B-897 | H | H | C₂H₅ | C₂H₅ | CH₃ | CH₃ |
| B-898 | H | H | C₂H₅ | C₂H₅ | CH₃ | C₂H₅ |
| B-899 | H | H | C₂H₅ | C₂H₅ | C₂H₅ | CH₃ |
| B-900 | H | H | C₂H₅ | C₂H₅ | C₂H₅ | C₂H₅ |
| B-901 | F | H | C₂H₅ | C₂H₅ | CH₃ | CH₃ |
| B-902 | F | H | C₂H₅ | C₂H₅ | CH₃ | C₂H₅ |
| B-903 | F | H | C₂H₅ | C₂H₅ | C₂H₅ | CH₃ |
| B-904 | F | H | C₂H₅ | C₂H₅ | C₂H₅ | C₂H₅ |
| B-905 | Cl | H | C₂H₅ | C₂H₅ | CH₃ | CH₃ |
| B-906 | Cl | H | C₂H₅ | C₂H₅ | CH₃ | C₂H₅ |
| B-907 | Cl | H | C₂H₅ | C₂H₅ | C₂H₅ | CH₃ |
| B-908 | Cl | H | C₂H₅ | C₂H₅ | C₂H₅ | C₂H₅ |
| B-909 | CH₃ | H | C₂H₅ | C₂H₅ | CH₃ | CH₃ |
| B-910 | CH₃ | H | C₂H₅ | C₂H₅ | CH₃ | C₂H₅ |
| B-911 | CH₃ | H | C₂H₅ | C₂H₅ | C₂H₅ | CH₃ |
| B-912 | CH₃ | H | C₂H₅ | C₂H₅ | C₂H₅ | C₂H₅ |
| B-913 | H | F | C₂H₅ | C₂H₅ | CH₃ | CH₃ |
| B-914 | H | F | C₂H₅ | C₂H₅ | CH₃ | C₂H₅ |
| B-915 | H | F | C₂H₅ | C₂H₅ | C₂H₅ | CH₃ |
| B-916 | H | F | C₂H₅ | C₂H₅ | C₂H₅ | C₂H₅ |
| B-917 | F | F | C₂H₅ | C₂H₅ | CH₃ | CH₃ |
| B-918 | F | F | C₂H₅ | C₂H₅ | CH₃ | C₂H₅ |
| B-919 | F | F | C₂H₅ | C₂H₅ | C₂H₅ | CH₃ |
| B-920 | F | F | C₂H₅ | C₂H₅ | C₂H₅ | C₂H₅ |
| B-921 | Cl | F | C₂H₅ | C₂H₅ | CH₃ | CH₃ |
| B-922 | Cl | F | C₂H₅ | C₂H₅ | CH₃ | C₂H₅ |
| B-923 | Cl | F | C₂H₅ | C₂H₅ | C₂H₅ | CH₃ |
| B-924 | Cl | F | C₂H₅ | C₂H₅ | C₂H₅ | C₂H₅ |
| B-925 | CH₃ | F | C₂H₅ | C₂H₅ | CH₃ | CH₃ |
| B-926 | CH₃ | F | C₂H₅ | C₂H₅ | CH₃ | C₂H₅ |
| B-927 | CH₃ | F | C₂H₅ | C₂H₅ | C₂H₅ | CH₃ |
| B-928 | CH₃ | F | C₂H₅ | C₂H₅ | C₂H₅ | C₂H₅ |
| B-929 | H | CH₃ | C₂H₅ | C₂H₅ | CH₃ | CH₃ |
| B-930 | H | CH₃ | C₂H₅ | C₂H₅ | CH₃ | C₂H₅ |
| B-931 | H | CH₃ | C₂H₅ | C₂H₅ | C₂H₅ | CH₃ |
| B-932 | H | CH₃ | C₂H₅ | C₂H₅ | C₂H₅ | C₂H₅ |
| B-933 | F | CH₃ | C₂H₅ | C₂H₅ | CH₃ | CH₃ |
| B-934 | F | CH₃ | C₂H₅ | C₂H₅ | CH₃ | C₂H₅ |
| B-935 | F | CH₃ | C₂H₅ | C₂H₅ | C₂H₅ | CH₃ |
| B-936 | F | CH₃ | C₂H₅ | C₂H₅ | C₂H₅ | C₂H₅ |
| B-937 | Cl | CH₃ | C₂H₅ | C₂H₅ | CH₃ | CH₃ |
| B-938 | Cl | CH₃ | C₂H₅ | C₂H₅ | CH₃ | C₂H₅ |
| B-939 | Cl | CH₃ | C₂H₅ | C₂H₅ | C₂H₅ | CH₃ |
| B-940 | Cl | CH₃ | C₂H₅ | C₂H₅ | C₂H₅ | C₂H₅ |
| B-941 | CH₃ | CH₃ | C₂H₅ | C₂H₅ | CH₃ | CH₃ |
| B-942 | CH₃ | CH₃ | C₂H₅ | C₂H₅ | CH₃ | C₂H₅ |
| B-943 | CH₃ | CH₃ | C₂H₅ | C₂H₅ | C₂H₅ | CH₃ |
| B-944 | CH₃ | CH₃ | C₂H₅ | C₂H₅ | C₂H₅ | C₂H₅ |
| B-945 | H | Cl | C₂H₅ | C₂H₅ | CH₃ | CH₃ |
| B-946 | H | Cl | C₂H₅ | C₂H₅ | CH₃ | C₂H₅ |
| B-947 | H | Cl | C₂H₅ | C₂H₅ | C₂H₅ | CH₃ |
| B-948 | H | Cl | C₂H₅ | C₂H₅ | C₂H₅ | C₂H₅ |
| B-949 | F | Cl | C₂H₅ | C₂H₅ | CH₃ | CH₃ |
| B-950 | F | Cl | C₂H₅ | C₂H₅ | CH₃ | C₂H₅ |
| B-951 | F | Cl | C₂H₅ | C₂H₅ | C₂H₅ | CH₃ |
| B-952 | F | Cl | C₂H₅ | C₂H₅ | C₂H₅ | C₂H₅ |
| B-953 | Cl | Cl | C₂H₅ | C₂H₅ | CH₃ | CH₃ |
| B-954 | Cl | Cl | C₂H₅ | C₂H₅ | CH₃ | C₂H₅ |
| B-955 | Cl | Cl | C₂H₅ | C₂H₅ | C₂H₅ | CH₃ |
| B-956 | Cl | Cl | C₂H₅ | C₂H₅ | C₂H₅ | C₂H₅ |
| B-957 | CH₃ | Cl | C₂H₅ | C₂H₅ | CH₃ | CH₃ |
| B-958 | CH₃ | Cl | C₂H₅ | C₂H₅ | CH₃ | C₂H₅ |
| B-959 | CH₃ | Cl | C₂H₅ | C₂H₅ | C₂H₅ | CH₃ |
| B-960 | CH₃ | Cl | C₂H₅ | C₂H₅ | C₂H₅ | C₂H₅ |
| B-961 | H | H | CH₃ | C₂H₅ | CH₃ | CH₃ |
| B-962 | H | H | CH₃ | C₂H₅ | CH₃ | C₂H₅ |
| B-963 | H | H | CH₃ | C₂H₅ | C₂H₅ | CH₃ |
| B-964 | H | H | CH₃ | C₂H₅ | C₂H₅ | C₂H₅ |

TABLE B-continued

| line | R$^1$ | R$^2$ | R$^3$ | R$^4$ | R$^9$ | R$^{10}$ |
|---|---|---|---|---|---|---|
| B-965 | F | H | CH$_3$ | C$_2$H$_5$ | CH$_3$ | CH$_3$ |
| B-966 | F | H | CH$_3$ | C$_2$H$_5$ | CH$_3$ | C$_2$H$_5$ |
| B-967 | F | H | CH$_3$ | C$_2$H$_5$ | C$_2$H$_5$ | CH$_3$ |
| B-968 | F | H | CH$_3$ | C$_2$H$_5$ | C$_2$H$_5$ | C$_2$H$_5$ |
| B-969 | Cl | H | CH$_3$ | C$_2$H$_5$ | CH$_3$ | CH$_3$ |
| B-970 | Cl | H | CH$_3$ | C$_2$H$_5$ | CH$_3$ | C$_2$H$_5$ |
| B-971 | Cl | H | CH$_3$ | C$_2$H$_5$ | C$_2$H$_5$ | CH$_3$ |
| B-972 | Cl | H | CH$_3$ | C$_2$H$_5$ | C$_2$H$_5$ | C$_2$H$_5$ |
| B-973 | CH$_3$ | H | CH$_3$ | C$_2$H$_5$ | CH$_3$ | CH$_3$ |
| B-974 | CH$_3$ | H | CH$_3$ | C$_2$H$_5$ | CH$_3$ | C$_2$H$_5$ |
| B-975 | CH$_3$ | H | CH$_3$ | C$_2$H$_5$ | C$_2$H$_5$ | CH$_3$ |
| B-976 | CH$_3$ | H | CH$_3$ | C$_2$H$_5$ | C$_2$H$_5$ | C$_2$H$_5$ |
| B-977 | H | F | CH$_3$ | C$_2$H$_5$ | CH$_3$ | CH$_3$ |
| B-978 | H | F | CH$_3$ | C$_2$H$_5$ | CH$_3$ | C$_2$H$_5$ |
| B-979 | H | F | CH$_3$ | C$_2$H$_5$ | C$_2$H$_5$ | CH$_3$ |
| B-980 | H | F | CH$_3$ | C$_2$H$_5$ | C$_2$H$_5$ | C$_2$H$_5$ |
| B-981 | F | F | CH$_3$ | C$_2$H$_5$ | CH$_3$ | CH$_3$ |
| B-982 | F | F | CH$_3$ | C$_2$H$_5$ | CH$_3$ | C$_2$H$_5$ |
| B-983 | F | F | CH$_3$ | C$_2$H$_5$ | C$_2$H$_5$ | CH$_3$ |
| B-984 | F | F | CH$_3$ | C$_2$H$_5$ | C$_2$H$_5$ | C$_2$H$_5$ |
| B-985 | Cl | F | CH$_3$ | C$_2$H$_5$ | CH$_3$ | CH$_3$ |
| B-986 | Cl | F | CH$_3$ | C$_2$H$_5$ | CH$_3$ | C$_2$H$_5$ |
| B-987 | Cl | F | CH$_3$ | C$_2$H$_5$ | C$_2$H$_5$ | CH$_3$ |
| B-988 | Cl | F | CH$_3$ | C$_2$H$_5$ | C$_2$H$_5$ | C$_2$H$_5$ |
| B-989 | CH$_3$ | F | CH$_3$ | C$_2$H$_5$ | CH$_3$ | CH$_3$ |
| B-990 | CH$_3$ | F | CH$_3$ | C$_2$H$_5$ | CH$_3$ | C$_2$H$_5$ |
| B-991 | CH$_3$ | F | CH$_3$ | C$_2$H$_5$ | C$_2$H$_5$ | CH$_3$ |
| B-992 | CH$_3$ | F | CH$_3$ | C$_2$H$_5$ | C$_2$H$_5$ | C$_2$H$_5$ |
| B-993 | H | CH$_3$ | CH$_3$ | C$_2$H$_5$ | CH$_3$ | CH$_3$ |
| B-994 | H | CH$_3$ | CH$_3$ | C$_2$H$_5$ | CH$_3$ | C$_2$H$_5$ |
| B-995 | H | CH$_3$ | CH$_3$ | C$_2$H$_5$ | C$_2$H$_5$ | CH$_3$ |
| B-996 | H | CH$_3$ | CH$_3$ | C$_2$H$_5$ | C$_2$H$_5$ | C$_2$H$_5$ |
| B-997 | F | CH$_3$ | CH$_3$ | C$_2$H$_5$ | CH$_3$ | CH$_3$ |
| B-998 | F | CH$_3$ | CH$_3$ | C$_2$H$_5$ | CH$_3$ | C$_2$H$_5$ |
| B-999 | F | CH$_3$ | CH$_3$ | C$_2$H$_5$ | C$_2$H$_5$ | CH$_3$ |
| B-1000 | F | CH$_3$ | CH$_3$ | C$_2$H$_5$ | C$_2$H$_5$ | C$_2$H$_5$ |
| B-1001 | Cl | CH$_3$ | CH$_3$ | C$_2$H$_5$ | CH$_3$ | CH$_3$ |
| B-1002 | Cl | CH$_3$ | CH$_3$ | C$_2$H$_5$ | CH$_3$ | C$_2$H$_5$ |
| B-1003 | Cl | CH$_3$ | CH$_3$ | C$_2$H$_5$ | C$_2$H$_5$ | CH$_3$ |
| B-1004 | Cl | CH$_3$ | CH$_3$ | C$_2$H$_5$ | C$_2$H$_5$ | C$_2$H$_5$ |
| B-1005 | CH$_3$ | CH$_3$ | CH$_3$ | C$_2$H$_5$ | CH$_3$ | CH$_3$ |
| B-1006 | CH$_3$ | CH$_3$ | CH$_3$ | C$_2$H$_5$ | CH$_3$ | C$_2$H$_5$ |
| B-1007 | CH$_3$ | CH$_3$ | CH$_3$ | C$_2$H$_5$ | C$_2$H$_5$ | CH$_3$ |
| B-1008 | CH$_3$ | CH$_3$ | CH$_3$ | C$_2$H$_5$ | C$_2$H$_5$ | C$_2$H$_5$ |
| B-1009 | H | Cl | CH$_3$ | C$_2$H$_5$ | CH$_3$ | CH$_3$ |
| B-1010 | H | Cl | CH$_3$ | C$_2$H$_5$ | CH$_3$ | C$_2$H$_5$ |
| B-1011 | H | Cl | CH$_3$ | C$_2$H$_5$ | C$_2$H$_5$ | CH$_3$ |
| B-1012 | H | Cl | CH$_3$ | C$_2$H$_5$ | C$_2$H$_5$ | C$_2$H$_5$ |
| B-1013 | F | Cl | CH$_3$ | C$_2$H$_5$ | CH$_3$ | CH$_3$ |
| B-1014 | F | Cl | CH$_3$ | C$_2$H$_5$ | CH$_3$ | C$_2$H$_5$ |
| B-1015 | F | Cl | CH$_3$ | C$_2$H$_5$ | C$_2$H$_5$ | CH$_3$ |
| B-1016 | F | Cl | CH$_3$ | C$_2$H$_5$ | C$_2$H$_5$ | C$_2$H$_5$ |
| B-1017 | Cl | Cl | CH$_3$ | C$_2$H$_5$ | CH$_3$ | CH$_3$ |
| B-1018 | Cl | Cl | CH$_3$ | C$_2$H$_5$ | CH$_3$ | C$_2$H$_5$ |
| B-1019 | Cl | Cl | CH$_3$ | C$_2$H$_5$ | C$_2$H$_5$ | CH$_3$ |
| B-1020 | Cl | Cl | CH$_3$ | C$_2$H$_5$ | C$_2$H$_5$ | C$_2$H$_5$ |
| B-1021 | CH$_3$ | Cl | CH$_3$ | C$_2$H$_5$ | CH$_3$ | CH$_3$ |
| B-1022 | CH$_3$ | Cl | CH$_3$ | C$_2$H$_5$ | CH$_3$ | C$_2$H$_5$ |
| B-1023 | CH$_3$ | Cl | CH$_3$ | C$_2$H$_5$ | C$_2$H$_5$ | CH$_3$ |
| B-1024 | CH$_3$ | Cl | CH$_3$ | C$_2$H$_5$ | C$_2$H$_5$ | C$_2$H$_5$ |
| B-1025 | H | H |  | Cl | CH$_3$ | CH$_3$ |
| B-1026 | H | H |  | Cl | CH$_3$ | C$_2$H$_5$ |
| B-1027 | H | H |  | Cl | C$_2$H$_5$ | CH$_3$ |
| B-1028 | H | H |  | Cl | C$_2$H$_5$ | C$_2$H$_5$ |
| B-1029 | F | H |  | Cl | CH$_3$ | CH$_3$ |
| B-1030 | F | H |  | Cl | CH$_3$ | C$_2$H$_5$ |
| B-1031 | F | H |  | Cl | C$_2$H$_5$ | CH$_3$ |
| B-1032 | F | H |  | Cl | C$_2$H$_5$ | C$_2$H$_5$ |
| B-1033 | Cl | H |  | Cl | CH$_3$ | CH$_3$ |
| B-1034 | Cl | H |  | Cl | CH$_3$ | C$_2$H$_5$ |
| B-1035 | Cl | H |  | Cl | C$_2$H$_5$ | CH$_3$ |
| B-1036 | Cl | H |  | Cl | C$_2$H$_5$ | C$_2$H$_5$ |
| B-1037 | CH$_3$ | H |  | Cl | CH$_3$ | CH$_3$ |
| B-1038 | CH$_3$ | H |  | Cl | CH$_3$ | C$_2$H$_5$ |
| B-1039 | CH$_3$ | H |  | Cl | C$_2$H$_5$ | CH$_3$ |
| B-1040 | CH$_3$ | H |  | Cl | C$_2$H$_5$ | C$_2$H$_5$ |
| B-1041 | H | F |  | Cl | CH$_3$ | CH$_3$ |
| B-1042 | H | F |  | Cl | CH$_3$ | C$_2$H$_5$ |
| B-1043 | H | F |  | Cl | C$_2$H$_5$ | CH$_3$ |
| B-1044 | H | F |  | Cl | C$_2$H$_5$ | C$_2$H$_5$ |
| B-1045 | F | F |  | Cl | CH$_3$ | CH$_3$ |
| B-1046 | F | F |  | Cl | CH$_3$ | C$_2$H$_5$ |
| B-1047 | F | F |  | Cl | C$_2$H$_5$ | CH$_3$ |
| B-1048 | F | F |  | Cl | C$_2$H$_5$ | C$_2$H$_5$ |
| B-1049 | Cl | F |  | Cl | CH$_3$ | CH$_3$ |
| B-1050 | Cl | F |  | Cl | CH$_3$ | C$_2$H$_5$ |
| B-1051 | Cl | F |  | Cl | C$_2$H$_5$ | CH$_3$ |
| B-1052 | Cl | F |  | Cl | C$_2$H$_5$ | C$_2$H$_5$ |
| B-1053 | CH$_3$ | F |  | Cl | CH$_3$ | CH$_3$ |
| B-1054 | CH$_3$ | F |  | Cl | CH$_3$ | C$_2$H$_5$ |
| B-1055 | CH$_3$ | F |  | Cl | C$_2$H$_5$ | CH$_3$ |
| B-1056 | CH$_3$ | F |  | Cl | C$_2$H$_5$ | C$_2$H$_5$ |
| B-1057 | H | CH$_3$ |  | Cl | CH$_3$ | CH$_3$ |
| B-1058 | H | CH$_3$ |  | Cl | CH$_3$ | C$_2$H$_5$ |
| B-1059 | H | CH$_3$ |  | Cl | C$_2$H$_5$ | CH$_3$ |
| B-1060 | H | CH$_3$ |  | Cl | C$_2$H$_5$ | C$_2$H$_5$ |
| B-1061 | F | CH$_3$ |  | Cl | CH$_3$ | CH$_3$ |
| B-1062 | F | CH$_3$ |  | Cl | CH$_3$ | C$_2$H$_5$ |
| B-1063 | F | CH$_3$ |  | Cl | C$_2$H$_5$ | CH$_3$ |
| B-1064 | F | CH$_3$ |  | Cl | C$_2$H$_5$ | C$_2$H$_5$ |
| B-1065 | Cl | CH$_3$ |  | Cl | CH$_3$ | CH$_3$ |
| B-1066 | Cl | CH$_3$ |  | Cl | CH$_3$ | C$_2$H$_5$ |
| B-1067 | Cl | CH$_3$ |  | Cl | C$_2$H$_5$ | CH$_3$ |
| B-1068 | Cl | CH$_3$ |  | Cl | C$_2$H$_5$ | C$_2$H$_5$ |
| B-1069 | CH$_3$ | CH$_3$ |  | Cl | CH$_3$ | CH$_3$ |
| B-1070 | CH$_3$ | CH$_3$ |  | Cl | CH$_3$ | C$_2$H$_5$ |
| B-1071 | CH$_3$ | CH$_3$ |  | Cl | C$_2$H$_5$ | CH$_3$ |
| B-1072 | CH$_3$ | CH$_3$ |  | Cl | C$_2$H$_5$ | C$_2$H$_5$ |
| B-1073 | H | Cl |  | Cl | CH$_3$ | CH$_3$ |
| B-1074 | H | Cl |  | Cl | CH$_3$ | C$_2$H$_5$ |
| B-1075 | H | Cl |  | Cl | C$_2$H$_5$ | CH$_3$ |
| B-1076 | H | Cl |  | Cl | C$_2$H$_5$ | C$_2$H$_5$ |
| B-1077 | F | Cl |  | Cl | CH$_3$ | CH$_3$ |
| B-1078 | F | Cl |  | Cl | CH$_3$ | C$_2$H$_5$ |
| B-1079 | F | Cl |  | Cl | C$_2$H$_5$ | CH$_3$ |
| B-1080 | F | Cl |  | Cl | C$_2$H$_5$ | C$_2$H$_5$ |
| B-1081 | Cl | Cl |  | Cl | CH$_3$ | CH$_3$ |
| B-1082 | Cl | Cl |  | Cl | CH$_3$ | C$_2$H$_5$ |
| B-1083 | Cl | Cl |  | Cl | C$_2$H$_5$ | CH$_3$ |
| B-1084 | Cl | Cl |  | Cl | C$_2$H$_5$ | C$_2$H$_5$ |
| B-1085 | H | H |  | Cl | CH$_3$ | CH$_3$ |
| B-1086 | H | H |  | Cl | CH$_3$ | C$_2$H$_5$ |
| B-1087 | H | H |  | Cl | C$_2$H$_5$ | CH$_3$ |
| B-1088 | H | H |  | Cl | C$_2$H$_5$ | C$_2$H$_5$ |
| B-1089 | F | H |  | Cl | CH$_3$ | CH$_3$ |
| B-1090 | F | H |  | Cl | CH$_3$ | C$_2$H$_5$ |
| B-1091 | F | H |  | Cl | C$_2$H$_5$ | CH$_3$ |
| B-1092 | F | H |  | Cl | C$_2$H$_5$ | C$_2$H$_5$ |
| B-1093 | Cl | H |  | Cl | CH$_3$ | CH$_3$ |
| B-1094 | Cl | H |  | Cl | CH$_3$ | C$_2$H$_5$ |
| B-1095 | Cl | H |  | Cl | C$_2$H$_5$ | CH$_3$ |
| B-1096 | Cl | H |  | Cl | C$_2$H$_5$ | C$_2$H$_5$ |
| B-1097 | CH$_3$ | H |  | Cl | CH$_3$ | CH$_3$ |
| B-1098 | CH$_3$ | H |  | Cl | CH$_3$ | C$_2$H$_5$ |
| B-1099 | CH$_3$ | H |  | Cl | C$_2$H$_5$ | CH$_3$ |
| B-1100 | CH$_3$ | H |  | Cl | C$_2$H$_5$ | C$_2$H$_5$ |
| B-1101 | H | F |  | Cl | CH$_3$ | CH$_3$ |
| B-1102 | H | F |  | Cl | CH$_3$ | C$_2$H$_5$ |
| B-1103 | H | F |  | Cl | C$_2$H$_5$ | CH$_3$ |
| B-1104 | H | F |  | Cl | C$_2$H$_5$ | C$_2$H$_5$ |
| B-1105 | F | F |  | Cl | CH$_3$ | CH$_3$ |
| B-1106 | F | F |  | Cl | CH$_3$ | C$_2$H$_5$ |
| B-1107 | F | F |  | Cl | C$_2$H$_5$ | CH$_3$ |
| B-1108 | F | F |  | Cl | C$_2$H$_5$ | C$_2$H$_5$ |
| B-1109 | Cl | F |  | Cl | CH$_3$ | CH$_3$ |
| B-1110 | Cl | F |  | Cl | CH$_3$ | C$_2$H$_5$ |
| B-1111 | Cl | F |  | Cl | C$_2$H$_5$ | CH$_3$ |
| B-1112 | Cl | F |  | Cl | C$_2$H$_5$ | C$_2$H$_5$ |
| B-1113 | CH$_3$ | F |  | Cl | CH$_3$ | CH$_3$ |
| B-1114 | CH$_3$ | F |  | Cl | CH$_3$ | C$_2$H$_5$ |
| B-1115 | CH$_3$ | F |  | Cl | C$_2$H$_5$ | CH$_3$ |
| B-1116 | CH$_3$ | F |  | Cl | C$_2$H$_5$ | C$_2$H$_5$ |
| B-1117 | H | CH$_3$ |  | Cl | CH$_3$ | CH$_3$ |
| B-1118 | H | CH$_3$ |  | Cl | CH$_3$ | C$_2$H$_5$ |
| B-1119 | H | CH$_3$ |  | Cl | C$_2$H$_5$ | CH$_3$ |
| B-1120 | H | CH$_3$ |  | Cl | C$_2$H$_5$ | C$_2$H$_5$ |

TABLE B-continued

| line | R¹ | R² | R³ | R⁴ | R⁹ | R¹⁰ |
|---|---|---|---|---|---|---|
| B-1121 | F | CH₃ | Cl | | CH₃ | CH₃ |
| B-1122 | F | CH₃ | Cl | | CH₃ | C₂H₅ |
| B-1123 | F | CH₃ | Cl | | C₂H₅ | CH₃ |
| B-1124 | F | CH₃ | Cl | | C₂H₅ | C₂H₅ |
| B-1125 | Cl | CH₃ | Cl | | CH₃ | CH₃ |
| B-1126 | Cl | CH₃ | Cl | | CH₃ | C₂H₅ |
| B-1127 | Cl | CH₃ | Cl | | C₂H₅ | CH₃ |
| B-1128 | Cl | CH₃ | Cl | | C₂H₅ | C₂H₅ |
| B-1129 | CH₃ | CH₃ | Cl | | CH₃ | CH₃ |
| B-1130 | CH₃ | CH₃ | Cl | | CH₃ | C₂H₅ |
| B-1131 | CH₃ | CH₃ | Cl | | C₂H₅ | CH₃ |
| B-1132 | CH₃ | CH₃ | Cl | | C₂H₅ | C₂H₅ |
| B-1133 | H | Cl | Cl | | CH₃ | CH₃ |
| B-1134 | H | Cl | Cl | | CH₃ | C₂H₅ |
| B-1135 | H | Cl | Cl | | C₂H₅ | CH₃ |
| B-1136 | H | Cl | Cl | | C₂H₅ | C₂H₅ |
| B-1137 | F | Cl | Cl | | CH₃ | CH₃ |
| B-1138 | F | Cl | Cl | | CH₃ | C₂H₅ |
| B-1139 | F | Cl | Cl | | C₂H₅ | CH₃ |
| B-1140 | F | Cl | Cl | | C₂H₅ | C₂H₅ |
| B-1141 | Cl | Cl | Cl | | CH₃ | CH₃ |
| B-1142 | Cl | Cl | Cl | | CH₃ | C₂H₅ |
| B-1143 | Cl | Cl | Cl | | C₂H₅ | CH₃ |
| B-1144 | Cl | Cl | Cl | | C₂H₅ | C₂H₅ |
| B-1145 | CH₃ | Cl | Cl | | CH₃ | CH₃ |
| B-1146 | CH₃ | Cl | Cl | | CH₃ | C₂H₅ |
| B-1147 | CH₃ | Cl | Cl | | C₂H₅ | CH₃ |
| B-1148 | CH₃ | Cl | Cl | | C₂H₅ | C₂H₅ |
| B-1149 | H | H | Cl | | CH₃ | CH₃ |
| B-1150 | H | H | Cl | | CH₃ | C₂H₅ |
| B-1151 | H | H | Cl | | C₂H₅ | CH₃ |
| B-1152 | H | H | Cl | | C₂H₅ | C₂H₅ |
| B-1153 | F | H | Cl | | CH₃ | CH₃ |
| B-1154 | F | H | Cl | | CH₃ | C₂H₅ |
| B-1155 | F | H | Cl | | C₂H₅ | CH₃ |
| B-1156 | F | H | Cl | | C₂H₅ | C₂H₅ |
| B-1157 | Cl | H | Cl | | CH₃ | CH₃ |
| B-1158 | Cl | H | Cl | | CH₃ | C₂H₅ |
| B-1159 | Cl | H | Cl | | C₂H₅ | CH₃ |
| B-1160 | Cl | H | Cl | | C₂H₅ | C₂H₅ |
| B-1161 | CH₃ | H | Cl | | CH₃ | CH₃ |
| B-1162 | CH₃ | H | Cl | | CH₃ | C₂H₅ |
| B-1163 | CH₃ | H | Cl | | C₂H₅ | CH₃ |
| B-1164 | CH₃ | H | Cl | | C₂H₅ | C₂H₅ |
| B-1165 | H | F | Cl | | CH₃ | CH₃ |
| B-1166 | H | F | Cl | | CH₃ | C₂H₅ |
| B-1167 | H | F | Cl | | C₂H₅ | CH₃ |
| B-1168 | H | F | Cl | | C₂H₅ | C₂H₅ |
| B-1169 | F | F | Cl | | CH₃ | CH₃ |
| B-1170 | F | F | Cl | | CH₃ | C₂H₅ |
| B-1171 | F | F | Cl | | C₂H₅ | CH₃ |
| B-1172 | F | F | Cl | | C₂H₅ | C₂H₅ |
| B-1173 | Cl | F | Cl | | CH₃ | CH₃ |
| B-1174 | Cl | F | Cl | | CH₃ | C₂H₅ |
| B-1175 | Cl | F | Cl | | C₂H₅ | CH₃ |
| B-1176 | Cl | F | Cl | | C₂H₅ | C₂H₅ |
| B-1177 | CH₃ | F | Cl | | CH₃ | CH₃ |
| B-1178 | CH₃ | F | Cl | | CH₃ | C₂H₅ |
| B-1179 | CH₃ | F | Cl | | C₂H₅ | CH₃ |
| B-1180 | CH₃ | F | Cl | | C₂H₅ | C₂H₅ |
| B-1181 | H | CH₃ | Cl | | CH₃ | CH₃ |
| B-1182 | H | CH₃ | Cl | | CH₃ | C₂H₅ |
| B-1183 | H | CH₃ | Cl | | C₂H₅ | CH₃ |
| B-1184 | H | CH₃ | Cl | | C₂H₅ | C₂H₅ |
| B-1185 | F | CH₃ | Cl | | CH₃ | CH₃ |
| B-1186 | F | CH₃ | Cl | | CH₃ | C₂H₅ |
| B-1187 | F | CH₃ | Cl | | C₂H₅ | CH₃ |
| B-1188 | F | CH₃ | Cl | | C₂H₅ | C₂H₅ |
| B-1189 | Cl | CH₃ | Cl | | CH₃ | CH₃ |
| B-1190 | Cl | CH₃ | Cl | | CH₃ | C₂H₅ |
| B-1191 | Cl | CH₃ | Cl | | C₂H₅ | CH₃ |
| B-1192 | Cl | CH₃ | Cl | | C₂H₅ | C₂H₅ |
| B-1193 | CH₃ | CH₃ | Cl | | CH₃ | CH₃ |
| B-1194 | CH₃ | CH₃ | Cl | | CH₃ | C₂H₅ |
| B-1195 | CH₃ | CH₃ | Cl | | C₂H₅ | CH₃ |
| B-1196 | CH₃ | CH₃ | Cl | | C₂H₅ | C₂H₅ |
| B-1197 | H | Cl | Cl | | CH₃ | CH₃ |
| B-1198 | H | Cl | Cl | | CH₃ | C₂H₅ |
| B-1199 | H | Cl | Cl | | C₂H₅ | CH₃ |
| B-1200 | H | Cl | Cl | | C₂H₅ | C₂H₅ |
| B-1201 | F | Cl | Cl | | CH₃ | CH₃ |
| B-1202 | F | Cl | Cl | | CH₃ | C₂H₅ |
| B-1203 | F | Cl | Cl | | C₂H₅ | CH₃ |
| B-1204 | F | Cl | Cl | | C₂H₅ | C₂H₅ |
| B-1205 | Cl | Cl | Cl | | CH₃ | CH₃ |
| B-1206 | Cl | Cl | Cl | | CH₃ | C₂H₅ |
| B-1207 | Cl | Cl | Cl | | C₂H₅ | CH₃ |
| B-1208 | Cl | Cl | Cl | | C₂H₅ | C₂H₅ |
| B-1209 | CH₃ | Cl | Cl | | CH₃ | CH₃ |
| B-1210 | CH₃ | Cl | Cl | | CH₃ | C₂H₅ |
| B-1211 | CH₃ | Cl | Cl | | C₂H₅ | CH₃ |
| B-1212 | CH₃ | Cl | Cl | | C₂H₅ | C₂H₅ |
| B-1213 | H | H | Cl | | CH₃ | CH₃ |
| B-1214 | H | H | Cl | | CH₃ | C₂H₅ |
| B-1215 | H | H | Cl | | C₂H₅ | CH₃ |
| B-1216 | H | H | Cl | | C₂H₅ | C₂H₅ |
| B-1217 | F | H | Cl | | CH₃ | CH₃ |
| B-1218 | F | H | Cl | | CH₃ | C₂H₅ |
| B-1219 | F | H | Cl | | C₂H₅ | CH₃ |
| B-1220 | F | H | Cl | | C₂H₅ | C₂H₅ |
| B-1221 | Cl | H | Cl | | CH₃ | CH₃ |
| B-1222 | Cl | H | Cl | | CH₃ | C₂H₅ |
| B-1223 | Cl | H | Cl | | C₂H₅ | CH₃ |
| B-1224 | Cl | H | Cl | | C₂H₅ | C₂H₅ |
| B-1225 | CH₃ | H | Cl | | CH₃ | CH₃ |
| B-1226 | CH₃ | H | Cl | | CH₃ | C₂H₅ |
| B-1227 | CH₃ | H | Cl | | C₂H₅ | CH₃ |
| B-1228 | CH₃ | H | Cl | | C₂H₅ | C₂H₅ |
| B-1229 | H | F | Cl | | CH₃ | CH₃ |
| B-1230 | H | F | Cl | | CH₃ | C₂H₅ |
| B-1231 | H | F | Cl | | C₂H₅ | CH₃ |
| B-1232 | H | F | Cl | | C₂H₅ | C₂H₅ |
| B-1233 | F | F | Cl | | CH₃ | CH₃ |
| B-1234 | F | F | Cl | | CH₃ | C₂H₅ |
| B-1235 | F | F | Cl | | C₂H₅ | CH₃ |
| B-1236 | F | F | Cl | | C₂H₅ | C₂H₅ |
| B-1237 | Cl | F | Cl | | CH₃ | CH₃ |
| B-1238 | Cl | F | Cl | | CH₃ | C₂H₅ |
| B-1239 | Cl | F | Cl | | C₂H₅ | CH₃ |
| B-1240 | Cl | F | Cl | | C₂H₅ | C₂H₅ |
| B-1241 | CH₃ | F | Cl | | CH₃ | CH₃ |
| B-1242 | CH₃ | F | Cl | | CH₃ | C₂H₅ |
| B-1243 | CH₃ | F | Cl | | C₂H₅ | CH₃ |
| B-1244 | CH₃ | F | Cl | | C₂H₅ | C₂H₅ |
| B-1245 | H | CH₃ | Cl | | CH₃ | CH₃ |
| B-1246 | H | CH₃ | Cl | | CH₃ | C₂H₅ |
| B-1247 | H | CH₃ | Cl | | C₂H₅ | CH₃ |
| B-1248 | H | CH₃ | Cl | | C₂H₅ | C₂H₅ |
| B-1249 | F | CH₃ | Cl | | CH₃ | CH₃ |
| B-1250 | F | CH₃ | Cl | | CH₃ | C₂H₅ |
| B-1251 | F | CH₃ | Cl | | C₂H₅ | CH₃ |
| B-1252 | F | CH₃ | Cl | | C₂H₅ | C₂H₅ |
| B-1253 | Cl | CH₃ | Cl | | CH₃ | CH₃ |
| B-1254 | Cl | CH₃ | Cl | | CH₃ | C₂H₅ |
| B-1255 | Cl | CH₃ | Cl | | C₂H₅ | CH3 |
| B-1256 | Cl | CH₃ | Cl | | C₂H₅ | C₂H₅ |
| B-1257 | CH₃ | CH₃ | Cl | | CH₃ | CH₃ |
| B-1258 | CH₃ | CH₃ | Cl | | CH₃ | C₂H₅ |
| B-1259 | CH₃ | CH₃ | Cl | | C₂H₅ | CH₃ |
| B-1260 | CH₃ | CH₃ | Cl | | C₂H₅ | C₂H₅ |
| B-1261 | H | Cl | Cl | | CH₃ | CH₃ |
| B-1262 | H | Cl | Cl | | CH₃ | C₂H₅ |
| B-1263 | H | Cl | Cl | | C₂H₅ | CH₃ |
| B-1264 | H | Cl | Cl | | C₂H₅ | C₂H₅ |
| B-1265 | F | Cl | Cl | | CH₃ | CH₃ |
| B-1266 | F | Cl | Cl | | CH₃ | C₂H₅ |
| B-1267 | F | Cl | Cl | | C₂H₅ | CH₃ |
| B-1268 | F | Cl | Cl | | C₂H₅ | C₂H₅ |
| B-1269 | Cl | Cl | Cl | | CH₃ | CH₃ |
| B-1270 | Cl | Cl | Cl | | CH₃ | C₂H₅ |
| B-1271 | Cl | Cl | Cl | | C₂H₅ | CH₃ |
| B-1272 | Cl | Cl | Cl | | C₂H₅ | C₂H₅ |
| B-1273 | CH₃ | Cl | Cl | | CH₃ | CH₃ |
| B-1274 | CH₃ | Cl | Cl | | CH₃ | C₂H₅ |
| B-1275 | CH₃ | Cl | Cl | | C₂H₅ | CH₃ |
| B-1276 | CH₃ | Cl | Cl | | C₂H₅ | C₂H₅ |

TABLE B-continued

| line | R¹ | R² | R³ | R⁴ | R⁹ | R¹⁰ |
|---|---|---|---|---|---|---|
| B-1277 | H | H | | C2 | CH₃ | CH₃ |
| B-1278 | H | H | | C2 | CH₃ | C₂H₅ |
| B-1279 | H | H | | C2 | C₂H₅ | CH₃ |
| B-1280 | H | H | | C2 | C₂H₅ | C₂H₅ |
| B-1281 | F | H | | C2 | CH₃ | CH₃ |
| B-1282 | F | H | | C2 | CH₃ | C₂H₅ |
| B-1283 | F | H | | C2 | C₂H₅ | CH₃ |
| B-1284 | F | H | | C2 | C₂H₅ | C₂H₅ |
| B-1285 | Cl | H | | C2 | CH₃ | CH₃ |
| B-1286 | Cl | H | | C2 | CH₃ | C₂H₅ |
| B-1287 | Cl | H | | C2 | C₂H₅ | CH₃ |
| B-1288 | Cl | H | | C2 | C₂H₅ | C₂H₅ |
| B-1289 | CH₃ | H | | C2 | CH₃ | CH₃ |
| B-1290 | CH₃ | H | | C2 | CH₃ | C₂H₅ |
| B-1291 | CH₃ | H | | C2 | C₂H₅ | CH₃ |
| B-1292 | CH₃ | H | | C2 | C₂H₅ | C₂H₅ |
| B-1293 | H | F | | C2 | CH₃ | CH₃ |
| B-1294 | H | F | | C2 | CH₃ | C₂H₅ |
| B-1295 | H | F | | C2 | C₂H₅ | CH₃ |
| B-1296 | H | F | | C2 | C₂H₅ | C₂H₅ |
| B-1297 | F | F | | C2 | CH₃ | CH₃ |
| B-1298 | F | F | | C2 | CH₃ | C₂H₅ |
| B-1299 | F | F | | C2 | C₂H₅ | CH₃ |
| B-1300 | F | F | | C2 | C₂H₅ | C₂H₅ |
| B-1301 | Cl | F | | C2 | CH₃ | CH₃ |
| B-1302 | Cl | F | | C2 | CH₃ | C₂H₅ |
| B-1303 | Cl | F | | C2 | C₂H₅ | CH₃ |
| B-1304 | Cl | F | | C2 | C₂H₅ | C₂H₅ |
| B-1305 | CH₃ | F | | C2 | CH₃ | CH₃ |
| B-1306 | CH₃ | F | | C2 | CH₃ | C₂H₅ |
| B-1307 | CH₃ | F | | C2 | C₂H₅ | CH₃ |
| B-1308 | CH₃ | F | | C2 | C₂H₅ | C₂H₅ |
| B-1309 | H | CH₃ | | C2 | CH₃ | CH₃ |
| B-1310 | H | CH₃ | | C2 | CH₃ | C₂H₅ |
| B-1311 | H | CH₃ | | C2 | C₂H₅ | CH₃ |
| B-1312 | H | CH₃ | | C2 | C₂H₅ | C₂H₅ |
| B-1313 | F | CH₃ | | C2 | CH₃ | CH₃ |
| B-1314 | F | CH₃ | | C2 | CH₃ | C₂H₅ |
| B-1315 | F | CH₃ | | C2 | C₂H₅ | CH₃ |
| B-1316 | F | CH₃ | | C2 | C₂H₅ | C₂H₅ |
| B-1317 | Cl | CH₃ | | C2 | CH₃ | CH₃ |
| B-1318 | Cl | CH₃ | | C2 | CH₃ | C₂H₅ |
| B-1319 | Cl | CH₃ | | C2 | C₂H₅ | CH₃ |
| B-1320 | Cl | CH₃ | | C2 | C₂H₅ | C₂H₅ |
| B-1321 | CH₃ | CH₃ | | C2 | CH₃ | CH₃ |
| B-1322 | CH₃ | CH₃ | | C2 | CH₃ | C₂H₅ |
| B-1323 | CH₃ | CH₃ | | C2 | C₂H₅ | CH₃ |
| B-1324 | CH₃ | CH₃ | | C2 | C₂H₅ | C₂H₅ |
| B-1325 | H | Cl | | C2 | CH₃ | CH₃ |
| B-1326 | H | Cl | | C2 | CH₃ | C₂H₅ |
| B-1327 | H | Cl | | C2 | C₂H₅ | CH₃ |
| B-1328 | H | Cl | | C2 | C₂H₅ | C₂H₅ |
| B-1329 | F | Cl | | C2 | CH₃ | CH₃ |
| B-1330 | F | Cl | | C2 | CH₃ | C₂H₅ |
| B-1331 | F | Cl | | C2 | C₂H₅ | CH₃ |
| B-1332 | F | Cl | | C2 | C₂H₅ | C₂H₅ |
| B-1333 | Cl | Cl | | C2 | CH₃ | CH₃ |
| B-1334 | Cl | Cl | | C2 | CH₃ | C₂H₅ |
| B-1335 | Cl | Cl | | C2 | C₂H₅ | CH₃ |
| B-1336 | Cl | Cl | | C2 | C₂H₅ | C₂H₅ |
| B-1337 | CH₃ | Cl | | C2 | CH₃ | CH₃ |
| B-1338 | CH₃ | Cl | | C2 | CH₃ | C₂H₅ |
| B-1339 | CH₃ | Cl | | C2 | C₂H₅ | CH₃ |
| B-1340 | CH₃ | Cl | | C2 | C₂H₅ | C₂H₅ |
| B-1341 | H | H | | C2 | CH₃ | CH₃ |
| B-1342 | H | H | | C2 | CH₃ | C₂H₅ |
| B-1343 | H | H | | C2 | C₂H₅ | CH₃ |
| B-1344 | H | H | | C2 | C₂H₅ | C₂H₅ |
| B-1345 | F | H | | C2 | CH₃ | CH₃ |
| B-1346 | F | H | | C2 | CH₃ | C₂H₅ |
| B-1347 | F | H | | C2 | C₂H₅ | CH₃ |
| B-1348 | F | H | | C2 | C₂H₅ | C₂H₅ |
| B-1349 | Cl | H | | C2 | CH₃ | CH₃ |
| B-1350 | Cl | H | | C2 | CH₃ | C₂H₅ |
| B-1351 | Cl | H | | C2 | C₂H₅ | CH₃ |
| B-1352 | Cl | H | | C2 | C₂H₅ | C₂H₅ |
| B-1353 | CH₃ | H | | C2 | CH₃ | CH₃ |
| B-1354 | CH₃ | H | | C2 | CH₃ | C₂H₅ |
| B-1355 | CH₃ | H | | C2 | C₂H₅ | CH₃ |
| B-1356 | CH₃ | H | | C2 | C₂H₅ | C₂H₅ |
| B-1357 | H | F | | C2 | CH₃ | CH₃ |
| B-1358 | H | F | | C2 | CH₃ | C₂H₅ |
| B-1359 | H | F | | C2 | C₂H₅ | CH₃ |
| B-1360 | H | F | | C2 | C₂H₅ | C₂H₅ |
| B-1361 | F | F | | C2 | CH₃ | CH₃ |
| B-1362 | F | F | | C2 | CH₃ | C₂H₅ |
| B-1363 | F | F | | C2 | C₂H₅ | CH₃ |
| B-1364 | F | F | | C2 | C₂H₅ | C₂H₅ |
| B-1365 | Cl | F | | C2 | CH₃ | CH₃ |
| B-1366 | Cl | F | | C2 | CH₃ | C₂H₅ |
| B-1367 | Cl | F | | C2 | C₂H₅ | CH₃ |
| B-1368 | Cl | F | | C2 | C₂H₅ | C₂H₅ |
| B-1369 | CH₃ | F | | C2 | CH₃ | CH₃ |
| B-1370 | CH₃ | F | | C2 | CH₃ | C₂H₅ |
| B-1371 | CH₃ | F | | C2 | C₂H₅ | CH₃ |
| B-1372 | CH₃ | F | | C2 | C₂H₅ | C₂H₅ |
| B-1373 | H | CH₃ | | C2 | CH₃ | CH₃ |
| B-1374 | H | CH₃ | | C2 | CH₃ | C₂H₅ |
| B-1375 | H | CH₃ | | C2 | C₂H₅ | CH₃ |
| B-1376 | H | CH₃ | | C2 | C₂H₅ | C₂H₅ |
| B-1377 | F | CH₃ | | C2 | CH₃ | CH₃ |
| B-1378 | F | CH₃ | | C2 | CH₃ | C₂H₅ |
| B-1379 | F | CH₃ | | C2 | C₂H₅ | CH₃ |
| B-1380 | F | CH₃ | | C2 | C₂H₅ | C₂H₅ |
| B-1381 | Cl | CH₃ | | C2 | CH₃ | CH₃ |
| B-1382 | Cl | CH₃ | | C2 | CH₃ | C₂H₅ |
| B-1383 | Cl | CH₃ | | C2 | C₂H₅ | CH₃ |
| B-1384 | Cl | CH₃ | | C2 | C₂H₅ | C₂H₅ |
| B-1385 | CH₃ | CH₃ | | C2 | CH₃ | CH₃ |
| B-1386 | CH₃ | CH₃ | | C2 | CH₃ | C₂H₅ |
| B-1387 | CH₃ | CH₃ | | C2 | C₂H₅ | CH₃ |
| B-1388 | CH₃ | CH₃ | | C2 | C₂H₅ | C₂H₅ |
| B-1389 | H | Cl | | C2 | CH₃ | CH₃ |
| B-1390 | H | Cl | | C2 | CH₃ | C₂H₅ |
| B-1391 | H | Cl | | C2 | C₂H₅ | CH₃ |
| B-1392 | H | Cl | | C2 | C₂H₅ | C₂H₅ |
| B-1393 | F | Cl | | C2 | CH₃ | CH₃ |
| B-1394 | F | Cl | | C2 | CH₃ | C₂H₅ |
| B-1395 | F | Cl | | C2 | C₂H₅ | CH₃ |
| B-1396 | F | Cl | | C2 | C₂H₅ | C₂H₅ |
| B-1397 | Cl | Cl | | C2 | CH₃ | CH₃ |
| B-1398 | Cl | Cl | | C2 | CH₃ | C₂H₅ |
| B-1399 | Cl | Cl | | C2 | C₂H₅ | CH₃ |
| B-1400 | Cl | Cl | | C2 | C₂H₅ | C₂H₅ |
| B-1401 | CH₃ | Cl | | C2 | CH₃ | CH₃ |
| B-1402 | CH₃ | Cl | | C2 | CH₃ | C₂H₅ |
| B-1403 | CH₃ | Cl | | C2 | C₂H₅ | CH₃ |
| B-1404 | CH₃ | Cl | | C2 | C₂H₅ | C₂H₅ |
| B-1405 | H | H | | C2 | CH₃ | CH₃ |
| B-1406 | H | H | | C2 | CH₃ | C₂H₅ |
| B-1407 | H | H | | C2 | C₂H₅ | CH₃ |
| B-1408 | H | H | | C2 | C₂H₅ | C₂H₅ |
| B-1409 | F | H | | C2 | CH₃ | CH₃ |
| B-1410 | F | H | | C2 | CH₃ | C₂H₅ |
| B-1411 | F | H | | C2 | C₂H₅ | CH₃ |
| B-1412 | F | H | | C2 | C₂H₅ | C₂H₅ |
| B-1413 | Cl | H | | C2 | CH₃ | CH₃ |
| B-1414 | Cl | H | | C2 | CH₃ | C₂H₅ |
| B-1415 | Cl | H | | C2 | C₂H₅ | CH₃ |
| B-1416 | Cl | H | | C2 | C₂H₅ | C₂H₅ |
| B-1417 | CH₃ | H | | C2 | CH₃ | CH₃ |
| B-1418 | CH₃ | H | | C2 | CH₃ | C₂H₅ |
| B-1419 | CH₃ | H | | C2 | C₂H₅ | CH₃ |
| B-1420 | CH₃ | H | | C2 | C₂H₅ | C₂H₅ |
| B-1421 | H | F | | C2 | CH₃ | CH₃ |
| B-1422 | H | F | | C2 | CH₃ | C₂H₅ |
| B-1423 | H | F | | C2 | C₂H₅ | CH₃ |
| B-1424 | H | F | | C2 | C₂H₅ | C₂H₅ |
| B-1425 | F | F | | C2 | CH₃ | CH₃ |
| B-1426 | F | F | | C2 | CH₃ | C₂H₅ |
| B-1427 | F | F | | C2 | C₂H₅ | CH₃ |
| B-1428 | F | F | | C2 | C₂H₅ | C₂H₅ |
| B-1429 | Cl | F | | C2 | CH₃ | CH₃ |
| B-1430 | Cl | F | | C2 | CH₃ | C₂H₅ |
| B-1431 | Cl | F | | C2 | C₂H₅ | CH₃ |
| B-1432 | Cl | F | | C2 | C₂H₅ | C₂H₅ |

TABLE B-continued

| line | R¹ | R² | R³ | R⁴ | R⁹ | R¹⁰ |
|---|---|---|---|---|---|---|
| B-1433 | CH₃ | F | | C2 | CH₃ | CH₃ |
| B-1434 | CH₃ | F | | C2 | CH₃ | C₂H₅ |
| B-1435 | CH₃ | F | | C2 | C₂H₅ | CH₃ |
| B-1436 | CH₃ | F | | C2 | C₂H₅ | C₂H₅ |
| B-1437 | H | CH₃ | | C2 | CH₃ | CH₃ |
| B-1438 | H | CH₃ | | C2 | CH₃ | C₂H₅ |
| B-1439 | H | CH₃ | | C2 | C₂H₅ | CH₃ |
| B-1440 | H | CH₃ | | C2 | C₂H₅ | C₂H₅ |
| B-1441 | F | CH₃ | | C2 | CH₃ | CH₃ |
| B-1442 | F | CH₃ | | C2 | CH₃ | C₂H₅ |
| B-1443 | F | CH₃ | | C2 | C₂H₅ | CH₃ |
| B-1444 | F | CH₃ | | C2 | C₂H₅ | C₂H₅ |
| B-1445 | Cl | CH₃ | | C2 | CH₃ | CH₃ |
| B-1446 | Cl | CH₃ | | C2 | CH₃ | C₂H₅ |
| B-1447 | Cl | CH₃ | | C2 | C₂H₅ | CH₃ |
| B-1448 | Cl | CH₃ | | C2 | C₂H₅ | C₂H₅ |
| B-1449 | CH₃ | CH₃ | | C2 | CH₃ | CH₃ |
| B-1450 | CH₃ | CH₃ | | C2 | CH₃ | C₂H₅ |
| B-1451 | CH₃ | CH₃ | | C2 | C₂H₅ | CH₃ |
| B-1452 | CH₃ | CH₃ | | C2 | C₂H₅ | C₂H₅ |
| B-1453 | H | CL | | C2 | CH₃ | CH₃ |
| B-1454 | H | Cl | | C2 | CH₃ | C₂H₅ |
| B-1455 | H | Cl | | C2 | C₂H₅ | CH₃ |
| B-1456 | H | Cl | | C2 | C₂H₅ | C₂H₅ |
| B-1457 | F | Cl | | C2 | CH₃ | CH₃ |
| B-1458 | F | Cl | | C2 | CH₃ | C₂H₅ |
| B-1459 | F | Cl | | C2 | C₂H₅ | CH₃ |
| B-1460 | F | Cl | | C2 | C₂H₅ | C₂H₅ |
| B-1461 | Cl | Cl | | C2 | CH₃ | CH₃ |
| B-1462 | Cl | Cl | | C2 | CH₃ | C₂H₅ |
| B-1463 | Cl | Cl | | C2 | C₂H₅ | CH₃ |
| B-1464 | Cl | Cl | | C2 | C₂H₅ | C₂H₅ |
| B-1465 | CH₃ | Cl | | C2 | CH₃ | CH₃ |
| B-1466 | CH₃ | Cl | | C2 | CH₃ | C₂H₅ |
| B-1467 | CH₃ | Cl | | C2 | C₂H₅ | CH₃ |
| B-1468 | CH₃ | Cl | | C2 | C₂H₅ | C₂H₅ |
| B-1469 | H | H | | C2 | CH₃ | CH₃ |
| B-1470 | H | H | | C2 | CH₃ | C₂H₅ |
| B-1471 | H | H | | C2 | C₂H₅ | CH₃ |
| B-1472 | H | H | | C2 | C₂H₅ | C₂H₅ |
| B-1473 | F | H | | C2 | CH₃ | CH₃ |
| B-1474 | F | H | | C2 | CH₃ | C₂H₅ |
| B-1475 | F | H | | C2 | C₂H₅ | CH₃ |
| B-1476 | F | H | | C2 | C₂H₅ | C₂H₅ |
| B-1477 | Cl | H | | C2 | CH₃ | CH₃ |
| B-1478 | Cl | H | | C2 | CH₃ | C₂H₅ |
| B-1479 | Cl | H | | C2 | C₂H₅ | CH₃ |
| B-1480 | Cl | H | | C2 | C₂H₅ | C₂H₅ |
| B-1481 | CH₃ | H | | C2 | CH₃ | CH₃ |
| B-1482 | CH₃ | H | | C2 | CH₃ | C₂H₅ |
| B-1483 | CH₃ | H | | C2 | C₂H₅ | CH₃ |
| B-1484 | CH₃ | H | | C2 | C₂H₅ | C₂H₅ |
| B-1485 | H | F | | C2 | CH₃ | CH₃ |
| B-1486 | H | F | | C2 | CH₃ | C₂H₅ |
| B-1487 | H | F | | C2 | C₂H₅ | CH₃ |
| B-1488 | H | F | | C2 | C₂H₅ | C₂H₅ |
| B-1489 | F | F | | C2 | CH₃ | CH₃ |
| B-1490 | F | F | | C2 | CH₃ | C₂H₅ |
| B-1491 | F | F | | C2 | C₂H₅ | CH3 |
| B-1492 | F | F | | C2 | C₂H₅ | C₂H₅ |
| B-1493 | Cl | F | | C2 | CH₃ | CH₃ |
| B-1494 | Cl | F | | C2 | CH₃ | C₂H₅ |
| B-1495 | Cl | F | | C2 | C₂H₅ | CH₃ |
| B-1496 | Cl | F | | C2 | C₂H₅ | C₂H₅ |
| B-1497 | CH₃ | F | | C2 | CH₃ | CH₃ |
| B-1498 | CH₃ | F | | C2 | CH₃ | C₂H₅ |
| B-1499 | CH₃ | F | | C2 | C₂H₅ | CH₃ |
| B-1500 | CH₃ | F | | C2 | C₂H₅ | C₂H₅ |
| B-1501 | H | CH₃ | | C2 | CH₃ | CH₃ |
| B-1502 | H | CH₃ | | C2 | CH₃ | C₂H₅ |
| B-1503 | H | CH₃ | | C2 | C₂H₅ | CH₃ |
| B-1504 | H | CH₃ | | C2 | C₂H₅ | C₂H₅ |
| B-1505 | F | CH₃ | | C2 | CH₃ | CH₃ |
| B-1506 | F | CH₃ | | C2 | CH₃ | C₂H₅ |
| B-1507 | F | CH₃ | | C2 | C₂H₅ | CH₃ |
| B-1508 | F | CH₃ | | C2 | C₂H₅ | C₂H₅ |
| B-1509 | Cl | CH₃ | | C2 | CH₃ | CH₃ |
| B-1510 | Cl | CH₃ | | C2 | CH₃ | C₂H₅ |
| B-1511 | Cl | CH₃ | | C2 | C₂H₅ | CH₃ |
| B-1512 | Cl | CH₃ | | C2 | C₂H₅ | C₂H₅ |
| B-1513 | CH₃ | CH₃ | | C2 | CH₃ | CH₃ |
| B-1514 | CH₃ | CH₃ | | C2 | CH₃ | C₂H₅ |
| B-1515 | CH₃ | CH₃ | | C2 | C₂H₅ | CH₃ |
| B-1516 | CH₃ | CH₃ | | C2 | C₂H₅ | C₂H₅ |
| B-1517 | H | Cl | | C2 | CH₃ | CH₃ |
| B-1518 | H | Cl | | C2 | CH₃ | C₂H₅ |
| B-1519 | H | Cl | | C2 | C₂H₅ | CH₃ |
| B-1520 | H | Cl | | C2 | C₂H₅ | C₂H₅ |
| B-1521 | F | Cl | | C2 | CH₃ | CH₃ |
| B-1522 | F | Cl | | C2 | CH₃ | C₂H₅ |
| B-1523 | F | Cl | | C2 | C₂H₅ | CH₃ |
| B-1524 | F | Cl | | C2 | C₂H₅ | C₂H₅ |
| B-1525 | Cl | Cl | | C2 | CH₃ | CH₃ |
| B-1526 | Cl | Cl | | C2 | CH₃ | C₂H₅ |
| B-1527 | Cl | Cl | | C2 | C₂H₅ | CH₃ |
| B-1528 | Cl | Cl | | C2 | C₂H₅ | C₂H₅ |
| B-1529 | CH₃ | Cl | | C2 | CH₃ | CH₃ |
| B-1530 | CH₃ | Cl | | C2 | CH₃ | C₂H₅ |
| B-1531 | CH₃ | Cl | | C2 | C₂H₅ | CH₃ |
| B-1532 | CH₃ | Cl | | C2 | C₂H₅ | C₂H₅ |

Particular embodiments of the compounds I are the following compounds I*, In this formula, the substituents $R^9$, $R^{10}$, $R^{78}$ and o are independently as defined or preferably defined herein:

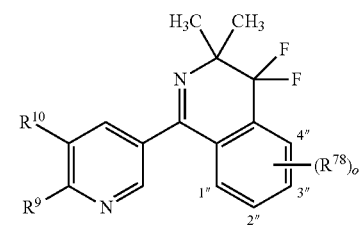

I*

Each of the groups mentioned for a substituent in the tables is furthermore per se, independently of the combination in which it is mentioned, a particularly preferred aspect of the substituent in question.

Particularly preferred embodiments of combinations of $R^9$ and $R^{10}$ in according to the invention are as compiled in Table B*-1 to B*-9, wherein lines of B*-1 to B*-9 are also in any combination with one another a preferred embodiment of the present invention.

Table B*1 Compounds of the formula I* in which o is 0 and the meaning for the combination of $R^9$ and $R^{10}$ for each individual compound corresponds in each case to one line of Table B*.

Table B*2 Compounds of formula I* in which o is 1, $R^{78}$ is 1"-F and the meaning for the combination of $R^9$ and $R^{10}$ for each individual compound corresponds in each case to one line of Table B*.

Table B*3 Compounds of formula I* in which o is 1, $R^{78}$ is 2"-F and the meaning for the combination of $R^9$ and $R^{10}$ for each individual compound corresponds in each case to one line of Table B*.

Table B*4 Compounds of formula I* in which o is 1, $R^{78}$ is 3-F and the meaning for the combination of $R^9$ and $R^{10}$ for each individual compound corresponds in each case to one line of Table B*.

Table B*5 Compounds of formula I* in which o is 1, $R^{78}$ is 4"-F and the meaning for the combination of $R^9$ and $R^{10}$ for each individual compound corresponds in each case to one line of Table B*.

Table B*6 Compounds of formula I* in which o is 1, $R^{78}$ is 1"-Cl and the meaning for the combination of $R^9$ and $R^{10}$ for each individual compound corresponds in each case to one line of Table B*.

Table B*7 Compounds of formula I* in which o is 1, $R^{78}$ is 2"-Cl and the meaning for the combination of $R^9$ and $R^{10}$ for each individual compound corresponds in each case to one line of Table B*.

Table B*8 Compounds of formula I* in which o is 1, $R^{78}$ is 3-Cl and the meaning for the combination of $R^9$ and $R^{10}$ for each individual compound corresponds in each case to one line of Table B*.

Table B*9 Compounds of formula I* in which o is 1, $R^{78}$ is 4"-Cl and the meaning for the combination $R^9$ and $R^{10}$ for each individual compound corresponds in each case to one line of Table B*.

TABLE B*

| line | $R^9$ | $R^{10}$ |
|---|---|---|
| B*-1 | H | H |
| B*-2 | H | $CH_3$ |
| B*-3 | H | $C_2H_5$ |
| B*-4 | H | F |
| B*-5 | H | Cl |
| B*-6 | H | Br |
| B*-7 | H | CN |
| B*-8 | H | $OCH_3$ |
| B*-9 | H | $OCHF_2$ |
| B*-10 | H | $CHF_2$ |
| B*-11 | H | $CF_3$ |
| B*-12 | H | $S-CH_3$ |
| B*-13 | H | $SO-CH_3$ |
| B*-14 | H | $SO_2-CH_3$ |
| B*-15 | H | $CO-NH_2$ |
| B*-16 | H | $CO-NH(CH_3)$ |
| B*-17 | H | $CO-N(CH_3)_2$ |
| B*-18 | $CH_3$ | H |
| B*-19 | $CH_3$ | $CH_3$ |
| B*-20 | $CH_3$ | $C_2H_5$ |
| B*-21 | $CH_3$ | F |
| B*-22 | $CH_3$ | Cl |
| B*-23 | $CH_3$ | Br |
| B*-24 | $CH_3$ | CN |
| B*-25 | $CH_3$ | $OCH_3$ |
| B*-26 | $CH_3$ | $OCHF_2$ |
| B*-27 | $CH_3$ | $CHF_2$ |
| B*-28 | $CH_3$ | $CF_3$ |
| B*-29 | $CH_3$ | $S-CH_3$ |
| B*-30 | $CH_3$ | $SO-CH_3$ |
| B*-31 | $CH_3$ | $SO_2-CH_3$ |
| B*-32 | $CH_3$ | $CO-NH_2$ |
| B*-33 | $CH_3$ | $CO-NH(CH_3)$ |
| B*-34 | $CH_3$ | $CO-N(CH_3)_2$ |
| B*-35 | $C_2H_5$ | H |
| B*-36 | $C_2H_5$ | $CH_3$ |
| B*-37 | $C_2H_5$ | $C_2H_5$ |
| B*-38 | $C_2H_5$ | F |
| B*-39 | $C_2H_5$ | Cl |
| B*-40 | $C_2H_5$ | Br |
| B*-41 | $C_2H_5$ | CN |
| B*-42 | $C_2H_5$ | $OCH_3$ |
| B*-43 | $C_2H_5$ | $OCHF_2$ |
| B*-44 | $C_2H_5$ | $CHF_2$ |
| B*-45 | $C_2H_5$ | $CF_3$ |
| B*-46 | $C_2H_5$ | $S-CH_3$ |
| B*-47 | $C_2H_5$ | $SO-CH_3$ |
| B*-48 | $C_2H_5$ | $SO_2-CH_3$ |
| B*-49 | $C_2H_5$ | $CO-NH_2$ |
| B*-50 | $C_2H_5$ | $CO-NH(CH_3)$ |
| B*-51 | $C_2H_5$ | $CO-N(CH_3)_2$ |
| B*-52 | F | H |
| B*-53 | F | $CH_3$ |
| B*-54 | F | $C_2H_5$ |
| B*-55 | F | F |
| B*-56 | F | Cl |
| B*-57 | F | Br |
| B*-58 | F | CN |
| B*-59 | F | $OCH_3$ |
| B*-60 | F | $OCHF_2$ |
| B*-61 | F | $CHF_2$ |
| B*-62 | F | $CF_3$ |
| B*-63 | F | $S-CH_3$ |
| B*-64 | F | $SO-CH_3$ |
| B*-65 | F | $SO_2-CH_3$ |
| B*-66 | F | $CO-NH_2$ |
| B*-67 | F | $CO-NH(CH_3)$ |
| B*-68 | F | $CO-N(CH_3)_2$ |
| B*-69 | Cl | H |
| B*-70 | Cl | $CH_3$ |
| B*-71 | Cl | $C_2H_5$ |
| B*-72 | Cl | F |
| B*-73 | Cl | Cl |
| B*-74 | Cl | Br |
| B*-75 | Cl | CN |
| B*-76 | Cl | $OCH_3$ |
| B*-77 | Cl | $OCHF_2$ |
| B*-78 | Cl | $CHF_2$ |
| B*-79 | Cl | $CF_3$ |
| B*-80 | Cl | $S-CH_3$ |
| B*-81 | Cl | $SO-CH_3$ |
| B*-82 | Cl | $SO_2-CH_3$ |
| B*-83 | Cl | $CO-NH_2$ |
| B*-84 | Cl | $CO-NH(CH_3)$ |
| B*-85 | Cl | $CO-N(CH_3)_2$ |
| B*-86 | Br | H |
| B*-87 | Br | $CH_3$ |
| B*-88 | Br | $C_2H_5$ |
| B*-89 | Br | F |
| B*-90 | Br | Cl |
| B*-91 | Br | Br |
| B*-92 | Br | CN |
| B*-93 | Br | $OCH_3$ |
| B*-94 | Br | $OCHF_2$ |
| B*-95 | Br | $CHF_2$ |
| B*-96 | Br | $CF_3$ |
| B*-97 | Br | $S-CH_3$ |
| B*-98 | Br | $SO-CH_3$ |
| B*-99 | Br | $SO_2-CH_3$ |
| B*-100 | Br | $CO-NH_2$ |
| B*-101 | Br | $CO-NH(CH_3)$ |
| B*-102 | Br | $CO-N(CH_3)_2$ |
| B*-103 | CN | H |
| B*-104 | CN | $CH_3$ |
| B*-105 | CN | $C_2H_5$ |
| B*-106 | CN | F |
| B*-107 | CN | Cl |
| B*-108 | CN | Br |
| B*-109 | CN | CN |
| B*-110 | CN | $OCH_3$ |
| B*-111 | CN | $OCHF_2$ |
| B*-112 | CN | $CHF_2$ |
| B*-113 | CN | $CF_3$ |
| B*-114 | CN | $S-CH_3$ |
| B*-115 | CN | $SO-CH_3$ |
| B*-116 | CN | $SO_2-CH_3$ |
| B*-117 | CN | $CO-NH_2$ |
| B*-118 | CN | $CO-NH(CH_3)$ |
| B*-119 | CN | $CO-N(CH_3)_2$ |
| B*-120 | $OCH_3$ | H |
| B*-121 | $OCH_3$ | $CH_3$ |
| B*-122 | $OCH_3$ | $C_2H_5$ |
| B*-123 | $OCH_3$ | F |
| B*-124 | $OCH_3$ | Cl |
| B*-125 | $OCH_3$ | Br |
| B*-126 | $OCH_3$ | CN |
| B*-127 | $OCH_3$ | $OCH_3$ |
| B*-128 | $OCH_3$ | $OCHF_2$ |
| B*-129 | $OCH_3$ | $CHF_2$ |
| B*-130 | $OCH_3$ | $CF_3$ |
| B*-131 | $OCH_3$ | $S-CH_3$ |
| B*-132 | $OCH_3$ | $SO-CH_3$ |
| B*-133 | $OCH_3$ | $SO_2-CH_3$ |
| B*-134 | $OCH_3$ | $CO-NH_2$ |
| B*-135 | $OCH_3$ | $CO-NH(CH_3)$ |

TABLE B*-continued

| line | R⁹ | R¹⁰ |
|---|---|---|
| B*-136 | OCH₃ | CO—N(CH₃)₂ |
| B*-137 | OCHF₂ | H |
| B*-138 | OCHF₂ | CH₃ |
| B*-139 | OCHF₂ | C₂H₅ |
| B*-140 | OCHF₂ | F |
| B*-141 | OCHF₂ | Cl |
| B*-142 | OCHF₂ | Br |
| B*-143 | OCHF₂ | CN |
| B*-144 | OCHF₂ | OCH₃ |
| B*-145 | OCHF₂ | OCHF₂ |
| B*-146 | OCHF₂ | CHF₂ |
| B*-147 | OCHF₂ | CF₃ |
| B*-148 | OCHF₂ | S—CH₃ |
| B*-149 | OCHF₂ | SO—CH₃ |
| B*-150 | OCHF₂ | SO₂—CH₃ |
| B*-151 | OCHF₂ | CO—NH₂ |
| B*-152 | OCHF₂ | CO—NH(CH₃) |
| B*-153 | OCHF₂ | CO—N(CH₃)₂ |
| B*-154 | CHF₂ | H |
| B*-155 | CHF₂ | CH₃ |
| B*-156 | CHF₂ | C₂H₅ |
| B*-157 | CHF₂ | F |
| B*-158 | CHF₂ | Cl |
| B*-159 | CHF₂ | Br |
| B*-160 | CHF₂ | CN |
| B*-161 | CHF₂ | OCH₃ |
| B*-162 | CHF₂ | OCHF₂ |
| B*-163 | CHF₂ | CHF₂ |
| B*-164 | CHF₂ | CF₃ |
| B*-165 | CHF₂ | S—CH₃ |
| B*-166 | CHF₂ | SO—CH₃ |
| B*-167 | CHF₂ | SO₂—CH₃ |
| B*-168 | CHF₂ | CO—NH₂ |
| B*-169 | CHF₂ | CO—NH(CH₃) |
| B*-170 | CHF₂ | CO—N(CH₃)₂ |
| B*-171 | CF₃ | H |
| B*-172 | CF₃ | CH₃ |
| B*-173 | CF₃ | C₂H₅ |
| B*-174 | CF₃ | F |
| B*-175 | CF₃ | Cl |
| B*-176 | CF₃ | Br |
| B*-177 | CF₃ | CN |
| B*-178 | CF₃ | OCH₃ |
| B*-179 | CF₃ | OCHF₂ |
| B*-180 | CF₃ | CHF₂ |
| B*-181 | CF₃ | CF₃ |
| B*-182 | CF₃ | S—CH₃ |
| B*-183 | CF₃ | SO—CH₃ |
| B*-184 | CF₃ | SO₂—CH₃ |
| B*-185 | CF₃ | CO—NH₂ |
| B*-186 | CF₃ | CO—NH(CH₃) |
| B*-187 | CF₃ | CO—N(CH₃)₂ |
| B*-188 | S—CH₃ | H |
| B*-189 | S—CH₃ | CH₃ |
| B*-190 | S—CH₃ | C₂H₅ |
| B*-191 | S—CH₃ | F |
| B*-192 | S—CH₃ | Cl |
| B*-193 | S—CH₃ | Br |
| B*-194 | S—CH₃ | CN |
| B*-195 | S—CH₃ | OCH₃ |
| B*-196 | S—CH₃ | OCHF₂ |
| B*-197 | S—CH₃ | CHF₂ |
| B*-198 | S—CH₃ | CF₃ |
| B*-199 | S—CH₃ | S—CH₃ |
| B*-200 | S—CH₃ | SO—CH₃ |
| B*-201 | S—CH₃ | SO₂—CH₃ |
| B*-202 | S—CH₃ | CO—NH₂ |
| B*-203 | S—CH₃ | CO—NH(CH₃) |
| B*-204 | S—CH₃ | CO—N(CH₃)₂ |
| B*-205 | SO—CH₃ | H |
| B*-206 | SO—CH₃ | CH₃ |
| B*-207 | SO—CH₃ | C₂H₅ |
| B*-208 | SO—CH₃ | F |
| B*-209 | SO—CH₃ | Cl |
| B*-210 | SO—CH₃ | Br |
| B*-211 | SO—CH₃ | CN |
| B*-212 | SO—CH₃ | OCH₃ |
| B*-213 | SO—CH₃ | OCHF₂ |
| B*-214 | SO—CH₃ | CHF₂ |
| B*-215 | SO—CH₃ | CF₃ |
| B*-216 | SO—CH₃ | S—CH₃ |
| B*-217 | SO—CH₃ | SO—CH₃ |
| B*-218 | SO—CH₃ | SO₂—CH₃ |
| B*-219 | SO—CH₃ | CO—NH₂ |
| B*-220 | SO—CH₃ | CO—NH(CH₃) |
| B*-221 | SO—CH₃ | CO—N(CH₃)₂ |
| B*-222 | SO₂—CH₃ | H |
| B*-223 | SO₂—CH₃ | CH₃ |
| B*-224 | SO₂—CH₃ | C₂H₅ |
| B*-225 | SO₂—CH₃ | F |
| B*-226 | SO₂—CH₃ | Cl |
| B*-227 | SO₂—CH₃ | Br |
| B*-228 | SO₂—CH₃ | CN |
| B*-229 | SO₂—CH₃ | OCH₃ |
| B*-230 | SO₂—CH₃ | OCHF₂ |
| B*-231 | SO₂—CH₃ | CHF₂ |
| B*-232 | SO₂—CH₃ | CF₃ |
| B*-233 | SO₂—CH₃ | S—CH₃ |
| B*-234 | SO₂—CH₃ | SO—CH₃ |
| B*-235 | SO₂—CH₃ | SO₂—CH₃ |
| B*-236 | SO₂—CH₃ | CO—NH₂ |
| B*-237 | SO₂—CH₃ | CO—NH(CH₃) |
| B*-238 | SO₂—CH₃ | CO—N(CH₃)₂ |
| B*-239 | CO—NH₂ | H |
| B*-240 | CO—NH₂ | CH₃ |
| B*-241 | CO—NH₂ | C₂H₅ |
| B*-242 | CO—NH₂ | F |
| B*-243 | CO—NH₂ | Cl |
| B*-244 | CO—NH₂ | Br |
| B*-245 | CO—NH₂ | CN |
| B*-246 | CO—NH₂ | OCH₃ |
| B*-247 | CO—NH₂ | OCHF₂ |
| B*-248 | CO—NH₂ | CHF₂ |
| B*-249 | CO—NH₂ | CF₃ |
| B*-250 | CO—NH₂ | S—CH₃ |
| B*-251 | CO—NH₂ | SO—CH₃ |
| B*-252 | CO—NH₂ | SO₂—CH₃ |
| B*-253 | CO—NH₂ | CO—NH₂ |
| B*-254 | CO—NH₂ | CO—NH(CH₃) |
| B*-255 | CO—NH₂ | CO—N(CH₃)₂ |
| B*-256 | CO—NH(CH₃) | H |
| B*-257 | CO—NH(CH₃) | CH₃ |
| B*-258 | CO—NH(CH₃) | C₂H₅ |
| B*-259 | CO—NH(CH₃) | F |
| B*-260 | CO—NH(CH₃) | Cl |
| B*-261 | CO—NH(CH₃) | Br |
| B*-262 | CO—NH(CH₃) | CN |
| B*-263 | CO—NH(CH₃) | OCH₃ |
| B*-264 | CO—NH(CH₃) | OCHF₂ |
| B*-265 | CO—NH(CH₃) | CHF₂ |
| B*-266 | CO—NH(CH₃) | CF₃ |
| B*-267 | CO—NH(CH₃) | S—CH₃ |
| B*-268 | CO—NH(CH₃) | SO—CH₃ |
| B*-269 | CO—NH(CH₃) | SO₂—CH₃ |
| B*-270 | CO—NH(CH₃) | CO—NH₂ |
| B*-271 | CO—NH(CH₃) | CO—NH(CH₃) |
| B*-272 | CO—NH(CH₃) | CO—N(CH₃)₂ |
| B*-273 | CO—N(CH₃)₂ | H |
| B*-274 | CO—N(CH₃)₂ | CH₃ |
| B*-275 | CO—N(CH₃)₂ | C₂H₅ |
| B*-276 | CO—N(CH₃)₂ | F |
| B*-277 | CO—N(CH₃)₂ | Cl |
| B*-278 | CO—N(CH₃)₂ | Br |
| B*-279 | CO—N(CH₃)₂ | CN |
| B*-280 | CO—N(CH₃)₂ | OCH₃ |
| B*-281 | CO—N(CH₃)₂ | OCHF₂ |
| B*-282 | CO—N(CH₃)₂ | CHF₂ |
| B*-283 | CO—N(CH₃)₂ | CF₃ |
| B*-284 | CO—N(CH₃)₂ | S—CH₃ |
| B*-285 | CO—N(CH₃)₂ | SO—CH₃ |
| B*-286 | CO—N(CH₃)₂ | SO₂—CH₃ |
| B*-287 | CO—N(CH₃)₂ | CO—NH₂ |
| B*-288 | CO—N(CH₃)₂ | CO—NH(CH₃) |
| B*-289 | CO—N(CH₃)₂ | CO—N(CH₃)₂ |

$R^9$, $R^{10}$ are independently selected from H, halogen, CN, NO2, $N(R^{91})(R^{92})$, $S(R^{93})$, $S(O)_{z94}(R^{94})$, $O(R^{95})$, C1-C6-alkyl, C2-C6-alkenyl, C2-C6-alkynyl, cycloalkyl, CO—$(R^{96})$;

$R^{91}$, $R^{92}$ are independently selected from H, alkyl, alkenyl, alkynyl, cycloalkyl, carbonyl-$R(^{911})$, $S(O)_{z91}R^{912}$;

$R^{911}$ is H or $R^{912}$;

$R^{912}$ is independently selected from alkyl, alkenyl, alkynyl, cycloalkyl, O—$R^{9111}$, $N(R^{9112})(R^{9113})$;

$R^{9111}$ is alkyl, alkenyl, alkynyl or cycloalkyl;

$R^{9112}$ $R^{9113}$ are independently selected from H, alkyl, alkenyl, alkynyl and cycloalkyl;

z91 is 1 or 2;

$R^{93}$ is independently selected from H, alkyl, alkenyl, alkynyl, cycloalkyl;

$R^{94}$ is independently selected from H, alkyl, alkenyl, alkynyl, cycloalkyl, O—$R^{941}$, $N(R^{942})(R^{943})$;

$R^{942}$, $R^{943}$ are independently selected from H or $R^{941}$;

$R^{941}$ is independently selected from alkyl, alkenyl, alkynyl, cycloalkyl;

$z^{94}$ is 1 or 2;

$R^{95}$ is independently selected from H, alkyl, alkenyl, alkynyl, cycloalkyl, carbonyl-$R(^{951})$, $S(O)_{z95}(R^{952})$ $R^{951}$ is H or $R^{952}$;

$R^{952}$ is independently selected from alkyl, alkenyl, alkynyl, cycloalkyl, O—$R^{9521}$, $N(R^{9522})(R^{9523})$;

$R^{9521}$ is independently selected from alkyl, alkenyl, alkynyl, cycloalkyl;

$R^{9522}$, $R^{9523}$ is independently selected from H and $R^{9521}$;

$z_{95}$ is 1 or 2;

$R^{96}$ is independently selected from H, alkyl, alkenyl, alkynyl, cycloalkyl, O—$R^{961}$, $N(R^{962})(R^{963})$;

$R^{961}$ is independently selected from H, alkyl, alkenyl, alkynyl, cycloalkyl;

$R^{962}$, $R^{963}$ are independently selected from H, alkyl, alkenyl, alkynyl, cycloalkyl;

wherein wherein the aliphatic moieties of $R^9$ and $R^{10}$ are independently unsubstituted or substituted; and with identical or different groups $R^{9a}$ or $R^{10a}$, respectively, which independently of one another are selected from:

$R^{9a},R^{10a}$ halogen, OH, CN, $C_1$-$C_6$-alkoxy, alkenyloxy, alkynyloxy, $C_3$-$C_6$-cycloalkyl, $C_3$-$C_6$-halogencycloalkyl, $C_1$-$C_4$-koxy, $C_1$-$C_6$-alkylthio;

or $R^9$ & $R^{10}$ together with the carbon atoms to which they are bound form a five-, six-, or seven-membered heterocyclic or heteroaromatic ring; wherein the ring contains one, two, three or four heteroatoms selected from N, O and S, wherein the heteroatom N may carry one substituent $R^N$ selected from $C_1$-$C_4$-alkyl, $C_1$-$C_4$-alkyl and $SO_2Ph$, wherein Ph is unsubstituted phenyl or phenyl that is substituted by one, two or three substituents selected from $C_1$-$C_4$-alkyl, and wherein the heteroatom S may be in the form of its oxide SO or $SO_2$; and wherein in each case one or two $CH_2$ groups of the carbo- or heterocycle may be replaced by a group independently selected from C(=O) and C(=S); and wherein the heterocyclic ring carries substituents $(R^{11})_m$, wherein m is 0, 1, 2, 3 or 4;

$R^{11}$ is in each case independently selected from halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; and wherein $R^x$ is $C_1$-$C_4$-alkyl, $C_1$-$C_4$-halogenalkyl, unsubstituted aryl or aryl that is substituted by one, two, three, four or five substituents $R^{x1}$ independently selected from $C_1$-$C_4$-alkyl; wherein in each case one or two $CH_2$ groups of carbocycle or heterocycle of $R^{11}$ may be replaced by a group independently selected from C(=O) and C(=S); and wherein the aliphatic moieties of $R^{11}$ are unsubstituted or substituted with identical or different groups $R^{11a}$ which independently of one another are selected from:

$R^{11a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or unsubstituted or substituted with $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heteroaryl and aryl moieties of $R^{11}$ are unsubstituted or substituted with identical or different groups $R^{11b}$ which independently of one another are selected from: $R^{11b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio; unsubstituted or substituted with According to one embodiment, $R^9$ is selected from hydrogen, halogen, OH, CN, SH, $C_1$-$C_6$-alkylthio, $NH_2$, $NH(C_1$-$C_4$-alkyl), $N(C_1$-$C_4$-alkyl)$_2$, NH—$SO_2$—$R^{912}$, $C_1$-$C_6$-alkyl, $C_2$-$C_6$-alkenyl, $C_2$-$C_6$-alkynyl, and $C_1$-$C_6$-alkoxy, in particular halogen, OH, CN, $C_1$-$C_4$-alkylthio, $C_1$-$C_6$-alkyl, $C_2$-$C_6$-alkenyl, $C_2$-$C_6$-alkynyl, $C_1$-$C_6$-alkoxy and, wherein $R^{912}$ is defined above; and wherein the aliphatic moieties of $R^9$ are unsubstituted or substituted with identical or different groups $R^{9a}$ as defined above.

According to a further embodiment, $R^9$ is selected from H, OH, CN, SH, $C_1$-$C_6$-alkylthio, $NH_2$, $NH(C_1$-$C_4$-alkyl), $N(C_1$-$C_4$-alkyl)$_2$, NH—$SO_2$—$R^{912}$, $C_1$-$C_6$-alkyl, $C_2$-$C_6$-alkenyl, $C_2$-$C_6$-alkynyl, and $C_1$-$C_6$-alkoxy, in particular OH, CN, $C_1$-$C_4$-alkylthio, $C_1$-$C_6$-alkyl, $C_2$-$C_6$-alkenyl, $C_2$-$C_6$-alkynyl, and $C_1$-$C_6$-alkoxy, wherein $R^{912}$ is defined below; and wherein the aliphatic moieties of $R^9$ are unsubstituted or substituted with identical or different groups $R^{9a}$ as defined above.

According to a further particular embodiment, $R^9$ is halogen or $C_1$-$C_6$-alkyl, such as C, F, Br, methyl, ethyl, n-propyl, i-propyl, n-butyl, i-butyl, tert-butyl, n-pentyl or i-pentyl.

According to a further particular embodiment, $R^9$ is $C_1$-$C_6$-alkyl, such as methyl, ethyl, n-propyl, i-propyl, n-butyl, i-butyl, tert-butyl, n-pentyl or i-pentyl.

According to a further particular embodiment, $R^9$ is CN, S-alkyl, S-alkynyl or S-alkenyl.

According to a further particular embodiment, $R^9$ is $NO_2$, $NH_2$, $SO_2$ $NH_2$, OH, OCO-alkyl, OCO-alkenyl or OCO-alkynyl.

According to a further particular embodiment, $R^9$ is halogen, CN, $NO_2$, $NH_2$, CO—$NH_2$, CO—$NH(CH_3)$; CO—N$(CH_3)_2$, $SO_2NH_2$, OH, OCO-alkyl, OCO-alkenyl or OCO-alkynyl, S-alkyl, SO-alkyl, $SO_2NH_2$ alkyl, SO-alkenyl, $SO_2$-alkenyl, SO-alkynyl$_2$ or $SO_2$-alkynyl.

According to a further particular embodiment, $R^9$ is S-alkyl such as S—$CH_3$.

According to a further particular embodiment, $R^9$ is SO-alkyl such as SO—$CH_3$.

According to a further particular embodiment, $R^9$ is $SO_2$-alkyl such as $SO_2$—$CH_3$.

According to a further particular embodiment, $R^9$ is alkoxy or halogen substituted alkoxy such as $OCH_3$ or $OCHF_2$.

According to a further particular embodiment, $R^9$ is alkyl or a halogen substituted alkyl such as methyl, ethyl, fluormethyl, difluoromethyl, trifluoromethyl, 2,2,2-trifluoroethyl, 1-fluorethyl or pentafluoroethyl.

According to a further particular embodiment, $R^9$ is CN, cycloalkyl such as cyclopropyl, cyclobutyl, cyclopentyl, cyclohexyl, cycloheptyl wherein the cycloalkyl may contain one or two heteroatoms such as O, S and N.

According to a further particular embodiment, $R^9$ is halogen such as F, Br, Cl or I.

According to a further particular embodiment, $R^9$ is NH—$C_1$-$C_6$-alkyl or NH—$CH_2$.

According to a further particular embodiment, $R^9$ is $C_1$-$C_6$-alkoxy, such as -methoxy, -ethoxy, -propoxy, -n Butoxy and ter-Butoxy.

According to a further particular embodiment, $R^9$ is an amide group such as CO—$NH_2$, CO—NH($CH_3$); CO—N$(H_3)_2$.

Particularly preferred embodiments of $R^9$ according to the invention are in Table P13 below, wherein each line of lines P13-1 to P13-40 corresponds to one particular embodiment of the invention, wherein P13-1 to P13-40 are also in any combination with P14-1 to P14-40a preferred embodiment of the present invention. The connection point to the carbon atom, to which $R^9$ is bound is marked with "#" in the drawings.

TABLE P13

| No. | $R^9$ |
| --- | --- |
| P13-1 | H |
| P13-2 | $CH_3$ |
| P13-3 | $CHF_2$ |
| P13-4 | $CF_3$ |
| P13-5 | $C_2H_5$ |
| P13-6 | $CH(CH_3)_2$ |
| P13-7 | $CH_2CH_2CH_3$ |
| P13-8 | $CH_2CH_2CH_2CH_3$ |
| P13-9 | $CH_2CH(CH_3)_2$ |
| P13-10 | $C(CH_3)_3$ |
| P13-11 | $CH_2CH_2CH_2CH_2CH_3$ |
| P13-12 | $CH_2CH_2CH(CH_3)_2$ |
| P13-13 | $SO(CH_3)_2$ |
| P13-14 | OH |
| P13-15 | $OCH_3$ |
| P13-16 | $OCHF_2$ |
| P13-17 | $OC_2H_5$ |
| P13-18 | CN |
| P13-19 | F |
| P13-20 | Cl |
| P13-21 | Br |
| P13-22 | $NO_2$ |
| P13-23 | $NH_2$ |
| P13-24 | CO—$NH_2$ |
| P13-25 | CO—NH($CH_3$) |
| P13-26 | CO—N($CH_3)_2$ |
| P13-27 | $HNCH_3$ |
| P13-28 | $HNC_2H_5$ |
| P13-29 | $(CH_3)_2N$ |
| P13-30 | $SO_2NH_2$ |
| P13-31 | $SO_2$—$CH_3$ |
| P13-32 | SO—$CH_3$ |
| P13-33 | S—$CH_3$ |
| P13-34 | (C1) |
| P13-35 | (C2) |
| P13-36 | (C3) |
| P13-37 | (C4) |
| P13-38 | (C5) |
| P13-39 | (C6) |
| P13-40 | (C7) |

According to one embodiment, $R^{10}$ is selected from H, halogen, OH, ON, SH, $C_1$-$C_6$-alkylthio, NH, NH($C_1$-$C_4$-alkyl), N($C_1$-$C_4$-alkyl)$_2$, NH—$SO_2$—$R^{912}$, $C_1$-$C_6$-alkyl, $C_2$-$C_6$-alkenyl, $C_2$-$C_6$-alkynyl, and $C_1$-$C_6$-alkoxy, in particular halogen, OH, CN, $C_1$-$C_4$-alkylthio, $C_1$-$C_6$-alkyl, $C_2$-$C_6$-alkenyl, $C_2$-$C_6$-alkynyl, $C_1$-$C_6$-alkoxy and, wherein $R^{912}$ is defined above; and wherein the aliphatic moieties of $R^{10}$ are unsubstituted or substituted with identical or different groups $R^{10a}$ as defined above.

According to a further embodiment, $R^{10}$ is selected from H, OH, CN, SH, $C_1$-$C_6$-alkylthio, $NH_2$, NH($C_1$-$C_4$-alkyl), N($C_1$-$C_4$-alkyl)$_2$, NH—$SO_2$—$R^{912}$, $C_1$-$C_6$-alkyl, $C_2$-$C_6$-alkenyl, $C_2$-$C_6$-alkynyl, and $C_1$-$C_6$-alkoxy, in particular OH, CN, $C_1$-$C_4$-alkylthio, $C_1$-$C_6$-alkyl, $C_2$-$C_6$-alkenyl, $C_2$-$C_6$-alkynyl, and $C_1$-$C_6$-alkoxy, wherein $R^{912}$ is defined above; and wherein the aliphatic moieties of $R^{10}$ are unsubstituted or substituted with identical or different groups $R^{10a}$ as defined above.

According to a further particular embodiment, $R^{10}$ is halogen or $C_1$-$C_6$-alkyl, such as Cl, F, Br, methyl, ethyl, n-propyl, i-propyl, n-butyl, i-butyl, tert-butyl, n-pentyl or i-pentyl.

According to a further particular embodiment, $R^{10}$ is $C_1$-$C_6$-alkyl, such as methyl, ethyl, n-propyl, i-propyl, n-butyl, i-butyl, tert-butyl, n-pentyl or i-pentyl.

According to a further particular embodiment, $R^{10}$ is CN, S-alkyl, S-alkynyl or S-alkenyl.

According to a further particular embodiment, $R^{10}$ is $NO_2$, $NH_2$, $SO_2NH_2$, OH, OCO-alkyl, OCO-alkenyl or OCO-alkynyl.

According to a further particular embodiment, $R^{10}$ is halogen, CN, $NO_2$, $NH_2$, CO—$NH_2$, CO—NH($CH_3$); CO—

N(CH$_3$)$_2$, SO$_2$NH$_2$, OH, OCO-alkyl, OCO-alkenyl or OCO-alkynyl, S-alkyl, SO-alkyl, SO$_2$-alkyl, SO-alkenyl, SO$_2$ alkenyl, SO-alkynyl or SO$_2$-alkynyl.

According to a further particular embodiment, R$^{10}$ is S-alkyl such as S—CH$_3$.

According to a further particular embodiment, R$^{10}$ is SO-alkyl such as SO—CH$_3$.

According to a further particular embodiment, R$^{10}$ is SO$_2$ alkyl such as SO$_2$—CH$_3$.

According to a further particular embodiment, R$^{10}$ is alkoxy or halogen substituted alkoxy such as OCH$_3$ or OCHF$_2$.

According to a further particular embodiment, R$^{10}$ is alkyl or a halogen substituted alkyl such as methyl, ethyl, fluormethyl, difluoromethyl, trifluoromethyl, 2,2,2-trifluoroethyl, 1-fluorethyl or pentafluoroethyl.

According to a further particular embodiment, R$^{10}$ is CN, cycloalkyl such as cyclopropyl, cyclobutyl, cyclopentyl, cyclohexyl, cycloheptyl wherein the cycloalkyl may contain one or two heteroatoms such as O, S and N.

According to a further particular embodiment, R$^{10}$ is halogen such as F, Br, Cl or I.

According to a further particular embodiment, R$^{10}$ is NH—C$_1$-C$_6$-alkyl or NH—CH$_2$.

According to a further particular embodiment, R$^{10}$ is an amide group such as CO—NH$_2$, CO—NH(CH$_3$); CO—N(CH$_3$)$_2$.

According to a further particular embodiment, R$^{10}$ is C$_1$-C$_6$-alkoxy, such as -methoxy, -ethoxy, -propoxy,-n Butoxy and ter Butoxy.

Particularly preferred embodiments of R$^{10}$ according to the invention are in Table P14 below, wherein each line of lines P14-1 to P14-40 corresponds to one particular embodiment of the invention, wherein P14-1 to P14-40 are also in any combination with P13-1 to P13-40 a preferred embodiment of the present invention. The connection point to the carbon atom, to which R$^{10}$ is bound is marked with "#" in the drawings.

TABLE P14

| No. | R$^{10}$ |
|---|---|
| P14-1 | H |
| P14-2 | CH$_3$ |
| P14-3 | CHF$_2$ |
| P14-4 | CF$_3$ |
| P14-5 | C$_2$H$_5$ |
| P14-6 | CH$_2$CH$_2$CH$_3$ |
| P14-7 | CH(CH$_3$)$_2$ |
| P14-8 | CH$_2$CH$_2$CH$_2$CH$_3$ |
| P14-9 | CH$_2$CH(CH$_3$)$_2$ |
| P14-10 | C(CH$_3$)$_3$ |
| P14-11 | CH$_2$CH$_2$CH$_2$CH$_2$CH$_3$ |
| P14-12 | CH$_2$CH$_2$CH(CH$_3$)$_2$ |
| P14-13 | SO(CH$_3$)$_2$ |
| P14-14 | OH |
| P14-15 | OCH$_3$ |
| P14-16 | OCHF$_2$ |
| P14-17 | OC$_2$H$_5$ |
| P14-18 | CN |
| P14-19 | F |
| P14-20 | Cl |
| P14-21 | Br |
| P14-22 | NO$_2$ |
| P14-23 | NH$_2$ |
| P14-24 | CO—NH$_2$ |
| P14-25 | CO—NH(CH$_3$) |
| P14-26 | CO—N(CH$_3$)$_2$ |
| P14-27 | HNCH$_3$ |
| P14-28 | HNC$_2$H$_5$ |
| P14-29 | (CH$_3$)$_2$N |

TABLE P14-continued

| No. | R$^{10}$ |
|---|---|
| P14-30 | SO$_2$NH$_2$ |
| P14-31 | SO$_2$—CH$_3$ |
| P14-32 | SO—CH$_3$ |
| P14-33 | S—CH$_3$ |
| P14-34 | 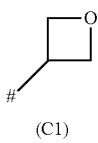 (C1) |
| P14-35 | 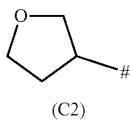 (C2) |
| P14-36 | 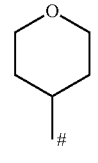 (C3) |
| P14-37 | 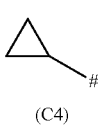 (C4) |
| P14-38 | 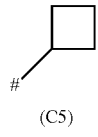 (C5) |
| P14-39 | 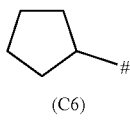 (C6) |
| P14-40 | 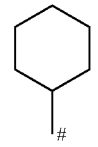 (C7) |

According to a further embodiment, R$^9$ and R$^{10}$ together with the carbon atoms to which they are bound form a saturated or partially unsaturated five-, six- or seven-, membered carbocycle, heterocycle or heteroaromatic ring; wherein the heterocycle and heteroaromatic ring contains one, two, three or four heteroatoms selected from N, O and S, wherein the heteroatom N may carry one substituent R$^N$ selected from C$_1$-C$_4$-alkyl, C$_1$-C$_4$-haloalkyl and SO$_2$Ph, wherein Ph is unsubstituted phenyl or phenyl that is substituted by one, two or three substituents selected from C$_1$-C$_4$-alkyl, and wherein the heteroatom S may be in the form of its oxide SO or SO$_2$,and wherein the carbocycle or heterocycle is substituted or carries one, two, three or four substituents R$^{94}$ independently selected from halogen, OH, OCN, NO, SH, NH, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_1$-C$_4$-alkoxy-C$_1$—C$_4$-alkyl, phenyl and phenoxy.

According to one embodiment, $R^9$ and $R^{10}$ together with the carbon atoms to which they are bound form a saturated or partially unsaturated five-, six- or seven-membered heterocycle that is unsubstituted or substituted.

According to a further embodiment, the heterocycle formed by $R^9$ and $R^{10}$ is saturated.

According to a further embodiment, the heterocycle formed by $R^9$ and $R^{10}$ is a saturated unsubstituted or substituted heterocycle, wherein the heterocycle contains one, two or three, more particularly one or two, specifically one, heteroatom(s) selected from NH, $NR^N$, O, S, S(=O) and S(=O)$_2$, wherein $R^N$ is defined and preferably defined above. According to one embodiment, this saturated heterocycle is unsubstituted. According to a further embodiment, the saturated heterocycle carries one, two, three or four substituents $R^{94}$. In one further particular embodiment, said heterocycle is four- or six-membered.

According to a further embodiment, the unsubstituted or substituted and saturated or partially unsaturated heterocycle is three-, four-, five- or six-membered and contains one, two or three, more particularly one or two, heteroatoms selected from NH, $NR^N$, O, S, S(=O) and S(=O)$_2$, wherein $R^N$ is as defined above or preferably selected from $C_1$-$C_2$-alkyl, $C_1$-$C_2$-haloalkyl and SO$_2$Ph, wherein Ph is unsubstituted phenyl or phenyl that is substituted by one $C_1$-$C_2$-alkyl. In one further particular embodiment, said heterocycle is four- or six-membered.

According to a further embodiment, the heterocycle formed by R and $R^{10}$ contains one, two or three, more specifically one or two, heteroatoms selected from NH and $NR^N$, wherein $R^N$ is as defined and preferably defined below, more particularly selected from $C_1$-$C_2$-alkyl, $C_1$-$C_2$-haloalkyl and SO$_2$Ph, wherein Ph is unsubstituted phenyl or phenyl that is substituted by one methyl. In one embodiment thereof, it contains one or two heteroatoms NH, in particular one NH. In another embodiment, it contains one or two heteroatoms $NR^N$, in particular one $NR^N$, wherein $R^N$ n each case is as defined and preferably defined above.

According to a further embodiment, the heterocycle formed by $R^9$ and $R^{10}$ contains one, two or three, more specifically one or two, in particular one, heteroatom(s) selected from S, S(=O) and S(=O)$_2$. In one embodiment thereof, it contains one or two heteroatoms S, in particular one S. In another embodiment, it contains one or two heteroatoms S(=O), in particular one S(=O). In still another embodiment, it contains one or two heteroatoms S(=O)$_2$, in particular one S(=O)$_2$.

According to a further embodiment, the heterocycle formed by $R^9$ and $R^{10}$ contains one or two heteroatoms O. In one embodiment thereof, it contains one heteroatom O. In another embodiment, it contains two heteroatoms O.

According to a further embodiment, the heterocycle formed by $R^9$ and $R^{10}$ is unsubstituted, i.e. it does not carry any substituent $R^{94}$. According to a further embodiment, it carries one, two, three or four $R^{94}$.

According to one particular embodiment, $R^9$ and $R^{10}$ together form a 4-membered saturated heterocycle which contains 1 or 2 heteroatoms, in particular 1 heteroatom, from the group consisting of NH, $NR^N$, O, S, S(=O) and S(=O)$_2$, as ring members, wherein $R^N$ is defined and preferably defined above. In one embodiment, the heterocycle contains one 0 as heteroatom. For example, the formed heterocycle is oxetane. According to one embodiment thereof, the heterocycle is unsubstituted, i.e. it does not carry any substituent $R^{94}$. According to a further embodiment, it carries one, two, three or four $R^{94}$.

According to a further particular embodiment, $R^9$ and $R^{10}$ together form a 5-membered saturated heterocycle which contains 1, 2 or 3, in particular 1 or 2, heteroatoms from the group consisting of NH, $NR^N$, O, S, S(=O) and S(=O)$_2$, as ring members, wherein $R^N$ is as defined and preferably defined above. According to one embodiment thereof, the heterocycle is unsubstituted, i.e. it does not carry any substituent $R^{94}$. According to a further embodiment, it carries one, two, three or four $R^{94}$.

According to a further particular embodiment, $R^9$ and $R^{10}$ together form a 6-membered saturated heterocycle which contains 1, 2 or 3, in particular 1 or 2, heteroatoms from the group consisting of NH, $NR^N$, O, S, S(=O) and S(=O)$_2$, as ring members, wherein $R^N$ is as defined and preferably defined below. According to one embodiment thereof, the heterocycle is unsubstituted, i.e. it does not carry any substituent $R^{94}$. According to a further embodiment, it carries one, two, three or four $R^{94}$. According to one specific embodiment thereof, said 6-membered saturated heterocycle contains 1 or 2 heteroatoms selected from NH and $NR^N$.

According to a further specific embodiment thereof, said 6-membered saturated heterocycle contains 1 or 2 heteroatoms O. According to a further specific embodiment thereof, said 6-membered saturated heterocycle contains 1 or 2 heteroatoms selected from S, S(=O) and S(=O)$_2$. According to one embodiment thereof, the respective 6-membered heterocycle is unsubstituted, i.e. it does not carry any substituent $R^{94}$. According to a further embodiment, it carries one, two, three or four $R^{94}$.

According to one further embodiment $R^9$ together with $R^{10}$ and with the carbon atom to which they are bound form a saturated three-, four-, five-, six- or seven-membered, in particular five- or six-membered carbocycle, that is unsubstituted or carries one, two, three or four substituents $R^{94}$ as defined below. According to one embodiment thereof, $R^9$ and $R^{10}$ form a cyclopropyl, that is unsubstituted or carries one, two, three or four substituents $R^{94}$ as defined below. According to a further embodiment thereof, $R^9$ and $R^{10}$ form a cyclobutyl, that is unsubstituted or carries one, two, three or four substituents $R^{94}$ as defined below. According to still a further embodiment thereof, $R^9$ and $R^{10}$ form a cyclopentyl, that is unsubstituted or carries one, two, three or four substituents $R^{94}$ as defined below. According to still a further embodiment thereof, $R^9$ and $R^{10}$ form a cyclohexyl, that is unsubstituted or carries one, two, three or four substituents $R^{94}$ as defined below. According to still a further embodiment thereof, $R^9$ and $R^{10}$ form a cycloheptyl, that is unsubstituted or carries one, two, three or four substituents $R^{94}$ as defined below.

$R^{94}$ are the possible substituents for the carbo- or heterocycle formed by $R^9$ and $R^{10}$ and are independently selected from halogen, OH, CN, NO$_2$, SH, NH$_2$, $C_1$-$C_6$-alkyl, $C_1$-$C_6$-haloalkyl, $C_1$-$C_6$-alkoxy, $C_1$-$C_6$-koxy, $C_1$-$C_6$-alkylthio, $C_1$-$C_6$ haloalkyl thio, $C_1$-$C_4$-alkoxy-$C_1$-$C_4$-alkyl, phenyl and phenoxy, wherein the phenyl groups are unsubstituted or substituted with substituents $R^{94a}$ selected from the group consisting of halogen, OH, $C_1$-$C_4$-alkyl, $C_1$-$C_4$-haloalkyl $C_1$-$C_4$-alkoxy and $C_1$-$C_4$-alkoxy; and wherein in each case one or two CH$_2$ groups of the carbo- or heterocycle may be replaced by a group independently selected from C(=O) and C(=S).

In one preferred embodiment, $R^{94}$ is in each case independently selected from halogen, OH, CN, SH, $C_1$-$C_6$-alkyl, $C_1$-$C_6$-haloalkyl, $C_1$-$C_6$-alkoxy, $C_1$-$C_6$-haloalkoxy and $C_1$-$C_6$-alkylthio. In one further preferred embodiment, $R^{94}$ is in each case independently selected from halogen, $C_1$-$C_6$-alkyl and $C_1$-$C_6$ haloalkyl. In one further particular embodiment, $R^{94}$ is in each case independently selected from $C_1$-$C_6$-alkyl, such as methyl and ethyl.

$R^N$ is the substituent of the heteroatom $NR^N$ that is contained in the heterocycle formed by $R^9$ and $R^{10}$ in some of the inventive compounds. $R^N$ is selected from $C_1$-$C_4$-alkyl, $C_1$-$C_4$-alkene and $SO_2Ph$, wherein Ph is unsubstituted phenyl or phenyl that is substituted by one, two or three substituents selected from $C_1$-$C_4$-alkyl. In one preferred embodiment, $R^N$ is in each case independently selected from $C_1$-$C_2$-alkyl, $C_1$-$C_2$ haloalkyl and $SO_2Ph$, wherein Ph is unsubstituted phenyl or phenyl that is substituted by one methyl substituents. In one particular embodiment, $R^N$ is in each case independently selected from $C_1$-$C_2$-alkyl, more particularly methyl. In one particular embodiment, $R^N$ is n each case independently selected from $SO_2Ph$, wherein Ph is unsubstituted phenyl or phenyl that is substituted by one methyl.

According to a further embodiment, $R^9$ and $R^{10}$ together with the carbon atoms to which they are bound form five-, six- or seven-, membered heteroaromatic ring; wherein heteroaromatic ring contains one, two, three or four heteroatoms selected from N, O and S, wherein the heteroatom N may carry one substituent $R^N$ selected from $C_1$-$C_4$-alkyl, $C_1$-$C_4$-haloalkyl and $SO_2Ph$, wherein Ph is unsubstituted phenyl or phenyl that is substituted by one, two or three substituents selected from $C_1$-$C_4$-alkyl, and wherein the heteroatom S may be in the form of its oxide SO or $SO_2$, and wherein the carbocycle or heterocycle is substituted or carries one, two, three or four substituents $R^{94}$ independently selected from halogen, OH, CN, $NO_2$, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_4$-alkoxy-$C_1$-$C_4$-alkyl, phenyl and phenoxy.

According to a further particular embodiment, $R^9$ and $R^{10}$ together form a 5-membered heteroaromatic ring which contains 1, 2 or 3, in particular 1 or 2, heteroatoms from the group consisting of NH, $NR^N$, 0, 5, S(=O) and S(=O)$_2$, as ring members, wherein $R^N$ is as defined and preferably defined above. According to one embodiment thereof, the heterocycle is unsubstituted, i.e. it does not carry any substituent $R^{94}$. According to a further embodiment, it carries one, two, three or four $R^{94}$.

According to a further particular embodiment, $R^9$ and $R^{10}$ together form a 5-membered heteroaromatic ring which contains 1, 2 or 3, in particular 1 or 2 N or S, preferably S. In an proffered embodiment, $R^9$ and $R^{10}$ together form thiophen.

According to one embodiment thereof, the heteroaromatic ring is unsubstituted, i.e. it does not carry any substituent $R^{94}$. According to a further embodiment, it carries one, two, three or four $R^{94}$.

According to a further particular embodiment, $R^9$ and $R^{10}$ together form a 6-membered heteroaromatic ring which contains 1, 2 or 3, in particular 1 or 2, heteroatoms from the group consisting of NH, $NR^N$, 0, 5, S(=O) and S(=O)$_2$, as ring members, wherein $R^N$ is as defined and preferably defined above. According to one embodiment thereof, the heterocycle is unsubstituted, i.e. it does not carry any substituent $R^{94}$. According to a further embodiment, it carries one, two, three or four $R^{94}$.

According to a further particular embodiment, $R^9$ and $R^{10}$ together form a 6-membered heteroaromatic ring which contains 1, 2 or 3, in particular 1 or 2 N. In an preferred embodiment, $R^9$ and $R^{10}$ together form pyridin.

According to one embodiment thereof, the heteroaromatic ring is unsubstituted, i.e. it does not carry any substituent $R^{94}$. According to a further embodiment, it carries one, two, three or four $R^{94}$.

Particularly preferred embodiments of combinations of $R^9$ and $R^{10}$ according to the invention are in Table P35 below, wherein each line of lines P35-1 to P35-406 corresponds to one particular embodiment of the invention, wherein P35-1 to P35-406 are also in any combination with one another a preferred embodiment of the present invention. The carbon atom, to which $R^9$ bound is marked with * in the drawings and the carbon atom, to which $R^{10}$ is bound is marked with # in the drawings. "Ts" in the drawings stands for the tosyl group $SO_2$-(p-$H_3$)phenyl. The abbreviations of the cycles (C1 to C7) are explained in Table P13 above.

TABLE P35

| line | $R^9$ | $R^{10}$ |
|---|---|---|
| P35-1 | H | H |
| P35-2 | H | $CH_3$ |
| P35-3 | H | $C_2H_5$ |
| P35-4 | H | F |
| P35-5 | H | Cl |
| P35-6 | H | Br |
| P35-7 | H | CN |
| P35-8 | H | $OCH_3$ |
| P35-9 | H | $OCHF_2$ |
| P35-10 | H | $CHF_2$ |
| P35-11 | H | $CF_3$ |
| P35-12 | H | S—$CH_3$ |
| P35-13 | H | SO—$CH_3$ |
| P35-14 | H | $SO_2$—$CH_3$ |
| P35-15 | H | CO—$NH_2$ |
| P35-16 | H | CO—NH($CH_3$) |
| P35-17 | H | CO—N($CH_3$)$_2$ |
| P35-18 | $CH_3$ | H |
| P35-19 | $CH_3$ | $CH_3$ |
| P35-20 | $CH_3$ | $C_2H_5$ |
| P35-21 | $CH_3$ | F |
| P35-22 | $CH_3$ | Cl |
| P35-23 | $CH_3$ | Br |
| P35-24 | $CH_3$ | CN |
| P35-25 | $CH_3$ | $OCH_3$ |
| P35-26 | $CH_3$ | $OCHF_2$ |
| P35-27 | $CH_3$ | $CHF_2$ |
| P35-28 | $CH_3$ | $CF_3$ |
| P35-29 | $CH_3$ | S—$CH_3$ |
| P35-30 | $CH_3$ | SO—$CH_3$ |
| P35-31 | $CH_3$ | $SO_2$—$CH_3$ |
| P35-32 | $CH_3$ | CO—$NH_2$ |
| P35-33 | $CH_3$ | CO—NH($CH_3$) |
| P35-34 | $CH_3$ | CO—N($CH_3$)$_2$ |
| P35-35 | $C_2H_5$ | H |
| P35-36 | $C_2H_5$ | $CH_3$ |
| P35-37 | $C_2H_5$ | $C_2H_5$ |
| P35-38 | $C_2H_5$ | F |
| P35-39 | $C_2H_5$ | Cl |
| P35-40 | $C_2H_5$ | Br |
| P35-41 | $C_2H_5$ | CN |
| P35-42 | $C_2H_5$ | $OCH_3$ |
| P35-43 | $C_2H_5$ | $OCHF_2$ |
| P35-44 | $C_2H_5$ | $CHF_2$ |
| P35-45 | $C_2H_5$ | $CF_3$ |
| P35-46 | $C_2H_5$ | S—$CH_3$ |
| P35-47 | $C_2H_5$ | SO—$CH_3$ |
| P35-48 | $C_2H_5$ | $SO_2$—$CH_3$ |
| P35-49 | $C_2H_5$ | CO—$NH_2$ |
| P35-50 | $C_2H_5$ | CO—NH($CH_3$) |
| P35-51 | $C_2H_5$ | CO—N($CH_3$)$_2$ |
| P35-52 | F | H |
| P35-53 | F | $CH_3$ |
| P35-54 | F | $C_2H_5$ |
| P35-55 | F | F |
| P35-56 | F | Cl |
| P35-57 | F | Br |

TABLE P35-continued

| line | R⁹ | R¹⁰ |
|---|---|---|
| P35-58 | F | CN |
| P35-59 | F | OCH₃ |
| P35-60 | F | OCHF₂ |
| P35-61 | F | CHF₂ |
| P35-62 | F | CF₃ |
| P35-63 | F | S—CH₃ |
| P35-64 | F | SO—CH₃ |
| P35-65 | F | SO₂—CH₃ |
| P35-66 | F | CO—NH₂ |
| P35-67 | F | CO—NH(CH₃) |
| P35-68 | F | CO—N(CH₃)₂ |
| P35-69 | Cl | H |
| P35-70 | Cl | CH₃ |
| P35-71 | Cl | C₂H₅ |
| P35-72 | Cl | F |
| P35-73 | Cl | Cl |
| P35-74 | Cl | Br |
| P35-75 | Cl | CN |
| P35-76 | Cl | OCH₃ |
| P35-77 | Cl | OCHF₂ |
| P35-78 | Cl | CHF₂ |
| P35-79 | Cl | CF₃ |
| P35-80 | Cl | S—CH₃ |
| P35-81 | Cl | SO—CH₃ |
| P35-82 | Cl | SO₂—CH₃ |
| P35-83 | Cl | CO—NH₂ |
| P35-84 | Cl | CO—NH(CH₃) |
| P35-85 | Cl | CO—N(CH₃)₂ |
| P35-86 | Br | H |
| P35-87 | Br | CH₃ |
| P35-88 | Br | C₂H₅ |
| P35-89 | Br | F |
| P35-90 | Br | Cl |
| P35-91 | Br | Br |
| P35-92 | Br | CN |
| P35-93 | Br | OCH₃ |
| P35-94 | Br | OCHF₂ |
| P35-95 | Br | CHF₂ |
| P35-96 | Br | CF₃ |
| P35-97 | Br | S—CH₃ |
| P35-98 | Br | SO—CH₃ |
| P35-99 | Br | SO₂—CH₃ |
| P35-100 | Br | CO—NH₂ |
| P35-101 | Br | CO—NH(CH₃) |
| P35-102 | Br | CO—N(CH₃)₂ |
| P35-103 | CN | H |
| P35-104 | CN | CH₃ |
| P35-105 | CN | C₂H₅ |
| P35-106 | CN | F |
| P35-107 | CN | Cl |
| P35-108 | CN | Br |
| P35-109 | CN | CN |
| P35-110 | CN | OCH₃ |
| P35-111 | CN | OCHF₂ |
| P35-112 | CN | CHF₂ |
| P35-113 | CN | CF₃ |
| P35-114 | CN | S—CH₃ |
| P35-115 | CN | SO—CH₃ |
| P35-116 | CN | SO₂—CH₃ |
| P35-117 | CN | CO—NH₂ |
| P35-118 | CN | CO—NH(CH₃) |
| P35-119 | CN | CO—N(CH₃)₂ |
| P35-120 | OCH₃ | H |
| P35-121 | OCH₃ | CH₃ |
| P35-122 | OCH₃ | C₂H₅ |
| P35-123 | OCH₃ | F |
| P35-124 | OCH₃ | Cl |
| P35-125 | OCH₃ | Br |
| P35-126 | OCH₃ | CN |
| P35-127 | OCH₃ | OCH₃ |
| P35-128 | OCH₃ | OCHF₂ |
| P35-129 | OCH₃ | CHF₂ |
| P35-130 | OCH₃ | CF₃ |
| P35-131 | OCH₃ | S—CH₃ |
| P35-132 | OCH₃ | SO—CH₃ |
| P35-133 | OCH₃ | SO₂—CH₃ |
| P35-134 | OCH₃ | CO—NH₂ |
| P35-135 | OCH₃ | CO—NH(CH₃) |
| P35-136 | OCH₃ | CO—N(CH₃)₂ |
| P35-137 | OCHF₂ | H |
| P35-138 | OCHF₂ | CH₃ |
| P35-139 | OCHF₂ | C₂H₅ |
| P35-140 | OCHF₂ | F |
| P35-141 | OCHF₂ | Cl |
| P35-142 | OCHF₂ | Br |
| P35-143 | OCHF₂ | CN |
| P35-144 | OCHF₂ | OCH₃ |
| P35-145 | OCHF₂ | OCHF₂ |
| P35-146 | OCHF₂ | CHF₂ |
| P35-147 | OCHF₂ | CF₃ |
| P35-148 | OCHF₂ | S—CH₃ |
| P35-149 | OCHF₂ | SO—CH₃ |
| P35-150 | OCHF₂ | SO₂—CH₃ |
| P35-151 | OCHF₂ | CO—NH₂ |
| P35-152 | OCHF₂ | CO—NH(CH₃) |
| P35-153 | OCHF₂ | CO—N(CH₃)₂ |
| P35-154 | CHF₂ | H |
| P35-155 | CHF₂ | CH₃ |
| P35-156 | CHF₂ | C₂H₅ |
| P35-157 | CHF₂ | F |
| P35-158 | CHF₂ | Cl |
| P35-159 | CHF₂ | Br |
| P35-160 | CHF₂ | CN |
| P35-161 | CHF₂ | OCH₃ |
| P35-162 | CHF₂ | OCHF₂ |
| P35-163 | CHF₂ | CHF₂ |
| P35-164 | CHF₂ | CF₃ |
| P35-165 | CHF₂ | S—CH₃ |
| P35-166 | CHF₂ | SO—CH₃ |
| P35-167 | CHF₂ | SO₂—CH₃ |
| P35-168 | CHF₂ | CO—NH₂ |
| P35-169 | CHF₂ | CO—NH(CH₃) |
| P35-170 | CHF₂ | CO—N(CH₃)₂ |
| P35-171 | CF₃ | H |
| P35-172 | CF₃ | CH₃ |
| P35-173 | CF₃ | C₂H₅ |
| P35-174 | CF₃ | F |
| P35-175 | CF₃ | Cl |
| P35-176 | CF₃ | Br |
| P35-177 | CF₃ | CN |
| P35-178 | CF₃ | OCH₃ |
| P35-179 | CF₃ | OCHF₂ |
| P35-180 | CF₃ | CHF₂ |
| P35-181 | CF₃ | CF₃ |
| P35-182 | CF₃ | S—CH₃ |
| P35-183 | CF₃ | SO—CH₃ |
| P35-184 | CF₃ | SO₂—CH₃ |
| P35-185 | CF₃ | CO—NH₂ |
| P35-186 | CF₃ | CO—NH(CH₃) |
| P35-187 | CF₃ | CO—N(CH₃)₂ |
| P35-188 | S—CH₃ | H |
| P35-189 | S—CH₃ | CH₃ |
| P35-190 | S—CH₃ | C₂H₅ |
| P35-191 | S—CH₃ | F |
| P35-192 | S—CH₃ | Cl |
| P35-193 | S—CH₃ | Br |
| P35-194 | S—CH₃ | CN |
| P35-195 | S—CH₃ | OCH₃ |
| P35-196 | S—CH₃ | OCHF₂ |
| P35-197 | S—CH₃ | CHF₂ |
| P35-198 | S—CH₃ | CF₃ |
| P35-199 | S—CH₃ | S—CH₃ |
| P35-200 | S—CH₃ | SO—CH₃ |
| P35-201 | S—CH₃ | SO₂—CH₃ |
| P35-202 | S—CH₃ | CO—NH₂ |
| P35-203 | S—CH₃ | CO—NH(CH₃) |
| P35-204 | S—CH₃ | CO—N(CH₃)₂ |
| P35-205 | SO—CH₃ | H |
| P35-206 | SO—CH₃ | CH₃ |
| P35-207 | SO—CH₃ | C₂H₅ |
| P35-208 | SO—CH₃ | F |
| P35-209 | SO—CH₃ | Cl |
| P35-210 | SO—CH₃ | Br |
| P35-211 | SO—CH₃ | CN |
| P35-212 | SO—CH₃ | OCH₃ |
| P35-213 | SO—CH₃ | OCHF₂ |

TABLE P35-continued

| line | R$^9$ | R$^{10}$ |
|---|---|---|
| P35-214 | SO—CH$_3$ | CHF$_2$ |
| P35-215 | SO—CH$_3$ | CF$_3$ |
| P35-216 | SO—CH$_3$ | S—CH$_3$ |
| P35-217 | SO—CH$_3$ | SO—CH$_3$ |
| P35-218 | SO—CH$_3$ | SO$_2$—CH$_3$ |
| P35-219 | SO—CH$_3$ | CO—NH$_2$ |
| P35-220 | SO—CH$_3$ | CO—NH(CH$_3$) |
| P35-221 | SO—CH$_3$ | CO—N(CH$_3$)$_2$ |
| P35-222 | SO$_2$—CH$_3$ | H |
| P35-223 | SO$_2$—CH$_3$ | CH$_3$ |
| P35-224 | SO$_2$—CH$_3$ | C$_2$H$_5$ |
| P35-225 | SO$_2$—CH$_3$ | F |
| P35-226 | SO$_2$—CH$_3$ | Cl |
| P35-227 | SO$_2$—CH$_3$ | Br |
| P35-228 | SO$_2$—CH$_3$ | CN |
| P35-229 | SO$_2$—CH$_3$ | OCH$_3$ |
| P35-230 | SO$_2$—CH$_3$ | OCHF$_2$ |
| P35-231 | SO$_2$—CH$_3$ | CHF$_2$ |
| P35-232 | SO$_2$—CH$_3$ | CF$_3$ |
| P35-233 | SO$_2$—CH$_3$ | S—CH$_3$ |
| P35-234 | SO$_2$—CH$_3$ | SO—CH$_3$ |
| P35-235 | SO$_2$—CH$_3$ | SO$_2$—CH$_3$ |
| P35-236 | SO$_2$—CH$_3$ | CO—NH$_2$ |
| P35-237 | SO$_2$—CH$_3$ | CO—NH(CH$_3$) |
| P35-238 | SO$_2$—CH$_3$ | CO—N(CH$_3$)$_2$ |
| P35-239 | CO—NH$_2$ | H |
| P35-240 | CO—NH$_2$ | CH$_3$ |
| P35-241 | CO—NH$_2$ | C$_2$H$_5$ |
| P35-242 | CO—NH$_2$ | F |
| P35-243 | CO—NH$_2$ | Cl |
| P35-244 | CO—NH$_2$ | Br |
| P35-245 | CO—NH$_2$ | CN |
| P35-246 | CO—NH$_2$ | OCH$_3$ |
| P35-247 | CO—NH$_2$ | OCHF$_2$ |
| P35-248 | CO—NH$_2$ | CHF$_2$ |
| P35-249 | CO—NH$_2$ | CF$_3$ |
| P35-250 | CO—NH$_2$ | S—CH$_3$ |
| P35-251 | CO—NH$_2$ | SO—CH$_3$ |
| P35-252 | CO—NH$_2$ | SO$_2$—CH$_3$ |
| P35-253 | CO—NH$_2$ | CO—NH$_2$ |
| P35-254 | CO—NH$_2$ | CO—NH(CH$_3$) |
| P35-255 | CO—NH$_2$ | CO—N(CH$_3$)$_2$ |
| P35-256 | CO—NH(CH$_3$) | H |
| P35-257 | CO—NH(CH$_3$) | CH$_3$ |
| P35-258 | CO—NH(CH$_3$) | C$_2$H$_5$ |
| P35-259 | CO—NH(CH$_3$) | F |
| P35-260 | CO—NH(CH$_3$) | Cl |
| P35-261 | CO—NH(CH$_3$) | Br |
| P35-262 | CO—NH(CH$_3$) | CN |
| P35-263 | CO—NH(CH$_3$) | OCH$_3$ |
| P35-264 | CO—NH(CH$_3$) | OCHF$_2$ |
| P35-265 | CO—NH(CH$_3$) | CHF$_2$ |
| P35-266 | CO—NH(CH$_3$) | CF$_3$ |
| P35-267 | CO—NH(CH$_3$) | S—CH$_3$ |
| P35-268 | CO—NH(CH$_3$) | SO—CH$_3$ |
| P35-269 | CO—NH(CH$_3$) | SO$_2$—CH$_3$ |
| P35-270 | CO—NH(CH$_3$) | CO—NH$_2$ |
| P35-271 | CO—NH(CH$_3$) | CO—NH(CH$_3$) |
| P35-272 | CO—NH(CH$_3$) | CO—N(CH$_3$)$_2$ |
| P35-273 | CO—N(CH$_3$)$_2$ | H |
| P35-274 | CO—N(CH$_3$)$_2$ | CH$_3$ |
| P35-275 | CO—N(CH$_3$)$_2$ | C$_2$H$_5$ |
| P35-276 | CO—N(CH$_3$)$_2$ | F |
| P35-277 | CO—N(CH$_3$)$_2$ | Cl |
| P35-278 | CO—N(CH$_3$)$_2$ | Br |
| P35-279 | CO—N(CH$_3$)$_2$ | CN |
| P35-280 | CO—N(CH$_3$)$_2$ | OCH$_3$ |
| P35-281 | CO—N(CH$_3$)$_2$ | OCHF$_2$ |
| P35-282 | CO—N(CH$_3$)$_2$ | CHF$_2$ |
| P35-283 | CO—N(CH$_3$)$_2$ | CF$_3$ |
| P35-284 | CO—N(CH$_3$)$_2$ | S—CH$_3$ |
| P35-285 | CO—N(CH$_3$)$_2$ | SO—CH$_3$ |
| P35-286 | CO—N(CH$_3$)$_2$ | SO$_2$—CH$_3$ |
| P35-287 | CO—N(CH$_3$)$_2$ | CO—NH$_2$ |
| P35-288 | CO—N(CH$_3$)$_2$ | CO—NH(CH$_3$) |
| P35-289 | CO—N(CH$_3$)$_2$ | CO—N(CH$_3$)$_2$ |
| P35-290 | C1 | H |
| P35-291 | C2 | H |
| P35-292 | C3 | H |
| P35-293 | C4 | H |
| P35-294 | C5 | H |
| P35-295 | C6 | H |
| P35-296 | C7 | H |
| P35-297 | C8 | H |
| P35-298 | C1 | CH$_3$ |
| P35-299 | C2 | CH$_3$ |
| P35-300 | C3 | CH$_3$ |
| P35-301 | C4 | CH$_3$ |
| P35-302 | C5 | CH$_3$ |
| P35-303 | C6 | CH$_3$ |
| P35-304 | C7 | CH$_3$ |
| P35-305 | C1 | C$_2$H$_5$ |
| P35-306 | C2 | C$_2$H$_5$ |
| P35-307 | C3 | C$_2$H$_5$ |
| P35-308 | C4 | C$_2$H$_5$ |
| P35-309 | C5 | C$_2$H$_5$ |
| P35-310 | C6 | C$_2$H$_5$ |
| P35-311 | C7 | C$_2$H$_5$ |
| P35-312 | C1 | CH(CH$_3$)$_2$ |
| P35-313 | C2 | CH(CH$_3$)$_2$ |
| P35-314 | C3 | CH(CH$_3$)$_2$ |
| P35-315 | C4 | CH(CH$_3$)$_2$ |
| P35-316 | C5 | CH(CH$_3$)$_2$ |
| P35-317 | C6 | CH(CH$_3$)$_2$ |
| P35-318 | C7 | CH(CH$_3$)$_2$ |
| P35-319 | C1 | CH$_2$CH$_2$CH$_3$ |
| P35-320 | C2 | CH$_2$CH$_2$CH$_3$ |
| P35-321 | C3 | CH$_2$CH$_2$CH$_3$ |
| P35-322 | C4 | CH$_2$CH$_2$CH$_3$ |
| P35-323 | C5 | CH$_2$CH$_2$CH$_3$ |
| P35-324 | C6 | CH$_2$CH$_2$CH$_3$ |
| P35-325 | C7 | CH$_2$CH$_2$CH$_3$ |
| P35-326 | C1 | CH(CH$_3$)$_2$ |
| P35-327 | C2 | CH(CH$_3$)$_2$ |
| P35-328 | C3 | CH(CH$_3$)$_2$ |
| P35-329 | C4 | CH(CH$_3$)$_2$ |
| P35-330 | C5 | CH(CH$_3$)$_2$ |
| P35-331 | C6 | CH(CH$_3$)$_2$ |
| P35-332 | C7 | CH(CH$_3$)$_2$ |
| P35-333 | C1 | CH$_2$CH$_2$CH$_2$CH$_3$ |
| P35-334 | C2 | CH$_2$CH$_2$CH$_2$CH$_3$ |
| P35-335 | C3 | CH$_2$CH$_2$CH$_2$CH$_3$ |
| P35-336 | C4 | CH$_2$CH$_2$CH$_2$CH$_3$ |
| P35-337 | C5 | CH$_2$CH$_2$CH$_2$CH$_3$ |
| P35-338 | C6 | CH$_2$CH$_2$CH$_2$CH$_3$ |
| P35-339 | C7 | CH$_2$CH$_2$CH$_2$CH$_3$ |
| P35-340 | C1 | CH$_2$CH(CH$_3$)$_2$ |
| P35-341 | C2 | CH$_2$CH(CH$_3$)$_2$ |
| P35-342 | C3 | CH$_2$CH(CH$_3$)$_2$ |
| P35-343 | C4 | CH$_2$CH(CH$_3$)$_2$ |
| P35-344 | C5 | CH$_2$CH(CH$_3$)$_2$ |
| P35-345 | C6 | CH$_2$CH(CH$_3$)$_2$ |
| P35-346 | C7 | CH$_2$CH(CH$_3$)$_2$ |
| P35-347 | C1 | C(CH$_3$)$_3$ |
| P35-348 | C2 | C(CH$_3$)$_3$ |
| P35-349 | C3 | C(CH$_3$)$_3$ |
| P35-350 | C4 | C(CH$_3$)$_3$ |
| P35-351 | C5 | C(CH$_3$)$_3$ |
| P35-352 | C6 | C(CH$_3$)$_3$ |
| P35-353 | C7 | C(CH$_3$)$_3$ |
| P35-354 | C1 | CH$_2$CH$_2$CH$_2$CH$_2$CH$_3$ |
| P35-355 | C2 | CH$_2$CH$_2$CH$_2$CH$_2$CH$_3$ |
| P35-356 | C3 | CH$_2$CH$_2$CH$_2$CH$_2$CH$_3$ |
| P35-357 | C4 | CH$_2$CH$_2$CH$_2$CH$_2$CH$_3$ |
| P35-358 | C5 | CH$_2$CH$_2$CH$_2$CH$_2$CH$_3$ |
| P35-359 | C6 | CH$_2$CH$_2$CH$_2$CH$_2$CH$_3$ |
| P35-360 | C7 | CH$_2$CH$_2$CH$_2$CH$_2$CH$_3$ |
| P35-361 | C1 | CH$_2$CH$_2$CH(CH$_3$)$_2$ |
| P35-362 | C2 | CH$_2$CH$_2$CH(CH$_3$)$_2$ |
| P35-363 | C3 | CH$_2$CH$_2$CH(CH$_3$)$_2$ |
| P35-364 | C4 | CH$_2$CH$_2$CH(CH$_3$)$_2$ |
| P35-365 | C5 | CH$_2$CH$_2$CH(CH$_3$)$_2$ |
| P35-366 | C6 | CH$_2$CH$_2$CH(CH$_3$)$_2$ |
| P35-367 | C7 | CH$_2$CH$_2$CH(CH$_3$)$_2$ |
| P35-368 | C1 | Cl |
| P35-369 | C2 | Cl |

TABLE P35-continued

| line | R⁹ | R¹⁰ |
|---|---|---|
| P35-370 | C3 | C1 |
| P35-371 | C4 | C1 |
| P35-372 | C5 | C1 |
| P35-373 | C6 | C1 |
| P35-374 | C7 | C1 |
| P35-375 | C2 | C2 |
| P35-376 | C3 | C2 |
| P35-377 | C4 | C2 |
| P35-378 | C5 | C2 |
| P35-379 | C6 | C2 |
| P35-380 | C7 | C2 |
| P35-381 | C3 | C3 |
| P35-382 | C4 | C3 |
| P35-383 | C5 | C3 |
| P35-384 | C6 | C3 |
| P35-385 | C7 | C3 |
| P35-386 | C4 | C4 |
| P35-387 | C5 | C4 |
| P35-388 | C6 | C4 |
| P35-389 | C7 | C4 |
| P35-390 | C5 | C5 |
| P35-391 | C6 | C5 |
| P35-392 | C7 | C5 |
| P35-393 | C6 | C6 |
| P35-394 | C7 | C6 |
| P35-395 | C7 | C7 |
| P35-396 | | (tetrahydropyran) |
| P35-397 | | (piperidine) |
| P35-398 | | (N-methylpiperidine) |
| P35-399 | | (N-tosylpiperidine) |
| P35-400 | | (thiane) |
| P35-401 | | (thiane S-oxide) |
| P35-402 | | (thiane S,S-dioxide) |
| P35-403 | | (2-oxopyrrolidinyl, NH) |
| P35-404 | | (N-methyl-2-oxopyrrolidinyl) |
| P35-405 | | (succinimidyl) |
| P35-406 | | (N-methylsuccinimidyl) |
| P35-407 | | (thiophen-2-yl) |
| P35-408 | | (thiophen-3-yl) |
| P35-409 | | (thiophen-2-yl) |
| P35-410 | | (pyridin-2-yl) |
| P35-411 | | (pyridin-3-yl) |
| P35-412 | | (pyridin-4-yl) |
| P35-413 | | (pyridin-3-yl) |

Particular Compounds of formula I according to the present invention are the following compounds I.Ka:

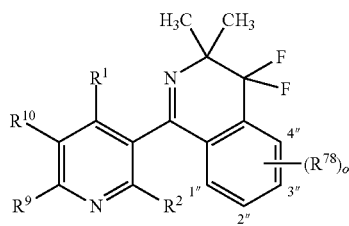

Particular embodiments thereof are compiled in the following Table C wherein $(R^{78})_o$ is specified:

TABLE C

| Specific compounds I.Ka (I.Ka-1 to I.Ka-10): | |
|---|---|
| compound No. | $(R^{78})_o$ |
| I.Ka-1 | o = 0 |
| I.Ka-2 | 1''-F |
| I.Ka-3 | 2''-F |
| I.Ka-4 | 3''-F |
| I.Ka-5 | 4''-F |
| I.Ka-6 | 1''-Cl |
| I.Ka-7 | 2''-Cl |
| I.Ka-8 | 3''-Cl |
| I.Ka-9 | 4''-Cl |
| I.Ka-10 | 2''-CHF$_2$ |

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (*Coleoptera*), two-winged insects (*Diptera*), and moths (*Lepidoptera*) and to nematodes (*Nematoda*).

Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Pro-*tecta*®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or brassicae), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Biplaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes* black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri* Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechsiera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyr*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans, and *F. verticilloides* on corn; *Gaeumannomyces graminis* (take-all) on cereals (e. g. wheat or barley) and corn; *Gibberella* spp. on cereals (e. g. *G. zeae*) and rice (e. g. *G. fujikuroi* Bakanae disease); *Glomerela cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochlobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseoina* (syn. *phaseoli*) (root and stem rot) on soybeans and cotton; *Microdochium* (syn. *Fusarium*) n/vale (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria blotch*) on wheat or *M. fijiensis* (black Sigatoka disease) on bananas; *Peronospora* spp. (downy mildew) on cabbage (e. g. *P. brassicae*), rape (e. g. *P. parastica*), onions (e. g. *P. destructo*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii*(orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora blotch*) on cereals; *Uncinula* (syn. *Erysiphe*) *necator*(powdery mildew, anamorph: *Oidium tuckeri*) on vines; *Setospaeria* spp. (leaf blight) on corn (e. g. *S. turcicum,* syn. *Helminthosporium turcicum*) and turf; *Sphacelotheca* spp. (smut) on corn, (e. g. *S. reliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: Leptosphaeria [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta*(stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpuia* spp. and *Tyromyces* spp., Deuteromycetes such as *Aspergllus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, lime-stone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides.

Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target.

Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-Soluble Concentrates (SL, LS)
10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.
ii) Dispersible Concentrates (DC)
5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.
iii) Emulsifiable Concentrates (EC)
15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.
iv) Emulsions (EW, EO, ES)
5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

Biopesticides have been defined as a form of pesticides based on microorganisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multicellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

When living microorganisms, such as microbial pesticides from groups L1), L3) and L5), form part of such kit, it must be taken care that choice and amounts of the components (e. g. chemical pesticides) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration Inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), tri-floxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate(A.1.22),1-[3-chloro-2-[[1-(4-chlorophenyl)-1H-pyrazol-3-yl]oxymethyl]phenyl]-4-methyl-tetrazol-5-one (A1.23),1-[3-bromo-2-[[1-(4-chlorophenyl)pyrazol-3-yl]oxymethyl] phenyl]-4-methyl-tetrazol-5-one (A.1.24),1-[2-[[1-(4-chlorophenyl)pyrazol-3-yl]oxymethyl]-3-methyl-phenyl]-4-methyl-tetrazol-5-one (A.1.25),1-[2-[[I-(4-chlorophenyl)pyrazol-3-yl]oxymethyl]-3-fluoro-phenyl]-4-methyl-tetrazol-5-one (A.1.26),1-[2-[[1-(2, 4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl])oxymethyl]phenyl]-4-methyl-tetrazol-5-one (A.1.29),1-[3-cyclopropyl-2-[[2-methyl-4-(1-methylpyrazol-3-yl)phenoxy]methyl] phenyl]-4-methyl-tetrazol-5-one (A.1.30),1-[3-(difluoromethoxy)-2-[[2-methyl-4-(1-methylpyrazol-3-yl)phenoxy]methyl]phenyl]-4-methyl-tetrazol-5-ne (A.1.31),1-methyl-4-[3-methyl-2-[[2-methyl-4-(1-methylpyrazol-3-yl)phenoxy]methyl]phenyl]tetrazol-5-one (A1.32) 1-methyl-4-[3-methyl-2-[[1-[3-(trifluormethyl)phenyl]-ethyl]phenyl]tetrazol-5-one (A.1.33), (Z,2E)-5-[1-(2,4-dichlorophenyl)pyrazol-3-yl]-oxy-2-methoxyimino-,3-dimethyl-pent-3-enamide ((A.1.34), (2E)-5-[1-(4-chlorophenyl)pyrazol-3-yl]oxy-2-methoxyimino-,3-dimethyl-pent-3-enamide (A.1.35), (Z,2E)-5-[1-(4-chloro-2-fluoro-phenyl)pyrazol-3-yl] oxy-2-methoxyimino-N,3-dimethyl-pent-3-enamide (A.1.36), inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl] amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6);

(3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinanido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e. g. complex, uncouplers): diflumetorim (A.4.1), (5,8-difluoro-quinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[re(2S,3R)-3-(2-chlorophenyl)-2-(2,4-difluorophenyl)-oxiranylmethyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chloro-phenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);
compounds affecting cell membrane permeability and fatty acids: propamocarb (G.4.1);
fatty acid amide hydrolase inhibitors: oxathiapiprolin (G.5.1), 2-{3-[2-(1-{[3,5-bis(di-fluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);
thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);
organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);
guanidines and others: guanidine (H.4.1), dodine (H.4.2), dodine free base (H.4.3), guazatine (H.4.4), guazatineacetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (1.1.1), polyoxin B (1.1.2);
melanin synthesis inhibitors: pyroquilon (1.2.1), tricyclazole (1.2.2), carpropamid (1.2.3), dicyclomet (1.2.4), fenoxanil (1.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclo-propylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-tri-methylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48);

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocadium catenulatum*), *Gliocadium roseum, Lysobacter antibioticus, L. enzymogenes, Metschnikowia fructicola, Microdochium dimerum, Microsphaeropsis ochracea, Muscodor albus, Paenibacillus alvei, Paenibacillus polymyxa, Pantoea vagans, Penicillium bilaiae, Phlebiopsis gigantea, Pseudomonas* sp., *Pseudomonas chlraphis, Pseudozyma flocculosa, Pichia anomala, Pythium oligandrum, Sphaerodes mycoparasitica, Streptomyces griseoviridis, S. lydicus, S. violaceusniger; Taaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Uocadium oudemansii, Verticilium dahlia,* zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium*

*radiobacter Bacillus cereus, B. firmus, B. thuringiensis, B. thuringiensis* ssp. *aizawai*, B. t. ssp. *israelensis*, B. t. ssp. *galleriae*, B. t. ssp. *kurstaki* B. t. ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrIeGV), *Flavobacterium* spp., *Helicoverpa armigera* nucleopolyhedrovirus (HearNPV), *Helicoverpazea nucleopolyhedro* virus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, Metarhizium anisopliae* var. *anisopliae, M. anisopliae* var. *acridum, Nomuraea rileyi, Paecilomyces fumosoroseus, P. liacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. japonicum, B. liaoningense, B. lupini, Delflia acidovorans, Glomus intraradices, Mesorhizobium* spp., *Rhizobium leguminosarum* bv. *phaseoli, R.* bv. *trifolii, R.* bv. *viciae, R. tropici, Sinorhizobium meliloti;*

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;

amino acid derivatives: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;

cyclohexanediones: butroxydim, clethodim (N.6.1), cycloxydim (N.6.2), profoxydim (N.6.3), sethoxydim (N.6.4), tepraloxydim (N.6.5), tralkoxydim;

dinitroanilines: benfluralin, ethalfluralin, oryzalin, pendimethalin (N.7.1), prodiamine (N.7.2), trifluralin (N.7.3);

diphenyl ethers: acifluorfen (N.8.1), aclonifen, bifenox, diclofop, ethoxyfen, fomesafen, lac-tofen, oxyfluorfen;

hydroxybenzonitriles: bomoxynil (N.9.1), dichlobenil, ioxynil;

imidazolinones: imazamethabenz, imazamox (N.10.1), imazapic (N.10.2), imazapyr (N.10.3), imazaquin (N.10.4), imazethapyr (N.10.5);

phenoxy acetic acids: clomeprop, 2,4-dichlorophenoxyacetic acid (2,4-D) (N.11.1), 2,4-DB, dichlorprop, MCPA, MCPA-thioethyl, MCPB, Mecoprop;

pyrazines: chloridazon (N.11.1), flufenpyr-ethyl, fluthiacet, norflurazon, pyridate;

pyridines: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam, trifludimoxazin (N.14.3);

ureas: chlorotoluron, daimuron, diuron (N.15.1), flumeturon, isoproturon, linuron, methabenzthiazuron, tebuthiuron;

other acetolactate synthase inhibitors: bispyribac-sodium, cloransulam-methyl, diclosulam, florasulam (N.16.1), flucarbazone, flumetsulam, metosulam, ortho-sulfamuron, penoxsulam, propoxycarbazone, pyribambenz-propyl, pyribenzoxim, pyriftalid, pyriminobacmethyl, pyrimisulfan, pyrithiobac, pyroxasulfone (N.16.2), pyroxsulam;

others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids: allethrin (O.3.1), bifenthrin (O.3.2), cyfluthrin (O.3.3), cyhalothrin (O.3.4), cy-phenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);

insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7);

macrocyclic lactone insecticides: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) I acaricides: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflumizone (O.14.2);

ryanodine receptor inhibitors: chlorantraniliprole (O.15.1), cyantraniliprole (O.15.2), flu-bendiamide (O.15.3), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.15.4); N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (O.15.5); N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.15.7); N-[4,6-dichloro-2-[(diethyl-lambda-4-sulfanylidene)carbamoyl]-phenyl]-2-(3-chloro-2-pyridyl)-5-(difluoromethyl)pyr-azole-3-carboxamide (O.15.8); N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide (O.15.9); N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide (O.15.11);

others: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15), 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester (O.16.16), tioxazafen (O.16.7).

Preferred two-component compositions comprising a compound of formula I according to the present invention are compiled in the following Table D:

TABLE D

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-1 | I.Ka-1 | Pyraclostrobin |
| D-2 | I.Ka-1 | Azoxystrobin |
| D-3 | I.Ka-1 | Trifloxystrobin |
| D-4 | I.Ka-1 | Picoxystrobin |
| D-5 | I.Ka-1 | Fluoxastrobin |
| D-6 | I.Ka-1 | Dimoxystrobin |
| D-7 | I.Ka-1 | Kresoxim-methyl |
| D-8 | I.Ka-1 | (2E,3Z)-5-[[1-(2,4-dichlorophenyl)-1H-pyrazol-3-yl]oxy]-2-(methoxyimino)-N,3-dimethyl-pent-3-enamide |
| D-9 | I.Ka-1 | (2E,3Z)-5-[[1-(4-chlorophenyl)-1H-pyrazol-3-yl]oxy]-2-(methoxyimino)-N,3-dimethyl-pent-3-enamide |
| D-10 | I.Ka-1 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-11 | I.Ka-1 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-12 | I.Ka-1 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-13 | I.Ka-1 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-14 | I.Ka-1 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-15 | I.Ka-1 | Fluxapyroxad |
| D-16 | I.Ka-1 | Boscalid |
| D-17 | I.Ka-1 | Bixafen |
| D-18 | I.Ka-1 | Isopyrazam |
| D-19 | I.Ka-1 | Benzovindiflupyr |
| D-20 | I.Ka-1 | Fluopyram |
| D-21 | I.Ka-1 | N-[(5-chloro-2-isopropyl-phenyl)methyl]-N-cyclopropyl-5-fluoro-1,3-dimethyl-pyrazole-4-carboxamide |
| D-22 | I.Ka-1 | Sedaxane |
| D-23 | I.Ka-1 | Penflufen |
| D-24 | I.Ka-1 | N-[2-(2,4-dichlorophenyl)-2-methoxy-1-methyl-ethyl]-3-(difluoromethyl)-1-methyl-pyrazole-4-carboxamide |
| D-25 | I.Ka-1 | 3 (difluoromethyl)-1-methyl-N-(1,1,3-trimethylindan-4-yl)pyrazole-4-carboxamide |
| D-26 | I.Ka-1 | 3 (trifluoromethyl)-1-methyl-N-(1,1,3-trimethylindan-4-yl)pyrazole-4-carboxamide |
| D-27 | I.Ka-1 | 1,3-dimethyl-N-(1,1,3-trimethylindan-4-yl)pyrazole-4-carboxamide |
| D-28 | I.Ka-1 | 3-(trifluorometh¬yl)-1,5-dimethyl-N-(1,1,3-trimethylindan-4-yl)pyrazole-4-carboxamide |
| D-29 | I.Ka-1 | 1,3,5-trimethyl-N-(1,1,3-trimethylindan-4-yl)pyrazole-4-carboxamide |
| D-30 | I.Ka-1 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-31 | I.Ka-1 | Ametoctradin |
| D-32 | I.Ka-1 | epoxiconazole |
| D-33 | I.Ka-1 | metconazole |
| D-34 | I.Ka-1 | prothioconazole |
| D-35 | I.Ka-1 | difenoconazole |
| D-36 | I.Ka-1 | fluquinconazole |
| D-37 | I.Ka-1 | propiconazole |
| D-38 | I.Ka-1 | tebuconazole |
| D-39 | I.Ka-1 | 2-[2-chloro-4-(4-chlorophenoxy)phenyl]-1 (1,2,4-triazol-1-yl)pentan-2-ol |
| D-40 | I.Ka-1 | 1-[4-(4-chlorophenoxy)-2-(trifluoromethyl)phenyl]-1 cyclopropyl-2-(1,2,4-triazol-1-yl)ethanol |
| D-41 | I.Ka-1 | 2-[4-(4-chlorophenoxy)-2-(trifluoromethyl)phenyl]-1-(1,2,4-triazol-1-yl)butan-2-ol |
| D-42 | I.Ka-1 | 2-[2-chloro-4-(4-chlorophenoxy)phenyl]-1-(1,2,4-triazol-1-yl)butan-2-ol |
| D-43 | I.Ka-1 | 2-[4-(4-chlorophenoxy)-2-(trifluoromethyl)phenyl]-3-methyl-1-(1,2,4-triazol-1-yl)butan-2-ol |
| D-44 | I.Ka-1 | 2-[4-(4-chlorophenoxy)-2-(trifluoromethyl)phenyl]-1-(1,2,4-triazol-1-yl)propan-2-ol |
| D-45 | I.Ka-1 | 2-[2-chloro-4-(4-chlorophenoxy)phenyl]-3-methyl-1-(1,2,4-triazol-1-yl)butan-2-ol |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-46 | I.Ka-1 | 2-[4-(4-chlorophenoxy)-2-(trifluoromethyl)phenyl]-1-(1,2,4-triazol-1-yl)pentan-2-ol |
| D-47 | I.Ka-1 | 2-[4-(4-fluorophenoxy)-2-(trifluoromethyl)phenyl]-1-(1,2,4-triazol-1-yl)propan-2-ol |
| D-48 | I.Ka-1 | 2-[2-chloro-4-(4-chlorophenoxy)phenyl]-1-(1,2,4-triazol-1-yl)pent-3-yn-2-ol |
| D-49 | I.Ka-1 | prochloraz |
| D-50 | I.Ka-1 | [3-(4-chloro-2-fluoro-phenyl)-5-(2,4-difluorophenyl)isoxazol-4-yl]-(3-pyridyl)methanol |
| D-51 | I.Ka-1 | fenpropimorph |
| D-52 | I.Ka-1 | Metalaxyl |
| D-53 | I.Ka-1 | Benalaxyl |
| D-54 | I.Ka-1 | Thiophanate-methyl |
| D-55 | I.Ka-1 | Carbendazim |
| D-56 | I.Ka-1 | Metrafenone |
| D-57 | I.Ka-1 | Pyrimethanil |
| D-58 | I.Ka-1 | Iprodione |
| D-59 | I.Ka-1 | Vinclozolin |
| D-60 | I.Ka-1 | Fludioxonil |
| D-61 | I.Ka-1 | dimethomorph |
| D-62 | I.Ka-1 | oxathiapiprolin |
| D-63 | I.Ka-1 | metiram |
| D-64 | I.Ka-1 | mancozeb |
| D-65 | I.Ka-1 | chlorothalonil |
| D-66 | I.Ka-1 | dithianon |
| D-67 | I.Ka-1 | Dipymetitrone |
| D-68 | I.Ka-1 | prohexadione-calcium |
| D-69 | I.Ka-1 | 3-(5-fluoro-3,3,4,4-tetramethyl-3,4-dihydroisoquinolin-1-yl)quinoline |
| D-70 | I.Ka-1 | 3-(4,4-difluoro-3,3-dimethyl-3,4-dihydroisoquinolin-1-yl)quinoline |
| D-71 | I.Ka-1 | 3-(4,4,5-trifluoro-3,3-dimethyl-3,4-dihydroisoquinolin-1-yl)quinoline |
| D-72 | I.Ka-1 | 9-fluoro-2,2-dimethyl-5-(3-quinolyl)-3H 1,4-benzoxazepine |
| D-73 | I.Ka-2 | Pyraclostrobin |
| D-74 | I.Ka-2 | Azoxystrobin |
| D-75 | I.Ka-2 | Trifloxystrobin |
| D-76 | I.Ka-2 | Picoxystrobin |
| D-77 | I.Ka-2 | Fluoxastrobin |
| D-78 | I.Ka-2 | Dimoxystrobin |
| D-79 | I.Ka-2 | Kresoxim-methyl |
| D-80 | I.Ka-2 | (2E,3Z)-5-[[1-(2,4-dichlorophenyl)-1H-pyrazol-3-yl]oxy]-2-(methoxyimino)-N,3-dimethyl-pent-3-enamide |
| D-81 | I.Ka-2 | (2E,3Z)-5-[[1-(4-chlorophenyl)-1H-pyrazol-3-yl]oxy]-2-(methoxyimino)-N,3-dimethyl-pent-3-enamide |
| D-82 | I.Ka-2 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-83 | I.Ka-2 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-84 | I.Ka-2 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-85 | I.Ka-2 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-86 | I.Ka-2 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-87 | I.Ka-2 | Fluxapyroxad |
| D-88 | I.Ka-2 | Boscalid |
| D-89 | I.Ka-2 | Bixafen |
| D-90 | I.Ka-2 | Isopyrazam |
| D-91 | I.Ka-2 | Benzovindiflupyr |
| D-92 | I.Ka-2 | Fluopyram |
| D-93 | I.Ka-2 | N-[(5-chloro-2-isopropyl-phenyl)methyl]-N-cyclopropyl-5-fluoro-1,3-dimethyl-pyrazole-4-carboxamide |
| D-94 | I.Ka-2 | Sedaxane |
| D-95 | I.Ka-2 | Penflufen |
| D-96 | I.Ka-2 | N-[2-(2,4-dichlorophenyl)-2-methoxy-1-methyl-ethyl]-3-(difluoromethyl)-1-methyl-pyrazole-4-carboxamide |
| D-97 | I.Ka-2 | 3 (difluoromethyl)-1-methyl-N-(1,1,3-trimethylindan-4-yl)pyrazole-4-carboxamide |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-98 | I.Ka-2 | 3 (trifluoromethyl)-1-methyl-N-(1,1,3-trimethylindan-4-yl)pyrazole-4-carboxamide |
| D-99 | I.Ka-2 | 1,3-dimethyl-N-(1,1,3-trimethylindan-4-yl)pyrazole-4-carboxamide |
| D-100 | I.Ka-2 | 3-(trifluorometh¬yl)-1,5-dimethyl-N-(1,1,3-trimethylindan-4-yl)pyrazole-4-carboxamide |
| D-101 | I.Ka-2 | 1,3,5-trimethyl-N-(1,1,3-trimethylindan-4-yl)pyrazole-4-carboxamide |
| D-102 | I.Ka-2 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-103 | I.Ka-2 | Ametoctradin |
| D-104 | I.Ka-2 | epoxiconazole |
| D-105 | I.Ka-2 | metconazole |
| D-106 | I.Ka-2 | prothioconazole |
| D-107 | I.Ka-2 | difenoconazole |
| D-108 | I.Ka-2 | fluquinconazole |
| D-109 | I.Ka-2 | propiconazole |
| D-110 | I.Ka-2 | tebuconazole |
| D-111 | I.Ka-2 | 2-[2-chloro-4-(4-chlorophenoxy)phenyl]-1 (1,2,4-triazol-1-yl)pentan-2-ol |
| D-112 | I.Ka-2 | 1-[4-(4-chlorophenoxy)-2-(trifluoromethyl)phenyl]-1 cyclopropyl-2-(1,2,4-triazol-1-yl)ethanol |
| D-113 | I.Ka-2 | 2-[4-(4-chlorophenoxy)-2-(trifluoromethyl)phenyl]-1-(1,2,4-triazol-1-yl)butan-2-ol |
| D-114 | I.Ka-2 | 2-[2-chloro-4-(4-chlorophenoxy)phenyl]-1-(1,2,4-triazol-1-yl)butan-2-ol |
| D-115 | I.Ka-2 | 2-[4-(4-chlorophenoxy)-2-(trifluoromethyl)phenyl]-3-methyl-1-(1,2,4-triazol-1-yl)butan-2-ol |
| D-116 | I.Ka-2 | 2-[4-(4-chlorophenoxy)-2-(trifluoromethyl)phenyl]-1-(1,2,4-triazol-1-yl)propan-2-ol |
| D-117 | I.Ka-2 | 2-[2-chloro-4-(4-chlorophenoxy)phenyl]-3-methyl-1-(1,2,4-triazol-1-yl)butan-2-ol |
| D-118 | I.Ka-2 | 2-[4-(4-chlorophenoxy)-2-(trifluoromethyl)phenyl]-1-(1,2,4-triazol-1-yl)pentan-2-ol |
| D-119 | I.Ka-2 | 2-[4-(4-fluorophenoxy)-2-(trifluoromethyl)phenyl]-1-(1,2,4-triazol-1-yl)propan-2-ol |
| D-120 | I.Ka-2 | 2-[2-chloro-4-(4-chlorophenoxy)phenyl]-1-(1,2,4-triazol-1-yl)pent-3-yn-2-ol |
| D-121 | I.Ka-2 | prochloraz |
| D-122 | I.Ka-2 | [3-(4-chloro-2-fluoro-phenyl)-5-(2,4-difluorophenyl)isoxazol-4-yl]-(3-pyridyl)methanol |
| D-123 | I.Ka-2 | fenpropimorph |
| D-124 | I.Ka-2 | Metalaxyl |
| D-125 | I.Ka-2 | Benalaxyl |
| D-126 | I.Ka-2 | Thiophanate-methyl |
| D-127 | I.Ka-2 | Carbendazim |
| D-128 | I.Ka-2 | Metrafenone |
| D-129 | I.Ka-2 | Pyrimethanil |
| D-130 | I.Ka-2 | Iprodione |
| D-131 | I.Ka-2 | Vinclozolin |
| D-132 | I.Ka-2 | Fludioxonil |
| D-133 | I.Ka-2 | dimethomorph |
| D-134 | I.Ka-2 | oxathiapiprolin |
| D-135 | I.Ka-2 | metiram |
| D-136 | I.Ka-2 | mancozeb |
| D-137 | I.Ka-2 | chlorothalonil |
| D-138 | I.Ka-2 | dithianon |
| D-139 | I.Ka-2 | Dipymetitrone |
| D-140 | I.Ka-2 | prohexadione-calcium |
| D-141 | I.Ka-2 | 3-(5-fluoro-3,3,4,4-tetramethyl-3,4-dihydroisoquinolin-1-yl)quinoline |
| D-142 | I.Ka-2 | 3-(4,4-difluoro-3,3-dimethyl-3,4-dihydroisoquinolin-1-yl)quinoline |
| D-143 | I.Ka-2 | 3-(4,4,5-trifluoro-3,3-dimethyl-3,4-dihydroisoquinolin-1-yl)quinoline |
| D-144 | I.Ka-2 | 9-fluoro-2,2-dimethyl-5-(3-quinolyl)-3H 1,4-benzoxazepine |
| D-145 | I.Ka-3 | Pyraclostrobin |
| D-146 | I.Ka-3 | Azoxystrobin |
| D-147 | I.Ka-3 | Trifloxystrobin |
| D-148 | I.Ka-3 | Picoxystrobin |
| D-149 | I.Ka-3 | Fluoxastrobin |
| D-150 | I.Ka-3 | Dimoxystrobin |
| D-151 | I.Ka-3 | Kresoxim-methyl |
| D-152 | I.Ka-3 | (2E,3Z)-5-[[1-(2,4-dichlorophenyl)-1H-pyrazol-3-yl]oxy]-2-(methoxyimino)-N,3-dimethyl-pent-3-enamide |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-153 | I.Ka-3 | (2E,3Z)-5-[[1-(4-chlorophenyl)-1H-pyrazol-3-yl]oxy]-2-(methoxyimino)-N,3-dimethyl-pent-3-enamide |
| D-154 | I.Ka-3 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-155 | I.Ka-3 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-156 | I.Ka-3 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-157 | I.Ka-3 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-158 | I.Ka-3 | (3S,6S,7R,8R)-3-[[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-159 | I.Ka-3 | Fluxapyroxad |
| D-160 | I.Ka-3 | Boscalid |
| D-161 | I.Ka-3 | Bixafen |
| D-162 | I.Ka-3 | Isopyrazam |
| D-163 | I.Ka-3 | Benzovindiflupyr |
| D-164 | I.Ka-3 | Fluopyram |
| D-165 | I.Ka-3 | N-[(5-chloro-2-isopropyl-phenyl)methyl]-N-cyclopropyl-5-fluoro-1,3-dimethyl-pyrazole-4-carboxamide |
| D-166 | I.Ka-3 | Sedaxane |
| D-167 | I.Ka-3 | Penflufen |
| D-168 | I.Ka-3 | N-[2-(2,4-dichlorophenyl)-2-methoxy-1-methyl-ethyl]-3-(difluoromethyl)-1-methyl-pyrazole-4-carboxamide |
| D-169 | I.Ka-3 | 3 (difluoromethyl)-1-methyl-N-(1,1,3-trimethylindan-4-yl)pyrazole-4-carboxamide |
| D-170 | I.Ka-3 | 3 (trifluoromethyl)-1-methyl-N-(1,1,3-trimethylindan-4-yl)pyrazole-4-carboxamide |
| D-171 | I.Ka-3 | 1,3-dimethyl-N-(1,1,3-trimethylindan-4-yl)pyrazole-4-carboxamide |
| D-172 | I.Ka-3 | 3-(trifluorometh¬yl)-1,5-dimethyl-N-(1,1,3-trimethylindan-4-yl)pyrazole-4-carboxamide |
| D-173 | I.Ka-3 | 1,3,5-trimethyl-N-(1,1,3-trimethylindan-4-yl)pyrazole-4-carboxamide |
| D-174 | I.Ka-3 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-175 | I.Ka-3 | Ametoctradin |
| D-176 | I.Ka-3 | epoxiconazole |
| D-177 | I.Ka-3 | metconazole |
| D-178 | I.Ka-3 | prothioconazole |
| D-179 | I.Ka-3 | difenoconazole |
| D-180 | I.Ka-3 | fluquinconazole |
| D-181 | I.Ka-3 | propiconazole |
| D-182 | I.Ka-3 | tebuconazole |
| D-183 | I.Ka-3 | 2-[2-chloro-4-(4-chlorophenoxy)phenyl]-1 (1,2,4-triazol-1-yl)pentan-2-ol |
| D-184 | I.Ka-3 | 1-[4-(4-chlorophenoxy)-2-(trifluoromethyl)phenyl]-1 cyclopropyl-2-(1,2,4-triazol-1-yl)ethanol |
| D-185 | I.Ka-3 | 2-[4-(4-chlorophenoxy)-2-(trifluoromethyl)phenyl]-1-(1,2,4-triazol-1-yl)butan-2-ol |
| D-186 | I.Ka-3 | 2-[2-chloro-4-(4-chlorophenoxy)phenyl]-1-(1,2,4-triazol-1-yl)butan-2-ol |
| D-187 | I.Ka-3 | 2-[4-(4-chlorophenoxy)-2-(trifluoromethyl)phenyl]-3-methyl-1-(1,2,4-triazol-1-yl)butan-2-ol |
| D-188 | I.Ka-3 | 2-[4-(4-chlorophenoxy)-2-(trifluoromethyl)phenyl]-1-(1,2,4-triazol-1-yl)propan-2-ol |
| D-189 | I.Ka-3 | 2-[2-chloro-4-(4-chlorophenoxy)phenyl]-3-methyl-1-(1,2,4-triazol-1-yl)butan-2-ol |
| D-190 | I.Ka-3 | 2-[4-(4-chlorophenoxy)-2-(trifluoromethyl)phenyl]-1-(1,2,4-triazol-1-yl)pentan-2-ol |
| D-191 | I.Ka-3 | 2-[4-(4-fluorophenoxy)-2-(trifluoromethyl)phenyl]-1-(1,2,4-triazol-1-yl)propan-2-ol |
| D-192 | I.Ka-3 | 2-[2-chloro-4-(4-chlorophenoxy)phenyl]-1-(1,2,4-triazol-1-yl)pent-3-yn-2-ol |
| D-193 | I.Ka-3 | prochloraz |
| D-194 | I.Ka-3 | [3-(4-chloro-2-fluoro-phenyl)-5-(2,4-difluorophenyl)isoxazol-4-yl]-(3-pyridyl)methanol |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
| --- | --- | --- |
| D-195 | I.Ka-3 | fenpropimorph |
| D-196 | I.Ka-3 | Metalaxyl |
| D-197 | I.Ka-3 | Benalaxyl |
| D-198 | I.Ka-3 | Thiophanate-methyl |
| D-199 | I.Ka-3 | Carbendazim |
| D-200 | I.Ka-3 | Metrafenone |
| D-201 | I.Ka-3 | Pyrimethanil |
| D-202 | I.Ka-3 | Iprodione |
| D-203 | I.Ka-3 | Vinclozolin |
| D-204 | I.Ka-3 | Fludioxonil |
| D-205 | I.Ka-3 | dimethomorph |
| D-206 | I.Ka-3 | oxathiapiprolin |
| D-207 | I.Ka-3 | metiram |
| D-208 | I.Ka-3 | mancozeb |
| D-209 | I.Ka-3 | chlorothalonil |
| D-210 | I.Ka-3 | dithianon |
| D-211 | I.Ka-3 | Dipymetitrone |
| D-212 | I.Ka-3 | prohexadione-calcium |
| D-213 | I.Ka-3 | 3-(5-fluoro-3,3,4,4-tetramethyl-3,4-dihydroisoquinolin-1-yl)quinoline |
| D-214 | I.Ka-3 | 3-(4,4-difluoro-3,3-dimethyl-3,4-dihydroisoquinolin-1-yl)quinoline |
| D-215 | I.Ka-3 | 3-(4,4,5-trifluoro-3,3-dimethyl-3,4-dihydroisoquinolin-1-yl)quinoline |
| D-216 | I.Ka-3 | 9-fluoro-2,2-dimethyl-5-(3-quinolyl)-3H 1,4-benzoxazepine |
| D-217 | I.Ka-4 | Pyraclostrobin |
| D-218 | I.Ka-4 | Azoxystrobin |
| D-219 | I.Ka-4 | Trifloxystrobin |
| D-220 | I.Ka-4 | Picoxystrobin |
| D-221 | I.Ka-4 | Fluoxastrobin |
| D-222 | I.Ka-4 | Dimoxystrobin |
| D-223 | I.Ka-4 | Kresoxim-methyl |
| D-224 | I.Ka-4 | (2E,3Z)-5-[[1-(2,4-dichlorophenyl)-1H-pyrazol-3-yl]oxy]-2-(methoxyimino)-N,3-dimethyl-pent-3-enamide |
| D-225 | I.Ka-4 | (2E,3Z)-5-[[1-(4-chlorophenyl)-1H-pyrazol-3-yl]oxy]-2-(methoxyimino)-N,3-dimethyl-pent-3-enamide |
| D-226 | I.Ka-4 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-227 | I.Ka-4 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-228 | I.Ka-4 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-229 | I.Ka-4 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-230 | I.Ka-4 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-231 | I.Ka-4 | Fluxapyroxad |
| D-232 | I.Ka-4 | Boscalid |
| D-233 | I.Ka-4 | Bixafen |
| D-234 | I.Ka-4 | Isopyrazam |
| D-235 | I.Ka-4 | Benzovindiflupyr |
| D-236 | I.Ka-4 | Fluopyram |
| D-237 | I.Ka-4 | N-[(5-chloro-2-isopropyl-phenyl)methyl]-N-cyclopropyl-5-fluoro-1,3-dimethyl-pyrazole-4-carboxamide |
| D-238 | I.Ka-4 | Sedaxane |
| D-239 | I.Ka-4 | Penflufen |
| D-240 | I.Ka-4 | N-[2-(2,4-dichlorophenyl)-2-methoxy-1-methyl-ethyl]-3-(difluoromethyl)-1-methyl-pyrazole-4-carboxamide |
| D-241 | I.Ka-4 | 3 (difluoromethyl)-1-methyl-N-(1,1,3-trimethylindan-4-yl)pyrazole-4-carboxamide |
| D-242 | I.Ka-4 | 3 (trifluoromethyl)-1-methyl-N-(1,1,3-trimethylindan-4-yl)pyrazole-4-carboxamide |
| D-243 | I.Ka-4 | 1,3-dimethyl-N-(1,1,3-trimethylindan-4-yl)pyrazole-4-carboxamide |
| D-244 | I.Ka-4 | 3-(trifluorometh¬yl)-1,5-dimethyl-N-(1,1,3-trimethylindan-4-yl)pyrazole-4-carboxamide |
| D-245 | I.Ka-4 | 1,3,5-trimethyl-N-(1,1,3-trimethylindan-4-yl)pyrazole-4-carboxamide |
| D-246 | I.Ka-4 | 1-[3-chloro-2-[[[1-(4-chlorophenyl)-1H-pyrazol-3-yl]oxy]methyl]phenyl]-1,4-dihydro-4-methyl-5H-tetrazol-5-one |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-247 | I.Ka-4 | Ametoctradin |
| D-248 | I.Ka-4 | epoxiconazole |
| D-249 | I.Ka-4 | metconazole |
| D-250 | I.Ka-4 | prothioconazole |
| D-251 | I.Ka-4 | difenoconazole |
| D-252 | I.Ka-4 | fluquinconazole |
| D-253 | I.Ka-4 | propiconazole |
| D-254 | I.Ka-4 | tebuconazole |
| D-255 | I.Ka-4 | 2-[2-chloro-4-(4-chlorophenoxy)phenyl]-1 (1,2,4-triazol-1-yl)pentan-2-ol |
| D-256 | I.Ka-4 | 1-[4-(4-chlorophenoxy)-2-(trifluoromethyl)phenyl]-1 cyclopropyl-2-(1,2,4-triazol-1-yl)ethanol |
| D-257 | I.Ka-4 | 2-[4-(4-chlorophenoxy)-2-(trifluoromethyl)phenyl]-1-(1,2,4-triazol-1-yl)butan-2-ol |
| D-258 | I.Ka-4 | 2-[2-chloro-4-(4-chlorophenoxy)phenyl]-1-(1,2,4-triazol-1-yl)butan-2-ol |
| D-259 | I.Ka-4 | 2-[4-(4-chlorophenoxy)-2-(trifluoromethyl)phenyl]-3-methyl-1-(1,2,4-triazol-1-yl)butan-2-ol |
| D-260 | I.Ka-4 | 2-[4-(4-chlorophenoxy)-2-(trifluoromethyl)phenyl]-1-(1,2,4-triazol-1-yl)propan-2-ol |
| D-261 | I.Ka-4 | 2-[2-chloro-4-(4-chlorophenoxy)phenyl]-3-methyl-1-(1,2,4-triazol-1-yl)butan-2-ol |
| D-262 | I.Ka-4 | 2-[4-(4-chlorophenoxy)-2-(trifluoromethyl)phenyl]-1-(1,2,4-triazol-1-yl)pentan-2-ol |
| D-263 | I.Ka-4 | 2-[4-(4-fluorophenoxy)-2-(trifluoromethyl)phenyl]-1-(1,2,4-triazol-1-yl)propan-2-ol |
| D-264 | I.Ka-4 | 2-[2-chloro-4-(4-chlorophenoxy)phenyl]-1-(1,2,4-triazol-1-yl)pent-3-yn-2-ol |
| D-265 | I.Ka-4 | prochloraz |
| D-266 | I.Ka-4 | [3-(4-chloro-2-fluoro-phenyl)-5-(2,4-difluorophenyl)isoxazol-4-yl]-(3-pyridyl)methanol |
| D-267 | I.Ka-4 | fenpropimorph |
| D-268 | I.Ka-4 | Metalaxyl |
| D-269 | I.Ka-4 | Benalaxyl |
| D-270 | I.Ka-4 | Thiophanate-methyl |
| D-271 | I.Ka-4 | Carbendazim |
| D-272 | I.Ka-4 | Metrafenone |
| D-273 | I.Ka-4 | Pyrimethanil |
| D-274 | I.Ka-4 | Iprodione |
| D-275 | I.Ka-4 | Vinclozolin |
| D-276 | I.Ka-4 | Fludioxonil |
| D-277 | I.Ka-4 | dimethomorph |
| D-278 | I.Ka-4 | oxathiapiprolin |
| D-279 | I.Ka-4 | metiram |
| D-280 | I.Ka-4 | mancozeb |
| D-281 | I.Ka-4 | chlorothalonil |
| D-282 | I.Ka-4 | dithianon |
| D-283 | I.Ka-4 | Dipymetitrone |
| D-284 | I.Ka-4 | prohexadione-calcium |
| D-285 | I.Ka-4 | 3-(5-fluoro-3,3,4,4-tetramethyl-3,4-dihydroisoquinolin-1-yl)quinoline |
| D-286 | I.Ka-4 | 3-(4,4-difluoro-3,3-dimethyl-3,4-dihydroisoquinolin-1-yl)quinoline |
| D-287 | I.Ka-4 | 3-(4,4,5-trifluoro-3,3-dimethyl-3,4-dihydroisoquinolin-1-yl)quinoline |
| D-288 | I.Ka-4 | 9-fluoro-2,2-dimethyl-5-(3-quinolyl)-3H 1,4-benzoxazepine |
| D-289 | I.Ka-5 | Pyraclostrobin |
| D-290 | I.Ka-5 | Azoxystrobin |
| D-291 | I.Ka-5 | Trifloxystrobin |
| D-292 | I.Ka-5 | Picoxystrobin |
| D-293 | I.Ka-5 | Fluoxastrobin |
| D-294 | I.Ka-5 | Dimoxystrobin |
| D-295 | I.Ka-5 | Kresoxim-methyl |
| D-296 | I.Ka-5 | (2E,3Z)-5-[[1-(2,4-dichlorophenyl)-1H-pyrazol-3-yl]oxy]-2-(methoxyimino)-N,3-dimethyl-pent-3-enamide |
| D-297 | I.Ka-5 | (2E,3Z)-5-[[1-(4-chlorophenyl)-1H-pyrazol-3-yl]oxy]-2-(methoxyimino)-N,3-dimethyl-pent-3-enamide |
| D-298 | I.Ka-5 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-299 | I.Ka-5 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-300 | I.Ka-5 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-301 | I.Ka-5 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-302 | I.Ka-5 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-303 | I.Ka-5 | Fluxapyroxad |
| D-304 | I.Ka-5 | Boscalid |
| D-305 | I.Ka-5 | Bixafen |
| D-306 | I.Ka-5 | Isopyrazam |
| D-307 | I.Ka-5 | Benzovindiflupyr |
| D-308 | I.Ka-5 | Fluopyram |
| D-309 | I.Ka-5 | N-[(5-chloro-2-isopropyl-phenyl)methyl]-N-cyclopropyl-5-fluoro-1,3-dimethyl-pyrazole-4-carboxamide |
| D-310 | I.Ka-5 | Sedaxane |
| D-311 | I.Ka-5 | Penflufen |
| D-312 | I.Ka-5 | N-[2-(2,4-dichlorophenyl)-2-methoxy-1-methyl-ethyl]-3-(difluoromethyl)-1-methyl-pyrazole-4-carboxamide |
| D-313 | I.Ka-5 | 3 (difluoromethyl)-1-methyl-N-(1,1,3-trimethylindan-4-yl)pyrazole-4-carboxamide |
| D-314 | I.Ka-5 | 3 (trifluoromethyl)-1-methyl-N-(1,1,3-trimethylindan-4-yl)pyrazole-4-carboxamide |
| D-315 | I.Ka-5 | 1,3-dimethyl-N-(1,1,3-trimethylindan-4-yl)pyrazole-4-carboxamide |
| D-316 | I.Ka-5 | 3-(trifluorometh¬yl)-1,5-dimethyl-N-(1,1,3-trimethylindan-4-yl)pyrazole-4-carboxamide |
| D-317 | I.Ka-5 | 1,3,5-trimethyl-N-(1,1,3-trimethylindan-4-yl)pyrazole-4-carboxamide |
| D-318 | I.Ka-5 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-319 | I.Ka-5 | Ametoctradin |
| D-320 | I.Ka-5 | epoxiconazole |
| D-321 | I.Ka-5 | metconazole |
| D-322 | I.Ka-5 | prothioconazole |
| D-323 | I.Ka-5 | difenoconazole |
| D-324 | I.Ka-5 | fluquinconazole |
| D-325 | I.Ka-5 | propiconazole |
| D-326 | I.Ka-5 | tebuconazole |
| D-327 | I.Ka-5 | 2-[2-chloro-4-(4-chlorophenoxy)phenyl]-1 (1,2,4-triazol-1-yl)pentan-2-ol |
| D-328 | I.Ka-5 | 1-[4-(4-chlorophenoxy)-2-(trifluoromethyl)phenyl]-1 cyclopropyl-2-(1,2,4-triazol-1-yl)ethanol |
| D-329 | I.Ka-5 | 2-[4-(4-chlorophenoxy)-2-(trifluoromethyl)phenyl]-1-(1,2,4-triazol-1-yl)butan-2-ol |
| D-330 | I.Ka-5 | 2-[2-chloro-4-(4-chlorophenoxy)phenyl]-1-(1,2,4-triazol-1-yl)butan-2-ol |
| D-331 | I.Ka-5 | 2-[4-(4-chlorophenoxy)-2-(trifluoromethyl)phenyl]-3-methyl-1-(1,2,4-triazol-1-yl)butan-2-ol |
| D-332 | I.Ka-5 | 2-[4-(4-chlorophenoxy)-2-(trifluoromethyl)phenyl]-1-(1,2,4-triazol-1-yl)propan-2-ol |
| D-333 | I.Ka-5 | 2-[2-chloro-4-(4-chlorophenoxy)phenyl]-3-methyl-1-(1,2,4-triazol-1-yl)butan-2-ol |
| D-334 | I.Ka-5 | 2-[4-(4-chlorophenoxy)-2-(trifluoromethyl)phenyl]-1-(1,2,4-triazol-1-yl)pentan-2-ol |
| D-335 | I.Ka-5 | 2-[4-(4-fluorophenoxy)-2-(trifluoromethyl)phenyl]-1-(1,2,4-triazol-1-yl)propan-2-ol |
| D-336 | I.Ka-5 | 2-[2-chloro-4-(4-chlorophenoxy)phenyl]-1-(1,2,4-triazol-1-yl)pent-3-yn-2-ol |
| D-337 | I.Ka-5 | prochloraz |
| D-338 | I.Ka-5 | [3-(4-chloro-2-fluoro-phenyl)-5-(2,4-difluorophenyl)isoxazol-4-yl]-(3-pyridyl)methanol |
| D-339 | I.Ka-5 | fenpropimorph |
| D-340 | I.Ka-5 | Metalaxyl |
| D-341 | I.Ka-5 | Benalaxyl |
| D-342 | I.Ka-5 | Thiophanate-methyl |
| D-343 | I.Ka-5 | Carbendazim |
| D-344 | I.Ka-5 | Metrafenone |
| D-345 | I.Ka-5 | Pyrimethanil |
| D-346 | I.Ka-5 | Iprodione |
| D-347 | I.Ka-5 | Vinclozolin |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-348 | I.Ka-5 | Fludioxonil |
| D-349 | I.Ka-5 | dimethomorph |
| D-350 | I.Ka-5 | oxathiapiprolin |
| D-351 | I.Ka-5 | metiram |
| D-352 | I.Ka-5 | mancozeb |
| D-353 | I.Ka-5 | chlorothalonil |
| D-354 | I.Ka-5 | dithianon |
| D-355 | I.Ka-5 | Dipymetitrone |
| D-356 | I.Ka-5 | prohexadione-calcium |
| D-357 | I.Ka-5 | 3-(5-fluoro-3,3,4,4-tetramethyl-3,4-dihydroisoquinolin-1-yl)quinoline |
| D-358 | I.Ka-5 | 3-(4,4-difluoro-3,3-dimethyl-3,4-dihydroisoquinolin-1-yl)quinoline |
| D-359 | I.Ka-5 | 3-(4,4,5-trifluoro-3,3-dimethyl-3,4-dihydroisoquinolin-1-yl)quinoline |
| D-360 | I.Ka-5 | 9-fluoro-2,2-dimethyl-5-(3-quinolyl)-3H 1,4-benzoxazepine |
| D-361 | I.Ka-6 | Pyraclostrobin |
| D-362 | I.Ka-6 | Azoxystrobin |
| D-363 | I.Ka-6 | Trifloxystrobin |
| D-364 | I.Ka-6 | Picoxystrobin |
| D-365 | I.Ka-6 | Fluoxastrobin |
| D-366 | I.Ka-6 | Dimoxystrobin |
| D-367 | I.Ka-6 | Kresoxim-methyl |
| D-368 | I.Ka-6 | (2E,3Z)-5-[[1-(2,4-dichlorophenyl)-1H-pyrazol-3-yl]oxy]-2-(methoxyimino)-N,3-dimethyl-pent-3-enamide |
| D-369 | I.Ka-6 | (2E,3Z)-5-[[1-(4-chlorophenyl)-1H-pyrazol-3-yl]oxy]-2-(methoxyimino)-N,3-dimethyl-pent-3-enamide |
| D-370 | I.Ka-6 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-371 | I.Ka-6 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-372 | I.Ka-6 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-373 | I.Ka-6 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-374 | I.Ka-6 | (3S,6S,7R,8R)-3-[[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-375 | I.Ka-6 | Fluxapyroxad |
| D-376 | I.Ka-6 | Boscalid |
| D-377 | I.Ka-6 | Bixafen |
| D-378 | I.Ka-6 | Isopyrazam |
| D-379 | I.Ka-6 | Benzovindiflupyr |
| D-380 | I.Ka-6 | Fluopyram |
| D-381 | I.Ka-6 | N-[(5-chloro-2-isopropyl-phenyl)methyl]-N-cyclopropyl-5-fluoro-1,3-dimethyl-pyrazole-4-carboxamide |
| D-382 | I.Ka-6 | Sedaxane |
| D-383 | I.Ka-6 | Penflufen |
| D-384 | I.Ka-6 | N-[2-(2,4-dichlorophenyl)-2-methoxy-1-methyl-ethyl]-3-(difluoromethyl)-1-methyl-pyrazole-4-carboxamide |
| D-385 | I.Ka-6 | 3 (difluoromethyl)-1-methyl-N-(1,1,3-trimethylindan-4-yl)pyrazole-4-carboxamide |
| D-386 | I.Ka-6 | 3 (trifluoromethyl)-1-methyl-N-(1,1,3-trimethylindan-4-yl)pyrazole-4-carboxamide |
| D-387 | I.Ka-6 | 1,3-dimethyl-N-(1,1,3-trimethylindan-4-yl)pyrazole-4-carboxamide |
| D-388 | I.Ka-6 | 3-(trifluorometh¬yl)-1,5-dimethyl-N-(1,1,3-trimethylindan-4-yl)pyrazole-4-carboxamide |
| D-389 | I.Ka-6 | 1,3,5-trimethyl-N-(1,1,3-trimethylindan-4-yl)pyrazole-4-carboxamide |
| D-390 | I.Ka-6 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-391 | I.Ka-6 | Ametoctradin |
| D-392 | I.Ka-6 | epoxiconazole |
| D-393 | I.Ka-6 | metconazole |
| D-394 | I.Ka-6 | prothioconazole |
| D-395 | I.Ka-6 | difenoconazole |
| D-396 | I.Ka-6 | fluquinconazole |
| D-397 | I.Ka-6 | propiconazole |
| D-398 | I.Ka-6 | tebuconazole |
| D-399 | I.Ka-6 | 2-[2-chloro-4-(4-chlorophenoxy)phenyl]-1 (1,2,4-triazol-1-yl)pentan-2-ol |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
| --- | --- | --- |
| D-400 | I.Ka-6 | 1-[4-(4-chlorophenoxy)-2-(trifluoromethyl)phenyl]-1 cyclopropyl-2-(1,2,4-triazol-1-yl)ethanol |
| D-401 | I.Ka-6 | 2-[4-(4-chlorophenoxy)-2-(trifluoromethyl)phenyl]-1-(1,2,4-triazol-1-yl)butan-2-ol |
| D-402 | I.Ka-6 | 2-[2-chloro-4-(4-chlorophenoxy)phenyl]-1-(1,2,4-triazol-1-yl)butan-2-ol |
| D-403 | I.Ka-6 | 2-[4-(4-chlorophenoxy)-2-(trifluoromethyl)phenyl]-3-methyl-1-(1,2,4-triazol-1-yl)butan-2-ol |
| D-404 | I.Ka-6 | 2-[4-(4-chlorophenoxy)-2-(trifluoromethyl)phenyl]-1-(1,2,4-triazol-1-yl)propan-2-ol |
| D-405 | I.Ka-6 | 2-[2-chloro-4-(4-chlorophenoxy)phenyl]-3-methyl-1-(1,2,4-triazol-1-yl)butan-2-ol |
| D-406 | I.Ka-6 | 2-[4-(4-chlorophenoxy)-2-(trifluoromethyl)phenyl]-1-(1,2,4-triazol-1-yl)pentan-2-ol |
| D-407 | I.Ka-6 | 2-[4-(4-fluorophenoxy)-2-(trifluoromethyl)phenyl]-1-(1,2,4-triazol-1-yl)propan-2-ol |
| D-408 | I.Ka-6 | 2-[2-chloro-4-(4-chlorophenoxy)phenyl]-1-(1,2,4-triazol-1-yl)pent-3-yn-2-ol |
| D-409 | I.Ka-6 | prochloraz |
| D-410 | I.Ka-6 | [3-(4-chloro-2-fluoro-phenyl)-5-(2,4-difluorophenyl)isoxazol-4-yl]-(3-pyridyl)methanol |
| D-411 | I.Ka-6 | fenpropimorph |
| D-412 | I.Ka-6 | Metalaxyl |
| D-413 | I.Ka-6 | Benalaxyl |
| D-414 | I.Ka-6 | Thiophanate-methyl |
| D-415 | I.Ka-6 | Carbendazim |
| D-416 | I.Ka-6 | Metrafenone |
| D-417 | I.Ka-6 | Pyrimethanil |
| D-418 | I.Ka-6 | Iprodione |
| D-419 | I.Ka-6 | Vinclozolin |
| D-420 | I.Ka-6 | Fludioxonil |
| D-421 | I.Ka-6 | dimethomorph |
| D-422 | I.Ka-6 | oxathiapiprolin |
| D-423 | I.Ka-6 | metiram |
| D-424 | I.Ka-6 | mancozeb |
| D-425 | I.Ka-6 | chlorothalonil |
| D-426 | I.Ka-6 | dithianon |
| D-427 | I.Ka-6 | Dipymetitrone |
| D-428 | I.Ka-6 | prohexadione-calcium |
| D-429 | I.Ka-6 | 3-(5-fluoro-3,3,4,4-tetramethyl-3,4-dihydroisoquinolin-1-yl)quinoline |
| D-430 | I.Ka-6 | 3-(4,4-difluoro-3,3-dimethyl-3,4-dihydroisoquinolin-1-yl)quinoline |
| D-431 | I.Ka-6 | 3-(4,4,5-trifluoro-3,3-dimethyl-3,4-dihydroisoquinolin-1-yl)quinoline |
| D-432 | I.Ka-6 | 9-fluoro-2,2-dimethyl-5-(3-quinolyl)-3H 1,4-benzoxazepine |
| D-433 | I.Ka-7 | Pyraclostrobin |
| D-434 | I.Ka-7 | Azoxystrobin |
| D-435 | I.Ka-7 | Trifloxystrobin |
| D-436 | I.Ka-7 | Picoxystrobin |
| D-437 | I.Ka-7 | Fluoxastrobin |
| D-438 | I.Ka-7 | Dimoxystrobin |
| D-439 | I.Ka-7 | Kresoxim-methyl |
| D-440 | I.Ka-7 | (2E,3Z)-5-[[1-(2,4-dichlorophenyl)-1H-pyrazol-3-yl]oxy]-2-(methoxyimino)-N,3-dimethyl-pent-3-enamide |
| D-441 | I.Ka-7 | (2E,3Z)-5-[[1-(4-chlorophenyl)-1H-pyrazol-3-yl]oxy]-2-(methoxyimino)-N,3-dimethyl-pent-3-enamide |
| D-442 | I.Ka-7 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-443 | I.Ka-7 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-444 | I.Ka-7 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-445 | I.Ka-7 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-446 | I.Ka-7 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-447 | I.Ka-7 | Fluxapyroxad |
| D-448 | I.Ka-7 | Boscalid |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-449 | I.Ka-7 | Bixafen |
| D-450 | I.Ka-7 | Isopyrazam |
| D-451 | I.Ka-7 | Benzovindiflupyr |
| D-452 | I.Ka-7 | Fluopyram |
| D-453 | I.Ka-7 | N-[(5-chloro-2-isopropyl-phenyl)methyl]-N-cyclopropyl-5-fluoro-1,3-dimethyl-pyrazole-4-carboxamide |
| D-454 | I.Ka-7 | Sedaxane |
| D-455 | I.Ka-7 | Penflufen |
| D-456 | I.Ka-7 | N-[2-(2,4-dichlorophenyl)-2-methoxy-1-methyl-ethyl]-3-(difluoromethyl)-1-methyl-pyrazole-4-carboxamide |
| D-457 | I.Ka-7 | 3 (difluoromethyl)-1-methyl-N-(1,1,3-trimethylindan-4-yl)pyrazole-4-carboxamide |
| D-458 | I.Ka-7 | 3 (trifluoromethyl)-1-methyl-N-(1,1,3-trimethylindan-4-yl)pyrazole-4-carboxamide |
| D-459 | I.Ka-7 | 1,3-dimethyl-N-(1,1,3-trimethylindan-4-yl)pyrazole-4-carboxamide |
| D-460 | I.Ka-7 | 3-(trifluorometh¬yl)-1,5-dimethyl-N-(1,1,3-trimethylindan-4-yl)pyrazole-4-carboxamide |
| D-461 | I.Ka-7 | 1,3,5-trimethyl-N-(1,1,3-trimethylindan-4-yl)pyrazole-4-carboxamide |
| D-462 | I.Ka-7 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-463 | I.Ka-7 | Ametoctradin |
| D-464 | I.Ka-7 | epoxiconazole |
| D-465 | I.Ka-7 | metconazole |
| D-466 | I.Ka-7 | prothioconazole |
| D-467 | I.Ka-7 | difenoconazole |
| D-468 | I.Ka-7 | fluquinconazole |
| D-469 | I.Ka-7 | propiconazole |
| D-470 | I.Ka-7 | tebuconazole |
| D-471 | I.Ka-7 | 2-[2-chloro-4-(4-chlorophenoxy)phenyl]-1 (1,2,4-triazol-1-yl)pentan-2-ol |
| D-472 | I.Ka-7 | 1-[4-(4-chlorophenoxy)-2-(trifluoromethyl)phenyl]-1 cyclopropyl-2-(1,2,4-triazol-1-yl)ethanol |
| D-473 | I.Ka-7 | 2-[4-(4-chlorophenoxy)-2-(trifluoromethyl)phenyl]-1-(1,2,4-triazol-1-yl)butan-2-ol |
| D-474 | I.Ka-7 | 2-[2-chloro-4-(4-chlorophenoxy)phenyl]-1-(1,2,4-triazol-1-yl)butan-2-ol |
| D-475 | I.Ka-7 | 2-[4-(4-chlorophenoxy)-2-(trifluoromethyl)phenyl]-3-methyl-1-(1,2,4-triazol-1-yl)butan-2-ol |
| D-476 | I.Ka-7 | 2-[4-(4-chlorophenoxy)-2-(trifluoromethyl)phenyl]-1-(1,2,4-triazol-1-yl)propan-2-ol |
| D-477 | I.Ka-7 | 2-[2-chloro-4-(4-chlorophenoxy)phenyl]-3-methyl-1-(1,2,4-triazol-1-yl)butan-2-ol |
| D-478 | I.Ka-7 | 2-[4-(4-chlorophenoxy)-2-(trifluoromethyl)phenyl]-1-(1,2,4-triazol-1-yl)pentan-2-ol |
| D-479 | I.Ka-7 | 2-[4-(4-fluorophenoxy)-2-(trifluoromethyl)phenyl]-1-(1,2,4-triazol-1-yl)propan-2-ol |
| D-480 | I.Ka-7 | 2-[2-chloro-4-(4-chlorophenoxy)phenyl]-1-(1,2,4-triazol-1-yl)pent-3-yn-2-ol |
| D-481 | I.Ka-7 | prochloraz |
| D-482 | I.Ka-7 | [3-(4-chloro-2-fluoro-phenyl)-5-(2,4-difluorophenyl)isoxazol-4-yl]-(3-pyridyl)methanol |
| D-483 | I.Ka-7 | fenpropimorph |
| D-484 | I.Ka-7 | Metalaxyl |
| D-485 | I.Ka-7 | Benalaxyl |
| D-486 | I.Ka-7 | Thiophanate-methyl |
| D-487 | I.Ka-7 | Carbendazim |
| D-488 | I.Ka-7 | Metrafenone |
| D-489 | I.Ka-7 | Pyrimethanil |
| D-490 | I.Ka-7 | Iprodione |
| D-491 | I.Ka-7 | Vinclozolin |
| D-492 | I.Ka-7 | Fludioxonil |
| D-493 | I.Ka-7 | dimethomorph |
| D-494 | I.Ka-7 | oxathiapiprolin |
| D-495 | I.Ka-7 | metiram |
| D-496 | I.Ka-7 | mancozeb |
| D-497 | I.Ka-7 | chlorothalonil |
| D-498 | I.Ka-7 | dithianon |
| D-499 | I.Ka-7 | Dipymetitrone |
| D-500 | I.Ka-7 | prohexadione-calcium |
| D-501 | I.Ka-7 | 3-(5-fluoro-3,3,4,4-tetramethyl-3,4-dihydroisoquinolin-1-yl)quinoline |
| D-502 | I.Ka-7 | 3-(4,4-difluoro-3,3-dimethyl-3,4-dihydroisoquinolin-1-yl)quinoline |

TABLE D-continued

Individual preferred pesticidal compositions D-1 to D-432 comprising a particular
compound of formula I, namely one of I.Aa-1 to I.Aa-5 and I.Ba-1 as component I (from Table C
above) and a particular second pesticidal compound as component II:

| composition | component I compound from Table B aove | component II |
|---|---|---|
| D-503 | I.Ka-7 | 3-(4,4,5-trifluoro-3,3-dimethyl-3,4-dihydroisoquinolin-1-yl)quinoline |
| D-504 | I.Ka-7 | 9-fluoro-2,2-dimethyl-5-(3-quinolyl)-3H 1,4-benzoxazepine |
| D-505 | I.Ka-8 | Pyraclostrobin |
| D-506 | I.Ka-8 | Azoxystrobin |
| D-507 | I.Ka-8 | Trifloxystrobin |
| D-508 | I.Ka-8 | Picoxystrobin |
| D-509 | I.Ka-8 | Fluoxastrobin |
| D-510 | I.Ka-8 | Dimoxystrobin |
| D-511 | I.Ka-8 | Kresoxim-methyl |
| D-512 | I.Ka-8 | (2E,3Z)-5-[[1-(2,4-dichlorophenyl)-1H-pyrazol-3-yl]oxy]-2-(methoxyimino)-N,3-dimethyl-pent-3-enamide |
| D-513 | I.Ka-8 | (2E,3Z)-5-[[1-(4-chlorophenyl)-1H-pyrazol-3-yl]oxy]-2-(methoxyimino)-N,3-dimethyl-pent-3-enamide |
| D-514 | I.Ka-8 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-515 | I.Ka-8 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-516 | I.Ka-8 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-517 | I.Ka-8 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-518 | I.Ka-8 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-519 | I.Ka-8 | Fluxapyroxad |
| D-520 | I.Ka-8 | Boscalid |
| D-521 | I.Ka-8 | Bixafen |
| D-522 | I.Ka-8 | Isopyrazam |
| D-523 | I.Ka-8 | Benzovindiflupyr |
| D-524 | I.Ka-8 | Fluopyram |
| D-525 | I.Ka-8 | N-[(5-chloro-2-isopropyl-phenyl)methyl]-N-cyclopropyl-5-fluoro-1,3-dimethyl-pyrazole-4-carboxamide |
| D-526 | I.Ka-8 | Sedaxane |
| D-527 | I.Ka-8 | Penflufen |
| D-528 | I.Ka-8 | N-[2-(2,4-dichlorophenyl)-2-methoxy-1-methyl-ethyl]-3-(difluoromethyl)-1-methyl-pyrazole-4-carboxamide |
| D-529 | I.Ka-8 | 3 (difluoromethyl)-1-methyl-N-(1,1,3-trimethylindan-4-yl)pyrazole-4-carboxamide |
| D-530 | I.Ka-8 | 3 (trifluoromethyl)-1-methyl-N-(1,1,3-trimethylindan-4-yl)pyrazole-4-carboxamide |
| D-531 | I.Ka-8 | 1,3-dimethyl-N-(1,1,3-trimethylindan-4-yl)pyrazole-4-carboxamide |
| D-532 | I.Ka-8 | 3-(trifluorometh¬yl)-1,5-dimethyl-N-(1,1,3-trimethylindan-4-yl)pyrazole-4-carboxamide |
| D-533 | I.Ka-8 | 1,3,5-trimethyl-N-(1,1,3-trimethylindan-4-yl)pyrazole-4-carboxamide |
| D-534 | I.Ka-8 | 1-[3-chloro-2-[[[1-(4-chlorophenyl)-1H-pyrazol-3-yl]oxy]methyl]phenyl]-1,4-dihydro-4-methyl5H-tetrazol-5-one |
| D-535 | I.Ka-8 | Ametoctradin |
| D-536 | I.Ka-8 | epoxiconazole |
| D-537 | I.Ka-8 | metconazole |
| D-538 | I.Ka-8 | prothioconazole |
| D-539 | I.Ka-8 | difenoconazole |
| D-540 | I.Ka-8 | fluquinconazole |
| D-541 | I.Ka-8 | propiconazole |
| D-542 | I.Ka-8 | tebuconazole |
| D-543 | I.Ka-8 | 2-[2-chloro-4-(4-chlorophenoxy)phenyl]-1 (1,2,4-triazol-1-yl)pentan-2-ol |
| D-544 | I.Ka-8 | 1-[4-(4-chlorophenoxy)-2-(trifluoromethyl)phenyl]-1 cyclopropyl-2-(1,2,4-triazol-1-yl)ethanol |
| D-545 | I.Ka-8 | 2-[4-(4-chlorophenoxy)-2-(trifluoromethyl)phenyl]-1-(1,2,4-triazol-1-yl)butan-2-ol |
| D-546 | I.Ka-8 | 2-[2-chloro-4-(4-chlorophenoxy)phenyl]-1-(1,2,4-triazol-1-yl)butan-2-ol |
| D-547 | I.Ka-8 | 2-[4-(4-chlorophenoxy)-2-(trifluoromethyl)phenyl]-3-methyl-1-(1,2,4-triazol-1-yl)butan-2-ol |
| D-548 | I.Ka-8 | 2-[4-(4-chlorophenoxy)-2-(trifluoromethyl)phenyl]-1-(1,2,4-triazol-1-yl)propan-2-ol |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-549 | I.Ka-8 | 2-[2-chloro-4-(4-chlorophenoxy)phenyl]-3-methyl-1-(1,2,4-triazol-1-yl)butan-2-ol |
| D-550 | I.Ka-8 | 2-[4-(4-chlorophenoxy)-2-(trifluoromethyl)phenyl]-1-(1,2,4-triazol-1-yl)pentan-2-ol |
| D-551 | I.Ka-8 | 2-[4-(4-fluorophenoxy)-2-(trifluoromethyl)phenyl]-1-(1,2,4-triazol-1-yl)propan-2-ol |
| D-552 | I.Ka-8 | 2-[2-chloro-4-(4-chlorophenoxy)phenyl]-1-(1,2,4-triazol-1-yl)pent-3-yn-2-ol |
| D-553 | I.Ka-8 | prochloraz |
| D-554 | I.Ka-8 | [3-(4-chloro-2-fluoro-phenyl)-5-(2,4-difluorophenyl)isoxazol-4-yl]-(3-pyridyl)methanol |
| D-555 | I.Ka-8 | fenpropimorph |
| D-556 | I.Ka-8 | Metalaxyl |
| D-557 | I.Ka-8 | Benalaxyl |
| D-558 | I.Ka-8 | Thiophanate-methyl |
| D-559 | I.Ka-8 | Carbendazim |
| D-560 | I.Ka-8 | Metrafenone |
| D-561 | I.Ka-8 | Pyrimethanil |
| D-562 | I.Ka-8 | Iprodione |
| D-563 | I.Ka-8 | Vinclozolin |
| D-564 | I.Ka-8 | Fludioxonil |
| D-565 | I.Ka-8 | dimethomorph |
| D-566 | I.Ka-8 | oxathiapiprolin |
| D-567 | I.Ka-8 | metiram |
| D-568 | I.Ka-8 | mancozeb |
| D-569 | I.Ka-8 | chlorothalonil |
| D-570 | I.Ka-8 | dithianon |
| D-571 | I.Ka-8 | Dipymetitrone |
| D-572 | I.Ka-8 | prohexadione-calcium |
| D-573 | I.Ka-8 | 3-(5-fluoro-3,3,4,4-tetramethyl-3,4-dihydroisoquinolin-1-yl)quinoline |
| D-574 | I.Ka-8 | 3-(4,4-difluoro-3,3-dimethyl-3,4-dihydroisoquinolin-1-yl)quinoline |
| D-575 | I.Ka-8 | 3-(4,4,5-trifluoro-3,3-dimethyl-3,4-dihydroisoquinolin-1-yl)quinoline |
| D-576 | I.Ka-8 | 9-fluoro-2,2-dimethyl-5-(3-quinolyl)-3H 1,4-benzoxazepine |
| D-577 | I.Ka-9 | Pyraclostrobin |
| D-578 | I.Ka-9 | Azoxystrobin |
| D-579 | I.Ka-9 | Trifloxystrobin |
| D-580 | I.Ka-9 | Picoxystrobin |
| D-581 | I.Ka-9 | Fluoxastrobin |
| D-582 | I.Ka-9 | Dimoxystrobin |
| D-583 | I.Ka-9 | Kresoxim-methyl |
| D-584 | I.Ka-9 | (2E,3Z)-5-[[1-(2,4-dichlorophenyl)-1H-pyrazol-3-yl]oxy]-2-(methoxyimino)-N,3-dimethyl-pent-3-enamide |
| D-585 | I.Ka-9 | (2E,3Z)-5-[[1-(4-chlorophenyl)-1H-pyrazol-3-yl]oxy]-2-(methoxyimino)-N,3-dimethyl-pent-3-enamide |
| D-586 | I.Ka-9 | [(3S,6S,7R,8R)-8-benzyl-3-[(3-acetoxy 4 methoxy-pyridine-2-carbonyl)amino]-6-methyl-4,9-dioxo-1,5-dioxonan-7-yl] 2 methylpropanoate |
| D-587 | I.Ka-9 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-588 | I.Ka-9 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-589 | I.Ka-9 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-590 | I.Ka-9 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-591 | I.Ka-9 | Fluxapyroxad |
| D-592 | I.Ka-9 | Boscalid |
| D-593 | I.Ka-9 | Bixafen |
| D-594 | I.Ka-9 | Isopyrazam |
| D-595 | I.Ka-9 | Benzovindiflupyr |
| D-596 | I.Ka-9 | Fluopyram |
| D-597 | I.Ka-9 | N-[(5-chloro-2-isopropyl-phenyl)methyl]-N-cyclopropyl-5-fluoro-1,3-dimethyl-pyrazole-4-carboxamide |
| D-598 | I.Ka-9 | Sedaxane |
| D-599 | I.Ka-9 | Penflufen |
| D-600 | I.Ka-9 | N-[2-(2,4-dichlorophenyl)-2-methoxy-1-methyl-ethyl]-3-(difluoromethyl)-1-methyl-pyrazole-4-carboxamide |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
|---|---|---|
| D-601 | I.Ka-9 | 3 (difluoromethyl)-1-methyl-N-(1,1,3-trimethylindan-4-yl)pyrazole-4-carboxamide |
| D-602 | I.Ka-9 | 3 (trifluoromethyl)-1-methyl-N-(1,1,3-trimethylindan-4-yl)pyrazole-4-carboxamide |
| D-603 | I.Ka-9 | 1,3-dimethyl-N-(1,1,3-trimethylindan-4-yl)pyrazole-4-carboxamide |
| D-604 | I.Ka-9 | 3-(trifluorometh¬yl)-1,5-dimethyl-N-(1,1,3-trimethylindan-4-yl)pyrazole-4-carboxamide |
| D-605 | I.Ka-9 | 1,3,5-trimethyl-N-(1,1,3-trimethylindan-4-yl)pyrazole-4-carboxamide |
| D-606 | I.Ka-9 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-607 | I.Ka-9 | Ametoctradin |
| D-608 | I.Ka-9 | epoxiconazole |
| D-609 | I.Ka-9 | metconazole |
| D-610 | I.Ka-9 | prothioconazole |
| D-611 | I.Ka-9 | difenoconazole |
| D-612 | I.Ka-9 | fluquinconazole |
| D-613 | I.Ka-9 | propiconazole |
| D-614 | I.Ka-9 | tebuconazole |
| D-615 | I.Ka-9 | 2-[2-chloro-4-(4-chlorophenoxy)phenyl]-1 (1,2,4-triazol-1-yl)pentan-2-ol |
| D-616 | I.Ka-9 | 1-[4-(4-chlorophenoxy)-2-(trifluoromethyl)phenyl]-1 cyclopropyl-2-(1,2,4-triazol-1-yl)ethanol |
| D-617 | I.Ka-9 | 2-[4-(4-chlorophenoxy)-2-(trifluoromethyl)phenyl]-1-(1,2,4-triazol-1-yl)butan-2-ol |
| D-618 | I.Ka-9 | 2-[2-chloro-4-(4-chlorophenoxy)phenyl]-1-(1,2,4-triazol-1-yl)butan-2-ol |
| D-619 | I.Ka-9 | 2-[4-(4-chlorophenoxy)-2-(trifluoromethyl)phenyl]-3-methyl-1-(1,2,4-triazol-1-yl)butan-2-ol |
| D-620 | I.Ka-9 | 2-[4-(4-chlorophenoxy)-2-(trifluoromethyl)phenyl]-1-(1,2,4-triazol-1-yl)propan-2-ol |
| D-621 | I.Ka-9 | 2-[2-chloro-4-(4-chlorophenoxy)phenyl]-3-methyl-1-(1,2,4-triazol-1-yl)butan-2-ol |
| D-622 | I.Ka-9 | 2-[4-(4-chlorophenoxy)-2-(trifluoromethyl)phenyl]-1-(1,2,4-triazol-1-yl)pentan-2-ol |
| D-623 | I.Ka-9 | 2-[4-(4-fluorophenoxy)-2-(trifluoromethyl)phenyl]-1-(1,2,4-triazol-1-yl)propan-2-ol |
| D-624 | I.Ka-9 | 2-[2-chloro-4-(4-chlorophenoxy)phenyl]-1-(1,2,4-triazol-1-yl)pent-3-yn-2-ol |
| D-625 | I.Ka-9 | prochloraz |
| D-626 | I.Ka-9 | [3-(4-chloro-2-fluoro-phenyl)-5-(2,4-difluorophenyl)isoxazol-4-yl]-(3-pyridyl)methanol |
| D-627 | I.Ka-9 | fenpropimorph |
| D-628 | I.Ka-9 | Metalaxyl |
| D-629 | I.Ka-9 | Benalaxyl |
| D-630 | I.Ka-9 | Thiophanate-methyl |
| D-631 | I.Ka-9 | Carbendazim |
| D-632 | I.Ka-9 | Metrafenone |
| D-633 | I.Ka-9 | Pyrimethanil |
| D-634 | I.Ka-9 | Iprodione |
| D-635 | I.Ka-9 | Vinclozolin |
| D-636 | I.Ka-9 | Fludioxonil |
| D-637 | I.Ka-9 | dimethomorph |
| D-638 | I.Ka-9 | oxathiapiprolin |
| D-639 | I.Ka-9 | metiram |
| D-640 | I.Ka-9 | mancozeb |
| D-641 | I.Ka-9 | chlorothalonil |
| D-642 | I.Ka-9 | dithianon |
| D-643 | I.Ka-9 | Dipymetitrone |
| D-644 | I.Ka-9 | prohexadione-calcium |
| D-645 | I.Ka-9 | 3-(5-fluoro-3,3,4,4-tetramethyl-3,4-dihydroisoquinolin-1-yl)quinoline |
| D-646 | I.Ka-9 | 3-(4,4-difluoro-3,3-dimethyl-3,4-dihydroisoquinolin-1-yl)quinoline |
| D-647 | I.Ka-9 | 3-(4,4,5-trifluoro-3,3-dimethyl-3,4-dihydroisoquinolin-1-yl)quinoline |
| D-648 | I.Ka-9 | 9-fluoro-2,2-dimethyl-5-(3-quinolyl)-3H 1,4-benzoxazepine |
| D-649 | I.Ka-10 | Pyraclostrobin |
| D-650 | I.Ka-10 | Azoxystrobin |
| D-651 | I.Ka-10 | Trifloxystrobin |
| D-652 | I.Ka-10 | Picoxystrobin |
| D-653 | I.Ka-10 | Fluoxastrobin |
| D-654 | I.Ka-10 | Dimoxystrobin |
| D-655 | I.Ka-10 | Kresoxim-methyl |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
| --- | --- | --- |
| D-656 | I.Ka-10 | (2E,3Z)-5-[[1-(2,4-dichlorophenyl)-1H-pyrazol-3-yl]oxy]-2-(methoxyimino)-N,3-dimethyl-pent-3-enamide |
| D-657 | I.Ka-10 | (2E,3Z)-5-[[1-(4-chlorophenyl)-1H-pyrazol-3-yl]oxy]-2-(methoxyimino)-N,3-dimethyl-pent-3-enamide |
| D-658 | I.Ka-10 | [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate |
| D-659 | I.Ka-10 | [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl] 2 methylpropanoate |
| D-660 | I.Ka-10 | [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl] 2-methylpropanoate |
| D-661 | I.Ka-10 | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| D-662 | I.Ka-10 | (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate |
| D-663 | I.Ka-10 | Fluxapyroxad |
| D-664 | I.Ka-10 | Boscalid |
| D-665 | I.Ka-10 | Bixafen |
| D-666 | I.Ka-10 | Isopyrazam |
| D-667 | I.Ka-10 | Benzovindiflupyr |
| D-668 | I.Ka-10 | Fluopyram |
| D-669 | I.Ka-10 | N-[(5-chloro-2-isopropyl-phenyl)methyl]-N-cyclopropyl-5-fluoro-1,3-dimethyl-pyrazole-4-carboxamide |
| D-670 | I.Ka-10 | Sedaxane |
| D-671 | I.Ka-10 | Penflufen |
| D-672 | I.Ka-10 | N-[2-(2,4-dichlorophenyl)-2-methoxy-1-methyl-ethyl]-3-(difluoromethyl)-1-methyl-pyrazole-4-carboxamide |
| D-673 | I.Ka-10 | 3 (difluoromethyl)-1-methyl-N-(1,1,3-trimethylindan-4-yl)pyrazole-4-carboxamide |
| D-674 | I.Ka-10 | 3 (trifluoromethyl)-1-methyl-N-(1,1,3-trimethylindan-4-yl)pyrazole-4-carboxamide |
| D-675 | I.Ka-10 | 1,3-dimethyl-N-(1,1,3-trimethylindan-4-yl)pyrazole-4-carboxamide |
| D-676 | I.Ka-10 | 3-(trifluorometh¬yl)-1,5-dimethyl-N-(1,1,3-trimethylindan-4-yl)pyrazole-4-carboxamide |
| D-677 | I.Ka-10 | 1,3,5-trimethyl-N-(1,1,3-trimethylindan-4-yl)pyrazole-4-carboxamide |
| D-678 | I.Ka-10 | 1-[3-chloro-2-[[[1-(4-chlorophenyl)-1H-pyrazol-3-yl]oxy]methyl]phenyl]-1,4-dihydro-4-methyl-5H-tetrazol-5-one |
| D-679 | I.Ka-10 | Ametoctradin |
| D-680 | I.Ka-10 | epoxiconazole |
| D-681 | I.Ka-10 | metconazole |
| D-682 | I.Ka-10 | prothioconazole |
| D-683 | I.Ka-10 | difenoconazole |
| D-684 | I.Ka-10 | fluquinconazole |
| D-685 | I.Ka-10 | propiconazole |
| D-686 | I.Ka-10 | tebuconazole |
| D-687 | I.Ka-10 | 2-[2-chloro-4-(4-chlorophenoxy)phenyl]-1 (1,2,4-triazol-1-yl)pentan-2-ol |
| D-688 | I.Ka-10 | 1-[4-(4-chlorophenoxy)-2-(trifluoromethyl)phenyl]-1 cyclopropyl-2-(1,2,4-triazol-1-yl)ethanol |
| D-689 | I.Ka-10 | 2-[4-(4-chlorophenoxy)-2-(trifluoromethyl)phenyl]-1-(1,2,4-triazol-1-yl)butan-2-ol |
| D-690 | I.Ka-10 | 2-[2-chloro-4-(4-chlorophenoxy)phenyl]-1-(1,2,4-triazol-1-yl)butan-2-ol |
| D-691 | I.Ka-10 | 2-[4-(4-chlorophenoxy)-2-(trifluoromethyl)phenyl]-3-methyl-1-(1,2,4-triazol-1-yl)butan-2-ol |
| D-692 | I.Ka-10 | 2-[4-(4-chlorophenoxy)-2-(trifluoromethyl)phenyl]-1-(1,2,4-triazol-1-yl)propan-2-ol |
| D-693 | I.Ka-10 | 2-[2-chloro-4-(4-chlorophenoxy)phenyl]-3-methyl-1-(1,2,4-triazol-1-yl)butan-2-ol |
| D-694 | I.Ka-10 | 2-[4-(4-chlorophenoxy)-2-(trifluoromethyl)phenyl]-1-(1,2,4-triazol-1-yl)pentan-2-ol |
| D-695 | I.Ka-10 | 2-[4-(4-fluorophenoxy)-2-(trifluoromethyl)phenyl]-1-(1,2,4-triazol-1-yl)propan-2-ol |
| D-696 | I.Ka-10 | 2-[2-chloro-4-(4-chlorophenoxy)phenyl]-1-(1,2,4-triazol-1-yl)pent-3-yn-2-ol |
| D-697 | I.Ka-10 | prochloraz |

TABLE D-continued

Individual preferred pesticidal compositions D-1 to D-432 comprising a particular compound of formula I, namely one of I.Aa-1 to I.Aa-5 and I.Ba-1 as component I (from Table C above) and a particular second pesticidal compound as component II:

| composition | component I compound from Table B aove | component II |
| --- | --- | --- |
| D-698 | I.Ka-10 | [3-(4-chloro-2-fluoro-phenyl)-5-(2,4-difluorophenyl)isoxazol-4-yl]-(3-pyridyl)methanol |
| D-699 | I.Ka-10 | fenpropimorph |
| D-700 | I.Ka-10 | Metalaxyl |
| D-701 | I.Ka-10 | Benalaxyl |
| D-702 | I.Ka-10 | Thiophanate-methyl |
| D-703 | I.Ka-10 | Carbendazim |
| D-704 | I.Ka-10 | Metrafenone |
| D-705 | I.Ka-10 | Pyrimethanil |
| D-706 | I.Ka-10 | Iprodione |
| D-707 | I.Ka-10 | Vinclozolin |
| D-708 | I.Ka-10 | Fludioxonil |
| D-709 | I.Ka-10 | dimethomorph |
| D-710 | I.Ka-10 | oxathiapiprolin |
| D-711 | I.Ka-10 | metiram |
| D-712 | I.Ka-10 | mancozeb |
| D-713 | I.Ka-10 | chlorothalonil |
| D-714 | I.Ka-10 | dithianon |
| D-715 | I.Ka-10 | Dipymetitrone |
| D-716 | I.Ka-10 | prohexadione-calcium |
| D-717 | I.Ka-10 | 3-(5-fluoro-3,3,4,4-tetramethyl-3,4-dihydroisoquinolin-1-yl)quinoline |
| D-718 | I.Ka-10 | 3-(4,4-difluoro-3,3-dimethyl-3,4-dihydroisoquinolin-1-yl)quinoline |
| D-719 | I.Ka-10 | 3-(4,4,5-trifluoro-3,3-dimethyl-3,4-dihydroisoquinolin-1-yl)quinoline |
| D-720 | I.Ka-10 | 9-fluoro-2,2-dimethyl-5-(3-quinolyl)-3H 1,4-benzoxazepine |

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303 WO 09/90181, WO 13/007767, WO 13/010862, WO 13/127704, WO 13/024009, WO 13/024010 and WO 13/047441, WO 13/162072, WO 13/092224, WO 11/135833).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a mixture comprising a pesticide II selected from group L), it is preferred that the pesticide II is applied as last treatment.

According to the invention, the solid material (dry matter) of the biopesticides (with the exception of oils such as Neem oil) are considered as active components (e. g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as Steinernema fetiae.

In the binary mixtures and compositions according to the invention the weight ratio of the component 1) and the component 2) generally depends from the properties of the active components used, usually it is in the range of from 1:10,000 to 10,000:1, often it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100: 1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to further embodiments of the mixtures and compositions, the weight ratio of the component 1) and the component 2) usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to further embodiments of the mixtures and compositions, the weight ratio of the component 1) and the component 2) usually is in the range of from 10:1 to 1:20,000, often in the range of from 1:1 to 1:10,000, regularly in the range of from 1:5 to 1:5,000, preferably in the range of from 1:10 to 1:5,000, more preferably in the range of from 1:30 to 1:2,000, even more preferably in the range of from 1:100 to 1:2,000 to and in particular in the range of from 1:100 to 1:1,000.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

When mixtures comprising microbial pesticides are employed in crop protection, the application rates preferably range from about $1\times10^6$ to $5\times10^{15}$ (or more) CFU/ha, preferably from about $1\times10^8$ to about $1\times10^{13}$ CFU/ha, and even more preferably from about $1\times10^9$ to about $1\times10^{12}$ CFU/ha. In the case of (entomopathogenic) nematodes as microbial pesticides (e. g. Steinernema feltiae), the application rates preferably range inform about $1\times10^5$ to $1\times10^{12}$ (or more), more preferably from $1\times10^8$ to $1\times10^{11}$, even more preferably from $5\times10^8$ to $1\times10^{10}$ individuals (e. g. in the form of eggs, juvenile or any other live stages, preferably in an infective juvenile stage) per ha.

When mixtures comprising microbial pesticides are employed in seed treatment, the application rates with respect to plant propagation material preferably range from about $1\times10^6$ to $1\times10^{12}$ (or more) CFU/seed. Preferably, the concentration is about $1\times10^6$ to about $1\times10^9$ CFU/seed.

In the case of the microbial pesticides II, the application rates with respect to plant propagation material also preferably range from about $1\times10^7$ to $1\times10^{14}$ (or more) CFU per 100 kg of seed, preferably from $1\times10^9$ to about $1\times10^{12}$ CFU per 100 kg of seed.

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection, for details see e. g. here: http://www.wfcc.info/ccinfo/collection/by_acronym/), are referred to in literature, registered and/or are commercially available: mixtures of Aureobasidium pullulans DSM 14940 and DSM 14941 isolated in 1989 in Konstanz, Germany (e. g. blastospores in BlossomProtect® from bio-ferm GmbH, Austria),Bacillus amyloliquefaciens strain AP-188 (NRRL B-50615 and B-50331; U.S. Pat. No. 8,445,255); B. amyloiquefaciens spp. plantarum D747 isolated from air in Kikugawa-shi, Japan (US 20130236522 A1; FERM BP-8234; e. g. Double Nickel™ 55 WDG from Certis LLC, USA), B. amyloliquefaciens spp. plantarum FZB24 isolated from soil in Brandenburg, Germany (also called SB3615; DSM 96-2; J. Plant Dis. Prot. 105, 181-197, 1998; e. g. Taegro® from Novozyme Biologicals, Inc., USA), B. amyloiquefaciens ssp. plantarum FZB42 isolated from soil in Brandenburg, Germany (DSM 23117; J. Plant Dis. Prot. 105, 181-197, 1998; e. g. RhizoVital® 42 from AbiTEP GmbH, Germany), B. amyloliquefaciens ssp. plantarum MBI600 isolated from faba bean in Sutton Bonington, Nottinghamshire, U.K. at least before 1988 (also called 1430; NRRL B-50595; US 2012/0149571 A1; e. g. Integral® from BASF Corp., USA),

*B. amyloiquefaciens* spp. *plantarum* QST-713 isolated from peach orchard in 1995 in California, U.S.A. (NRRL B-21661; e. g. Serenade® MAX from Bayer Crop Science LP, USA), *B. amyloiquefaciens* spp. *plantarum* TJ1000 isolated in 1992 in South Dakota, U.S.A. (also called 1BE; ATCC BAA-390; CA 2471555 A1; e. g. QuickRoots™ from TJ Technologies, Watertown, S. Dak., USA), *B. firmus* CNCM I-1582, a variant of parental strain EIP-N1 (CNCM I-1556) isolated from soil of central plain area of Israel (WO 2009/126473, U.S. Pat. No. 6,406,690; e. g. Votivo® from Bayer CropScience LP, USA), *B. pumilus* GHA 180 isolated from apple tree rhizosphere in Mexico (IDAC 260707-01; e. g. PRO-MIX® BX from Premier Horticulture, Quebec, Canada), *B. pumilus* INR-7 otherwise referred to as BU-F22 and BU-F33 isolated at least before 1993 from cucumber infested by *Erwinia racheiphila* (NRRL B-50185, NRRL B-50153; U.S. Pat. No. 8,445,255), *B. pumilus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B-50304; U.S. Pat. No. 8,445, 255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* sp. *aizawai* ABTS-1857 isolated from soil taken from a lawn in Ephraim, Wis., U.S.A., in 1987 (also called ABG-6346; ATCC SD-1372; e. g. XenTari® from BioFa AG, Munsingen, Germany), B. t. ssp. *kurstaki* ABTS-351 identical to HD-1 isolated in 1967 from diseased Pink Bollworm black larvae in Brownsville, Tex., U.S.A. (ATCC SD-1275; e. g. Dipel® DF from Valent BioSciences, IL, USA), B. t. ssp. *tenebrionis* NB-176-1, a mutant of strain NB-125, a wild type strain isolated in 1982 from a dead pupa of the beetle *Tenebrio molitor* (DSM 5383; EP 585 215 B1; e. g. Novodor from Valent BioSciences, Switzerland), *Beauveria bassiana* GHA (ATCC 74250; e. g. BotaniGard®22WGP from Laverlam Int. Corp., USA), *B. bassiana* JW-1 (ATCC 74040; e. g. Naturalis® from CBC (Europe) S.r.I., Italy),*Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Helicoverpa zeasingle* capsid nucleopolyhedrovirus (HzSNPV) (e. g. Gemstar® from Certis LLC, USA), *Helicoverpa zea* nucleopolyhedrovirus ABA-NPV-U (e. g. Heligen® from AgBiTech Pty Ltd., Queensland, Australia), *Heterorhabditis bacteriophora* (e. g. Nemasys® G from BASF Agricultural Specialities Limited, UK), *Isaria fumosorosea* Apopka-97 isolated from mealy bug on gynura in Apopka, Fla., U.S.A. (ATCC 20874; Biocontrol Science Technol. 22(7), 747-761, 2012; e. g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e. g. Met52@ from Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e. g. BioAct® from Bayer CropScience AG, Germany and MeloCon® from Certis, USA), *Pasteur/a nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilaiae*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutria sachalinensis* extract (EP 0307510 B1; e. g. Regalia® SC from Marrone BioInnovations, Davis, Calif., USA or Milsana® from BioFa AG, Germany), *Steinernema carpocapsae* (e. g. Millenium® from BASF Agricultural Specialities Limited, UK), S. felt/ae (e. g. Nemashield® from BioWorks, Inc., USA; Nemasys® from BASF Agricultural Specialities Limited, UK), *Streptomyce smicroflavus* NRRL B-50550 (WO 2014/124369; Bayer CropScience, Germany), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, OH, USA).

The mixtures of active substances can be prepared as compositions comprising besides the active ingredients at least one inert ingredient (auxiliary) by usual means, e. g. by the means given for the compositions of compounds I. Concerning usual ingredients of such compositions reference is made to the explanations given for the compositions containing compounds I.

According to one embodiment, the microbial pesticides selected from groups L1), L3) and L5) embrace not only the isolated, pure cultures of the respective microorganism as defined herein, but also its cell-free extract, its suspensions in a whole broth culture or as a metabolite-containing culture medium or a purified metabolite obtained from a whole broth culture of the microorganism.

When living microorganisms, such as pesticides II from groups L1), L3) and L5), form part of the compositions, such compositions can be prepared as compositions comprising besides the active ingredients at least one auxiliary by usual means (e. g. H. D. Burges: Formulation of Micobial Biopesticides, Springer, 1998). Suitable customary types of such compositions are suspensions, dusts, powders, pastes, granules, pressings, capsules, and mixtures thereof. Examples for composition types are suspensions, capsules, pastes, pastilles, wettable powders or dusts, pressings, granules, insecticidal articles, as well as gel formulations. Herein, it has to be taken into account that each formulation type or choice of auxiliary should not influence the viability of the microorganism during storage of the composition and when finally applied to the soil, plant or plant propagation material. Suitable formulations are e. g. mentioned in WO 2008/002371, U.S. Pat. Nos. 6,955,912, 5,422,107.

SYNTHESIS EXAMPLES

With due modification of the starting compounds, the procedures shown in the synthesis examples below were used to obtain further compounds I. The resulting compounds, together with physical data, are listed in Table I below.

Example 1

1. Synthesis of 1-(2-chloro-3-pyridyl)-4,4-difluoro-3,3-dimethyl-isoquinoline

1.1 1-(2-Chloro-3-pyridyl)-3,3-dimethyl-4H-isoquinoline 10.8 g of trifluoromethane sulfonic acid was added dropwise to a mixture of 2 g (10 mmol) 2-chloropyridine-3-carbonitrile and 2.17 g (10 mmol) 2-methyl-1-phenyl-propan-2-ol in 40 ml dichloromethane at −10° C. After 30 minutes the reaction mixture was poured onto sodium hydrogencarbonate solution, the organic layer was separated and the aqueous layer was extracted twice with dichloromethane. The combined organic extracts were evaporated and the residue was purified via silica gel chromatography with heptane/ethyl acetate mixtures to yield 1,42 g (36%) of the title compound as a colorless solid.

$^1$H-NMR (CDCl$_3$, δ in ppm):

8.5 (s, broad, 1H); 7,75 (d, 1H); 7,4 (m, 2H); 7,2 (m, 2H); 6,85 (d, 1H); 2,9 (s, very broad, 2H); 1,4 (s, very broad, 3H); 1,3 (s, very broad, 3H).

1.2. 4,4-Dibromo-1-(2-chloro-3-pyridyl)-3,3-dimethyl-isoquinoline

A mixture of 1,2 g (4.43 mmol) 1-(2-chloro-3-pyridyl)-3,3-dimethyl-4H-isoquinoline (example 1.1.), 1,39 g (4.88 mmol) 1,3-dibromo-5,5-dimethyl-imidazolidine-2,4-dione and 0,23 g 2-[(E)-(1-cyano-1-methyl-ethyl)azo]-2-methyl-propanenitrile in 10 ml carbon tetrachloride was heated upon stirring to 80° C. After 30 min the starting material was consumed (HPLC). The reaction mixture was cooled to 0° C. and the precipitated solid was filtered off. The solvent was evaporated and the residue (2,52 g) was used in the subsequent reaction without further purification.

1.3. 1-(2-Chloro-3-pyridyl)-4,4-difluoro-3,3-dimethyl-isoquinoline 0,86 g triethylamine×3 HF (5.3 mmol) was added dropwise to a mixture of 1,9 g crude 4,4-dibromo-1-(2-chloro-3-pyridyl)-3,3-dimethyl-isoquinoline (example 1.2.) in 10 ml acetonitrile. Afterwards the reaction mixture was heated 30 min to reflux. Having cooled to room temperature the reaction mixture was diluted with saturated sodium hydrogencarbonate solution. The organic phase was separated and volatiles were evaporated. The obtained residue was purified via silica gel chromatography with heptane/ethyl acetate mixtures to yield 0,45 g (33%) of the title compound as a yellow solid (mp=99° C.).

$^1$H-NMR (CDCl$_3$, δ in ppm):

8,55 (s, broad, 1H); 7,85 (d, 1H); 7,75 (d, 1H); 7,65 (t, 1H); 7,5 (t, 1H); 7,4 (m, 1H); 7,0 (d, 1H); 1,5 (s, very broad, 6H).

2. Synthesis of 1-(5,6-dimethoxy-3-pyridyl)-4,4-difluoro-3,3-dimethyl-isoquinoline

2.1. 1-(5,6-Dimethoxy-3-pyridyl)-3,3-dimethyl-4H-isoquinoline 5,49 g of trifluoromethane sulfonic acid was added dropwise to a mixture of 1,2 g (7.3 mmol) 5,6-dimethoxy-pyridine-3-carbonitrile and 1,1 g (7.3 mmol)) 2-methyl-1-phenyl-propan-2-ol in 50 ml dichloromethane at −5° C. After 30 minutes the reaction mixture was poured onto sodium hydrogencarbonate solution, the organic layer was separated and the aqueous layer was extracted twice with dichloromethane. The combined organic extracts were evaporated and the residue was purified via silica gel chromatography with heptane/ethyl acetate mixtures to yield 1,8 g (83%) of the title compound as a yellow oil.

$^1$H-NMR (CDCl$_3$, δ in ppm):

7,9 (d, 1H); 7,4 (m, 1H); 7,35 (d, 1H); 7,25 (m, 3H); 4,1 (s, 3H); 3,95 (s, 3H); 2,8 (s, 2H); 1,3 (s, 6H).

2.2. 4,4-Dibromo-1-(5,6-dimethoxy-3-pyridyl)-3,3-dimethyl-isoquinoline

A mixture of 1,62 g (5.47 mmol) 1-(5,6-Dimethoxy-3-pyridyl)-3,3-dimethyl-4H-isoquinoline (example 2.1.), 1,72 g (6.0 mmol) 1,3-dibromo-5,5-dimethyl-imidazolidine-2,4-dione and 0,28 g 2-[(E)-(1-cyano-1-methyl-ethyl)azo]-2-methyl-propanenitrile in 40 ml carbon tetrachloride was heated upon stirring to 80° C. After 1,5 h the starting material was consumed (HPLC). The reaction mixture was cooled to 0° C. and the precipitated solid was filtered off. The solvent was evaporated and the residue (2,6 g) was used in the subsequent reaction without further purification. 2.3. 1-(5,6-Dimethoxy-3-pyridyl)-4,4-difluoro-3,3-dimethyl-isoquinoline 1,2 g triethylamine×3 HF (7.4 mmol) was added dropwise to a mixture of 2,6 g crude 4,4-Dibromo-1-(5,6-dimethoxy-3-pyridyl)-3,3-dimethyl-isoquinoline (example 2.2.) in 50 ml acetonitrile. Afterwards the reaction mixture was heated 30 min to reflux. Having cooled to room temperature the reaction mixture was diluted with saturated sodium hydrogencarbonate solution. The organic phase was separated and volatiles were evaporated. The obtained residue was purified via silica gel chromatography with heptane/ethyl acetate mixtures to yield 1,2 g (63%) of the title compound as a yellow solid (mp=179° C.).

$^1$H-NMR (CDCl$_3$, δ in ppm):

7,95 (d, 1H); 7,85 (d, 1H); 7,65 (t, 1H); 7,55 (t, 1H); 7,4 (d, 1H); 7,3 (d, 1H); 4,1 (s, 3H); 3,95 (s, 3H); 1,6 (s, 3H); 1,4 (s, 3H)

Analytical values of compound of formula I are provided in Table D.

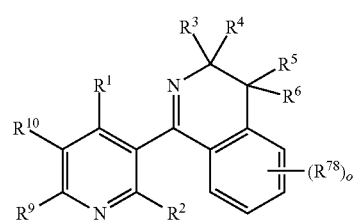

I

TABLE D

| No. | R¹ | R² | R³ | R⁴ | R⁵ | R⁶ | R⁹ | R¹⁰ | (R⁷⁸)ₒ | Fp [° C.]; HPLC-MS* (EI (M⁺ + H), R$_t$ [min]); ¹H-NMR (δ in ppm) |
|---|---|---|---|---|---|---|---|---|---|---|
| D-1 | H | H | CH₃ | CH₃ | F | F | Cl | Cl | H | 81° C. |
| D-2 | H | Cl | CH₃ | CH₃ | F | F | H | H | H | 99° C. |
| D-3 | Cl | Cl | CH₃ | CH₃ | F | F | H | H | H | R$_t$ = 1,252; M + H = 340,9 |
| D-4 | H | H | CH₃ | CH₃ | F | F | H | H | H | R$_t$ = 0,859; M + H = 273 |
| D-5 | H | H | CH₃ | CH₃ | F | F | OCH₃ | OCH₃ | H | 179° C. |
| D-6 | CF₃ | H | CH₃ | CH₃ | F | F | H | H | H | R$_t$ = 1,169; M + H = 341 |
| D-7 | H | Cl | CH₃ | CH₃ | F | F | Cl | H | H | R$_t$ = 1,260; M + H = 341 |
| D-8 | H | H | CH₃ | CH₃ | F | F | H | Br | H | R$_t$ = 1,231; M + H = 352,9 |
| D-9 | H | H | CH₃ | CH₃ | F | F | Cl | H | H | R$_t$ = 1,235; M + H = 306,9 |
| D-10 | H | H | CH₃ | CH₃ | F | F | OCH₃ | Cl | H | R$_t$ = 0,972; M + H = 337 |
| D-11 | H | H | CH₃ | CH₃ | F | F | CH₃ | CH₃ | H | R$_t$ = 0,864; M + H = 301 |
| D-12 | H | Cl | CH₃ | CH₃ | F | F | CH₃—CH(Br) | H | H | 125° C. |
| D-13 | H | H | CH₃ | CH₃ | Br | Br | Br | Br | H | 147° C. |
| D-14 | H | H | CH₃ | CH₃ | F | F | Br | H | H | R$_t$ = 1,244; M + H = 351 |
| D-15 | H | H | CH₃ | CH₃ | F | F | Br | CH₃ | H | R$_t$ = 1,298; M + H = 365 |
| D-16 | H | H | CH₃ | CH₃ | F | F | Br | CH₂CH₃ | H | R$_t$ = 1,252; M + H = 350,6 |
| D-17 | H | H | CH₃ | CH₃ | F | F | OCH₃ | CH₃ | H | R$_t$ = 1,126; M + H = 317,1 |
| D-18 | H | H | CH₃ | CH₃ | F | F | CN | CH₃ | H | R$_t$ = 1,225; M + H = 311,8 |
| D-19 | H | H | CH₃ | CH₃ | F | F | OCH₃ | Br | H | R$_t$ = 1,339; M + H = 380,6 |
| D-20 | H | H | CH₃ | CH₃ | F | F | CH₃ | Br | H | R$_t$ = 1,274; M + H = 367 |
| D-21 | H | H | CH₃ | CH₃ | F | F | Br | Br | H | R$_t$ = 1,402; M + H = 430,5 |
| D-22 | H | H | CH₃ | CH₃ | F | F | Br | CF₃ | H | 8,7 (s, 1H); 8,15 (s, 1H); 7,8 (d, 1H); 7,6 (t, 1H); 7,5 (t, 1H); 7,15 (d, 1H); 1,35 (s, 6H) |
| D-23 | H | H | CH₃ | CH₃ | F | F | Cl | CF₃ | H | 8,8 (s, 1H); 8,35 (s, 1H); 7,95 (d, 1H); 7,8 (t, 1H); 7,65 (t, 1H); 7,3 (d, 1H); 1,5 (s, 6H) |
| D-24 | H | H | CH₃ | CH₃ | F | F | F | CF₃ | H | 8,65 (s, 1H); 8,35 (d, 1H); 7,95 (d, 1H); 7,75 (t, 1H); 7,65 (t, 1H); 7,25 (d, 1H); 1,45 (s, 6H) |
| D-25 | H | H | CH₃ | CH₃ | F | F | CH₃ | CF₃ | H | 8,95 (s, 1H); 8,25 (s, 1H); 7,9 (d, 1H); 7,7 (t, 1H); 7,6 (t, 1H); 7,25 (d, 1H); 2,85 (s, 3H); 1.4 (s, 6H) |
| D-26 | H | H | CH₃ | CH₃ | F | F | CH₃ | CN | H | R$_t$ = 1,164; M + H = 312,1 |
| D-27 | H | H | CH₃ | CH₃ | F | F | CH₃ | CH₂CH₃ | H | R$_t$ = 0,946; M + H = 315,3 |
| D-28 | H | CH₃ | CH₃ | CH₃ | F | F | CH₃ | CH₃ | H | ¹H-NMR (CDCl₃): 7,84 (d, 1H); 7,63 (t, 1H); 7,49 (t, 1H); 7,34 (s, 1H); 7,0 (d, 1H); 2,56 (s, 3H); 2,33 (s, 3H); 2,31 (s, 3H); 1,46 (s, 6H) |
| D-29 | H | H | CH₃ | CH₃ | F | F | OCH₃ | CF₃ | H | ¹H-NMR (CDCl₃): 8.48 (d, J = 1.76 Hz, 1 H) 8.08 (d, J = 2.21 Hz, 1 H) 7.78 (d, J = 7.50 Hz, 1 H) 7.59 (t, J = 7.50 Hz, 1 H) 7.49 (t, J = 7.50 Hz, 1 H) 7.23 (d, J = 7.50 Hz, 1 H) 4.04 (s, 3 H) 1.33 (s, 6 H) |
| D-30 | H | H | CH₃ | CH₃ | F | F | C₂H₅ | CF₃ | H | ¹H-NMR (CDCl₃): 8.94 (d, J = 12.79 Hz, 1 H) 8.12 (s, 1 H) 7.81 (d, J = 7.50 Hz, 1 H) 7.61 (t, J = 7.50 Hz, 1 H) 7.51 (t, J = 7.50 Hz, 1 H) 7.16 (d, J = 7.50 Hz, 1 H) 1.30-1.39 (m, 7 H) |
| D-31 | H | H | CH₃ | CH₃ | F | F | H | CF₃ | H | ¹H-NMR (CDCl₃): 8,94 (m, 2H); 8,12 (s, 1H); 7,81 (d, 1H); 7,61 (t, 1H); 7,51 (t, 2H); 7,15 (d, 1H); 1,35 (s, 6H) |
| D-32 | H | H | CH₃ | CH₃ | F | F | SCH₃ | CF₃ | H | ¹H-NMR (CDCl₃): 8.81 (d, J = 2.01 Hz, 1 H) 8.11 (d, J = 1.51 Hz, 1 H) 7.90 (d, J = 7.53 Hz, 1 H) 7.73 (t, J = 7.28 Hz, 1 H) 7.62 (t, J = 7.78 Hz, 1 H) 7.34 (d, J = 7.03 Hz, 1 H) 2.63-2.71 (m, 3 H) 1.46 (s, 6 H) |
| D-33 | H | H | CH₃ | CH₃ | F | F | CONH₂ | CH₃ | H | 156 |
| D-34 | H | H | CH₃ | CH₃ | F | F | CONH(CH₃) | CH₃ | H | R$_t$ = 1,084 min M⁺ + H = 344,1 |

TABLE D-continued

| No. | R¹ | R² | R³ | R⁴ | R⁵ | R⁶ | R⁹ | R¹⁰ | (R⁷⁸)ₒ | Fp [° C.]; HPLC-MS* (EI (M⁺ + H), Rₜ [min]); ¹H-NMR (δ in ppm) |
|---|---|---|---|---|---|---|---|---|---|---|
| D-35 | H | H | $CH_3$ | $CH_3$ | F | F | $CH_3$ | $CONH_2$ | H | Rₜ = 0,843 min<br>M⁺ + H = 330,1 |
| D-36 | H | H | $CH_3$ | $CH_3$ | F | F | $CH_3$ | $CONH(CH_3)$ | H | Rₜ = 0,881 min<br>M⁺ + H = 344,1 |
| D-37 | H | H | $CH_3$ | $CH_3$ | F | F | $CH_3$ | $CON(CH_3)_2$ | H | Rₜ = 0,936 min<br>M⁺ + H = 358,3 |
| D-38 | H | H | $CH_3$ | $CH_3$ | F | F | $CF_3$ | $CF_3$ | H | ¹H-NMR (CDCl₃):<br>9.00 (s, 1 H) 8.38 (s, 1 H) 7.83 (d, J = 7.94 Hz, 1 H) 7.64 (t, J = 7.50 Hz, 1 H) 7.52 (t, J = 7.72 Hz, 1 H) 7.15 (d, J = 7.50 Hz, 1 H) 1.91-1.96 (s, 6 H) |
| D-39 | H | H | $CH_3$ | $CH_3$ | F | F | CN | $CF_3$ | H | ¹H-NMR (CDCl₃):<br>9.13 (d, J = 2.10 Hz, 1 H) 8.40 (d, J = 2.01 Hz, 1 H) 7.92 (d, J = 8.03 Hz, 1 H) 7.75 (t, J = 7.78 Hz, 1 H) 7.59-7.66 (m, 1 H) 7.21 (d, J = 7.03 Hz, 1 H) 1.43-1.49 (m, 6 H) |
| D-40 | H | H | $CH_3$ | $CH_3$ | F | F | $N(CH_3)_2$ | $CF_3$ | H | ¹H-NMR (CDCl₃):<br>8.57 (d, J = 2.01 Hz, 1 H) 8.13 (d, J = 2.01 Hz, 1 H) 7.86 (d, J = 7.53 Hz, 1 H) 7.66 (t, J = 7.53 Hz, 1 H) 7.54-7.61 (m, 1 H) 7.40 (d, J = 7.53 Hz, 1 H) 3.16 (s, 6 H) 1.41 (s, 6 H) |
| D-41 | H | H | $CH_3$ | $CH_3$ | F | F | $SOCH_3$ | $CF_3$ | H | ¹H-NMR (CDCl₃):<br>9.20 (s, 1 H) 8.33 (s, 1 H) 7.89 (d, J = 8.03 Hz, 1 H) 7.71 (t, J = 7.53 Hz, 1 H) 7.55-7.63 (m, 1 H) 7.23 (d, J = 8.03 Hz, 1 H) 2.87 (s, 3 H) 1.47 (s, 3 H) 1.38 (s, 3 H) |
| D-42 | H | H | $CH_3$ | $CH_3$ | F | F | $SO_2CH_3$ | $CF_3$ | H | ¹H-NMR (CDCl₃):<br>9.01 (s, 1 H) 8.48 (s, 1 H) 7.93 (d, J = 7.53 Hz, 1 H) 7.76 (t, J = 7.53 Hz, 1 H) 7.64 (t, J = 7.53 Hz, 1 H) 7.22 (d, J = 7.53 Hz, 1 H) 3.46 (s, 3 H) 1.47 (s, 6 H) |
| D-43 | H | H | $CH_3$ | $CH_3$ | F | F | $CHF—CH_3$ | $CF_3$ | H | ¹H-NMR (CDCl₃):<br>9.05-9.14 (m, 1 H) 8.27 (s, 1 H) 7.90 (d, J = 7.53 Hz, 1 H) 7.71 (t, J = 7.53 Hz, 1 H) 7.60 (t, J = 7.53 Hz, 1 H) 7.27 (s, 1 H) 6.00-6.20 (m, 1 H) 1.75-1.85 (m, 3 H) 1.47 (s, 3 H) 1.43 (s, 3 H) |
| D-44 | H | H | $CH_3$ | $CH_3$ | F | F | $CONH(CH_3)$ | $CF_3$ | H | ¹H-NMR (CDCl₃):<br>8.85 (s, 1 H) 8.31 (d, J = 7.16 Hz, 1 H) 7.86 (d, J = 7.50 Hz, 1 H) 7.72 (t, J = 7.28 Hz, 1 H) 7.65 (br. s., 1 H) 7.57 (t, J = 7.50 Hz, 1 H) 7.17 (s, 1 H) 6.66 (br. s., 2 H) 3.02 (d, J = 5.29 Hz, 3 H) 1.43 (s, 6 H) |
| D-45 | H | H | $CH_3$ | $CH_3$ | F | F | $COCH_3$ | $CF_3$ | H | ¹H-NMR (CDCl₃):<br>8.96 (s, 1 H) 8.30 (s, 1 H) 7.86 (d, J = 7.50 Hz, 1 H) 7.67 (t, J = 7.50 Hz, 1 H) 7.20 (d, J = 7.94 Hz, 1 H) 2.70 (s, 3 H) 1.40 (s, 6 H) |
| D-46 | H | H | $CH_3$ | $CH_3$ | F | F | $n-C_4H_9$ | $CH_3$ | H | Rₜ = 1,033 min<br>M⁺ + H = 343,3 |
| D-47 | H | H | $CH_3$ | $CH_3$ | F | F | $CF_3$ | $CH_3$ | H | 97 |
| D-48 | H | H | $CH_3$ | $CH_3$ | F | F | $CHF_2$ | Br | H | 104 |
| D-49 | H | H | $CH_3$ | $CH_3$ | F | F | $CHF_2$ | CN | H | Rₜ = 1,238 min<br>M⁺ + H = 348,1 |
| D-50 | H | H | $CH_3$ | $CH_3$ | F | F | $CHF_2$ | $CF_3$ | H | ¹H-NMR (CDCl₃):<br>9.08 (s, 1 H) 8.35 (s, 1 H) 7.89 (d, J = 7.50 Hz, 1 H) 7.70 (t, J = 7.50 Hz, 1 H) 7.59 (t, J = 7.50 Hz, 1 H) 7.22 (d, J = 7.50 Hz, 1 H) 6.81-7.12 (m, 1 H) 1.38-1.49 (m, 6 H) |
| D-51 | H | H | $CH_3$ | $CH_3$ | F | F | $SCH_3$ | $CH_3$ | H | Rₜ = 1,281 min<br>M⁺ + H = 333,2 |

TABLE D-continued

| No. | R¹ | R² | R³ | R⁴ | R⁵ | R⁶ | R⁹ | R¹⁰ | (R⁷⁸)ₒ | Fp [° C.]; HPLC-MS* (EI (M⁺ + H), Rₜ [min]); ¹H-NMR (δ in ppm) |
|---|---|---|---|---|---|---|---|---|---|---|
| D-52 | H | H | $CH_3$ | $CH_3$ | F | F | $CH_2F$ | H | H | Rₜ = 1,151 min<br>M⁺ + H = 305 |
| D-53 | H | H | $CH_3$ | $CH_3$ | F | F | $CH_3$ | $SCH_3$ | H | Rₜ = 1,042 min<br>M⁺ + H = 333,1 |
| D-54 | H | H | $CH_3$ | $CH_3$ | F | F | $CH_3$ | $OCH_3$ | H | 133 |
| D-55 | H | H | $CH_3$ | $CH_3$ | F | F | $CHF_2$ | $CH_3$ | H | Rₜ = 1,261 min<br>M⁺ + H = 337,2 |
| D-56 | H | H | $CH_3$ | $CH_3$ | F | F | c-$C_3H_5$ | $CH_3$ | H | Rₜ = 0,984 min<br>M⁺ + H = 327,1 |
| D-57 | H | H | $CH_3$ | $CH_3$ | F | F | Ethinyl | $CH_3$ | H | Rₜ = 1,165 min<br>M⁺ + H = 311,1 |
| D-58 | H | H | $CH_3$ | $CH_3$ | F | F | $CH_3$ | Ethinyl | H | Rₜ = 1,139 min<br>M⁺ + H = 311,1 |
| D-59 | H | H | $CH_3$ | $CH_3$ | F | F | Cl | $CH_3$ | H | 83 |
| D-60 | H | H | $CH_3$ | $CH_3$ | F | F | $CH_3$ | F | H | Rₜ = 1,14 min<br>M⁺ + H = 305 |
| D-61 | H | H | $CH_3$ | $CH_3$ | F | F | $CH_3$ | Cl | H | Rₜ = 1,275 min<br>M⁺ + H = 322 |
| D-62 | H | H | $CH_3$ | $CH_3$ | F | F | $CH_2CN$ | Br | H | Rₜ = 1,189 min<br>M⁺ + H = 390 |
| D-63 | H | H | $CH_3$ | $CH_3$ | F | F | $CH_3$ | $CHF_2$ | N | Rₜ = 1,128 min<br>M⁺ + H = 337,1 |
| D-64 | H | H | $CH_3$ | $CH_3$ | F | F | $CH_3$ | $SOCH_3$ | H | Rₜ = 0,96 min<br>M⁺ + H = 349,1 |
| D-65 | H | H | $CH_3$ | $CH_3$ | F | F | CN | CN | H | ¹H-NMR (CDCl₃):<br>9.07 (d, J = 2.01 Hz, 1 H) 8.34 (d, J = 2.01 Hz, 1 H) 7.83 (d, J = 7.65 Hz, 1 H) 7.66 (t, J = 7.53 Hz, 1 H) 7.50-7.60 (m, 1 H) 7.13 (d, J = 7.53 Hz, 1 H) 1.28-1.41 (s, 6 H) |
| D-66 | H | H | $CH_3$ | $CH_3$ | F | F | $CH_3$ | $SO_2CH_3$ | H | Rₜ = 1,092 min<br>M⁺ + H = 365,2 |
| D-67 | H | H | $CH_3$ | $CH_3$ | F | F | $C_2H_5$ | $CH_3$ | H | Rₜ = 0,908 min<br>M⁺ + H = 315,1 |
| D-68 | H | H | $CH_3$ | $CH_3$ | F | F | $CHF_2$ | $CHF_2$ | H | Rₜ = 1,299 min<br>M⁺ + H = 373,1 |
| D-69 | H | H | $CH_3$ | $CH_3$ | F | F | $CHF_2$ | $C_2H_5$ | H | 73 |
| D-70 | H | H | $CH_3$ | $CH_3$ | F | F | $CHF_2$ | $OCH_3$ | H | Rₜ = 1,152 min<br>M⁺ + H = 353 |
| D-71 | H | H | $CH_3$ | $CH_3$ | F | F | $CHF_2$ | Cl | H | 95 |
| D-72 | H | H | $CH_3$ | $CH_3$ | F | F | $CH_3$ | $OCHF_2$ | H | Rₜ = 1,155 min<br>M⁺ + H = 353 |
| D-73 | H | H | $CH_3$ | $CH_3$ | F | F | $CH_2F$ | $CH_3$ | H | 84 |
| D-74 | H | H | $CH_3$ | $CH_3$ | F | F | $CHCl_2$ | $CH_3$ | H | 107 |
| D-75 | H | H | $CH_3$ | $CH_3$ | F | F | $CH_3$ | $CH_2=CH$ | H | Rₜ = 0,942 min<br>M⁺ + H = 313,1 |
| D-76 | H | H | $CH_3$ | $CH_3$ | F | F | $CH_3$ | c-$C_3H_5$ | H | Rₜ = 0,943 min<br>M⁺ + H = 327,1 |
| D-77 | H | H | $CH_3$ | $CH_3$ | F | F | c-$C_3H_5$ | Br | H | 110 |
| D-78 | H | H | $CH_3$ | $CH_3$ | F | F | Br | Cl | H | 96 |
| D-79 | H | H | $CH_3$ | $CH_3$ | F | F | Br | $OCH_3$ | H | Rₜ = 1, min<br>M⁺ + H = 381 |
| D-80 | H | H | $CH_3$ | $CH_3$ | F | F | CHF—$CH_3$ | CH3 | H | Rₜ = 1,207 min<br>M⁺ + H = 333,1 |
| D-81 | H | H | $CH_3$ | $CH_3$ | F | F | $CH_3$ | $CHFCH_3$ | H | Rₜ = 1,002 min<br>M⁺ + H = 333,1 |
| D-82 | H | CN | $CH_3$ | $CH_3$ | F | F | $CH_3$ | $CH_3$ | H | ¹H-NMR (CDCl₃):<br>7,87 (d, 1H); 7,66 (t, 1H); 7,55 (m, 2H); 7,03 (d, 1 H); 2,61 (s, 3H); 2,41 (s, 3H); 1,48 (s, 6H) |
| D-83 | H | H | $CH_3$ | $CH_3$ | F | F | $CH_3$ | $CH_2F$ | H | Rₜ = 0,982 min<br>M⁺ + H = 319 |
| D-84 | H | H | $CH_3$ | $CH_3$ | F | F | Br | CHF—$CH_3$ | H | Rₜ = 1,35 min<br>M⁺ + H = 398,9 |
| D-85 | H | H | $CH_3$ | $CH_3$ | F | F | $CHF_2$ | Ethinyl | H | 112 |
| D-86 | H | H | $CH_3$ | $CH_3$ | F | F | $CH_3$ | $CH_3$ | 2″-F | Rₜ = 0,938 min<br>M⁺ + H = 319,1 |
| D-87 | H | H | $CH_3$ | $CH_3$ | F | F | $CH_3$ | $CH_3$ | 3″-F | Rₜ = 0,953 min<br>M⁺ + H = 319,1 |
| D-88 | H | H | $CH_3$ | $CH_3$ | F | F | F | F | H | Rₜ = 1,267 min<br>M⁺ + H = 309 |
| D-89 | H | H | $CH_3$ | $CH_3$ | Br | H | Br | Br | 4″-F | Rₜ = 1,401 min<br>M⁺ + H = 490,8 |

TABLE D-continued

| No. | R¹ | R² | R³ | R⁴ | R⁵ | R⁶ | R⁹ | R¹⁰ | (R⁷⁸)ₒ | Fp [° C.]; HPLC-MS* (EI (M⁺ + H), $R_t$ [min]); ¹H-NMR (δ in ppm) |
|---|---|---|---|---|---|---|---|---|---|---|
| D-90 | H | H | CH₃ | CH₃ | F | F | Cl | Br | H | 95 |
| D-91 | CN | H | CH₃ | CH₃ | F | F | CH₃ | CH₃ | H | ¹H-NMR (CDCl₃): 7,86 (d, 1H); 7,82 (s, 1H); 7,66 (t, 1H); 7,52 (t, 1H); 6,91 (d, 1H); 2,81 (s, 3H); 2,42 (s, 3H); 1,44 (s, 6H) |
| D-92 | CN | H | CH₃ | CH₃ | F | F | CH₃ | (CH₃)₂N | H | ¹H-NMR (CDCl₃): 7,82 (d, 1H); 7,68 (s, 1H); 7,63 (t, 1H); 7,49 (t, 1H); 6,94 (d, 1H); 2,89 (s, 6H); 2,64 (s, 3H); 1,62 (s, broad, 3H); 1,19 (s, broad, 3H) |
| D-93 | CN | H | CH₃ | CH₃ | F | F | CH₃ | H | H | ¹H-NMR (CDCl₃): 8,91 (s, 1H); 8,19 (s, 1H); 8,0 (d, 1H); 7,69 (t, 1H); 7,58 (t, 1H); 7,24 (d, 1H); 2,87 (s, 3H); 1,41 (s, 6H) |
| D-94 | H | H | CH₃ | CH₃ | F | F | CH₃ | CH₃ | H | $R_t$ = 1,015 min M⁺ + H = 315,1 |
| D-95 | H | H | CH₃ | CH₃ | F | F | Br | CH₂F | H | 118 |
| D-96 | H | H | CH₃ | CH₃ | F | F | CHF₂ | CH₂F | H | $R_t$ = 1,264 min M⁺ + H = 355 |
| D-97 | H | H | CH₃ | CH₃ | F | F | Cl | CH₂F | H | $R_t$ = 1,247 min M⁺ + H = 339 |
| D-98 | H | H | CH₃ | CH₃ | F | F | CH₂F | Br | H | $R_t$ = 1,27 min M⁺ + H = 383 |
| D-99 | H | H | CH₃ | CH₃ | F | F | CH₂F | OCH₃ | H | 131 |
| D-100 | H | H | CH₃ | CH₃ | F | F | CH₂F | CH₂F | H | $R_t$ = 1,149 min M⁺ + H = 337,1 |

Analytical values of compound of formula I are provided in Table E.

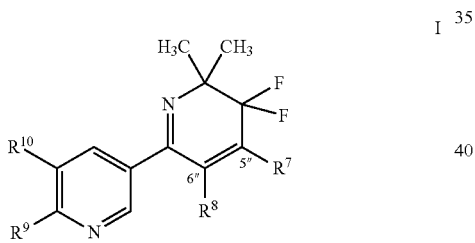

I

| No. | R⁷ | R⁸ | R⁹ | R¹⁰ | Fp [° C.]; HPLC-MS* (EI (M⁺ + H), $R_t$ [min]); ¹H-NMR (δ in ppm) |
|---|---|---|---|---|---|
| E-1 |  | 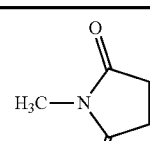 | | | ¹H (CDCl₃): 9.20 (d, J = 2.01 Hz, 1H) 8.43 (d, J = 1.51 Hz, 1H) 7.91 (d, J = 7.53 Hz, 1H) 7.72 (t, J = 7.78 Hz, 1H) 7.57-7.63 (m, 1H) 7.23 (d, J = 7.53 Hz, 1H) 3.32 (s, 3H) 1.45 (s, 6H) |
| E-2 |  | 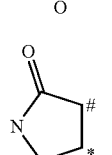 | | | ¹H (CDCl₃): 9.24 (s, 1H) 8.58 (br. s., 1H) 8.46 (s, 1H) 7.92 (d, J = 7.4 Hz, 1H) 7.75 (t, J = 7.6 Hz, 1H) 7.62 (t, J = 7.4 Hz, 1H) 7.23 (d, J = 7.8 Hz,1H) 1.47 (s, 6H) |

| No. | R⁷ | R⁸ | R⁹ | R¹⁰ | Fp [° C.]; HPLC-MS* (EI (M⁺ + H), $R_t$ [min]); ¹H-NMR (δ in ppm) |
|---|---|---|---|---|---|
| E-3 | #6'-phenyl-#5' | | #9-thiophene-#10 | | $R_t$ = 1,082 min; M⁺ + H = 329 |
| E-4 | #6'-thiophene-#5' | | #9-thiophene-#10 | | 147 |
| E-5 | #6'-phenyl-#5' | | 2-iminopyrrolidinyl (HN=, HN-) | | ¹H (CDCl₃): 8.68 (d, J = 1.76 Hz, 1H) 8.09-8.15 (m, 1H) 7.85 (d, J = 7.50 Hz, 1H) 7.63-7.69 (m, 1H) 7.56 (t, J = 7.72 Hz, 1H) 7.28-7.31 (m, 1H) 4.60 (d, J = 4.41 Hz, 2H) 1.49 (s, 9H) 1.40 (s, 6H) |
| E-6 | #6'-phenyl-#5' | | 2-oxopyrrolidinyl (O=, HN-) | | ¹H (CDCl₃): 8.68 (d, J = 1.76 Hz, 1H) 8.09-8.15 (m, 1H) 7.85 (d, J = 7.50 Hz, 1H) 7.63-7.69 (m, 1H) 7.56 (t, J = 7.72 Hz, 1H) 7.28-7.31 (m, 1H) 4.60 (d, J = 4.41 Hz, 2H) 1.49 (s, 9H) 1.40 (s, 6H) |
| E-7 | #6'-phenyl-#5' | | #10-thiophene-#9 | | $R_t$ = 1,186 min; M⁺ + H = 329 |
| E-8 | #6'-thiophene-#5' | | #10-thiophene-#9 | | $R_t$ = 1,250 min; M⁺ + H = 335 |
| E-9 | #6'-thiophene-#5' | | CH₃, CH₃ | | $R_t$ = 0,852 min; M⁺ + H = 307, 1 |

*HPLC-MS: HPLC-column Kinetex XB 018 1,7µ (50 × 2,1 mm); eluent: acetonitrile/water + 0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

Green House

The spray solutions were prepared in several steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml.

Water was then added to total volume of 100 ml.

This stock solution was diluted with the described solvent-emulsifier-water mixture to the given concentration.

Example 1—Long Lasting Control of *Borytis cinerea* on Leaves of Green Pepper

Young seedlings of green pepper were grown in pots to the 4 to 5 leaf stage. These plants were sprayed to run-off with an aqueous suspension, containing the concentration of active ingredient or their mixture mentioned in the table below. The plants were then cultivated in the greenhouse for 7 days and then inoculated with an aqueous biomalt solution containing the spore suspension of *Botrytis cinerea*. Then the plants were immediately transferred to a humid chamber. After 5 days at 22 to 24° C. and a relative humidity close to 100% the extent of fungal attack on the leaves was visually assessed as % diseased leaf area.

In this test, the samples which had been treated with 250 ppm of the active substance from examples E-8, E-9 and E-10 respectively, showed up at most 8% growth of the pathogen, whereas the untreated plants were 80% infected.

In this test, the samples which had been treated with 250 ppm of the active substance from examples D-11, D-15, D-20, D-47, D-48, D-49, D-51, D-52, D-53, D-54, D-55, D-56, D-18, D-26, D-59, D-61, D-62, D-63, D-67, D-71, D-79, D-83, D-87 respectively, showed up to at most 15% growth of the pathogen whereas the untreated plants were 80% infected.

Microtest

The active compounds were formulated separately as a stock solution having a concentration of 10000 ppm in dimethyl sulfoxide.

Example 1—Activity Against the Grey Mold Botrytis cinerea in the Microtiterplate Test The stock solutions were mixed according to the ratio, pipetted onto a micro titer plate (MTP) and diluted with water to the stated concentrations. A spore suspension of Botrci cinerea in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

In this test, the samples which had been treated with 8 ppm of the active substance from examples E-8 and E-10 respectively, showed up to at most 14% growth of the pathogen.

In this test, the samples which had been treated with 31 ppm of the active substance from examples D-8, D-11, D-15, D-17, D-18, D-20, D-26, D-27, D-45, D-47, D-48, D-51, D-52, D-53, D-54, D-55, D-56, D-59, D-60, D-61, D-62, D-63, D-67, D-69, D-70, D-71, D-73, D-74, D-75, D-76, D-79, D-80, D-81, D-82, D-83, D-84, D-85, D-86, D-87, D-90 and D-96, respectively, showed up to at most 19% growth of the pathogen.

Example 2—Activity Against Rice Blast Pyricularia oryzae in the Microtiterplate Test The stock solutions were mixed according to the ratio, pipetted onto a micro titer plate (MTP) and diluted with water to the stated concentrations. A spore suspension of Pyricularia oryzae in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation.

In this test, the samples which had been treated with 8 ppm of the active substance from examples E-8 and E-10 respectively, showed up to at most 1% growth of the pathogen.

In this test, the samples which had been treated with 31 ppm of the active substance from examples D-1, D-2, D-3, D-5, D-8, D-9, D-11, D-13, D-15, D-16, D-17, D-18, D-19, D-20, D-22, D-23, D-27, D-28, D-29, D-31, D-32, D-33, D-34, D-38, D-39, D-43, D-44, D-45, D-46, D-47, D-48, D-49, D-50, D-51, D-52, D-53, D-54, D-55, D-56, D-61, D-62, D-64, D-65, D-66, D-67, D-72, D-73, D-74, D-75, D-76, D-77, D-78, D-79, D-80, D-86, D-87, D-88, D-89, D-90, D-91, D-93 respectively, showed up to at most 22% growth of the pathogen.

Example 3—Activity Against Leaf Blotch on Wheat Caused by Septoria tritici

The stock solutions were mixed according to the ratio, pipetted onto a micro titer plate (MTP) and diluted with water to the stated concentrations. A spore suspension of Septoria tritici in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

In this test, the samples which had been treated with 31 ppm of the active substance from examples D-16, D-17, D-19, D-20, D-45, D-49, D-51, D-53, D-55, D-61, D-71, D-73, D-87, D-88, D-89, D-90, D-91, D-93 respectively, showed up to at most 18% growth of the pathogen.

The measured parameters were compared to the growth of the active compound-free control variant (100%) and the fungus-free and active compound-free blank value to determine the relative growth in % of the pathogens in the respective active compounds.

The invention claimed is:
1. A compound of the formula I

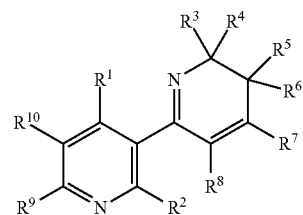

wherein
$R^1$ is in each case independently selected from hydrogen, halogen, CN, $C_1$-$C_6$-alkyl,
wherein the aliphatic moieties of $R^1$ are unsubstituted or substituted with identical or different groups $R^{1a}$ which independently of one another are selected from:
$R^{1a}$ halogen;
$R^2$ is in each case independently selected from the substituents as defined for $R^1$;
$R^3$, $R^4$ are $C_1$-$C_6$-alkyl;
$R^5$ is halogen;
$R^6$ is selected from H and halogen;
$R^9$, $R^{10}$ are independently selected from H, halogen, CN, $N(R^9)(R^{92})$, $S(R^{93})$, $S(O)_{z94}(R^{94})$, $O(R^{95})$, $C_1$-$C_6$-alkyl, $C_2$-$C_6$-alkenyl, $C_2$-$C_6$-alkynyl, cycloalkyl, CO—($R^{96}$);
$R^{91}$, $R^{92}$ are independently selected from H, alkyl;
$R^{93}$ is alkyl;
$R^{94}$ is alkyl;
$z^{94}$ is 1 or 2;
$R^{95}$ is alkyl;
$R^{96}$ is independently selected from alkyl, $N(R^{962})(R^{963})$;
$R^{962}$, $R^{963}$ are independently selected from H, alkyl;
wherein the aliphatic moieties of $R^9$, $R^{10}$ are unsubstituted or substituted by identical or different groups of $R^{9a}$, wherein $R^{9a}$ independently of one another are selected from: halogen, CN;
or
$R^7$ and $R^8$ together with the carbon atoms to which they are bound form a ring A, wherein the ring A is phenyl, and wherein the ring A is substituent by $(R^{78})_o$ wherein o is 0, 1, 2; and
$R^{78}$ are independently selected from halogen, $C_1$-$C_6$-alkyl, $C_1$-$C_6$-alkoxy, $C_1$-$C_6$-halogenalkoxy;
and
wherein the aliphatic moieties of $R^{78}$ are not further substituted or carry 1, 2, 3 or up to the maximum possible number of identical or different groups $R^{78a}$ which independently of one another are selected from:
$R^{78a}$ halogen;
and an N-oxide and an agriculturally acceptable salt thereof.

2. The compound of claim 1, wherein $R^3$ and $R^4$ are independently selected from $C_1$-$C_4$-alkyl.

3. The compound of claim 1, wherein $R^5$ and $R^6$ independently are selected from the group consisting of F, Cl, and Br.

4. The compound of claim 1, wherein $R^9$ and $R^{10}$ independently are selected from the group consisting of H and $C_1$-$C_4$-alkyl.

5. The compound of claim 1, wherein $R^9$ and $R^{10}$ independently are selected from the group consisting of CN and halogen.

6. The compound of claim 1, wherein $R^9$ and $R^{10}$ independently are selected from the group consisting of CO—$NH_2$, CO—NH($C_1$-$C_4$-alkyl) and CO—N($C_1$-$C_4$-alkyl)$_2$.

7. The compound of claim 1, wherein $R^9$ and $R^{10}$ independently are selected from the group consisting of S—($C_1$-$C_4$-alkyl), SO—($C_1$-$C_4$-alkyl) and $SO_2$—($C_1$-$C_4$-alkyl).

8. The compound of claim 1, wherein $R^9$ and $R^{10}$ independently are selected from the group consisting of H, CN, halogen, $C_1$-$C_4$-alkyl, $C_1$-$C_4$-haloalkyl, $C_1$-$C_4$-alkoxy, $C_1$-$C_4$-haloalkoxy, CO—$NH_2$, CO—NH($C_1$-$C_4$-alkyl), CO—N($C_1$-$C_4$-alkyl)$_2$, S—($C_1$-$C_4$-alkyl), SO—($C_1$-$C_4$-alkyl) and $SO_2$—($C_1$-$C_4$-alkyl).

9. A composition comprising one compound of formula I, as defined in claim 1, an N-oxide or an agriculturally acceptable salt thereof.

10. A method for combating phytopathogenic fungi comprising treating the fungi or the materials, plants, the soil or seeds to be protected against fungal attack with an effective amount of at least one compound of formula I, as defined in claim 1.

11. A seed coated with at least one compound of the formula I, as defined in claim 1 or an agriculturally acceptable salt thereof, in an amount of from 0.1 to 10 kg per 100 kg of seed.

12. A method for combating phytopathogenic fungi comprising treating the fungi or the materials, plants, the soil or seeds to be protected against fungal attack with the composition of claim 9.

13. A seed coated with the composition of claim 9 in an amount of from 0.1 to 10 kg per 100 kg of seed.

* * * * *